(12) United States Patent
Yasuma et al.

(10) Patent No.: US 8,557,805 B2
(45) Date of Patent: Oct. 15, 2013

(54) FUSED RING COMPOUND AND USE THEREOF

(75) Inventors: Tsuneo Yasuma, Osaka (JP); Nobuyuki Takakura, Osaka (JP); Yasufumi Miyamoto, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 134 days.

(21) Appl. No.: 13/142,507

(22) PCT Filed: Dec. 28, 2009

(86) PCT No.: PCT/JP2009/071811
§ 371 (c)(1),
(2), (4) Date: Jun. 28, 2011

(87) PCT Pub. No.: WO2010/076884
PCT Pub. Date: Jul. 8, 2010

(65) Prior Publication Data
US 2012/0035163 A1    Feb. 9, 2012

Related U.S. Application Data

(60) Provisional application No. 61/193,826, filed on Dec. 29, 2008.

(51) Int. Cl.
*A61K 31/535* (2006.01)
*C07D 277/04* (2006.01)

(52) U.S. Cl.
USPC ........ 514/228.2; 514/365; 514/342; 548/146; 546/269.7

(58) Field of Classification Search
USPC .................. 514/228.2, 365, 342; 548/146; 546/269.7
See application file for complete search history.

(56) References Cited

U.S. PATENT DOCUMENTS

| | | | |
|---|---|---|---|
| 7,799,820 B2* | 9/2010 | Takahashi et al. | 514/415 |
| 7,851,501 B2* | 12/2010 | Aydt et al. | 514/438 |
| 2009/0118304 A1 | 5/2009 | Takahashi et al. | |
| 2009/0247746 A1 | 10/2009 | Yasuma et al. | |

FOREIGN PATENT DOCUMENTS

| | | |
|---|---|---|
| JP | 2007-99630 | 4/2007 |
| KR | 2009-033752 | 4/2009 |
| WO | 2005/049019 | 6/2005 |
| WO | 2006/089397 | 8/2006 |
| WO | 2006/112549 | 10/2006 |
| WO | 2007/037534 | 4/2007 |
| WO | 2008/050821 | 5/2008 |
| WO | 2009/025477 | 2/2009 |
| WO | 2009/125873 | 10/2009 |

OTHER PUBLICATIONS

Caixach et al. CAS: 92: 146563, 1980.*
Takahashi et al. CAS: 146: 379952, 2007.*
International Search Report issued Jan. 26, 2010 in International (PCT) Application No. PCT/JP2009/071811.
M. J. Oila et al., "Mild and Efficient Synthesis of 2-Indole-2'-Oxazolines at Room Temperature—A Simple Access to Novel IndOX Ligands", Synthetic Communications, vol. 38, No. 3, pp. 361-370, 2008.
English translation of the International Preliminary Report on Patentability and Written Opinion dated Aug. 16, 2011.

* cited by examiner

*Primary Examiner* — Rei-tsang Shiao
(74) *Attorney, Agent, or Firm* — Wenderoth, Lind & Ponack, L.L.P.

(57) ABSTRACT

The present invention provides an agent for the prophylaxis or treatment of diabetes, obesity and the like, a glucokinase activator, containing a compound represented by the formula (I):

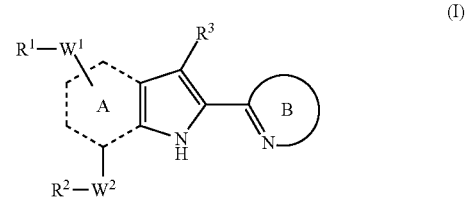

wherein each symbol is as defined in the description, or a salt thereof or a prodrug thereof.

21 Claims, No Drawings

SEQUENCE LISTING

<160> NUMBER OF SEQ ID NOS: 4

<210> SEQ ID NO 1
<211> LENGTH: 27
<212> TYPE: DNA
<213> ORGANISM: Artificial sequence
<220> FEATURE:
<223> OTHER INFORMATION: Synthetic construct; primer for cloning
      glucokinase

<400> SEQUENCE: 1
cagctctcca tccaagcagc cgttgct                                        27

<210> SEQ ID NO 2
<211> LENGTH: 21
<212> TYPE: DNA
<213> ORGANISM: Artificial sequence
<220> FEATURE:
<223> OTHER INFORMATION: Synthetic construct; primer for cloning
      glucokinase

<400> SEQUENCE: 2
ggcggcctgg gtcctgacaa g                                              21

<210> SEQ ID NO 3
<211> LENGTH: 69
<212> TYPE: DNA
<213> ORGANISM: Artificial sequence
<220> FEATURE:
<223> OTHER INFORMATION: Synthetic construct; primer for cloning
      glucokinase

<400> SEQUENCE: 3
ggatccatgc ccagaccaag atcccaactc ccacaaccca actcccaggt agagcagatc    60
ctggcagag                                                            69

<210> SEQ ID NO 4
<211> LENGTH: 24
<212> TYPE: DNA
<213> ORGANISM: Artificial sequence
<220> FEATURE:
<223> OTHER INFORMATION: Synthetic construct; primer for cloning
      glucokinase

<400> SEQUENCE: 4
gaattcctgg cccagcatac aggc                                           24

FUSED RING COMPOUND AND USE THEREOF

This application is a U.S. national stage of International Application No. PCT/JP2009/071811 filed Dec. 28, 2009, which claims the benefit of U.S. provisional application Ser. No. 61/193,826 filed Dec. 29, 2008.

TECHNICAL FIELD OF THE INVENTION

The present invention relates to a compound having a glucokinase activating action and useful as a therapeutic agent for diabetes, etc. and the like.

BACKGROUND OF THE INVENTION

Glucokinase (sometimes to be abbreviated to GK in the present specification) (EC2.7.1.1) is one of the four kinds of hexokinases found in mammals, and is also called hexokinase IV. GK is an enzyme that catalyzes the conversion of glucose to glucose-6-phosphate, which is the first step of glycolysis. GK is mainly present in the pancreatic β cell and the liver, and acts in the pancreatic β cell as a sensor of extracellular glucose concentration that regulates the glucose-stimulated insulin secretion. In the liver, the enzyme reaction of GK is a rate determining factor which regulates glycogen synthesis and glycolysis. The three hexokinases (I, II, III) other than GK reach the maximum enzyme activity at a glucose concentration of 1 mM or below. In contrast, GK shows low affinity for glucose and has a Km value of 8-15 mM which is close to a physiological blood glucose level. Accordingly, GK-mediated promotion of intracellular glucose metabolism occurs in conjunction with blood glucose changes from normal blood glucose (5 mM) to postprandial hyperglycemia (10-15 mM).

The hypothesis proposed by Matschinsky et al. in 1984 that GK acts as a glucose sensor in the pancreatic β cell and hepatocytes has been demonstrated by the analysis of glucokinase transgenic mouse in recent years (see The Journal of Biological Chemistry (J. Biol. Chem.), 1995, vol. 270, page 30253-30256; The Journal of Biological Chemistry (J. Biol. Chem.), 1997, vol. 272, page 22564-22569; The Journal of Biological Chemistry (J. Biol. Chem.), 1997, vol. 272, page 22570-22575; NIHONRINSHO, 2002, vol. 60, page 523-534; and Cell, 1995, vol. 83, page 69-78). That is, GK heterozygous deficient mouse showed a hyperglycemic condition, and further, a disordered glucose-stimulated insulin secretion response. GK homozygous deficient mouse dies shortly after birth with manifestations of marked hyperglycemia and urinary sugar. On the other hand, GK overexpressed mouse (hetero type) showed decreased blood glucose level, increased blood glucose clearance rate, increased liver glycogen content and the like. From these findings, it has been clarified that GK plays an important role in the systemic glucose homeostasis. In other words, decreased GK activity causes insulin secretion failure and lower liver glucose metabolism, which develops impaired glucose tolerance and diabetes. Conversely, GK activation or increased GK activity due to overexpression causes promoted insulin secretion and promoted liver glucose metabolism, which in turn increases the systemic use of glucose to improve glucose tolerance.

In addition, it has been clarified from the analysis of a report on GK gene abnormality mainly in the family of MODY2 (Maturity Onset Diabetes of the Young) that GK also acts as a glucose sensor in human, and plays a key role in glucose homeostasis (see Nature, 1992, vol. 356, page 721-722). In GK gene abnormality, due to the decreased affinity of GK for glucose (increased Km value) and the decreased Vmax, the blood glucose threshold value of insulin secretion increases and the insulin secretory capacity decreases. In the liver, decreased glucose uptake, promoted gluconeogenesis, decreased glycogen synthesis and liver insulin resistance are observed due to the decreased GK activity. On the other hand, a family with a mutation increasing the GK activity has also been found. In such a family, fasting hypoglycemia associated with increased plasma insulin concentration is observed (see New England Journal Medicine, 1998, vol. 338, page 226-230).

As mentioned above, GK acts as a glucose sensor in mammals including human, and plays an important role in blood glucose regulation. On the other hand, the control of blood glucose utilizing the glucose sensor system of GK is considered to open a new way to treat diabetes in many type 2 diabetes patients. Particularly, since a GK activating substance is expected to show insulin secretagogue action in the pancreatic β cell and glucose uptake promotion and glucose release suppressive action in the liver, it will be useful as a prophylactic or therapeutic drug for type 2 diabetes.

In recent years, it has been clarified that pancreatic β cell type glucokinase expresses locally in the feeding center (Ventromedial Hypothalamus: VMH) of rat brain. A subset of nerve cell present in VMH is called glucose responsive neuron, and plays an important role in the body weight control. From electrophysiological experiments, the neuron is activated in response to physiological changes in the glucose concentration (5-20 mM). However, since the glucose concentration sensor system of VHM is assumed to have a mechanism mediated by glucokinase as in the case of insulin secretion in the pancreatic β cell, different from the pancreatic β cell and the liver, a medicament capable of activating glucokinase of VHM has a possibility of providing not only a blood glucose corrective effect but also improvement of obesity.

As mentioned above, a medicament capable of activating GK is useful as a prophylactic or therapeutic drug for diabetes, diabetic complications, obesity and the like.

The following compounds have been reported.

(1) It has been reported that a compound represented by the formula:

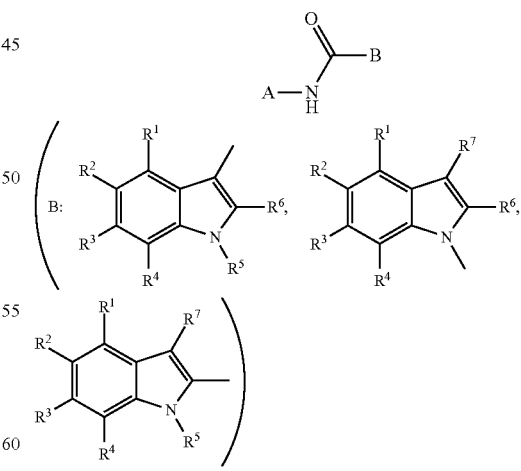

wherein

R¹, R², R³, R⁴, R⁶ and R⁷ are each independently a hydrogen atom, a halogen atom, nitro, —CN, —OH, —COOH, —CF₃, —NR¹⁰R11 (R¹⁰ and R¹¹ are each independently a hydrogen atom, a $C_{1-6}$ alkyl group, —CO—$_{1-6}$ alkyl, carboxy-$C_{1-6}$ alkyl, —C—$C_{1-6}$ alkyl-COOH, —$SO_2CH_3$, an aryl group etc.), a $C_{1-6}$ alkyl group, a $C_{3-8}$ cycloalkyl group, a heteroaryl group and the like;

$R^5$ is a $C_{1-6}$ alkyl group and the like; and

A is optionally substituted thiazolyl and the like is a glucokinase activator, and useful for the treatment of diabetes and the like (patent document 1).

(2) It has been reported that a compound represented by the formula:

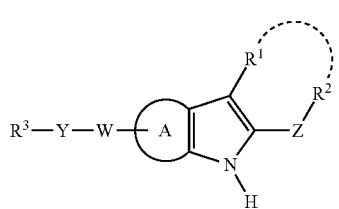

wherein ring A is an optionally substituted 6-membered ring,

W is O, $S(O)_m$ (m is 0, 1 or 2), $CR^5R^6$ ($R^5$ and $R^6$ are each independently a hydrogen atom or a $C_{1-6}$ alkyl group) or $NR^7$ ($R^7$ is a hydrogen atom or $R^{3'}$—Y'— ($R^{3'}$ is an optionally substituted hydrocarbon group, an optionally substituted hydroxy group, an optionally substituted mercapto group, an optionally substituted amino group or an optionally substituted heterocyclic group, Y' is a bond, CO, $S(O)_q$ (q is 0, 1 or 2) or $CR^{8'}R^{9'}$ ($R^{8'}$ and $R^{9'}$ are each independently a hydrogen atom or a $C_{1-6}$ alkyl group), Y is a bond, CO, $S(O)_p$ (p is 0, 1 or 2) or $CR^8R^9$ ($R^8$ and $R^9$ are each independently a hydrogen atom or a $C_{1-6}$ alkyl group), $R^3$ is an optionally substituted hydrocarbon group, an optionally substituted hydroxy group, an optionally substituted mercapto group, an optionally substituted amino group or an optionally substituted heterocyclic group, Z is a bond, CO, O, $S(O)_n$ (n is 0, 1 or 2) or $NR^{10}$ ($R^{10}$ is a hydrogen atom or a $C_{1-6}$ alkyl group), $R^1$ is a hydrogen atom, a halogen atom, an optionally substituted hydrocarbon group, an optionally substituted hydroxy group or an optionally substituted mercapto group, $R^2$ is a hydrogen atom, an optionally substituted hydrocarbon group, an optionally substituted hydroxy group, an optionally substituted mercapto group, an optionally substituted amino group or an optionally substituted heterocyclic group, and $R^1$ and $R^2$ are bonded to each other to form an optionally substituted ring, is a glucokinase activator (patent document 2).

(3) It has been reported that a compound represented by the formula:

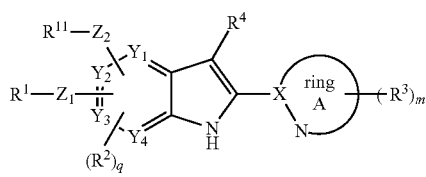

wherein $R^1$ is an optionally substituted aryl group or an optionally substituted heteroaryl group;

$R^{11}$ is an optionally substituted aryl group, a 5- to 7-membered aliphatic heterocyclic group, or an optionally substituted 5- or 6-membered heteroaryl group;

$R^2$ is formyl, OH, a $C_{1-6}$ alkyl group, —$CH_{3-a}F_a$, —$OCH_{3-a}F_a$ (a is 1-3), amino, cyano, a halogen atom or —$(CH_2)_{1-4}$—OH;

$R^3$ is a $C_{1-6}$ alkyl group, —$(CH_2)_{1-6}$—OH, —C(O)—$OC_{1-6}$ alkyl, —$(CH_2)_{1-6}$—$OC_{1-6}$ alkyl, —$(CH_2)_{1-6}$—$NH_2$, cyano, —C(O)—$C_{1-6}$ alkyl, a halogen atom, a $C_{2-6}$ alkenyl group, —O—$C_{1-6}$ alkyl, —COOH or OH;

$R^4$ is a hydrogen atom or a $C_{1-6}$ alkyl group;

Y is a carbon atom or a nitrogen atom;

$Z_1$ is —O—, —S—, —S(O)— or $S(O)_2$—;

$Z_2$ is —O—, —S—, —S(O)—, $S(O)_2$— or —$CH_2$— (optionally substituted by a halogen atom, a $C_{1-6}$ alkyl group etc.), or a single bond;

at least two of $Y_1$, $Y_2$, $Y_3$ and $Y_4$ are each independently a carbon atom and the rest is a carbon atom or a nitrogen atom;

ring A is a heteroaryl group;

X is a carbon atom or a nitrogen atom;

m is 0-2; and q is 0-2, is a glucokinase activator and useful for the treatment of diabetes, obesity and the like (patent document 3).

(4) It has been reported that a compound represented by the formula:

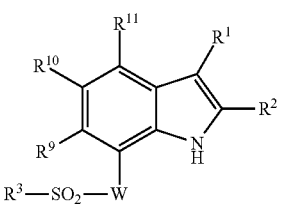

wherein $R^1$ is a hydrogen atom or halogen;

$R^2$ is

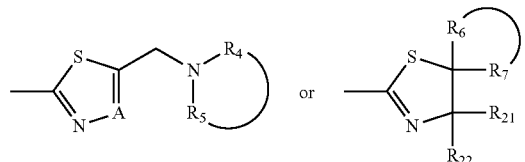

wherein

A is CH or N;

$R^4$ and $R^5$ are each an optionally substituted $C_{1-6}$ alkyl or optionally substituted $C_{3-10}$ cycloalkyl, and $R^4$ and $R^5$ form an optionally substituted ring (the ring is not morpholine);

$R^6$, $R^7$, $R^{21}$ and $R^{22}$ are each a hydrogen atom, an optionally substituted hydrocarbon group, a cyano group or an acyl group, and $R^6$ and $R^7$ form an optionally substituted ring;

W is an oxygen atom or $NR^8$ ($R^8$ is a hydrogen atom, an optionally substituted $C_{1-6}$ alkyl group or an optionally substituted $C_{3-10}$ cycloalkyl group);

$R^3$ is an optionally substituted heterocyclic group or an optionally substituted $C_{6-14}$ aryl group; and $R^9$, $R^{10}$ and $R^{11}$ are each a hydrogen atom, halogen, an optionally substituted $C_{1-6}$ alkyl group or an optionally substituted $C_{1-6}$ alkoxy group;

provided that when $R^{21}$ is a hydrogen atom or $C_{1-6}$ alkoxycarbonyl and $R^{22}$ is a hydrogen atom, then $R^6$ and $R^7$ are not simultaneously hydrogen atoms or methyl groups, is a glucokinase activator and useful for the treatment of diabetes, obesity and the like (patent document 4).

(5) It has been reported in patent document 5 that an indole derivative represented by the formula:

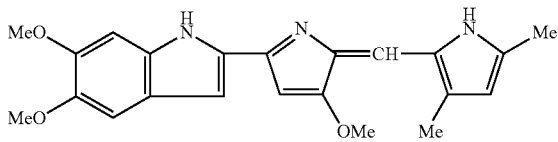 [SMILES: COC1=CC(c2cc3cc(OC)c(OC)cc3[nH]2)=NC1=Cc1[nH]c(C)cc1C]

is useful for an antirheumatism treatment, an anticancer treatment and an antivirus infection treatment (patent document 5).

(6) It has been reported in patent document 6 that an indole derivative represented by the formula:

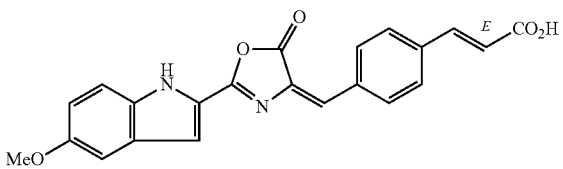 [SMILES: COc1ccc2[nH]c(C3=N/C(=C/c4ccc(/C=C/C(=O)O)cc4)C(=O)O3)cc2c1]

is a PDGF antagonist (patent document 6).

(7) In non-patent document 1, an indole derivative represented by the formula

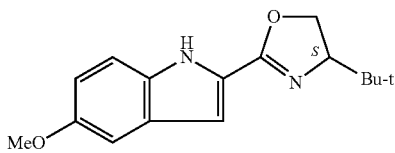

(non-patent document 1) is reported.

(8) It has been reported that a compound represented by

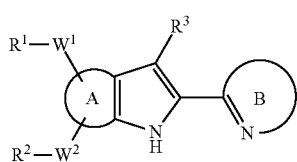

wherein ring A is a 6-membered ring which may be further substituted;

ring B is an optionally substituted 5- or 7-membered nitrogen-containing heterocycle;

W1 and W2 are each independently O, S, SO, $SO_2$ or $NR^4$ ($R^4$ is a hydrogen atom or a $C_{1-6}$ alkyl group);

$R^1$ is a substituted methyl group, an optionally substituted $C_{2-6}$ alkyl group, an optionally substituted $C_{3-10}$ cycloalkyl group, an optionally substituted $C_{6-14}$ aryl group or an optionally substituted heterocyclic group;

$R^2$ is an optionally substituted $C_{1-6}$ alkyl group or an optionally substituted $C_{3-10}$ cycloalkyl group;

$R^3$ is a hydrogen atom or a halogen atom, (excluding N-methyl-4-[(1-methyl-1H-tetrazol-5-yl)thio]-2-(1,3-thiazol-2-yl)-1H-indole-7-amine) is a glucokinase activator, and useful for the treatment of diabetes, obesity and the like (patent document 7).

However, none of the documents disclose a compound represented by the following formula (I).

patent document 1: WO2005/049019
patent document 2: WO2006/112549
patent document 3: WO2007/037534
patent document 4: WO2008/050821
patent document 5: WO2006/089397
patent document 6: JP-A-2007-099630
patent document 7: WO2009/125873
non-patent document 1: Synthetic Communications, 38(3), 361-370, 2008

SUMMARY OF THE INVENTION

Problems to be Solved by the Invention

The present invention aims to provide a glucokinase activator useful as a medicament such as an agent for the prophylaxis or treatment of diabetes, obesity etc. and the like.

Means of Solving the Problems

As a result of various intensive studies, the present inventors have found that a compound represented by the formula (I):

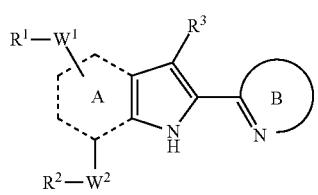

wherein ring A is a 6-membered ring which is optionally further substituted;

ring B is an optionally substituted 5- to 7-membered non-aromatic nitrogen-containing heterocycle;

$W^1$ is O, S, SO, $SO_2$, an optionally substituted $C_{1-6}$ alkylene group or $NR^4$ wherein $R^4$ is a hydrogen atom or a $C_{1-6}$ alkyl group;

$R^1$ is an optionally substituted $C_{6-14}$ aryl group or an optionally substituted heterocyclic group;

$R^3$ is a hydrogen atom or a halogen atom;

(1) when $W^2$ is O, S, SO or $SO_2$, $R^2$ is an optionally substituted heterocyclic group; and (2) when $W^2$ is a bond, $R^2$ is a hydrogen atom, a halogen atom, an optionally substituted $C_{1-6}$ alkyl group, an optionally substituted $C_{3-10}$ cycloalkyl group or an optionally substituted heterocyclic group, or a salt thereof [hereinafter sometimes to be abbreviated as compound (I)]

unexpectedly has a superior glucokinase activating action as well as superior properties as a pharmaceutical product such as stability and the like, and can be a safe and useful medicament, which resulted in the completion of the present invention.

Accordingly, the present invention relates to

[1] compound (I);

[2] the compound of the above-mentioned [1], wherein $W^2$ is O, S, SO or $SO_2$;

[3] the compound of the above-mentioned [1], wherein ring A is is a benzene ring;

[4] the compound of the above-mentioned [1], wherein $R^3$ is a hydrogen atom;

[5] the compound of the above-mentioned [1], wherein ring B is a thiazoline ring optionally substituted by a $C_{1-6}$ alkyl group optionally substituted by 1 to 3 substituents selected from
(1) a hydroxy group,
(2) a carbamoyl group optionally mono- or di-substituted by $C_{1-6}$ alkyl group(s) optionally substituted by 1 to 3 substituents selected from
(i) a hydroxy group,
(ii) a halogen atom,
(iii) a $C_{1-6}$ alkoxy group,
(iv) a $C_{1-6}$ alkylsulfonyl group, and
(v) a cyano group,
(3) a carboxy group, and
(4) a $C_{1-6}$ alkoxy-carbonyl group;

[6] the compound of the above-mentioned [1], wherein $W^1$ is O;

[7] the compound of the above-mentioned [1], wherein $R^1$ is a phenyl group or a pyridyl group each optionally substituted by 1 to 3 substituents selected from
(1) a $C_{1-6}$ alkyl group optionally substituted by 1 to 3 substituents selected from
(i) a $C_{1-6}$ alkoxy group optionally substituted by a $C_{1-6}$ alkoxy group, and
(ii) a $C_{1-6}$ alkylsulfonyl group, and
(2) a $C_{1-6}$ alkylsulfonyl group;

[8] the compound of the above-mentioned [1], wherein $W^2$ is O, and $R^2$ is a tetrahydropyranyl group;

[9] the compound of the above-mentioned [1], wherein $W^2$ is a bond, and $R^2$ is a hydrogen atom or a $C_{1-6}$ alkyl group;

[10] the compound of the above-mentioned [1], wherein
ring A is a benzene ring;
ring B is a thiazoline ring optionally substituted by a $C_{1-6}$ alkyl group optionally substituted by 1 to 3 substituents selected from
(1) a hydroxy group,
(2) a carbamoyl group optionally mono- or di-substituted by $C_{1-6}$ alkyl group(s) optionally substituted by 1 to 3 substituents selected from
(i) a hydroxy group,
(ii) a halogen atom,
(iii) a $C_{1-6}$ alkoxy group,
(iv) a $C_{1-6}$ alkylsulfonyl group, and
(v) a cyano group,
(3) a carboxy group, and
(4) a $C_{1-6}$ alkoxy-carbonyl group;
$W^1$ is O;
$R^1$ is a phenyl group or a pyridyl group each optionally substituted by 1 to 3 substituents selected from
(1) a $C_{1-6}$ alkyl group optionally substituted by 1 to 3 substituents selected from
(i) a $C_{1-6}$ alkoxy group optionally substituted by a $C_{1-6}$ alkoxy group, and
(ii) a $C_{1-6}$ alkylsulfonyl group, and
(2) a $C_{1-6}$ alkylsulfonyl group;
$R^3$ is a hydrogen atom;
$W^2$ is O; and
$R^2$ is a tetrahydropyranyl group;

[11] the compound of the above-mentioned [1], wherein
ring A is a benzene ring;
ring B is a thiazoline ring optionally substituted by a $C_{1-6}$ alkyl group optionally substituted by 1 to 3 substituents selected from
(1) a hydroxy group,
(2) a carbamoyl group optionally mono- or di-substituted by $C_{1-6}$ alkyl group(s) optionally substituted by 1 to 3 substituents selected from
(i) a hydroxy group,
(ii) a halogen atom,
(iii) a $C_{1-6}$ alkoxy group,
(iv) a $C_{1-6}$ alkylsulfonyl group, and
(v) a cyano group,
(3) a carboxy group, and
(4) a $C_{1-6}$ alkoxy-carbonyl group;
$W^1$ is O;
$R^1$ is a phenyl group or a pyridyl group each optionally substituted by 1 to 3 substituents selected from
(1) a $C_{1-6}$ alkyl group optionally substituted by 1 to 3 substituents selected from
(i) a $C_{1-6}$ alkoxy group optionally substituted by a $C_{1-6}$ alkoxy group, and
(ii) a $C_{1-6}$ alkylsulfonyl group, and
(2) a $C_{1-6}$ alkylsulfonyl group;
$R^3$ is a hydrogen atom;
$W^2$ is a bond; and
$R^2$ is a hydrogen atom or a $C_{1-6}$ alkyl group;

[12] N-methyl-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide or a salt thereof;

[13] N-methyl-2-[2-(5-{[6-(methylsulfonyl)pyridin-3-yl]oxy}-1H-indol-2-yl)-4,5-dihydro-1,3-thiazol-5-yl]acetamide or a salt thereof;

[14] N,N-dimethyl-2-[2-(5-{[6-(methylsulfonyl)pyridin-3-yl]oxy}-1H-indol-2-yl)-4,5-dihydro-1,3-thiazol-5-yl]acetamide or a salt thereof;

[15] N-(2-methoxyethyl)-2-[2-(5-{[6-(methylsulfonyl)pyridin-3-yl]oxy}-1H-indol-2-yl)-4,5-dihydro-1,3-thiazol-5-yl]acetamide or a salt thereof;

[16] 2-[2-(7-ethyl-5-{[6-(methylsulfonyl)pyridin-3-yl]oxy}-1H-indol-2-yl)-4,5-dihydro-1,3-thiazol-5-yl]-N-methylacetamide or a salt thereof;

[17] a prodrug of the compound of the above-mentioned [1];

[18] a medicament comprising the compound of the above-mentioned [1] or a prodrug thereof;

[19] the medicament of the above-mentioned [18], which is a glucokinase activator;

[20] the medicament of the above-mentioned [18], which is an agent for the prophylaxis or treatment of diabetes or obesity;

[21] a method for the prophylaxis or treatment of diabetes or obesity in a mammal, comprising administering an effective amount of the compound of the above-mentioned [1] or a prodrug thereof to the mammal;

[22] use of the compound of the above-mentioned [1] or a prodrug thereof for the production of a prophylactic or therapeutic agent for diabetes or obesity;

[23] the compound of the above-mentioned [1] or a prodrug thereof for use in a prophylactic or therapeutic agent for diabetes or obesity;

and the like.

Effect of the Invention

Since compound (I) has a superior glucokinase activating action, compound (I) is useful as a medicament such as an agent for the prophylaxis or treatment of diabetes, obesity and the like, and the like.

DETAILED DESCRIPTION OF THE INVENTION

Unless otherwise specified, the "halogen atom" in the present specification means a fluorine atom, a chlorine atom, a bromine atom or an iodine atom.

Unless otherwise specified, the "$C_{1-3}$ alkylenedioxy group" in the present specification means methylenedioxy, ethylenedioxy or the like.

Unless otherwise specified, the "$C_{1-6}$ alkyl group" in the present specification means methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

Unless otherwise specified, the "$C_{1-6}$ alkylene group" in the present specification means methylene, ethylene, propylene, 1-methylpropylene, butylene, pentamethylene, 3-methylbutylene, 1,1-dimethylpropylene, hexamethylene or the like.

Unless otherwise specified, the "$C_{1-6}$ alkoxy group" in the present specification means methoxy, ethoxy, propoxy, isopropoxy, butoxy, isobutoxy, sec-butoxy, tert-butoxy or the like.

Unless otherwise specified, the "$C_{1-6}$ alkoxy-carbonyl group" in the present specification means methoxycarbonyl, ethoxycarbonyl, propoxycarbonyl, tert-butoxycarbonyl or the like.

Unless otherwise specified, the "$C_{1-6}$ alkyl-carbonyl group" in the present specification means acetyl, propanoyl, butanoyl, isobutanoyl, pentanoyl, isopentanoyl, hexanoyl or the like.

Unless otherwise specified, the "$C_{3-10}$ cycloalkyl group" in the present specification means cyclopropyl, cyclobutyl, cyclopentyl, cyclohexyl, cycloheptyl, cyclooctyl or the like. The $C_{3-10}$ cycloalkyl group also includes cross-linking type cycloalkyl groups such as bicyclo[3.1.1]heptyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

Unless otherwise specified, the "$C_{6-14}$ aryl group" in the present specification means phenyl, naphthyl, anthryl, phenanthryl, acenaphthylenyl, biphenylyl or the like.

The definition of each symbol used in the formula (I) is explained in detail in the following.

Ring A is a 6-membered ring which is optionally further substituted.

Examples of the "6-membered ring" of the "6-membered ring which is optionally further substituted" for ring A include benzene, cyclohexane, cyclohexene, cyclohexadiene, 6-membered aromatic heterocycle and 6-membered non-aromatic heterocycle.

Here, examples of the 6-membered aromatic heterocycle include a 6-membered aromatic heterocycle containing, as a ring-constituting atom besides carbon atoms, 1 to 4 hetero atoms such as a nitrogen atom and the like.

Preferable examples of the 6-membered aromatic heterocycle include pyridine, pyrimidine, pyridazine, pyrazine and the like.

Examples of the 6-membered non-aromatic heterocycle include a 6-membered non-aromatic heterocycle containing, as a ring-constituting atom besides carbon atoms, 1 to 4 hetero atoms selected from an oxygen atom, a sulfur atom (the sulfur atom is optionally oxidized) and a nitrogen atom.

Preferable examples of the 6-membered non-aromatic heterocycle include piperidine, piperazine, morpholine, thiomorpholine, pyran, tetrahydropyran, thiopyran, tetrahydrothiopyran, 1-oxidotetrahydrothiopyran, 1,1-dioxidotetrahydrothiopyran, tetrahydropyrimidine, dioxane and the like.

The "6-membered ring" of the "6-membered ring which is optionally further substituted" for ring A may have 1 or 2 substituents at substitutable position(s). Examples of such substituent include (1) an optionally substituted $C_{1-6}$ alkyl group;
(2) a $C_{3-10}$ cycloalkyl group (e.g., cyclopropyl, cyclohexyl);
(3) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
(4) an aromatic heterocyclic group (e.g., thienyl, furyl, pyridyl, pyrimidinyl, pyridazinyl, oxazolyl, thiazolyl, tetrazolyl, oxadiazolyl, pyrazinyl, quinolyl, indolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
(5) a $C_{1-6}$ alkyl-carbonyl group optionally substituted by 1 to 3 halogen atoms;
(6) a $C_{1-6}$ alkoxy-carbonyl group optionally substituted by 1 to 3 halogen atoms;
(7) an aromatic heterocyclyl-carbonyl group (e.g., thienylcarbonyl, indolylcarbonyl) optionally substituted by 1 to 3 amino groups [the amino groups are each optionally mono- or di-substituted by substituent(s) selected from a $C_{1-6}$ alkyl group and an aromatic heterocyclyl-sulfonyl group (e.g., thienylsulfonyl)];
(8) a non-aromatic heterocyclyl-carbonyl group (e.g., piperidinylcarbonyl, piperazinylcarbonyl, morpholinylcarbonyl, thiomorpholinylcarbonyl, 1-oxidothiomorpholinylcarbonyl, 1,1-dioxidothiomorpholinylcarbonyl, pyrrolidinylcarbonyl, azetidinylcarbonyl) optionally substituted by 1 to 3 substituents selected from
  (a) a hydroxy group,
  (b) a $C_{1-6}$ alkyl group optionally substituted by 1 to 3 hydroxy groups,
  (c) a halogen atom,
  (d) a carboxy group,
  (e) a $C_{1-6}$ alkoxy-carbonyl group,
  (f) an amino group, and
  (g) a $C_{1-6}$ alkylsulfonyl group;
(9) a carbamoyl group optionally mono- or di-substituted by substituent(s) selected from
  (a) a $C_{1-6}$ alkyl group optionally substituted by 1 to 3 substituents selected from a hydroxy group, a $C_{1-6}$ alkoxy group, a $C_{1-6}$ alkylsulfonyl group (e.g., methylsulfonyl) and an aromatic heterocyclic group (e.g., furyl),
  (b) a $C_{6-14}$ aryl group (e.g., phenyl),
  (c) a $C_{7-13}$ aralkyl group (e.g., benzyl),
  (d) a $C_{1-6}$ alkoxy group, (e) a $C_{3-10}$ cycloalkyl group (e.g., cyclopropyl),
(f) a $C_{1-6}$ alkylsulfonyl group (e.g., methylsulfonyl),
(g) an aromatic heterocyclic group (e.g., triazolyl, tetrazolyl), and
(h) a non-aromatic heterocyclic group (e.g., tetrahydropyranyl);

(10) a thiocarbamoyl group optionally mono- or di-substituted by $C_{1-6}$ alkyl group(s) optionally substituted by 1 to 3 halogen atoms;

(11) a sulfamoyl group optionally mono- or di-substituted by $C_{1-6}$ alkyl group(s) optionally substituted by 1 to 3 halogen atoms;

(12) a carboxy group;

(13) a hydroxy group;

(14) a $C_{2-6}$ alkenyloxy group (e.g., ethenyloxy) optionally substituted by 1 to 3 halogen atoms;

(15) a $C_{7-13}$ aralkyloxy group (e.g., benzyloxy) optionally substituted by 1 to 3 halogen atoms;

(16) a $C_{6-14}$ aryloxy group (e.g., phenyloxy, naphthyloxy);

(17) a $C_{1-6}$ alkyl-carbonyloxy group (e.g., acetyloxy, tert-butylcarbonyloxy);

(18) a mercapto group;

(19) a $C_{6-14}$ arylthio group (e.g., phenylthio, naphthylthio);

(20) an aromatic heterocyclyl-thio group (e.g., tetrazolylthio) optionally substituted by 1 to 3 $C_{1-6}$ alkyl groups;

(21) a sulfo group;

(22) a cyano group;

(23) an azido group;

(24) a nitro group;

(25) a nitroso group;

(26) a halogen atom;

(27) an aromatic heterocyclyl-carbonylthio group (e.g., indolylcarbonylthio) optionally substituted by 1 to 3 amino groups [the amino groups are each optionally mono- or di-substituted by substituent(s) selected from a $C_{1-6}$ alkyl group and an aromatic heterocyclyl-sulfonyl group (e.g., thienylsulfonyl)];

(28) a formyl group;

(29) an aromatic heterocyclyl-oxy group (e.g., pyrimidyloxy, pyrazinyloxy);

(30) a $C_{1-6}$ alkylsulfonyloxy group (e.g., methylsulfonyloxy);

(31) a $C_{2-6}$ alkenyl-carbonyl group (e.g., vinylcarbonyl);

(32) a non-aromatic heterocyclyl-carbonyloxy group (e.g., morpholinylcarbonyloxy) optionally substituted by 1 to 3 $C_{1-6}$ alkyl groups;

(33) a di-tert-butylphenylsilyloxy group;

and the like (hereinafter to be referred to as substituent group A). When the number of the substituents is two or more, the respective substituents may be the same or different.

The "$C_{1-6}$ alkyl group" as the "substituent" of the "6-membered ring which is optionally further substituted" for ring A may have 1 to 3 substituents at substitutable position(s).

As such substituent, for example, (1) a $C_{3-10}$ cycloalkyl group (e.g., cyclopropyl, cyclohexyl);

(2) a $C_{6-14}$ aryl group (e.g., phenyl, naphthyl) optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group, and
(d) a halogen atom;

(3) an aromatic heterocyclic group (e.g., thienyl, furyl, pyridyl, pyrimidinyl, pyridazinyl, oxazolyl, thiazolyl, tetrazolyl, oxadiazolyl, pyrazinyl, quinolyl, indolyl) optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group, and
(d) a halogen atom;

(4) a non-aromatic heterocyclic group (e.g., tetrahydrofuryl, morpholinyl, thiomorpholinyl, piperidinyl, pyrrolidinyl, piperazinyl, dioxolyl, dioxolanyl, 1,3-dihydro-2-benzofuranyl, thiazolidinyl, thiazolinyl) optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group,
(d) a $C_{1-6}$ alkyl-carbonyl group,
(e) a $C_{1-6}$ alkylsulfonyl group,
(f) an oxo group, and
(g) a halogen atom;

(5) an amino group optionally mono- or di-substituted by substituent(s) selected from
(a) a $C_{1-6}$ alkyl group optionally substituted by 1 to 3 substituents selected from a hydroxy group and a $C_{1-6}$ alkylsulfonyl group (e.g., methylsulfonyl),
(b) a $C_{1-6}$ alkyl-carbonyl group,
(c) a $C_{1-6}$ alkoxy-carbonyl group optionally substituted by 1 to 3 $C_{6-14}$ aryl groups (e.g., phenyl),
(d) a $C_{6-14}$ aryl-carbonyl group (e.g., benzoyl),
(e) a $C_{7-13}$ aralkyl-carbonyl group (e.g., benzylcarbonyl, phenethylcarbonyl),
(f) a carbamoyl group optionally mono- or di-substituted by substituent(s) selected from a $C_{1-6}$ alkyl group, a $C_{6-14}$ aryl group (e.g., phenyl) and a $C_{7-13}$ aralkyl group (e.g., benzyl),
(g) a $C_{1-6}$ alkylsulfonyl group (e.g., methylsulfonyl, ethylsulfonyl, isopropylsulfonyl),
(h) a $C_{6-14}$ arylsulfonyl group (e.g., benzenesulfonyl, 1-naphthalenesulfonyl, 2-naphthalenesulfonyl) optionally substituted by 1 to 3 $C_{1-6}$ alkyl groups,
(i) a $C_{7-13}$ aralkylsulfonyl group (e.g., benzylsulfonyl)
(j) a $C_{3-10}$ cycloalkyl group (e.g., cyclohexyl) optionally substituted by 1 to 3 substituents selected from a hydroxy group and a $C_{1-6}$ alkyl group,
(k) an aromatic heterocyclic group (e.g., triazolyl), and
(l) a non-aromatic heterocyclic group (e.g., tetrahydrothiopyranyl, 1-oxidotetrahydrothiopyranyl, 1,1-dioxidotetrahydrothiopyranyl);

(6) an amidino group;

(7) a $C_{1-6}$ alkyl-carbonyl group optionally substituted by 1 to 3 halogen atoms;

(8) a $C_{1-6}$ alkoxy-carbonyl group optionally substituted by 1 to 3 halogen atoms;

(9) an aromatic heterocyclyl-carbonyl group (e.g., thienylcarbonyl, indolylcarbonyl) optionally substituted by 1 to 3 amino groups [the amino groups are each optionally mono- or di-substituted by substituent(s) selected from a $C_{1-6}$ alkyl group and an aromatic heterocyclyl-sulfonyl group (e.g., thienylsulfonyl)];

(10) a non-aromatic heterocyclyl-carbonyl group (e.g., piperidinylcarbonyl, piperazinylcarbonyl, morpholinylcarbonyl, thiomorpholinylcarbonyl, 1-oxidothiomorpholinylcarbonyl, 1,1-dioxidothiomorpholinylcarbonyl, pyrrolidinylcarbonyl, azetidinylcarbonyl) optionally substituted by 1 to 3 substituents selected from
(a) a hydroxy group,
(b) a $C_{1-6}$ alkyl group optionally substituted by 1 to 3 hydroxy groups,
(c) a halogen atom,
(d) a carboxy group,
(e) a $C_{1-6}$ alkoxy-carbonyl group, (f) an amino group,
(g) a $C_{1-6}$ alkylsulfonyl group, and
(h) an oxo group;
(11) a $C_{1-6}$ alkylsulfonyl group (e.g., methylsulfonyl, ethylsulfonyl) optionally substituted by 1 to 3 halogen atoms;
(12) a carbamoyl group optionally mono- or di-substituted by substituent(s) selected from
   (a) a $C_{1-6}$ alkyl group optionally substituted by 1 to 3 substituents selected from a hydroxy group, a halogen atom, a $C_{1-6}$ alkoxy group, a $C_{1-6}$ alkylsulfonyl group (e.g., methylsulfonyl), a cyano group, a non-aromatic heterocyclic group optionally substituted by a $C_{1-6}$ alkyl group and an aromatic heterocyclic group (e.g., furyl),
   (b) a $C_{6-14}$ aryl group (e.g., phenyl),
   (c) a $C_{7-13}$ aralkyl group (e.g., benzyl),
   (d) a $C_{1-6}$ alkoxy group,
   (e) a $C_{3-10}$ cycloalkyl group (e.g., cyclopropyl),
   (f) a $C_{1-6}$ alkylsulfonyl group (e.g., methylsulfonyl),
   (g) an aromatic heterocyclic group (e.g., triazolyl, tetrazolyl), and
   (h) a non-aromatic heterocyclic group (e.g., tetrahydropyranyl);
(13) a thiocarbamoyl group optionally mono- or di-substituted by $C_{1-6}$ alkyl group(s) optionally substituted by 1 to 3 halogen atoms;
(14) a sulfamoyl group optionally mono- or di-substituted by $C_{1-6}$ alkyl group(s) optionally substituted by 1 to 3 halogen atoms;
(15) a carboxy group;
(16) a hydroxy group;
(17) a $C_{1-6}$ alkoxy group optionally substituted by 1 to 3 substituents selected from
   (a) a halogen atom,
   (b) a carboxy group,
   (c) a $C_{1-6}$ alkoxy group, and
   (d) a $C_{1-6}$ alkoxy-carbonyl group;
(18) a $C_{2-6}$ alkenyloxy group (e.g., ethenyloxy) optionally substituted by 1 to 3 halogen atoms;
(19) a $C_{3-10}$ cycloalkyloxy group (e.g., cyclohexyloxy);
(20) a $C_{7-13}$ aralkyloxy group (e.g., benzyloxy) optionally substituted by 1 to 3 halogen atoms;
(21) a $C_{6-14}$ aryloxy group (e.g., phenyloxy, naphthyloxy);
(22) a $C_{1-6}$ alkyl-carbonyloxy group (e.g., acetyloxy, tert-butylcarbonyloxy);
(23) a mercapto group;
(24) a $C_{1-6}$ alkylthio group (e.g., methylthio, ethylthio) optionally substituted by 1 to 3 substituents selected from
   (a) a halogen atom,
   (b) a $C_{6-14}$ aryl group, and
   (c) a carboxy group;
(25) a $C_{6-14}$ arylthio group (e.g., phenylthio, naphthylthio);
(26) an aromatic heterocyclyl-thio group (e.g., tetrazolylthio) optionally substituted by 1 to 3 $C_{1-6}$ alkyl groups;
(27) a sulfo group;
(28) a cyano group;
(29) an azido group;
(30) a nitro group;
(31) a nitroso group;
(32) a halogen atom;
(33) a $C_{1-6}$ alkylsulfinyl group (e.g., methylsulfinyl);
(34) a $C_{3-10}$ cycloalkyl-$C_{1-6}$ alkyloxy group (e.g., cyclopropylmethyloxy);
(35) a $C_{1-3}$ alkylenedioxy group;
(36) an aromatic heterocyclyl-carbonylthio group (e.g., indolylcarbonylthio) optionally substituted by 1 to 3 amino groups [the amino groups are each optionally mono- or di-substituted by substituent(s) selected from a $C_{1-6}$ alkyl group and an aromatic heterocyclyl-sulfonyl group (e.g., thienylsulfonyl)];
(37) a formyl group;
(38) an aromatic heterocyclyl-oxy group (e.g., pyrimidyloxy, pyrazinyloxy);
(39) a $C_{1-6}$ alkylsulfonyloxy group (e.g., methylsulfonyloxy);
(40) a $C_{2-6}$ alkenyl-carbonyl group (e.g., vinylcarbonyl);
(41) a non-aromatic heterocyclyl-carbonyloxy group (e.g., morpholinylcarbonyloxy) optionally substituted by 1 to 3 $C_{1-6}$ alkyl groups;
(42) a di-tert-butylphenylsilyloxy group; and the like (hereinafter to be referred to as substituent group B) can be mentioned. When the number of the substituents is two or more, the respective substituents may be the same or different.

Ring A is preferably benzene which is further optionally substituted.

Ring A is more preferably benzene.

Ring B is an optionally substituted 5- to 7-membered non-aromatic nitrogen-containing heterocycle.

Examples of the "5- to 7-membered non-aromatic nitrogen-containing heterocycle" of the "optionally substituted 5- to 7-membered non-aromatic nitrogen-containing heterocycle" for ring B include a 5- to 7-membered (preferably 5- or 6-membered) non-aromatic nitrogen-containing heterocycle containing 1 to 4 nitrogen atoms as a ring-constituting atom besides carbon atoms, and optionally further containing 1 to 4 hetero atoms selected from an oxygen atom and a sulfur atom (the sulfur atom is optionally oxidized).

Preferable examples of the non-aromatic nitrogen-containing heterocycle include oxazoline, thiazoline, imidazoline, dihydropyrrole (e.g., 3,4-dihydro-2H-pyrrole), dihydrooxadiazole (e.g., 4,5-dihydro-1,2,4-oxadiazole), pyrazolidine, tetrahydropyrimidine and the like.

The "5- to 7-membered non-aromatic nitrogen-containing heterocycle" of the "optionally substituted 5- to 7-membered non-aromatic nitrogen-containing heterocycle" for ring B may have 1 to 3 substituents at substitutable position(s). Examples of such substituent include those similar to substituent group A recited as the substituents that the "6-membered ring" of the "6-membered ring which is optionally further substituted" for ring A optionally has. When the number of the substituents is two or more, the respective substituents may be the same or different.

The "substituent" of the "optionally substituted 5- to 7-membered non-aromatic nitrogen-containing heterocycle" for ring B is preferably (1) a $C_{1-6}$ alkyl group (preferably, methyl, ethyl, isobutyl) optionally substituted by 1 to 3 substituents selected from
   (a) a hydroxy group,
   (b) a carbamoyl group optionally mono- or di-substituted by substituent(s) selected from a $C_{1-6}$ alkyl group optionally substituted by 1 to 3 substituents selected from a hydroxy group, a halogen atom (e.g., a fluorine atom), a $C_{1-6}$ alkoxy group (e.g., methoxy), a $C_{1-6}$ alkylsulfonyl group (e.g., methylsulfonyl), a cyano group and a non-aromatic heterocyclic group (e.g., oxetanyl) optionally substituted by a $C_{1-6}$ alkyl group, and a $C_{3-10}$ cycloalkyl group,
   (c) a carboxy group,
   (d) a $C_{1-6}$ alkoxy group,
   (e) a $C_{1-6}$ alkoxy-carbonyl group (preferably, ethoxycarbonyl),
   (f) a non-aromatic heterocyclic group (preferably, thiomorpholinyl, 1-oxidothiomorpholinyl) optionally substituted by a hydroxy group or an oxo group, and (g) a non-aromatic heterocyclyl-carbonyl group (preferably, morpholinylcarbonyl, azetinylcarbonyl, thiomorpholinylcarbonyl, 1-oxidothiomorpholinylcarbonyl, 1,1-dioxidothiomorpholinylcarbonyl) optionally substituted by a hydroxy group or an oxo group;

(2) a $C_{1-6}$ alkoxy-carbonyl group (preferably, ethoxycarbonyl) optionally substituted by 1 to 3 halogen atoms; and (3) a non-aromatic heterocyclyl-carbonyl group optionally substituted by 1 to 3 substituents selected from
  (a) a hydroxy group,
  (b) a $C_{1-6}$ alkyl group optionally substituted by 1 to 3 hydroxy groups,
  (c) a halogen atom,
  (d) a carboxy group,
  (e) a $C_{1-6}$ alkoxy-carbonyl group,
  (f) an amino group, and
  (g) a $C_{1-6}$ alkylsulfonyl group, more preferably, a $C_{1-6}$ alkyl group optionally substituted by 1 to 3 substituents selected from
(1) a hydroxy group,
(2) a carbamoyl group optionally mono- or di-substituted by $C_{1-6}$ alkyl group(s) optionally substituted by 1 to 3 substituents selected from
  (a) a hydroxy group,
  (b) a halogen atom,
  (c) a $C_{1-6}$ alkoxy group,
  (d) a $C_{1-6}$ alkylsulfonyl group, and
  (e) a cyano group,
(3) a carboxy group, and
(4) a $C_{1-6}$ alkoxy-carbonyl group.

In addition, when the number of the substituents is two or more, two substituents present on the same atom or the adjacent atoms may in combination form an "optionally substituted ring".

Examples of the "ring" of such "optionally substituted ring" include $C_{3-10}$ cycloalkane, $C_{3-10}$ cycloalkene, $C_{4-10}$ cycloalkadiene, $C_{6-14}$ aryl, heterocycle and the like.

Examples of the $C_{3-10}$ cycloalkane include a ring corresponding to the "$C_{3-10}$ cycloalkyl group" recited as the substituent of the "6-membered ring" of the "6-membered ring which is optionally further substituted" for the above-mentioned ring A.

Examples of the $C_{6-14}$ aryl include a ring corresponding to the "$C_{6-14}$ aryl group" recited as the substituent of the "6-membered ring" of the "6-membered ring which is optionally further substituted" for the above-mentioned ring A.

Examples of the heterocycle include a ring corresponding to the "heterocyclic group" of the "optionally substituted heterocyclic group" for the following $R^1$.

Examples of the $C_{3-10}$ cycloalkene include cyclopropene, cyclobutene, cyclopentene, cyclohexene, cycloheptene, cyclooctene and the like.

Examples of the $C_{4-10}$ cycloalkadiene include 1,3-cyclopentadiene, 1,3-cyclohexadiene, 1,4-cyclohexadiene, 1,3-cycloheptadiene and the like.

The "ring" of the "optionally substituted ring" may have 1 to 3 substituents at substitutable position(s). Examples of such substituent include those similar to substituent group A recited as the substituent of the "6-membered ring" of the "6-membered ring which is optionally further substituted" for the above-mentioned ring A.

The "5- to 7-membered non-aromatic nitrogen-containing heterocycle" of the "optionally substituted 5- to 7-membered non-aromatic nitrogen-containing heterocycle" for ring B is preferably a 5-membered non-aromatic nitrogen-containing heterocycle (preferably, thiazoline).

Ring B is preferably a 5-membered non-aromatic nitrogen-containing heterocycle (preferably, thiazoline) optionally substituted by 1 to 3 substituents selected from (1) a $C_{1-6}$ alkyl group (preferably, methyl, ethyl, isobutyl) optionally substituted by 1 to 3 substituents selected from
  (a) a hydroxy group,
  (b) a carbamoyl group optionally mono- or di-substituted by substituent(s) selected from a $C_{1-6}$ alkyl group optionally substituted by 1 to 3 substituents selected from a hydroxy group, a halogen atom (preferably, a fluorine atom), a $C_{1-6}$ alkoxy group (preferably, methoxy), a $C_{1-6}$ alkylsulfonyl group (preferably, methylsulfonyl), a cyano group and a non-aromatic heterocyclic group (preferably, oxetanyl) optionally substituted by a $C_{1-6}$ alkyl group, and a $C_{3-10}$ cycloalkyl group,
  (c) a carboxy group,
  (d) a $C_{1-6}$ alkoxy group,
  (e) a $C_{1-6}$ alkoxy-carbonyl group (preferably, ethoxycarbonyl),
  (f) a non-aromatic heterocyclic group (preferably, thiomorpholinyl, 1-oxidothiomorpholinyl) optionally substituted by a hydroxy group or an oxo group, and
  (g) a non-aromatic heterocyclyl-carbonyl group (preferably, morpholinylcarbonyl, azetinylcarbonyl, thiomorpholinylcarbonyl, 1-oxidothiomorpholinylcarbonyl, 1,1-dioxidothiomorpholinylcarbonyl) optionally substituted by a hydroxy group or an oxo group, and (2) a $C_{1-6}$ alkoxy-carbonyl group (preferably, ethoxycarbonyl).

Ring B is more preferably thiazoline optionally substituted by a $C_{1-6}$ alkyl group optionally substituted by 1 to 3 substituents selected from
(1) a hydroxy group,
(2) a carbamoyl group optionally mono- or di-substituted by $C_{1-6}$ alkyl group(s) optionally substituted by 1 to 3 substituents selected from
  (i) a hydroxy group,
  (ii) a halogen atom,
  (iii) a $C_{1-6}$ alkoxy group,
  (iv) a $C_{1-6}$ alkylsulfonyl group, and
  (v) a cyano group,
(3) a carboxy group, and
(4) a $C_{1-6}$ alkoxy-carbonyl group.

$W^1$ is O, S, SO, $SO_2$, an optionally substituted $C_{1-6}$ alkylene group or $NR^4$ ($R^4$ is a hydrogen atom or a $C_{1-6}$ alkyl group).

The "$C_{1-6}$ alkylene group" of the "optionally substituted $C_{1-6}$ alkylene group" for $W^1$ may have 1 to 3 substituents at substitutable position(s). Examples of such substituents include those similar to substituent group B recited as the substituent that the "$C_{1-6}$ alkyl group" as the "substituent" of the "6-membered ring which is optionally further substituted" for ring A optionally has. When the number of the substituents is two or more, the respective substituents may be the same or different.

$W^1$ is preferably O.

$R^1$ is an optionally substituted $C_{6-14}$ aryl group or an optionally substituted heterocyclic group.

Examples of the "$C_{6-14}$ aryl group" of the "optionally substituted $C_{6-14}$ aryl group" for $R^1$ include phenyl, naphthyl, anthryl, phenanthryl, acenaphthylenyl, biphenylyl and the like.

Examples of the "heterocyclic group" of the "optionally substituted heterocyclic group" for $R^1$ include an aromatic heterocyclic group and a non-aromatic heterocyclic group.

As used herein, as the aromatic heterocyclic group, for example, a 4- to 7-membered (preferably 5- or 6-membered)

monocyclic aromatic heterocyclic group containing 1 to 4 hetero atoms selected from an oxygen atom, a sulfur atom (the sulfur atom is optionally oxidized) and a nitrogen atom as a ring-constituting atom besides carbon atoms, and a fused aromatic heterocyclic group can be mentioned. As the fused aromatic heterocyclic group, for example, a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, and the like can be mentioned.

As preferable examples of the aromatic heterocyclic group, monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 4-isothiazolyl), oxazolyl (e.g., 2-oxazolyl, 4-oxazolyl, 5-oxazolyl), isoxazolyl, oxadiazolyl (e.g., 1,2,4-oxadiazol-3-yl, 1,2,4-oxadiazol-5-yl, 1,3,4-oxadiazol-2-yl), thiadiazolyl (e.g., 1,3,4-thiadiazol-2-yl, 1,2,4-thiadiazol-3-yl, 1,2,4-thiadiazol-5-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like;

fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), azaindazolyl (e.g., 1H-6-azaindazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), imidazothiazolyl (e.g., imidazo[2,1-b]thiazol-5-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like;
and the like can be mentioned.

As the non-aromatic heterocyclic group, for example, a 4- to 7-membered (preferably 5- or 6-membered) monocyclic non-aromatic heterocyclic group containing 1 to 4 heteroatoms selected from an oxygen atom, a sulfur atom (the sulfur atom is optionally oxidized) and a nitrogen atom as a ring-constituting atom besides carbon atoms, and a fused non-aromatic heterocyclic group can be mentioned. As the fused non-aromatic heterocyclic group, for example, a group derived from a fused ring wherein a ring corresponding to the 4- to 7-membered monocyclic non-aromatic heterocyclic group and 1 or 2 rings selected from a 5- or 6-membered aromatic or non-aromatic heterocycle containing 1 or 2 nitrogen atoms (e.g., pyrrole, imidazole, pyrazole, pyrazine, pyridine, pyrimidine, pyrrolidine, imidazolidine, pyrazolidine, piperidine, piperazine), a 5-membered aromatic or non-aromatic heterocycle containing one sulfur atom (e.g., thiophene, tetrahydrothiophene) and a benzene ring are fused, a group wherein the above-mentioned group is partially saturated, and the like can be mentioned.

As preferable examples of the non-aromatic heterocyclic group,
monocyclic non-aromatic heterocyclic groups such as tetrahydrofuranyl (e.g., 2-tetrahydrofuranyl), pyrrolidinyl (e.g., 1-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), 1-oxidothiomorpholinyl (e.g., 1-oxidothiomorpholin-4-yl), 1,1-dioxidothiomorpholinyl (e.g., 1,1-dioxidothiomorpholin-4-yl), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), thioxooxazolidinyl (e.g., 2-thioxo-1,3-oxazolidin-5-yl), pyranyl (e.g., 4-pyranyl), tetrahydropyranyl (e.g., 4-tetrahydropyranyl), thiopyranyl (e.g., 4-thiopyranyl), tetrahydrothiopyranyl (e.g., 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), pyrazolidinyl (e.g., pyrazolidin-1-yl), tetrahydropyrimidinyl, dioxanyl (e.g., 1,3-dioxan-2-yl, 1,3-dioxan-4-yl, 1,3-dioxan-5-yl, 1,4-dioxan-2-yl), dioxinyl (e.g., 4H-1,3-dioxin-2-yl, 4H-1,3-dioxin-4-yl, 4H-1,3-dioxin-5-yl, 4H-1,3-dioxin-6-yl, 2,3-dihydro-1,4-dioxin-2-yl, 2,3-dihydro-1,4-dioxin-5-yl) and the like;

fused non-aromatic heterocyclic groups such as dihydroindolyl (e.g., 2,3-dihydro-1H-isoindol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl), hexahydropyrazinooxazinyl (e.g., hexahydropyrazino[2,1-c][1,4]oxazinyl) and the like;
and the like can be mentioned.

The "$C_{6-14}$ aryl group" of the "optionally substituted $C_{6-14}$ aryl group" and "heterocyclic group" of the "optionally substituted heterocyclic group" for $R^1$ may have 1 to 3 substituents at substitutable position(s). Examples of such substituents include
(1) a $C_{1-6}$ alkyl group (e.g., methyl) optionally substituted by an optionally substituted $C_{1-6}$ alkoxy group (e.g., methoxy, ethoxy) or a $C_{1-6}$ alkylsulfonyl group (e.g., methylsulfonyl) (preferably, a $C_{1-6}$ alkyl group (e.g., methyl) optionally substituted by (i) a $C_{1-6}$ alkoxy group (e.g., methoxy, ethoxy) optionally substituted by 1 to 3 substituents selected from a halogen atom, a carboxy group, a $C_{1-6}$ alkoxy group, and a $C_{1-6}$ alkoxy-carbonyl group or (ii) a $C_{1-6}$ alkylsulfonyl group (e.g., methylsulfonyl));

(2) a $C_{1-6}$ alkylsulfonyl group (e.g., methylsulfonyl, ethylsulfonyl) optionally substituted by 1 to 3 halogen atoms; and (3) a non-aromatic heterocyclyl-carbonyl group optionally substituted by 1 to 3 substituents selected from
(a) a hydroxy group,
(b) a $C_{1-6}$ alkyl group optionally substituted by 1 to 3 hydroxy groups,
(c) a halogen atom,
(d) a carboxy group,
(e) a $C_{1-6}$ alkoxy-carbonyl group,
(f) an amino group, and
(g) a $C_{1-6}$ alkylsulfonyl group. When the number of the substituents is two or more, the respective substituents may be the same or different.

The "$C_{1-6}$ alkoxy group" of the "optionally substituted $C_{1-6}$ alkoxy group" recited as the substituent of the $C_{1-6}$ alkyl group as the "substituent" of the "$C_{6-14}$ aryl group" of the "optionally substituted $C_{6-14}$ aryl group" and the "heterocyclic group" of the "optionally substituted heterocyclic group" for $R^1$ is optionally substituted by 1 to 3 substituents selected from a halogen atom, a carboxy group, a $C_{1-6}$ alkoxy group, and a $C_{1-6}$ alkoxy-carbonyl group.

The "substituent" of the "$C_{6-14}$ aryl group" of the "optionally substituted $C_{6-14}$ aryl group" and the "heterocyclic group" of "optionally substituted heterocyclic group" for $R^1$ is preferably (1) a $C_{1-6}$ alkyl group (e.g., methyl) optionally substituted by 1 to 3 substituents selected from a $C_{1-6}$ alkoxy group (e.g., methoxy, ethoxy) optionally substituted by a $C_{1-6}$ alkoxy group (e.g., methoxy) and a $C_{1-6}$ alkylsulfonyl group (e.g., methylsulfonyl, ethylsulfonyl); or (2) a $C_{1-6}$ alkylsulfonyl group (e.g., methylsulfonyl, ethylsulfonyl).

$R^1$ is preferably phenyl or pyridyl each of which is optionally substituted.

$R^1$ is more preferably a phenyl group or a pyridyl group each optionally substituted by 1 to 3 substituents selected from (1) a $C_{1-6}$ alkyl group optionally substituted by 1 to 3 substituents selected from
(i) a $C_{1-6}$ alkoxy group optionally substituted by a $C_{1-6}$ alkoxy group, and
(ii) a $C_{1-6}$ alkylsulfonyl group, and
(2) a $C_{1-6}$ alkylsulfonyl group.

$R^3$ is a hydrogen atom or a halogen atom. $R^3$ is preferably a hydrogen atom.

$W^2$ is O, S, SO, $SO_2$ or a bond.

Here, when $W^2$ is O, S, SO or $SO_2$, $R^2$ is a hydrogen atom or an optionally substituted heterocyclic group. When $W^2$ is a bond, $R^2$ is a hydrogen atom, a halogen atom, an optionally substituted $C_{1-6}$ alkyl group, optionally substituted $C_{3-10}$ cycloalkyl or an optionally substituted heterocyclic group.

Examples of the "heterocyclic group" of the "optionally substituted heterocyclic group" for $R^2$ include an aromatic heterocyclic group and a non-aromatic heterocyclic group. For example, the aromatic heterocyclic group and non-aromatic heterocyclic group recited as the "heterocyclic group" of the "optionally substituted heterocyclic group" for $R^1$ can be mentioned.

The "heterocyclic group" of the "optionally substituted heterocyclic group" for $R^2$ may have 1 to 3 substituents at substitutable position(s). Examples of such substituent include substituent group B. When the number of the substituents is two or more, the respective substituents may be the same or different.

The "$C_{1-6}$ alkyl group" of the "optionally substituted $C_{1-6}$ alkyl group" and the "$C_{3-10}$ cycloalkyl group" of the "optionally substituted $C_{3-10}$ cycloalkyl group" for $R^2$ when $W^2$ is a bond may have 1 to 3 substituents at substitutable position(s). Examples of such substituent include substituent group B. When the number of the substituents is two or more, the respective substituents may be the same or different.

The "substituent" of the "$C_{1-6}$ alkyl group" of the "optionally substituted $C_{1-6}$ alkyl group", the "$C_{3-10}$ cycloalkyl group" of the "optionally substituted $C_{3-10}$ cycloalkyl group" and the "heterocyclic group" of the "optionally substituted heterocyclic group" for $R^2$ is preferably (1) a $C_{1-6}$ alkylsulfonyl group (e.g., methylsulfonyl, ethylsulfonyl) optionally substituted by 1 to 3 halogen atoms;
(2) a halogen atom; or
(3) a $C_{1-6}$ alkoxy group.

When $W^2$ is O, S, SO or $SO_2$, $R^2$ is preferably an optionally substituted 5- or 6-membered heterocyclic group (preferably, pyridyl or tetrahydropyranyl, more preferably tetrahydropyranyl), more preferably a 5- or 6-membered heterocyclic group (preferably, pyridyl or tetrahydropyranyl, more preferably tetrahydropyranyl).

When $W^2$ is a bond, $R^2$ is preferably a hydrogen atom or a $C_{1-6}$ alkyl group (preferably, methyl or ethyl).

A structure represented by

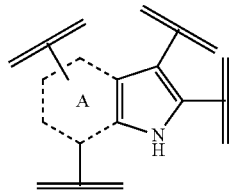

in the formula (I) is a group derived from a bicyclic ring formed by ring A and a pyrrole ring having one common side of each ring (i.e., fused). Here, the side of ring A and the side of the pyrrole ring forming the bicyclic ring form a bond having the same multiplicity. For example, when a structure represented by

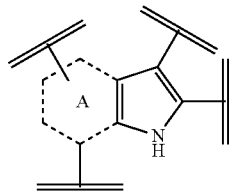

is a structure represented by

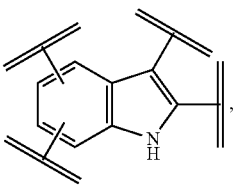

ring A is a "benzene ring".

As compound (I), the following compound is preferable.
[Compound (A)]
Compound (I) wherein
ring A is a 6-membered ring (preferably, benzene ring) substituted only by —W$^1$—R$^1$ and —W$^2$—R$^2$;
ring B is a 5-membered non-aromatic nitrogen-containing heterocycle (preferably, thiazoline) optionally substituted by 1 to 3 substituents selected from
(1) a $C_{1-6}$ alkyl group (preferably, methyl, ethyl, isobutyl) optionally substituted by 1 to 3 substituents selected from
  (a) a hydroxy group,
  (b) a carbamoyl group optionally mono- or di-substituted by substituent(s) selected from a $C_{1-6}$ alkyl group optionally substituted by 1 to 3 substituents selected from a hydroxy group, a halogen atom (preferably, a fluorine atom), a $C_{1-6}$ alkoxy group (preferably, methoxy), a $C_{1-6}$ alkylsulfonyl group (preferably, methylsulfonyl), a cyano group and a non-aromatic heterocyclic group (preferably, oxetanyl) optionally substituted by $C_{1-6}$ alkyl group, and $C_{3-10}$ cycloalkyl group,
  (c) a carboxy group,
  (d) a $C_{1-6}$ alkoxy group,
  (e) a $C_{1-6}$ alkoxy-carbonyl group (preferably, ethoxycarbonyl),
  (f) a non-aromatic heterocyclic group (preferably, thiomorpholinyl, 1-oxidothiomorpholinyl) optionally substituted by a hydroxy group or an oxo group, and
  (g) a non-aromatic heterocyclyl-carbonyl group (preferably, morpholinylcarbonyl, azetinylcarbonyl, thiomorpholinylcarbonyl, 1-oxidothiomorpholinylcarbonyl, 1,1-dioxidothiomorpholinylcarbonyl) optionally substituted by a hydroxy group or an oxo group, and
(2) a $C_{1-6}$ alkoxy-carbonyl group (preferably, ethoxycarbonyl);
W$^1$ is O; and
R$^1$ is a $C_{6-14}$ aryl group (preferably, phenyl) or a heterocyclic group (preferably, pyridyl) each optionally substituted by 1 to 3 substituents selected from
(1) a $C_{1-6}$ alkyl group (preferably, methyl) optionally substituted by 1 to 3 substituents selected from a $C_{1-6}$ alkoxy group (preferably, methoxy, ethoxy) optionally substituted by a $C_{1-6}$ alkoxy group (preferably, methoxy) and a $C_{1-6}$ alkylsulfonyl group (preferably, methylsulfonyl, ethylsulfonyl), and
(2) a $C_{1-6}$ alkylsulfonyl group (preferably, methylsulfonyl);
when W$^2$ is O, then R$^2$ is an optionally substituted 5- or 6-membered heterocycle (preferably, tetrahydropyranyl);
when W$^2$ is a bond, then R$^2$ is a hydrogen atom or a $C_{1-6}$ alkyl group (preferably, methyl or ethyl); and
R$^3$ is a hydrogen atom.
[Compound (B)]
Compound (I) wherein
ring A is a benzene ring;
ring B is a thiazoline ring optionally substituted by a $C_{1-6}$ alkyl group (preferably, methyl, ethyl, isobutyl) optionally substituted by 1 to 3 substituents selected from
(1) (a) a hydroxy group,
  (b) a carbamoyl group optionally mono- or di-substituted by $C_{1-6}$ alkyl group(s) optionally substituted by 1 to 3 substituents selected from a hydroxy group, a halogen atom (preferably, a fluorine atom), a $C_{1-6}$ alkoxy group (preferably, methoxy), a $C_{1-6}$ alkylsulfonyl group (preferably, methylsulfonyl), and a cyano group,
  (c) a carboxy group, and
  (d) a $C_{1-6}$ alkoxy-carbonyl group (preferably, ethoxycarbonyl);
W$^1$ is O;
R$^1$ is a phenyl group or a pyridyl group, each of which is optionally substituted by 1 to 3 substituents selected from
(1) a $C_{1-6}$ alkyl group (preferably, methyl) optionally substituted by 1 to 3 substituents selected from a $C_{1-6}$ alkoxy group (preferably, methoxy, ethoxy) optionally substituted by a $C_{1-6}$ alkoxy group (preferably, methoxy) and a $C_{1-6}$ alkylsulfonyl group (preferably, methylsulfonyl, ethylsulfonyl), and
(2) a $C_{1-6}$ alkylsulfonyl group (preferably, methylsulfonyl);
when W$^2$ is O, then R$^2$ is a tetrahydropyranyl group;
when W$^2$ is a bond, then R$^2$ is a hydrogen atom or a $C_{1-6}$ alkyl group; and
R$^3$ is a hydrogen atom.
[Compound (C)]
Compound (I) wherein
ring A is a benzene ring;
ring B is
(1) a thiazoline ring optionally substituted by a $C_{1-6}$ alkyl group (preferably, methyl, ethyl, isobutyl) optionally substituted by 1 to 3 substituents selected from
  (a) a hydroxy group,
  (b) a carbamoyl group optionally mono- or di-substituted by $C_{1-6}$ alkyl group(s) optionally substituted by 1 to 3 substituents selected from a hydroxy group, a halogen atom (preferably, a fluorine atom), a $C_{1-6}$ alkoxy group (preferably, methoxy), a $C_{1-6}$ alkylsulfonyl group (preferably, methylsulfonyl), and a cyano group,
  (c) a carboxy group, and
  (d) a $C_{1-6}$ alkoxy-carbonyl group (preferably, ethoxycarbonyl);
W$^1$ is O;
R$^1$ is a phenyl group or a pyridyl group, each of which is optionally substituted by 1 to 3 substituents selected from
(1) a $C_{1-6}$ alkyl group (preferably, methyl) optionally substituted by 1 to 3 substituents selected from a $C_{1-6}$ alkoxy group (preferably, methoxy, ethoxy) optionally substituted by a $C_{1-6}$ alkoxy group (preferably, methoxy) and a $C_{1-6}$ alkylsulfonyl group (preferably, methylsulfonyl, ethylsulfonyl), and
(2) a $C_{1-6}$ alkylsulfonyl group (preferably, methylsulfonyl);
R$^3$ is a hydrogen atom;
W$^2$ is O; and
R$^2$ is a tetrahydropyranyl group.
[Compound (D)]
Compound (I) wherein
ring A is a benzene ring;
ring B is a thiazoline ring optionally substituted by a $C_{1-6}$ alkyl group (preferably, methyl, ethyl, isobutyl) optionally substituted by 1 to 3 substituents selected from
(1) (a) a hydroxy group,
  (b) a carbamoyl group optionally mono- or di-substituted by $C_{1-6}$ alkyl group(s) optionally substituted by 1 to 3 substituents selected from a hydroxy group, a halogen atom (preferably, a fluorine atom), a $C_{1-6}$ alkoxy group (preferably, methoxy), a $C_{1-6}$ alkylsulfonyl group (preferably, methylsulfonyl), and a cyano group,
  (c) a carboxy group, and
  (d) a $C_{1-6}$ alkoxy-carbonyl group (preferably, ethoxycarbonyl);
W$^1$ is O;
R$^1$ is a phenyl group or a pyridyl group, each of which is optionally substituted by 1 to 3 substituents selected from
(1) a $C_{1-6}$ alkyl group (preferably, methyl) optionally substituted by 1 to 3 substituents selected from a $C_{1-6}$ alkoxy group (preferably, methoxy, ethoxy) optionally substituted by a $C_{1-6}$ alkoxy group (preferably, methoxy) and a $C_{1-6}$ alkylsulfonyl group (preferably, methylsulfonyl, ethylsulfonyl), and (2) a $C_{1-6}$ alkylsulfonyl group (preferably, methylsulfonyl);

$R^3$ is a hydrogen atom;

$W^2$ is a bond; and $R^2$ is a hydrogen atom or a $C_{1-6}$ alkyl group.

[Compound (F)]

N-methyl-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide or a salt thereof;

N-methyl-2-[2-(5-{[6-(methylsulfonyl)pyridin-3-yl]oxy}-1H-indol-2-yl)-4,5-dihydro-1,3-thiazol-5-yl]acetamide or a salt thereof;

N,N-dimethyl-2-[2-(5-{[6-(methylsulfonyl)pyridin-3-yl]oxy}-1H-indol-2-yl)-4,5-dihydro-1,3-thiazol-5-yl]acetamide or a salt thereof;

N-(2-methoxyethyl)-2-[2-(5-{[6-(methylsulfonyl)pyridin-3-yl]oxy}-1H-indol-2-yl)-4,5-dihydro-1,3-thiazol-5-yl]acetamide or a salt thereof;

2-[2-(7-ethyl-5-{[6-(methylsulfonyl)pyridin-3-yl]oxy}-1H-indol-2-yl)-4,5-dihydro-1,3-thiazol-5-yl]-N-methylacetamide or a salt thereof.

When compound (I) is a salt, as such salts, for example, a salt with inorganic base, a salt with organic base, a salt with inorganic acid, a salt with organic acid, a salt with basic or acidic amino acid and the like can be mentioned.

Preferable examples of salts with inorganic base include alkali metal salts such as sodium salt, potassium salt and the like; alkaline earth metal salts such as calcium salt, magnesium salt and the like; and aluminum salts; ammonium salts and the like.

Preferable examples of the salt with organic base include a salt with trimethylamine, triethylamine, pyridine, picoline, ethanolamine, diethanolamine, triethanolamine, dicyclohexylamine, N,N-dibenzylethylenediamine and the like.

Preferable examples of the salt with inorganic acid include a salt with hydrochloric acid, hydrobromic acid, nitric acid, sulfuric acid, phosphoric acid and the like.

Preferable examples of the salt with organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include a salt with arginine, lysine, ornithine and the like.

Preferable examples of the salt with acidic amino acid include a salt with aspartic acid, glutamic acid and the like.

A prodrug of the compound (I) means a compound which is converted to the compound (I) with a reaction due to an enzyme, a gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc. A prodrug of compound (I) may be a compound obtained by subjecting an amino group in compound (I) to an acylation, alkylation, sulfonylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, toluenesulfonylation, etc.); a compound obtained by subjecting a hydroxy group or a mercapto group in compound (I) to an acylation, alkylation, phosphorylation or boration (e.g., a compound obtained by subjecting a hydroxy group or a mercapto group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug of compound (I) may be a compound which is converted to compound (I) under physiological conditions as described in Development of Pharmaceutical Products, vol. 7, Molecule Design, 163-198, Hirokawa Shoten (1990).

Specific preferable examples of the prodrug of compound (I) include a compound of the formula (I) wherein an amino group of the pyrrole moiety of a structure represented by

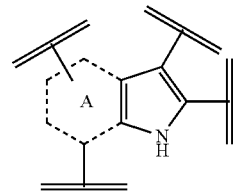

is acylated, alkylated, sulfonylated or phosphorylated.

In addition, compound (I) may be labeled with an isotope (e.g., $^3H$, $^{14}C$, $^{35}S$, $^{125}I$, etc.) and the like.

Furthermore, compound (I) may be a non-solvate or a solvate, and may be an anhydrate or a hydrate.

Deuterium-converted compound wherein $^1H$ has been converted to $^2H(D)$ is also encompassed in the compound (I).

Compound (I) or a prodrug thereof (hereinafter sometimes to be simply abbreviated as the compound of the present invention) shows low toxicity and can be used as an agent for the prophylaxis or treatment of various diseases to be mentioned later for mammals (e.g., humans, mice, rats, rabbits, dogs, cats, bovines, horses, pigs, monkeys etc.) as they are or by admixing with a pharmacologically acceptable carrier and the like to give a pharmaceutical composition.

Here, various organic or inorganic carriers conventionally used as materials for pharmaceutical preparations are used as a pharmacologically acceptable carrier, which are added as excipient, lubricant, binder and disintegrant for solid preparations; or solvent, solubilizing agent, suspending agent, isotonicity agent, buffer and soothing agent for liquid preparations, and the like. Where necessary, an additive for pharmaceutical preparations such as preservative, antioxidant, colorant, sweetening agent and the like can be used.

Preferable examples of the excipient include lactose, sucrose, D-mannitol, D-sorbitol, starch, α-starch, dextrin, crystalline cellulose, low-substituted hydroxypropylcellulose, sodium carboxymethylcellulose, gum arabic, pullulan, light anhydrous silicic acid, synthetic aluminum silicate, magnesium aluminate metasilicate and the like.

Preferred examples of the lubricant include magnesium stearate, calcium stearate, talc, colloidal silica and the like.

Preferable examples of the binder include α-starch, saccharose, gelatin, gum acacia, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose, polyvinylpyrrolidone and the like.

Preferable examples of the disintegrant include lactose, sucrose, starch, carboxymethylcellulose, calcium carboxymethylcellulose, sodium croscarmellose, sodium carboxymethylstarch, light anhydrous silicic acid, low-substituted hydroxypropylcellulose and the like.

Preferable examples of the solvent include water for injection, physiological brine, Ringer's solution, alcohol, propylene glycol, polyethylene glycol, sesame oil, corn oil, olive oil, cottonseed oil and the like.

Preferred examples of the solubilizing agents include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferred examples of the suspending agent include surfactants such as stearyltriethanolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, polyoxyethylene hydrogenated castor oil and the like.

Preferred examples of the isotonicity agent include sodium chloride, glycerol, D-mannitol, D-sorbitol, glucose and the like.

Preferred examples of the buffer include buffers such as phosphate, acetate, carbonate, citrate and the like.

Preferred examples of the soothing agent include benzyl alcohol and the like.

Preferred examples of the preservative include p-oxybenzoates, chlorobutanol, benzyl alcohol, phenethyl alcohol, dehydroacetic acid, sorbic acid and the like.

Preferred examples of the antioxidant include sulfite, ascorbate and the like.

Preferable examples of the colorant include water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment), natural pigments (e.g., beta carotene, chlorophil, ferric oxide red) and the like.

Preferable examples of the sweetening agent include saccharin sodium, dipotassium glycyrrhizinate, aspartame, stevia and the like.

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

The pharmaceutical composition can be produced according to a method conventionally used in the field of pharmaceutical preparation, such as the method described in Japan Pharmacopoeia and the like. Concrete production methods of preparations are described in detail in the following.

While the content of the compound of the present invention in the pharmaceutical composition varies depending on the dosage form, dose of the compound of the present invention and the like, it is, for example, about 0.1 to 100 wt %.

The compound of the present invention has a superior GK activating action, and can be used as an agent for the prophylaxis or treatment of various diseases for mammals (e.g., human, bovine, horse, dog, cat, monkey, mouse, rat, specifically human). In addition, as the compound of the present invention has a selective GK activating action, it shows low toxicity (e.g., acute toxicity, chronic toxicity, cardiotoxicity, carcinogenic, genetic toxicity), which causes fewer side effects.

The compound of the present invention can be used, for example, as an agent for the prophylaxis or treatment of diabetes (e.g., type 1 diabetes, type 2 diabetes, gestational diabetes, obesity type diabetes); an agent for the prophylaxis or treatment of obesity, an agent for the prophylaxis or treatment of hyperlipidemia (e.g., hypertriglyceridemia, hypercholesterolemia, hypoHDL-emia, postprandial hyperlipemia); an agent for the prophylaxis or treatment of arteriosclerosis; an agent for the prophylaxis or treatment of impaired glucose tolerance (IGT); and an agent for preventing progression from impaired glucose tolerance to diabetes.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported diagnostic criteria of diabetes and WHO.

According to these reports, diabetes is a condition showing a fasting blood glucose level (glucose concentration of intravenous plasma) of not less than 126 mg/dl or a 75 g oral glucose tolerance test 2 h level (glucose concentration of intravenous plasma) of not less than 200 mg/dl.

In addition, according to the above-mentioned reports of ADA and WHO, impaired glucose tolerance is a condition showing a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 100 mg/dl and less than 126 mg/dl is called IFG (Impaired Fasting Glucose). According to the report of WHO, among the IFG (Impaired Fasting Glucose), a condition showing fasting blood glucose level (glucose concentration of intravenous plasma) of not less than 110 mg/dl and less than 126 mg/dl is called IFG (Impaired Fasting Glycemia).

The compound of the present invention can also be used as an agent for improving or the prophylaxis or treatment of diabetes, borderline type, impaired glucose tolerance, IFG (Impaired Fasting Glucose) and IFG (Impaired Fasting Glycemia), as determined according to the above-mentioned diagnostic criteria. Moreover, the compound of the present invention can prevent progress of borderline type, impaired glucose tolerance, IFG (Impaired Fastig Gluvose) or (IFG (Impaired Fasting Glycemia) into diabetes.

The compound of the present invention can also be used as an agent for the prophylaxis or treatment of, for example, diabetic complications [e.g., neuropathy, nephropathy, retinopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic foot lesion (e.g., gangrene, ulcer), xerostomia, hypacusis, cerebrovascular disorder, peripheral blood circulation disorder, diabetic diarrhea], obesity, osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, hypertension, polycystic ovary syndrome, kidney disease (e.g., diabetic nephropathy, glomerular nephritis, glomerulosclerosis, nephrotic syndrome, hypertensive nephrosclerosis, end stage kidney disease, pyelonephritis, hydronephrosis), muscular dystrophy, myocardial infarction, angina pectoris, cerebrovascular accident (e.g., cerebral infarction, cerebral apoplexy), abnormal sugar metabolism, abnormal lipid metabolism, insulin resistance syndrome, Syndrome X, metabolic syndrome (according to the above-mentioned report by WHO, state concurrently associated with at least one of type 2 diabetes, impaired glucose tolerance and insulin resistance, and at least two from obesity, abnormal lipid metabolism, hypertension and trace albumin urine), Cushing's syndrome, hyperinsulinemia, hyperinsulinemia-induced sensory disorder, tumor (e.g., leukemia, breast cancer, prostate cancer, skin cancer), irritable bowel syndrome, acute or chronic diarrhea, inflammatory diseases (e.g., rheumatoid arthritis, spondylitis deformans, osteoarthritis, lumbago, gout, postoperative or traumatic inflammation, swelling, neuralgia, pharyngolaryngitis, cystitis, hepatitis (inclusive of non-alcoholic steatohepatitis), pneumonia, pancreatitis, inflammatory intestine disease, ulcerative colitis, stomach mucosainjury (including stomach mucosainjury caused by aspirin)), visceral fat syndrome, Alzheimer's disease, cerebrovascular dementia, depression and the like.

The compound of the present invention can also be used for improvement of insulin resistance, promotion or increase of insulin secretion, decrease of visceral fat, suppression of accumulation of visceral fat, improvement of glucose metabolism, improvement of lipid metabolism (including suppression of oxidative LDL production, improvement of lipoprotein metabolism, lowering of blood remnant), improvement of coronary metabolism, prophylaxis or treatment of cardiovascular complication, prophylaxis or treatment of heart failure complication, prophylaxis or treatment of anovulation, prophylaxis or treatment of hirsutism, prophylaxis or treatment of hyperandrogenism, improvement of pancreatic (β cell) function, regeneration of pancreas (β cell), promotion of regeneration of pancreas (β cell) and the like.

The compound of the present invention can also be used for the secondary prevention and suppression of progression of various diseases mentioned above (e.g., cardiovascular event such as myocardial infarction etc.).

The compound of the present invention is particularly useful as an agent for the prophylaxis or treatment of type-2 diabetes, obese diabetes and the like.

While the dose of the compound of the present invention varies depending on the administration subject, administration route, target disease, condition and the like, the compound of the present invention is generally given in a single dose of about 0.01-100 mg/kg body weight, preferably 0.05-30 mg/kg body weight, more preferably 0.1-10 mg/kg, further preferably 0.5-5 mg/kg body weight, in the case of, for example, oral administration to adult diabetic patients. This dose is desirably given 1 to 3 times a day.

The compound of the present invention can be used in combination with drugs such as a therapeutic agent for diabetes, a therapeutic agent for diabetic complications, a therapeutic agent for hyperlipidemia, an antihypertensive agent, an antiobestic agent, a diuretic, a chemotherapeutic agent, an immunotherapeutic agent, an antithrombotic agent, a therapeutic agent for osteoporosis, a antidementia agent, an erectile dysfunction improver, a therapeutic agent for pollakiuria or urinary incontinence, a therapeutic agent for dysuria and the like (hereinafter to be referred to as a combination drug). In this case, the timing of administration of the compound of the present invention and a combination drug is not limited. These may be simultaneously administered to an administration subject or administered in a staggered manner. Moreover, the compound of the present invention and a combination drug may be administered as two kinds of preparations each containing an active ingredient, or may be administered as a single preparation containing both active ingredients.

The dose of the concomitant drug can be appropriately determined based on the dose clinically employed. The mixing ratio of the compound of the present invention and the concomitant drug can be appropriately selected according to the administration subject, administration route, target disease, condition, combination, and other factors. In cases where the administration subject is human, for example, the concomitant drug may be used in an amount of 0.01 to 100 parts by weight per part by weight of the compound of the present invention.

Examples of other therapeutic agent for diabetes include insulin preparations (e.g., animal insulin preparations extracted from pancreas of bovine and swine; human insulin preparations genetically synthesized using *Escherichia coli*, yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, the compounds described in WO2007/013694, WO2007/018314, WO2008/093639 and WO2008/099794), α-glucosidase inhibitor (e.g., voglibose, acarbose, miglitol, emiglitate), biguanide (e.g., metformin, buforminor a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof), dipeptidyl peptidase IV inhibitors (e.g., Alogliptin or a salt thereof (preferably, benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compounds described in WO2004/041266, WO2004/106276, WO2005/063729, WO2005/063725, WO2005/087710, WO2005/095338, WO2007/013689 and WO2008/001931), GLP-1receptor agonists (e.g., GLP-1, GLP-1MR agent, Liraglutide, Exenatide, AVE-0010, BIM-51077, Aib(8,35)hGLP-1(7,37)NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitor, glucose-6-phosphatase inhibitors, glucagon antagonists, FBPase inhibitor), SGLT2 (sodium-glucose cotransporter 2) inhibitors (e.g., Depagliflozin, AVE2268, TS-033, YM543, TA-7284, Remogliflozin, ASP1941), SGLT1 inhibitor, 11β-hydroxysteroid dehydrogenase inhibitors (e.g., BVT-3498, INCB-13739), adiponectin or an agonist thereof, IKK inhibitors (e.g., AS-2868), leptin resistance improving drugs, somatostatin receptor agonists, glucokinase activators (e.g., Piragliatin, AZD1656, AZD6370, TTP-355, compounds described in WO2006/112549, WO2007/028135, WO2008/047821, WO2008/050821, WO2008/136428 and WO2008/156757), GIP (Glucose-dependent insulinotropic peptide), GPR119 agonists (e.g., PSN821), FGF21, FGF analogue and the like.

Examples of the therapeutic agent for diabetic complications include aldose reductase inhibitors (e.g., tolrestat, epalrestat, zopolrestat, fidarestat, CT-112, ranirestat (AS-3201), Lidorestat), neurotrophic factor and an increasing drug thereof (e.g., NGF, NT-3, BDNF, neurotrophic factors described in WO01/14372 and increasing drugs thereof (e.g., 4-(4-chlorophenyl)-2-(2-methyl-1-imidazolyl)-5-[3-(2-methylphenoxy)propyl]oxazole), a compound described in WO2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, Pregabalin), serotonin.noradrenaline reuptake inhibitors (e.g., duloxetine), sodium channel inhibitors (e.g., Lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitors and the like.

Examples of the therapeutic agent for hyperlipidemia include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, γ-oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the anti-hypertensive agent include angiotensin converting enzyme inhibitors (e.g., captopril, enalapril, delapril etc.), angiotensin II antagonists (e.g., candesartan cilexetil, candesartan, losartan, losartan potassium, eprosartan, valsartan, termisartan, irbesartan, tasosartan, olmesartan, olmesartan medoxomil, azilsartan, azilsartan medoxomil etc.), calcium antagonists (e.g., manidipine, nifedipine, amlodipine, efonidipine, nicardipine, amlodipine, Cilnidipine etc.), β-blocker (e.g., metoprolol, atenolol, propranolol, carvedilol, pindolol etc.), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptors, GABA-modulating agents (e.g., topiramate), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetyl CoA carboxylase (ACC) inhibitors, stearoyl-CoA desaturation enzyme inhibitors, microsomal triglyceride transfer protein inhibitors (e.g., R-256918), Na-glucose cotransport carrier inhibitors (e.g., JNJ-28431754, remogliflozin), NFK inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparation extracted from pancreas of bovine and swine; human GLP-1 preparations genetically synthesized using *Escherichia coli*, yeast; fragment or derivative of GLP-1 (e.g., exenatide, liraglutide)), amylin preparations (e.g., pramlintide, AC-2307), neuropeptide Y agonists (e.g., PYY3-36, derivative of PYY3-36, obinepitide, TM-30339, TM-30335), oxyntomodulin preparations: FGF21 preparations (e.g., animal FGF21 preparation extracted from pancreas of bovine and swine; human FGF21 preparations genetically synthesized using *Escherichia coli*, yeast; fragment or derivative of FGF21)), anorexigenic agents (e.g., P-57) and the like.

Examples of the diuretic include xanthine derivatives (e.g., sodium salicylate and theobromine, calcium salicylate and theobromine etc.), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonate dehydratase inhibitors (e.g., acetazolamide and the like), chlorobenzenesulfonamide preparations (e.g., chlortalidone, mefruside, indapamide etc.), azosemide, isosorbide, etacrynic acid, piretanide, bumetanide, furosemide and the like.

Examples of the chemotherapeutic agent include alkylating agents (e.g., cyclophosphamide, ifosfamide), metabolic antagonists (e.g., methotrexate, 5-fluorouracil or a derivative thereof), antitumor antibiotics (e.g., mitomycin, adriamycin), plant-derived antitumor agent (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agent include microorganism or bacterial components (e.g., muramyl dipeptide derivative, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukin such as IL-1, IL-2, IL-12 and the like.

Examples of the antithrombotic agent include heparin (e.g., heparin sodium, heparin calcium, enoxaparin sodium, dalteparin sodium), warfarin (e.g., warfarin potassium), antithrombin drugs (e.g., aragatroban, dabigatran), FXa inhibitors (e.g., rivaroxaban, apixaban, edoxaban, YM150, compounds described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the therapeutic agent for osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of the anti-dementia agent include tacrine, donepezil, rivastigmine, galanthamine, memantine and the like.

Examples of the erectile dysfunction amelioration agent include apomorphine, sildenafil citrate and the like.

Examples of the therapeutic agent for pollakiuria or urinary incontinence include flavoxate hydrochloride, oxybutynin hydrochloride, propiverine hydrochloride and the like.

Examples of the therapeutic agent for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like, can be used in combination with the compound of the present invention.

The combination drug preferably includes an insulin preparation, an insulin sensitizer, an α-glucosidase inhibitor, a biguanide agent, an insulin secretagogue (preferably sulfonylurea agent) and the like.

The above-mentioned combination drug may be a combination of two or more kinds thereof combined at appropriate ratios.

When the compound of the present invention is used in combination with a drug for combined use, the amount of each drug can be reduced within a safe range in consideration of the opposite effect of these drugs. Particularly, the dose of the insulin sensitizer, insulin secretagogue (preferably a sulfonylurea) and biguanide can be reduced from conventional level. As a result, the side effects possibly caused by the combination of these agents can be prevented safely. In addition, the dose of the therapeutic agent for diabetic complications, anti-hyperlipidemia agent or anti-hypertensive agent can be reduced and, as a result, the side effects possibly caused by these drugs can be effectively prevented.

Compound (I) can be produced by, for example, the methods shown in the following reaction schemes 1-7. In each of the following production methods, the starting compound used may be in the form of a salt, and as such salt, those exemplified as the salt of the aforementioned compound (I) are used.

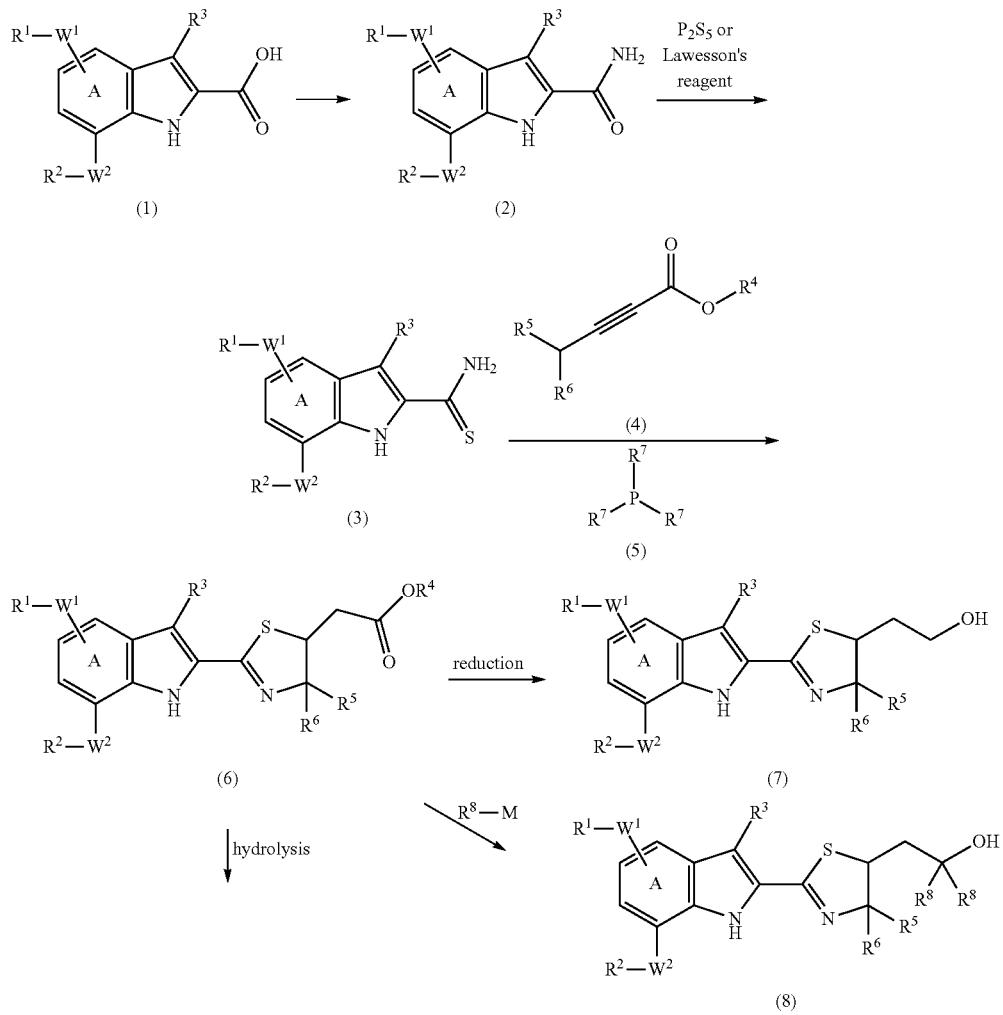

Reaction scheme 1

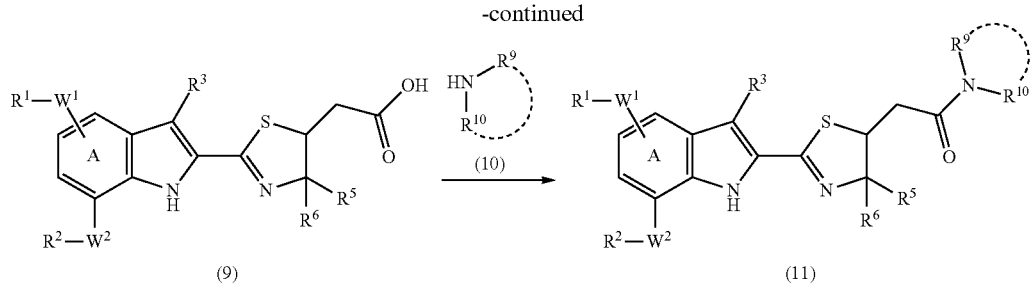

wherein $R^6$ is an optionally substituted $C_{1-6}$ alkyl group, an optionally substituted $C_{3-10}$ cycloalkyl group, an optionally substituted $C_{6-14}$ aryl group or an optionally substituted heterocyclic group, $R^4$ is an optionally substituted $C_{1-6}$ alkyl group or an optionally substituted $C_{3-10}$ cycloalkyl group, $R^5$ and $R^6$ are independently a hydrogen atom, an optionally substituted $C_{1-6}$ alkyl group or an optionally substituted $C_{3-10}$ cycloalkyl group, $R^7$ is an optionally substituted $C_{1-6}$ alkyl group or an optionally substituted aryl group, $R^9$ and $R^{10}$ are independently a hydrogen atom, an optionally substituted $C_{1-6}$ alkyl group or an optionally substituted $C_{3-10}$ cycloalkyl group, $R^9$ and $R^{10}$ may form an optionally substituted ring each other, and the other each symbol is as defined above.

Compound (6) can be produced by 3 steps using compound (1).

In the first step, compound (2) is produced by subjecting compound (1) to an amidation reaction. This reaction is performed by a method known per se, for example, a method to directly condense compound (1) and ammonia or a salt thereof with a condensing agent (e.g., dicyclohexylcarbodiimide etc.), a method to appropriately react a reactive derivative of compound (1) or a salt thereof with ammonia or a salt thereof, or the like. Examples of the reactive derivative of compound (1) include
1) an acid halide;
2) an acid azide;
3) a mixed acid anhydride with an acid (e.g., substituted phosphoric acids such as dialkylphosphoric acid, phenylphosphoric acid, diphenylphosphoric acid, dibenzylphosphoric acid, halogenated phosphoric acid and the like; dialkylphosphorous acid; sulfurous acid; thiosulfuric acid; sulfuric acid; sulfonic acids such as methanesulfonic acid and the like; aliphatic carboxylic acids such as formic acid, acetic acid, propionic acid, butyric acid, isobutyric acid, pivalic acid, pentanoic acid, isopentanoic acid, trichloroacetic acid and the like; aromatic carboxylic acids such as benzoic acid and the like);
4) a symmetric acid anhydride;
5) an activated amide with imidazole, 4-substituted imidazole, dimethylpyrazole, triazole or tetrazole;
6) an activated ester such as cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenylthioester, p-nitrophenyl ester, p-cresyl thioester, carboxymethyl thioester, pyranyl ester, pyridyl ester, piperidyl ester, 8-quinolylthio ester and the like;
7) a ester with a N-hydroxy compound (e.g., N,N-dimethylhydroxyamine, 1-hydroxy-2-(1H)-pyridone, N-hydroxysuccinimide, N-hydroxyphthalimide, 1-hydroxy-1H-benzotriazole);
and the like. These reactive derivatives are appropriately determined according to the kind of compound (1) to be used.

As preferable salt of compound (1) or a reactive derivative of the carboxy group, for example, salts with a base, such as alkali metal salts (e.g., sodium salt, potassium salt and the like), alkaline earth metal salts (e.g., calcium salt, magnesium salt and the like), ammonium salts, organic base salts (e.g., trimethylamine salt, triethylamine salt, pyridine salt, picoline salt, dicyclohexylamine salt, N,N-dibenzylethylenediamine salt and the like) and the like can be mentioned.

Examples of the ammonia or a salt thereof include aqueous ammonia, ammonium acetate, ammonium chloride, 1-hydroxybenztriazole.ammonia complex and the like.

For example, in the case of using acid halide, the reaction is performed in a solvent which does not influence the reaction in the presence of a base.

Examples of the base include alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogen carbonates such as sodium hydrogen carbonate, potassium hydrogen carbonate and the like; alkali metal $C_{1-6}$ alkoxide such as sodium methoxide, sodium ethoxide, potassium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithiums such as methyllithium, n-butyllithium, sec-butyllithium, tert-butyllithium and the like; lithium amides such as lithium diisopropylamide etc. and the like.

This reaction is preferably performed in a solvent which is inert to the reaction. Examples of the solvent that does not influence the reaction include solvents, for example, halogenated hydrocarbons such as chloroform, dichloromethane and the like; aromatic hydrocarbons such as benzene, toluene and the like; ethers such as tetrahydrofuran, 1,4-dioxane, diethyl ether and the like; amides such as N,N-dimethylformamide, N,N-dimethylacetamide, hexamethylphosphoric triamide and the like; sulfoxides such as dimethyl sulfoxide and the like; and the like, ethyl acetate, water and the like. Two or more kinds of these solvents may be mixed in an appropriate ratio and used.

The amount of ammonia or a salt thereof to be used is 1 to 10 molar equivalents, preferably 1 to 5 molar equivalents, relative to compound (1). The amount of the base to be used is generally 0.5 to 10 mol, preferably 0.5 to 3 mol, per 1 mol of compound (1). The reaction temperature is generally −30° C. to 100° C. The reaction time is generally 0.5 to 20 hr.

When a mixed acid anhydride is used, compound (1) is reacted with chlorocarbonate (e.g., methyl chlorocarbonate, ethyl chlorocarbonate, isobutyl chlorocarbonate and the like) in the presence of a base (e.g., triethylamine, N-methylmorpholine, N,N-dimethylaniline, sodium hydrogen carbonate, sodium carbonate, potassium carbonate etc.), and further reacted with ammonia.

The amount of ammonia or a salt thereof to be used is generally 1 to 10 molar equivalents, preferably 0.3 to 3 molar equivalents, relative to compound (1). The amount of chlorocarbonate to be used is generally, 0.5 to 10 mol, preferably 0.5 to 3 mol, per 1 mol of compound (1). The reaction temperature is generally −30° C. to 100° C. The reaction time is generally 0.5 to 20 hr.

In the reaction, when compound (1) is used in the form of a free acid or a salt thereof, the reaction is preferably performed in the presence of a conventional condensing agent such as carbodiimides (e.g., N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide and the like), N,N'-carbonylbis(2-methylimidazole), trialkyl phosphite, polyphosphates (e.g., ethyl polyphosphate, isopropyl polyphosphate and the like), phosphorus oxychloride, diphenylphosphoryl azide, thionyl chloride, oxalyl chloride, lower alkyl haloformate (e.g., ethyl chloroformate, isopropyl chloroformate and the like), triphenylphosphine, N-hydroxybenzotriazole, 1-(p-chlorobenzenesulfonyloxy)-6-chloro-1H-benzotriazole, Vilsmeier-reagent (prepared by the reaction of N,N'-dimethylformamide and thionyl chloride, phosgene, trichloromethyl chloroformate, phosphorus oxychloride and the like), and the like. The amount of the condensing agent to be used is generally, 0.5 to 10 mol, preferably 0.5 to 3 mol, per 1 mol of compound (1). The reaction temperature is generally −70° C. to 100° C. The reaction time is generally 0.5 to 20 hr.

This reaction can be performed in the presence of a base, as necessary. Examples of the base include triethylamine, N-methylmorpholine, N,N-dimethylaniline, sodium hydrogen carbonate, sodium carbonate, potassium carbonate and the like. The amount of the base to be used is generally 0.5 to 10 mol, preferably 0.5 to 3 mol, per 1 mol of compound (1). The reaction temperature is generally −30° C. to 100° C. The reaction time is generally 0.5 to 20 hr.

When, for example, an ester of an N-hydroxy compound is used, compound (1) is reacted with an N-hydroxy compound (e.g., N,N-dimethylhydroxyamine, 1-hydroxy-2-(1H)-pyridone, N-hydroxysuccinimide, N-hydroxyphthalimide, 1-hydroxy-1H-benzotriazole) in the presence of a condensing agent such as 1-[3-(dimethylamino)propyl-3-ethylcarbodiimide hydrochloride (WSC) and the like, and then reacted with ammonia. The reaction may be performed in the presence of a base. Examples of the base include alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogen carbonates such as sodium hydrogen carbonate, potassium hydrogen carbonate and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; and the like. This reaction is preferably performed in a solvent inert to the reaction. Examples of the solvent that does not influence the reaction include solvents, for example, halogenated hydrocarbons such as chloroform, dichloromethane and the like; aromatic hydrocarbons such as benzene, toluene and the like; ethers such as tetrahydrofuran, 1,4-dioxane, diethyl ether and the like; amides such as N,N-dimethylformamide, N,N-dimethylacetamide, hexamethylphosphoric triamide and the like; sulfoxides such as dimethyl sulfoxide and the like; and the like, ethyl acetate, water and the like. Two or more kinds of these solvents may be mixed in an appropriate ratio and used.

The thus-obtained compound (2) can be isolated and purified by a known separation and purification means, for example, concentration, concentration under reduced pressure, solvent extraction, crystallization, recrystallization, phase transfer, chromatography and the like.

In step 2, compound (2) is reacted with diphosphorus pentasulfide or the Lawesson's reagent to give compound (3).

This reaction is performed without a solvent or in a solvent which is inert to the reaction. While the solvent is not particularly limited as long as the reaction proceeds, as such solvent, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; halogenated hydrocarbons such as dichloromethane, chloroform, carbon tetrachloride, trichloroethylene and the like; bases such as pyridine, N,N-dimethylaniline and the like; and the like can be mentioned. Two or more kinds of these solvents may be mixed in an appropriate ratio and used.

The amount of diphosphorus pentasulfide or Lawesson's reagent to be used is generally 0.5 to 10 mol, preferably 0.5 to 3 mol, per 1 mol of compound (2).

The reaction temperature is generally −30° C. to 100° C. The reaction time is generally 0.5 to 20 hr.

The thus-obtained compound (3) can be isolated and purified by a known separation and purification means, for example, concentration, concentration under reduced pressure, solvent extraction, crystallization, recrystallization, phase transfer, chromatography and the like.

In step 3, compound (3) is reacted with compound (4) in the presence of compound (5) to give compound (6). This reaction can be performed according to the method described in J. Org. Chem., 2002, vol. 67, page 4595.

This reaction is performed without a solvent or in a solvent which is inert to the reaction. While the solvent is not particularly limited as long as the reaction proceeds, as such solvent, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; halogenated hydrocarbons such as dichloromethane, chloroform, carbon tetrachloride, trichloroethylene and the like; and the like can be mentioned. Two or more kinds of these solvents may be mixed in an appropriate ratio and used.

The amount of compound (4) to be used is generally 1 to 10 mol, preferably 1 to 4 mol, per 1 mol of compound (3).

The amount of compound (5) to be used is generally 0.1 to 10 mol, preferably 0.1 to 4 mol, per 1 mol of compound (3).

The reaction temperature is generally −30° C. to 100° C. The reaction time is generally 0.5 to 20 hr.

The thus-obtained compound (6) can be isolated and purified by a known separation and purification means, for example, concentration, concentration under reduced pressure, solvent extraction, crystallization, recrystallization, phase transfer, chromatography and the like.

Compound (7) can be produced by subjecting compound (6) to a reduction reaction.

Examples of the reducing agent to be used in this reaction include metal hydrides such as aluminum hydride, diisobutylaluminum hydride, tributyltin hydride and the like; metal hydride complex compounds such as lithium aluminum hydride, sodium borohydride, lithium borohydride, calcium borohydride and the like; borane complexes such as borane tetrahydrofuran complex, borane dimethyl sulfide complex and the like; alkyl boranes such as thexyl borane, disiamyl borane and the like; diborane and the like. The amount of the reducing agent to be used is appropriately determined according to the kind of the reducing agent. For example, the amount of metal hydride or the metal hydride complex compound to be used is 0.25 to 10 mol, preferably 0.5 to 5 mol, per 1 mol of compound (6), and the amount of the borane complex, alkylboranes or diborane to be used is 1 to 10 mol, preferably 1 to 5 mol, per 1 mol of compound (6).

The reduction reaction is advantageously performed in a solvent which is inert to the reaction. Such solvent is not particularly limited as long as the reaction proceeds and, for example, solvents, for example, alcohols such as methanol, ethanol, 1-propanol, 2-propanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like; organic acids such as formic acid, acetic acid, propionic acid, trifluoroacetic acid, methanesulfonic acid and the like; and the like or a mixed solvent thereof and the like are preferable.

While the reaction time varies depending on the kind and amount of the reducing agent or activity and amount of the catalyst to be used, it is generally 0.5 hr to 100 hr, preferably 1 hr to 50 hr. The reaction temperature is generally −20 to 120° C., preferably 0 to 80° C.

The thus-obtained compound (7) can be isolated and purified by a known separation and purification means, for example, concentration, concentration under reduced pressure, solvent extraction, crystallization, recrystallization, phase transfer, chromatography and the like.

Compound (8) can be produced by reacting compound (6) with an organic metal reagent. Preferable examples of the organic metal reagent include organic lithiums such as butyllithium, methyllithium and the like; Grignard reagents such as methylmagnesium bromide, ethylmagnesium chloride and the like.

This reaction is advantageously performed in a solvent which is inert to the reaction. Such solvent is not particularly limited as long as the reaction proceeds and, for example, solvents, for example, ethers such as diethyl ether, diisopropyl ether, diphenyl ether, tetrahydrofuran, 1,4-dioxane, 1,2-dimethoxyethane and the like; saturated hydrocarbons such as cyclohexane, hexane and the like; amides such as N,N-dimethylformamide, N,N-dimethylacetamide, hexamethylphosphoric triamide and the like; halogenated hydrocarbons such as dichloromethane, chloroform, carbon tetrachloride, 1,2-dichloroethane and the like; sulfoxides such as dimethyl sulfoxide and the like; and the like or a mixed solvent thereof and the like are preferable.

While the reaction time varies depending on the reagent and solvent to be used, it is generally 10 min to 100 hr, preferably 30 min to 50 hr. The reaction temperature is generally −70 to 100° C., preferably 0 to 80° C.

The amount of the alkyl metal reagent to be used is about 0.5 to about 20 mol, preferably about 1 to about 10 mol, per 1 mol of compound (6).

The thus-obtained compound (8) can be isolated and purified by a known separation and purification means, for example, concentration, concentration under reduced pressure, solvent extraction, crystallization, recrystallization, phase transfer, chromatography and the like.

Compound (9) can be produced by subjecting compound (6) to hydrolysis. The hydrolysis is performed using an acid or a base according to a conventional method.

As the acid, for example, mineral acids such as hydrochloric acid, sulfuric acid and the like; Lewis acids such as boron trichloride, boron tribromide and the like; organic acids such as trifluoroacetic acid, p-toluenesulfonic acid and the like, and the like can be mentioned. The Lewis acid can be used together with thiols or sulfides.

As the base, for example, alkali metal hydroxides such as lithium hydroxide, sodium hydroxide, potassium hydroxide, barium hydroxide and the like; alkali metal carbonates such as sodium carbonate, potassium carbonate and the like; alkali metal $C_{1-6}$ alkoxides such as sodium methoxide, sodium ethoxide, potassium tert-butoxide and the like; organic bases such as triethylamine, imidazole, formamidine and the like, and the like can be mentioned.

The amount of the acid or base to be used is generally 0.5 to 10 mol, preferably 0.5 to 6 mol, per 1 mol of compound (6).

The hydrolysis is performed without a solvent or in a solvent which is inert to the reaction. While the solvent is not particularly limited as long as the reaction proceeds, as such solvent, for example, alcohols such as methanol, ethanol, propanol and the like; aromatic hydrocarbons such as benzene, toluene and the like; saturated hydrocarbons such as cyclohexane, hexane and the like; organic acids such as formic acid, acetic acid and the like; ethers such as tetrahydrofuran, 1,4-dioxane, 1,2-dimethoxyethane and the like; amides such as N,N-dimethylformamide, N,N-dimethylacetamide and the like; halogenated hydrocarbons such as dichloromethane, chloroform, carbon tetrachloride, 1,2-dichloroethane and the like; nitriles such as acetonitrile, propionitrile and the like; ketones such as acetone, methyl ethyl ketone and the like; sulfoxides such as dimethyl sulfoxide and the like; water and the like can be mentioned. Two or more kinds of these solvents may be mixed in an appropriate ratio and used.

The reaction time is generally 10 min to 60 hr, preferably 10 min to 12 hr. The reaction temperature is generally −10 to 200° C., preferably 0 to 120° C.

The thus-obtained compound (9) can be isolated and purified by a known separation and purification means, for example, concentration, concentration under reduced pressure, solvent extraction, crystallization, recrystallization, phase transfer, chromatography and the like.

Compound (11) can be produced by reacting compound (9) or a reactive derivative at the carboxy group thereof or a salt thereof with compound (10).

This reaction is performed in the same manner as in the reaction to produce compound (2) from compound (1) in reaction scheme 1. As the reactive derivative at the carboxy group of compound (9), those recited for the reaction to produce compound (2) from compound (1) in reaction scheme 1 can be mentioned.

The amount of compound (10) to be used is generally 1 to 10 molar equivalents, preferably 1 to 5 molar equivalents, relative to compound (9).

The reaction temperature is generally −30° C. to 100° C. The reaction time is generally 0.5 to 20 hr.

The thus-obtained compound (11) can be isolated and purified by a known separation and purification means, for example, concentration, concentration under reduced pressure, solvent extraction, crystallization, recrystallization, phase transfer, chromatography and the like.

Compounds (4), (5) and (10) and R⁸-M to be used as starting materials in reaction scheme 1 can each be produced by a method known per se.

Compound (1) used as a starting material in reaction scheme 1 can be produced by, for example, the method shown in the following reaction scheme 2.

The amount of the organic phosphorus compound or the electrophile to be used is preferably 1 to 5 molar equivalents relative to compound (12) or compound (13).

The amount of compound (14) or compound (15) to be used is generally 1 to 10 mol, preferably 1 to 3 mol, per 1 mol of compound (12) or compound (13).

Reaction scheme 2

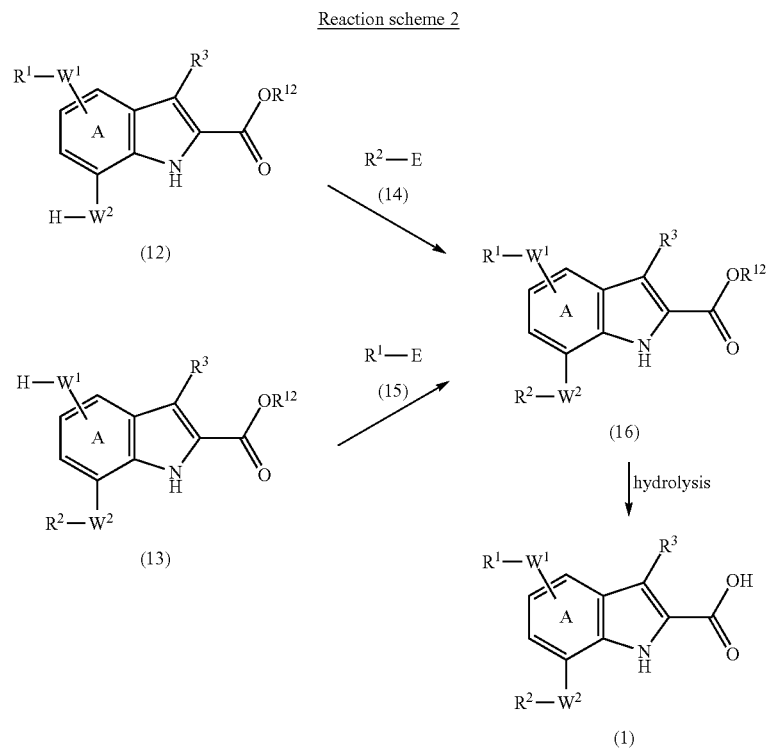

wherein $R^{12}$ is an optionally substituted $C_{1-6}$ alkyl group, E is a hydroxyl group or a leaving group, and the other symbols are as defined above.

Examples of the "leaving group" for E include a halogen atom; an optionally halogenated $C_{1-6}$ alkylsulfonyloxy group (e.g., methanesulfonyloxy, ethanesulfonyloxy, trichloromethanesulfonyloxy, trifluoromethanesulfonyloxy); a $C_{6-10}$ arylsulfonyloxy group optionally having 1 to 3 substituents selected from a $C_{1-6}$ alkyl group, a $C_{1-6}$ alkoxy group and a nitro group (e.g., phenylsulfonyloxy, m-nitrophenylsulfonyloxy, p-toluenesulfonyloxy); $C_{1-6}$ alkoxysulfonyloxy group; a $C_{6-10}$ aryloxysulfonyloxy group and the like.

Compound (1) can be produced in 2 steps using compound (12) or compound (13) as a starting material.

In step 1, compound (16) is produced by reacting compound (12) with compound (14), or reacting compound (13) with compound (15).

When E is a hydroxyl group, this reaction is performed by a method known per se, for example, the method described in Synthesis, page 1 (1981) or a method analogous thereto. This reaction is generally performed in the presence of an organic phosphorus compound and an electrophile in a solvent that does not adversely influence the reaction.

Examples of the organic phosphorus compound include triphenylphosphine, tributylphosphine and the like.

Examples of the electrophile include diethyl azodicarboxylate, diisopropyl azodicarboxylate, azodicarbonyl dipiperazine and the like.

Examples of the solvent that does not adversely influence the reaction include ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide and the like; and the like. These solvents may be mixed in an appropriate ratio.

The reaction temperature is generally −50 to 150° C., preferably −10 to 100° C.

The reaction time is generally 0.5 to 20 hr.

When E is a leaving group, this reaction is performed according to a conventional method in the presence of a base in a solvent that does not adversely influence the reaction.

Examples of the base include alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogen carbonates such as sodium hydrogen carbonate, potassium hydrogen carbonate and the like; alkali metal hydrides such as sodium hydride, potassium hydride and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; and the like.

The amount of the base to be used is preferably about 1 to about 5 molar equivalents relative to compound (12) or compound (13).

The amount of compound (14) or compound (15) to be used is generally 1 to 10 mol, preferably 1 to 3 mol, per 1 mol of compound (12) or compound (13).

Examples of the solvent that does not adversely influence the reaction include aromatic hydrocarbons such as benzene, toluene, xylene and the like; ethers such as tetrahydrofuran, dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide and the like; nitriles such as acetonitrile, propionitrile and the like; ketones such as acetone, methyl ethyl ketone and the like; and the like. These solvents may be mixed in an appropriate ratio and used.

The reaction temperature is generally −50 to 150° C., preferably −10 to 100° C.

The reaction time is generally 0.5 to 20 hr.

The thus-obtained compound (16) can be isolated and purified by a known separation and purification means, for example, concentration, concentration under reduced pressure, solvent extraction, crystallization, recrystallization, phase transfer, chromatography and the like.

In step 2, compound (1) is produced by subjecting compound (16) to hydrolysis. This reaction is performed in the same manner as in the method of producing compound (9) by hydrolysis of compound (6) in reaction scheme 1.

The thus-obtained compound (1) can be isolated and purified by a known separation and purification means, for example, concentration, concentration under reduced pressure, solvent extraction, crystallization, recrystallization, phase transfer, chromatography and the like.

Compounds (14) and (15) to be used as starting materials in reaction scheme 2 can each be produced by a method known per se.

Compound (12) used as a starting material in reaction scheme 2 can be produced, for example, by the method shown in the following reaction scheme 3.

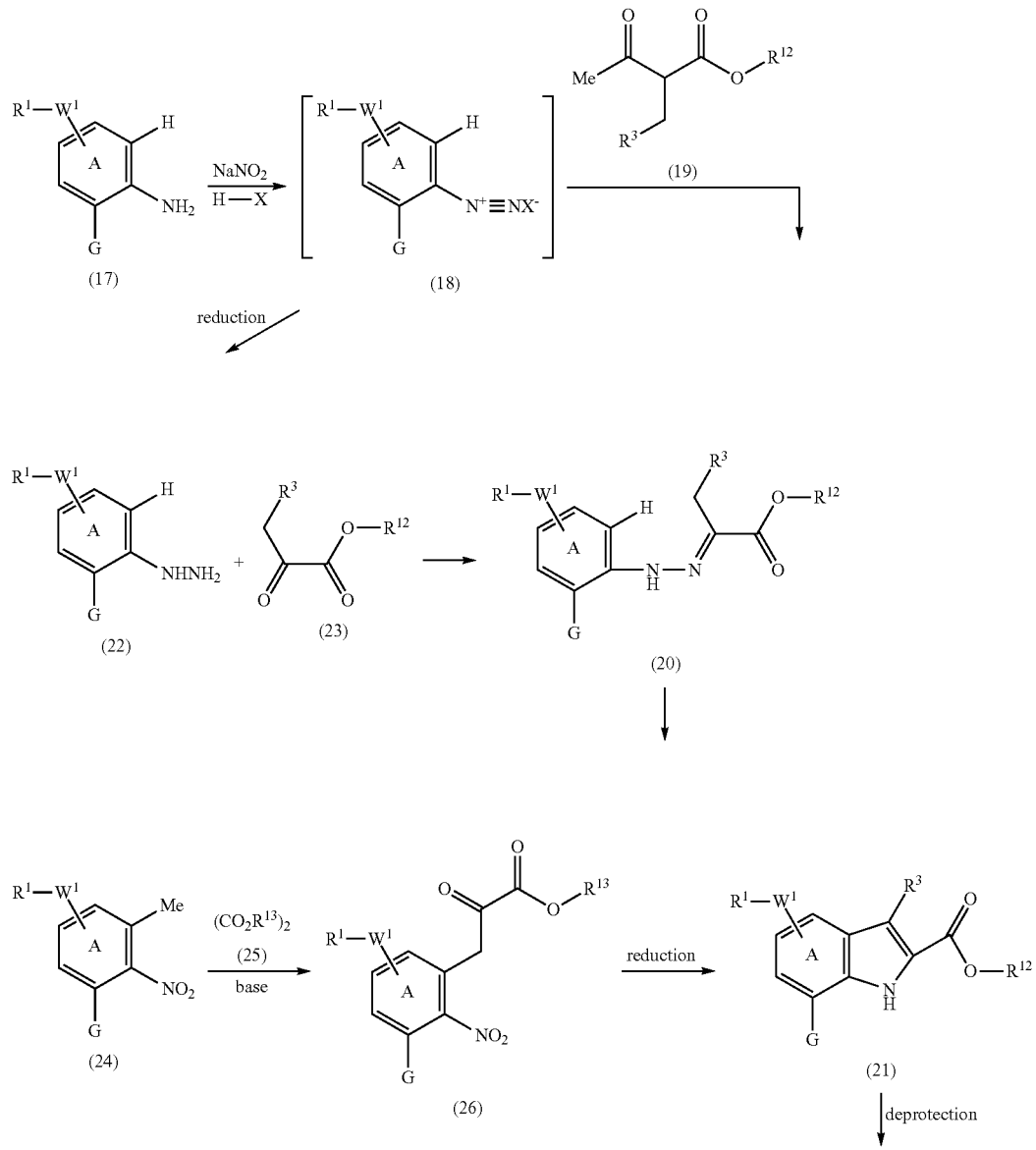

Reaction scheme 3

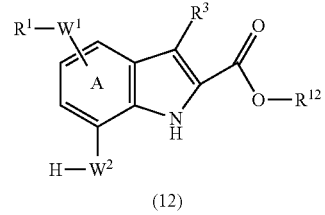

(12)

wherein G is an optionally protected sulfanyl group or an to optionally protected hydroxy group, H—X is mineral acid such as hydrochloric acid, sulfuric acid and the like; or organic acid such as acetic acid, formic acid, trifluoroacetic acid and the like, and the other symbols are as defined above.

As for the "optionally protected sulfanyl group" for G, examples of the sulfanyl-protecting group include a $C_{1-6}$ alkyl-carbonyl group, a phenylcarbonyl group, a $C_{1-6}$ alkoxy-carbonyl group, an allyloxycarbonyl group, a phenyloxycarbonyl group, a fluorenylmethyloxycarbonyl group, a $C_{7-10}$ aralkyl-carbonyl group (e.g., benzylcarbonyl), a $C_{7-10}$ aralkyloxy-carbonyl group (e.g., benzyloxycarbonyl), a $C_{7-20}$ aralkyl group (e.g., benzyl, trityl), an alkyl group (e.g., methoxymethyl, tert-butyl) and the like, each of which optionally has substituent(s). Here, examples of the substituent include a phenyl group, a halogen atom, a $C_{1-6}$ alkyl-carbonyl group, a $C_{1-6}$ alkoxy group optionally substituted by a halogen atom, a nitro group and the like, and the number of the substituents is 1 to 4.

As for the "optionally protected hydroxy group" for G, examples of the hydroxy-protecting group include a $C_{1-6}$ alkyl group, a $C_{7-20}$ aralkyl group (e.g., benzyl, trityl), formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a tetrahydrofuranyl group, a trialkylsilyl group (e.g., trimethylsilyl, tert-butyldimethylsilyl, diisopropylethylsilyl), for example, $C_{1-6}$ alkylsulfonyl (e.g., methylsulfonyl group), arylsulfonyl group (e.g., p-toluenesulfonyl group) and the like, each of which optionally has substituent(s). Here, examples of the substituent include a halogen atom, a $C_{1-6}$ alkyl group, a phenyl group, a $C^{7-10}$ aralkyl group (e.g., benzyl etc.), a $C_{1-6}$ alkoxy group, a nitro group and the like, and the number of the substituents is 1 to 4.

Compound (21) can be produced by subjecting compound (20) to the Fischer method [Berichte, 1883, vol. 16, page 2241]. In this reaction, compound (20) is reacted with an acid with heating.

Examples of the acid include zinc chloride, hydrogen chloride, sulfuric acid, conc. sulfuric acid, hydrogen chloride, acetic acid, formic acid, boron fluoride, polyphosphoric acid, diphosphorus pentoxide, methanesulfonic acid, toluenesulfonic acid and the like. Two or more kinds of these may be mixed in an appropriate ratio and used.

The amount of acid to be used is generally 0.1 to 10 mol, preferably 0.5 to 3 mol, per 1 mol of compound (20).

This reaction is preferably performed without solvent or in a solvent which is inert to the reaction. While such solvent is not particularly limited as long as the reaction proceeds, for example, alcohols such as methanol, ethanol, propanol, isopropanol, butanol, tert-butanol and the like; ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, naphthalene, toluene and the like; amides such as formamide, N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide; water and the like can be mentioned. Two or more kinds of these solvents may be mixed in an appropriate ratio and used.

While the reaction time varies depending on the kind and amount of the acid to be used, it is generally 0.5 hr to 100 hr, preferably 1 hr to 50 hr. The reaction temperature is generally 0 to 200° C., preferably 20 to 190° C.

The thus-obtained compound (21) can be isolated and purified by a known separation and purification means, for example, concentration, concentration under reduced pressure, solvent extraction, crystallization, recrystallization, phase transfer, chromatography and the like.

Compound (21) can also be produced in 2 steps by subjecting compound (24) to the Reissert method (Berichte, 1897, vol. 30, page 1030).

In the first step, compound (24) is reacted with compound (25) in the presence of a base to give compound (26). In step 2, compound (21) can be produced by subjecting compound (26) to a reduction reaction.

Examples of the base to be used in the first step include alkali metal $C_{1-6}$ alkoxide such as sodium methoxide, sodium ethoxide, potassium ethoxide, potassium tert-butoxide and the like, alkali metal hydride such as sodium hydride, potassium hydride and the like, and the like.

This reaction is preferably performed in a solvent which is inert to the reaction. While such solvent is not particularly limited as long as the reaction proceeds, for example, alcohols such as methanol, ethanol, propanol, isopropanol, butanol, tert-butanol and the like; ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide; water and the like can be mentioned. Two or more kinds of these solvents may be mixed in an appropriate ratio and used.

The amount of compound (25) or the base to be used is generally 1 to 10 mol, preferably 1 to 3 mol, per 1 mol of compound (24).

The reaction temperature is generally −30° C. to 100° C. The reaction time is generally 0.5 to 20 hr.

The reduction reaction in the second step is performed using a reducing agent. As the reducing agent, for example, metals such as iron, zinc, tin and the like; sulfides such as sodium dithionite and the like; and the like can be mentioned.

The amount of the reducing agent to be used is appropriately determined according to the kind of the reducing agent. This reaction can also be promoted by addition of a metal salt. As the metal salt, for example, calcium chloride, calcium bromide and the like can be mentioned.

The amount of the reducing agent to be used is generally 1 to 20 equivalents, preferably 1 to 5 equivalents, relative to 1 equivalent of compound (26).

The amount of the metal salt to be added is generally 0.05 to 10 equivalents, preferably 0.1 to 5 equivalents, relative to 1 equivalent of compound (26).

The reduction reaction can also be performed by a hydrogenation reaction. In this case, for example, catalysts such as palladium carbon, palladium black, platinum dioxide, Raney-nickel, Raney-cobalt, iron trichloride and the like can be used. The amount of the catalyst to be used is generally about 5 to 1000 wt %, preferably about 10 to 300 wt %, relative to compound (26). The hydrogenation reaction can also be performed using various hydrogen sources instead of hydrogen gas. As such hydrogen source, for example, formic acid, ammonium formate, triethylammonium formate, sodium phosphinate, hydrazine and the like can be mentioned. The amount of the hydrogen source to be used is generally about 1 to 100 mol, preferably about 1 to 5 mol, per 1 mol of compound (26).

The reduction reaction is preferably performed in a solvent which is inert to the reaction. While the solvent is not particularly limited as long as the reaction proceeds, as such solvent, for example, alcohols such as methanol, ethanol, 1-propanol, 2-propanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethyiphosphoramide and the like; organic acids such as formic acid, acetic acid, propionic acid, trifluoroacetic acid, methanesulfonic acid and the like, water and the like can be mentioned. Two or more kinds of these solvents may be mixed in an appropriate ratio and used.

While the reaction time varies depending on the kind and amount of the reducing agent to be used, it is generally 0.5 hr to 100 hr, preferably 1 hr to 50 hr. The reaction temperature is generally −20 to 120° C., preferably 0 to 80° C.

The thus-obtained compound (21) can be isolated and purified by a known separation and purification means, for example, concentration, concentration under reduced pressure, solvent extraction, crystallization, recrystallization, phase transfer, chromatography and the like.

Compound (12) can be produced by subjecting compound (21) wherein G is a protected sulfanyl group or a protected hydroxy group to a conventional deprotection reaction such as an acid treatment, an alkali treatment, a catalytic hydrogenation and the like, as necessary.

Compound (20) can be produced by subjecting compound (22) and compound (23) to a dehydrating reaction.

This reaction is performed without a solvent or in a solvent inert to the reaction. While the solvent is not particularly limited as long as the reaction proceeds, as such solvent, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; and the like can be mentioned. Two or more kinds of these solvents may be mixed in an appropriate ratio and used.

This reaction can be generally promoted by using an acid catalyst. Examples of the acid catalyst include mineral acids such as hydrochloric acid, sulfuric acid and the like; Lewis acids such as boron trihalide (e.g., boron trichloride, boron trifluoride), titanium tetrahalide (e.g., titanium tetrachloride, titanium tetrabromide), aluminum halide (e.g., aluminum chloride, aluminum bromide) and the like; organic acids such as acetic acid, formic acid, trifluoroacetic acid and the like; and the like.

The amount of compound (23) to be used is generally 1 to 10 mol, preferably 1 to 3 mol, per 1 mol of compound (22).

The amount of the acid catalyst to be used is generally 0.1 to 5 mol, preferably 0.5 to 3 mol, per 1 mol of compound (22).

While the reaction time varies depending on the kind and amount of compound (22), compound (23) and acid catalyst, it is generally 0.5 hr to 100 hr, preferably 1 hr to 50 hr. The reaction temperature is generally −20 to 120° C., preferably 0 to 80° C.

The thus-obtained compound (20) can be isolated and purified by a known separation and purification means, for example, concentration, concentration under reduced pressure, solvent extraction, crystallization, recrystallization, phase transfer, chromatography and the like.

Compound (22) can be produced by the following method and using compound (17) as a starting material.

In this reaction, the compound can be produced by reducing compound (18) produced by a method known per se using compound (17), acid (H—X) and sodium nitrite. The reduction reaction is performed using a reducing agent. Examples of the reducing agent include metals such as iron, zinc, tin and the like; metal halides such as tin chloride and the like; sulfides such as sodium dithonite and the like; and the like. The amount of the reducing agent to be used is appropriately determined according to the kind of the reducing agent.

The amount of the reducing agent to be used is generally 1 to 20 equivalents, preferably 1 to 5 equivalents, relative to 1 equivalent of compound (17).

This reaction is preferably performed in a solvent which is inert to the reaction. While such solvent is not particularly limited as long as the reaction proceeds, for example, alcohols such as methanol, ethanol, propanol, isopropanol, butanol, tert-butanol and the like; ethers such as 1,4-dioxane, tetrahydrofuran, diethyl ether, tert-butyl methyl ether, diisopropyl ether, 1,2-dimethoxyethane and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; water and the like can be mentioned. Two or more kinds of these solvents may be mixed in an appropriate ratio and used.

The reaction time is generally 0.5 hr to 100 hr, preferably 1 hr to 50 hr. The reaction temperature is generally 0 to 200° C., preferably 20 to 190° C.

The thus-obtained compound (22) can be isolated and purified by a known separation and purification means, for example, concentration, concentration under reduced pressure, solvent extraction, crystallization, recrystallization, phase transfer, chromatography and the like.

Compound (20) can also be produced by subjecting compound (17) to Japp-Klingemann reaction (Org. Reactions, 1959, vol. 10, page 143; J. Chem. Soc., 1927, page 1).

In this reaction, compound (18) produced by a method known per se and using compound (17), acid (H—X) and sodium nitrite is reacted with compound (19) in the presence of a base.

Examples of the base include alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogen carbonates such as sodium hydrogen carbonate, potassium hydrogen carbonate and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; and the like.

This reaction is preferably performed in a solvent which is inert to the reaction. While such solvent is not particularly limited as long as the reaction proceeds, for example, alcohols such as methanol, ethanol, propanol, isopropanol, butanol, tert-butanol and the like; ethers such as 1,4-dioxane, tetrahydrofuran, diethyl ether, tert-butyl methyl ether, diisopropyl ether, 1,2-dimethoxyethane and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; water and the like can be mentioned. Two or more kinds of these solvents may be mixed in an appropriate ratio and used.

The amount of compound (19) to be used is generally 1 to 10 mol, preferably 1 to 3 mol, per 1 mol of compound (18). The amount of the base to be used is generally 1 to 10 mol, preferably 1 to 3 mol, per 1 mol of compound (18).

The reaction time is generally about 1 hr to about 100 hr, preferably about 1 hr to about 50 hr. The reaction temperature is generally about −20 to about 120° C., preferably about 0 to about 80° C.

The thus-obtained compound (20) can be isolated and purified by a known separation and purification means, for example, concentration, concentration under reduced pressure, solvent extraction, crystallization, recrystallization, phase transfer, chromatography and the like.

Compounds (19), (22), (23), (24) and (25) to be used as starting materials in reaction scheme 3 can each be produced by a method known per se.

Compound (13) used as a starting material in reaction scheme 2 can be produced, for example, from compound (50) shown in the below-mentioned reaction scheme 7 as a starting material and in the same manner as in the method of reaction scheme 4 shown below and the method shown in the aforementioned reaction scheme 3.

Compound (17) to be used as a starting material in reaction scheme 3 can also be produced, for example, by the method of the following reaction scheme 4.

Reaction scheme 4

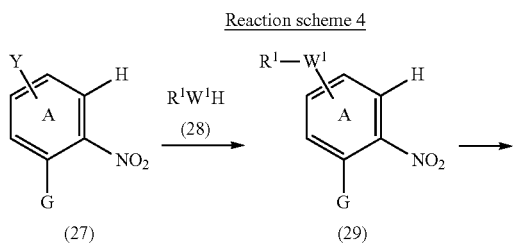

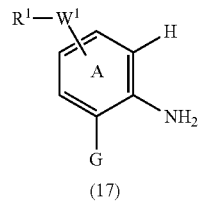

wherein Y is a halogen group, and other symbols are as defined above.

Compound (17) can be produced in 2 steps by using compound (27) as a starting material.

In step 1, compound (27) is reacted with compound (28) to give compound (29).

This reaction is performed in the presence of a base when desired.

Examples of the base include organic bases such as triethylamine, pyridine, 4-dimethylaminopyridine, diisopropylethylamine and the like; inorganic bases such as sodium hydroxide, potassium hydroxide, sodium carbonate, potassium carbonate, sodium hydride, potassium hydride and the like; and the like.

This reaction is performed without a solvent or in a solvent which is inert to the reaction. While the solvent is not particularly limited as long as the reaction proceeds, as such solvent, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like, and the like; nitriles such as acetonitrile, propionitrile and the like; ketones such as acetone, methyl ethyl ketone and the like can be mentioned. Two or more kinds of these solvents may be mixed in an appropriate ratio and used.

When a base is used, the amount of compound (28) and the base to be used is generally 1 to 10 mol, preferably 1 to 3 mol, per 1 mol of compound (27).

While the reaction time varies depending on the kind and amount of compound (27), compound (28), and the base, it is generally 0.5 hr to 100 hr, preferably 1 hr to 50 hr. The reaction temperature is generally −20 to 120° C., preferably 0 to 80° C.

The thus-obtained compound (29) can be isolated and purified by a known separation and purification means, for example, concentration, concentration under reduced pressure, solvent extraction, crystallization, recrystallization, phase transfer, chromatography and the like.

In step 2, compound (29) is subjected to a reduction reaction to give compound (17). The reduction reaction is performed in the same manner as in the method of producing compound (21) from compound (26) in the aforementioned reaction scheme 3.

The thus-obtained compound (17) can be isolated and purified by a known separation and purification means, for example, concentration, concentration under reduced pressure, solvent extraction, crystallization, recrystallization, phase transfer, chromatography and the like.

Compounds (27) and (28) to be used as starting materials in reaction scheme 4 can be produced by a method known per se.

Compound (16) in reaction scheme 2 can also be produced, for example, by the method of the following reaction scheme 5.

Reaction scheme 5

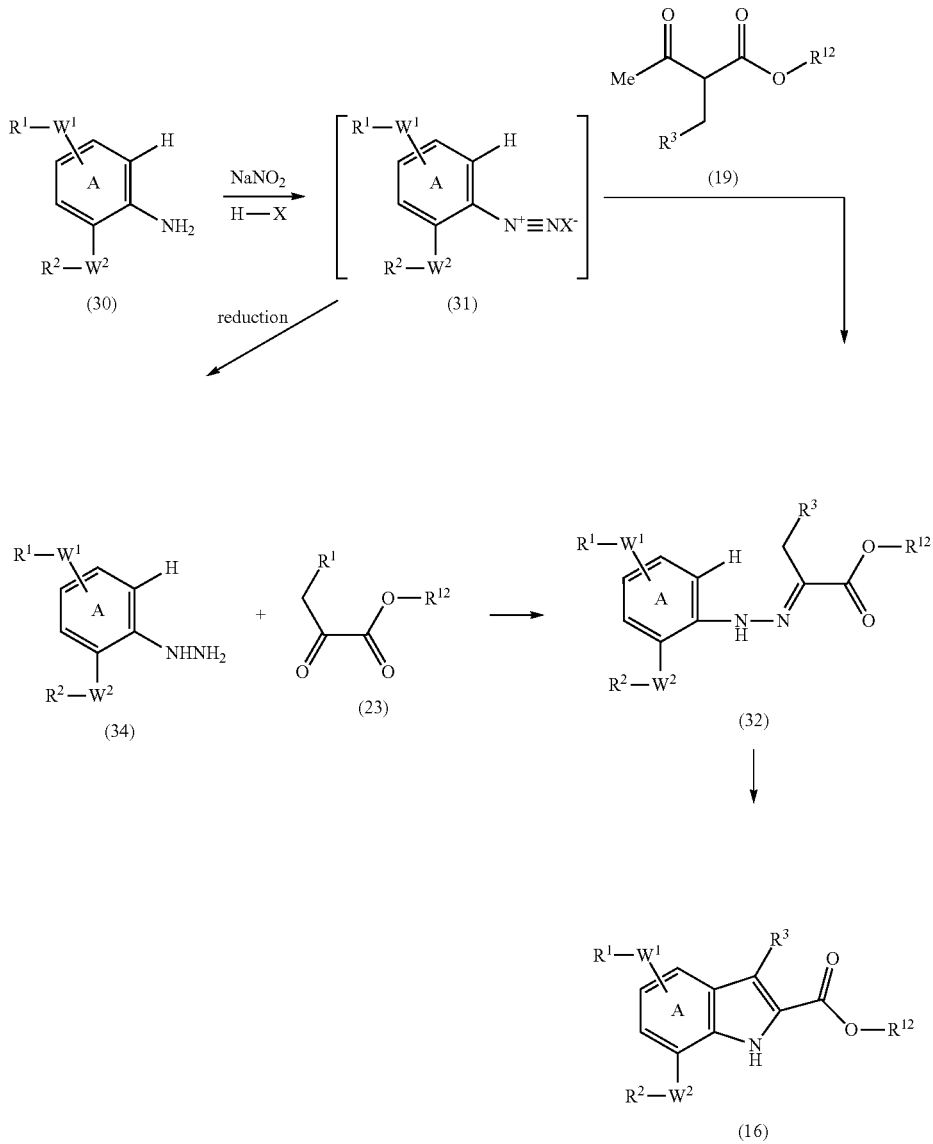

wherein each symbol is as defined above.

Compound (16) can be produced by subjecting compound (32) to the Fischer method (Berichte, 1883, vol. 16, page 2241). This reaction can be performed in the same manner as in the method of producing compound (21) from compound (20) in reaction scheme 3.

Compound (32) can be produced by subjecting compound (30) to Japp-Klingemann reaction (Org. Reactions, 1959, vol. 10, page 143; J. Chem. Soc., 1927, page 1). This reaction is performed in the same manner as in the method of producing compound (20) from compound (17) in reaction scheme 3 using compound (30) instead of compound (17).

Compound (32) can also be produced by subjecting compound (34) and compound (23) to a dehydration reaction. This reaction is performed in the same manner as in the method of producing compound (20) from compound (22) in reaction scheme 3 using compound (34) instead of compound (22).

Compound (34) can be produced from compound (30) in the same manner as in the method of producing compound (22) from compound (17) in reaction scheme 3.

Compounds (19) and (23) to be used as starting materials in reaction scheme 5 can each be produced by a method known per se.

Compound (30) to be used as a starting material in reaction scheme 5 can be produced, for example, by the method of reaction scheme 6 shown below.

Compound (30) used as a starting material in reaction scheme 5, wherein $R^2$ is an optionally substituted $C_{2-6}$ alkyl group and $W^2$ is a bond, can also be produced by, for example, the following method.

Reaction scheme 6

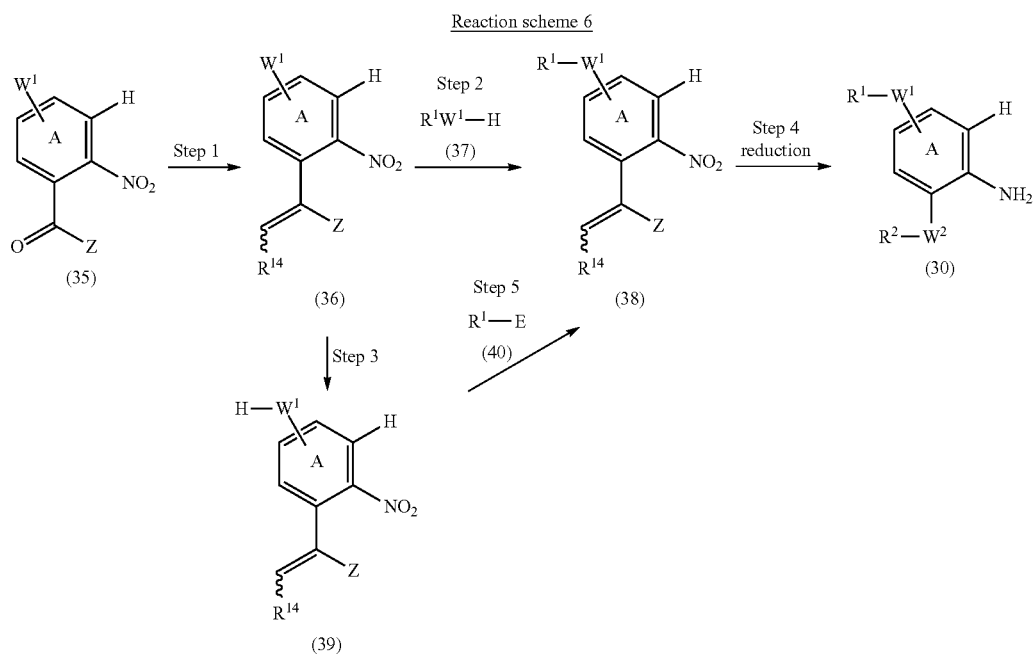

wherein X is a halogen group, Z is hydrogen or an optionally substituted alkyl group, $R^{14}$ is an optionally substituted alkyl group, an optionally substituted cycloalkyl group, an optionally substituted aryl group, or an optionally substituted heterocyclic group, and the other symbols are as defined above.

In step 1, compound (35) is reacted with an organic phosphorus reagent to give compound (36).

Examples of the organic phosphorus reagent include a phosphonium salt, a phosphonate compound and the like.

Examples of the phosphonium salt include a compound represented by the formula: $R^{14}$—$CH_2P(C_6H_5)_3Ea$ (Ea is a halogen atom).

Examples of the halogen atom for Ea include a chlorine atom, a bromine atom and an iodine atom. Phosphonium salt can be produced by a method known per se.

Examples of the phosphonate compound include a compound represented by the formula:) $R^{14}$—$CH_2PO(OR^2)$ ($OR^{21}$) ($R^{20}$ and $R^{21}$ are the same or different and each is a hydrogen atom or an optionally substituted hydrocarbon group, and they may be bonded to each other to form an optionally substituted ring). Phosphonate compound can be produced by a method known per se.

The reaction of compound (35) and an organic phosphorus reagent is performed by a conventional method in the presence of a base, in a solvent that does not adversely influence the reaction.

The amount of the organic phosphorus reagent is generally about 1 to about 5 molar equivalents, preferably about 1 to about 3 molar equivalents relative to compound (35).

Examples of the base include alkali metal salts such as sodium hydroxide, potassium hydroxide, potassium carbonate, sodium carbonate, sodium hydrogen carbonate and the like; amines such as pyridine, triethylamine, N,N-dimethylaniline and the like; metal hydrides such as sodium hydride, potassium hydride and the like; alkali metal alkoxides such as sodium ethoxide, sodium methoxide, potassium tert-butoxide and the like; alkyl metal reagents such as n-butyllithium, methyllithium and the like; and the like.

The amount of the base to be used is generally about 0.5 to 10 molar equivalents, preferably about 1 to about 5 molar equivalents, relative to compound (35).

Examples of the solvent that does not adversely influence the reaction include aromatic hydrocarbons such as benzene, toluene, xylene and the like; ethers such as dioxane, tetrahydrofuran, dimethoxyethane and the like; alcohols such as methanol, ethanol, propanol and the like; amides such as N,N-dimethylformamide and the like; sulfoxides such as dimethyl sulfoxide and the like; halogenated hydrocarbons such as chloroform, dichloromethane, 1,2-dichloroethane, 1,1,2,2-tetrachloroethane and the like; and the like. Two or more kinds of these solvents may be mixed in an appropriate ratio and used.

The reaction temperature is generally about −50° C. to about 150° C., preferably about −10° C. to about 100° C.

The reaction time is, for example, about 0.5 to about 30 hr.

The thus-obtained compound (36) can be isolated and purified by a known separation and purification means, for example, concentration, concentration under reduced pressure, solvent extraction, crystallization, recrystallization, phase transfer, chromatography and the like.

In addition, without isolation of compound (36), a reaction mixture containing compound (36) can also be used directly as a starting material for the next step.

Compound (30) can be produced in 2 steps by using compound (36) as a starting material.

In step 2, compound (36) is reacted with compound (37) to give compound (38).

This reaction is performed in the presence of a base, when desired.

Examples of the base include organic bases such as triethylamine, pyridine, 4-dimethylaminopyridine, diisopropylethylamine and the like; inorganic bases such as sodium hydroxide, potassium hydroxide, sodium carbonate, potassium carbonate and the like and the like.

This reaction is performed without a solvent or in a solvent which is inert to the reaction. While the solvent is not particularly limited as long as the reaction proceeds, as such solvent, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like, and the like can be mentioned. Two or more kinds of these solvents may be mixed in an appropriate ratio and used.

When a base is used, the amount of compound (37) or the base to be used is generally 1 to 10 mol, preferably 1 to 3 mol, per 1 mol of compound (36).

While the reaction time varies depending on the kind and amount of compound (36) and compound (37), it is generally 0.5 hr to 100 hr, preferably 1 hr to 50 hr. The reaction temperature is generally −20 to 120° C., preferably 0 to 80° C.

The thus-obtained compound (38) can be isolated and purified by a known separation and purification means, for example, concentration, concentration under reduced pressure, solvent extraction, crystallization, recrystallization, phase transfer, chromatography and the like.

In addition, compound (38) can also be produced by reacting compound (36) with compound (37) in the presence of a metal catalyst and, when desired, in the presence of a ligand, a base and molecular sieves.

As the metal catalyst, palladium catalysts (e.g., palladium acetate(II), tris(dibenzylideneacetone)dipalladium(0), bis(dibenzylideneacetone)palladium(0), tetrakis(triphenylphosphine)palladium(0), [1,1'-bis(diphenylphosphino)ferrocene]dichloropalladium dichloromethane(II) adduct etc.), nickel catalysts (e.g., tetrakis(triphenylphosphine)nickel (0), dichloro[1,3-bis(diphenylphosphino)propane]nickel (II), dichloro[1,4-bis(diphenylphosphino)butane(II)]nickel etc.), copper catalysts (e.g., copper(II) acetate, copper(I) iodide, copper(I) bromide, copper(I) chloride etc.) and the like can be mentioned.

As the ligand, phosphorus ligands (e.g., 2,2'-bis(diphenylphosphino)-1,1'-binaphthyl, 4,5-bis(diphenylphosphino)-9,9-dimethylxanthene etc.) can be mentioned.

When an organic metal catalyst or ligand which is unstable to oxygen is used in this reaction, the reaction is preferably performed in an inert gas such as argon and the like.

Examples of the base include alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate, cesium carbonate and the like; phosphoric acid metals such as sodium phosphate, potassium phosphate and the like; alkali metal hydrogen carbonates such as sodium hydrogen carbonate, potassium hydrogen carbonate and the like; alkali metal alkoxides having 1 to 6 carbon atoms such as sodium methoxide, sodium ethoxide, potassium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; and the like.

This reaction is advantageously performed without solvent or a solvent which is inert to the reaction. While such solvent is not particularly limited as long as the reaction proceeds, for example, solvents, for example, alcohols such as methanol, ethanol, propanol, isopropanol, butanol, tert-butanol and the like; ethers such as 1,4-dioxane, tetrahydrofuran, diethyl ether, tert-butyl methyl ether, diisopropyl ether, ethylene glycol dimethyl ether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide and the like, a mixed solvent thereof and the like are preferable.

The amount of the base to be used is generally 1 to 10 mol, preferably 1 to 5 mol, per 1 mol of compound (36) or compound (37).

The amount of the metal catalyst to be used is generally 0.01 to 0.5 mol, preferably 0.03 to 0.1 mol, per 1 mol of compound (36) or compound (37).

The amount of the ligand to be used is generally 0.01 to 1 mol, preferably 0.05 to 0.3 mol, per 1 mol of compound (36) or compound (37).

The amount of the molecular sieves to be used is 50 mg to 1000 mg, per 1 g of compound (36) or compound (37).

The reaction temperature is generally −30° C. to 150° C., preferably 25° C. to 120° C. The reaction time is generally 0.5 to 20 hr.

The thus-obtained compound (38) can be isolated and purified by a known separation and purification means, for example, concentration, concentration under reduced pressure, solvent extraction, crystallization, recrystallization, phase transfer, chromatography and the like.

In step 4, compound (38) is subjected to a reduction reaction to give compound (30). The reduction reaction is performed in the same manner as in the method of producing compound (21) from compound (26) in the aforementioned reaction scheme 3.

The thus-obtained compound (30) can be isolated and purified by a known separation and purification means, for example, concentration, concentration under reduced pressure, solvent extraction, crystallization, recrystallization, phase transfer, chromatography and the like.

Compound (38) can be produced in 2 steps by using compound (36) as a starting material.

In step 3, compound (39) is produced from compound (36). This step can be performed according to the methods described in J. Am. Chem. Soc, 1951, vol. 73, page 5125 and WO200397641A2 (Novartis).

In step 5, compound (39) is reacted with compound (40) to give compound (38). This reaction is performed in the same manner as in the method of producing compound (16) from compound (13) in the aforementioned reaction scheme 2 or a method analogous thereto.

The thus-obtained compound (38) can be isolated and purified by a known separation and purification means, for example, concentration, concentration under reduced pressure, solvent extraction, crystallization, recrystallization, phase transfer, chromatography and the like.

Compounds (35), (37) and (40) to be used as starting materials in reaction scheme 6 can each be produced by a method known per se.

Compounds (30) and compound (50) used as starting materials in reaction scheme 5 can also be produced by the method of the following reaction scheme 7.

Reaction scheme 7

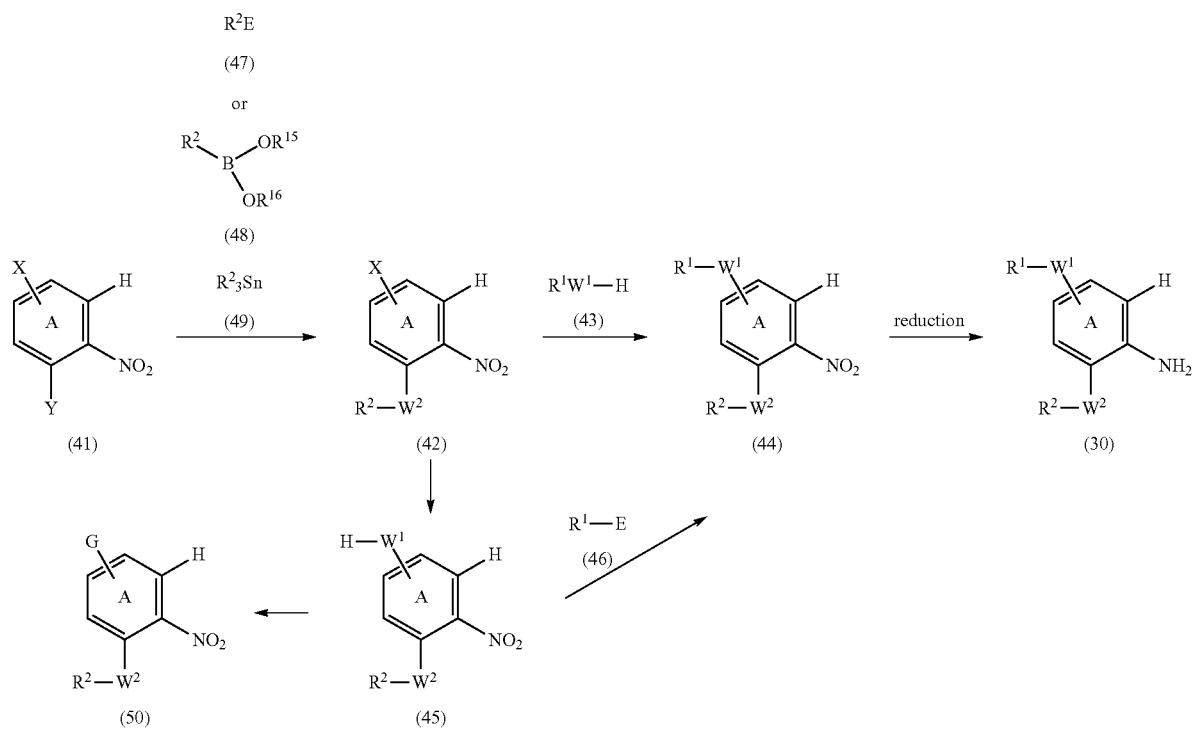

wherein X is a halogen atom, Y is a halogen atom or W²H, E is a hydroxyl group or a leaving group, $R^{15}$ and $R^{16}$ are each a hydrogen atom, an optionally substituted alkyl group, an optionally substituted aryl group or an optionally substituted cycloalkyl group, $R^{15}$ and $R^{16}$ may be bonded to each other to form an optionally substituted ring, and the other symbols are as defined above.

In the step for producing compound (42) from compound (41) and compound (47), when Y is a hydroxyl group or a sulfanyl group, and E is a leaving group, the reaction is performed in the presence of a base, when desired.

Examples of the base include organic bases such as triethylamine, pyridine, 4-dimethylaminopyridine, diisopropylethylamine and the like; inorganic bases such as sodium hydroxide, potassium hydroxide, sodium carbonate, potassium carbonate, sodium hydride, potassium hydride and the like; and the like.

This reaction is performed without a solvent or in a solvent which is inert to the reaction. While the solvent is not particularly limited as long as the reaction proceeds, as such solvent, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like, and the like; nitriles such as acetonitrile, propionitrile and the like; ketones such as acetone, methyl ethyl ketone and the like can be mentioned. Two or more kinds of these solvents may be mixed in an appropriate ratio and used.

When a base is used, the amount of the base to be used is generally 1 to 10 mol, preferably 1 to 3 mol, per 1 mol of compound (41).

The amount of compound (47) to be used is generally 1 to 10 mol, preferably 1 to 3 mol, per 1 mol of compound (41).

While the reaction time varies depending on the kind and amount of the base and compound (41), it is generally 0.5 hr to 100 hr, preferably 1 hr to 50 hr. The reaction temperature is generally −20 to 120° C., preferably 0 to 80° C.

when Y is a hydroxyl group and E is a hydroxyl group, this reaction can also be produced by a method known per se, for example, the method described in Synthesis, page 1 (1981), or a method analogous thereto. That is, this reaction is generally performed in the presence of an organic phosphorus compound and an electrophile, in a solvent that does not adversely influence the reaction.

Examples of the organic phosphorus compound include triphenylphosphine, tri-n-butylphosphine and the like.

Examples of the electrophile include diethyl azodicarboxylate, diisopropyl azodicarboxylate, azodicarbonyl dipiperazine and the like.

The amount of the organic phosphorus compound or electrophile to be used is preferably about 1 to about 5 molar equivalents relative to compound (41).

Examples of the solvent that does not adversely influence the reaction include ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide and the like; and the like can be mentioned. Two or more kinds of these solvents may be mixed in an appropriate ratio and used.

The reaction temperature is generally about −50 to about 150° C., preferably about −10 to about 100° C.

The reaction time is generally about 0.5 to about 20 hr.

In addition, when Y of compound (41) is a halogen atom, compound (42) can be produced by performing a reaction of compound (41) with a boric acid compound (48) such as methylboronic acid and the like, borate compound (48) represented by diisopropoxymethylborane and the like, a tetraalkyltin compound (49) represented by tetramethyltin and the like, and the like, in the presence of a metal catalyst and, when desired, in the presence of a ligand, a base and molecular sieves.

As the metal catalyst, palladium catalysts (e.g., palladium acetate(II), tris(dibenzylideneacetone)dipalladium(0), bis(dibenzylideneacetone)palladium(0), tetrakis(triphenylphosphine)palladium(0), [1,1'-bis(diphenylphosphino)ferrocene]dichloropalladium dichloromethane(II) adduct etc.), and nickel catalysts (e.g., tetrakis(triphenylphosphine)nickel (0), dichloro[1,3-bis(diphenylphosphino)propane]nickel (II), dichloro[1,4-bis(diphenylphosphino)butane(II)]nickel etc.) can be mentioned.

As the ligand, phosphorus ligands (e.g., 2,2'-bis(diphenylphosphino)-1,1'-binaphthyl, 4,5-bis(diphenylphosphino)-9,9-dimethylxanthene etc.) can be mentioned.

When an organic metal catalyst or ligand which is unstable to oxygen is used in this reaction, the reaction is preferably performed in an inert gas such as argon and the like.

Examples of the base include alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate, cesium carbonate and the like; alkali metal hydrogen carbonates such as sodium hydrogen carbonate, potassium hydrogen carbonate and the like; alkali metal alkoxides having 1 to 6 carbon atoms such as sodium methoxide, sodium ethoxide, potassium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; and the like.

This reaction is advantageously performed without solvent, or in a solvent which is inert reaction. While such solvent is not particularly limited as long as the reaction proceeds, for example, solvents, for example, alcohols such as methanol, ethanol, propanol, isopropanol, butanol, tert-butanol and the like; ethers such as 1,4-dioxane, tetrahydrofuran, diethyl ether, tert-butyl methyl ether, diisopropyl ether, ethylene glycol dimethyl ether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide and the like, and a mixed solvent thereof and the like are preferable.

The amount of the base to be used is generally 1 to 10 mol, preferably 1 to 5 mol, per 1 mol of compound (41).

The amount of the metal catalyst to be used is generally 0.01 to 0.5 mol, preferably 0.03 to 0.1 mol, per 1 mol of compound (41).

The amount of the ligand to be used is generally 0.01 to 1 mol, preferably 0.05 to 0.3 mol, per 1 mol of compound (41).

The amount of the molecular sieves to be used is 50 mg to 1000 mg, per 1 g of compound (41).

The reaction temperature is generally −30° C. to 150° C., preferably 25° C. to 120° C. The reaction time is generally 0.5 to 20 hr.

The thus-obtained compound (42) can be isolated and purified by a known separation and purification means, for example, concentration, concentration under reduced pressure, solvent extraction, crystallization, recrystallization, phase transfer, chromatography and the like.

Compound (30) can be produced in 2 steps by using compound (42) as a starting material.

In step 1, compound (42) is reacted with compound (43) to give compound (44). The reaction is performed in the same manner as in the method of producing compound (38) from compound (36) and compound (37) in reaction scheme 6 or a method analogous thereto.

In step 2, compound (44) is subjected to a reduction reaction to give compound (30). The reduction reaction is performed in the same manner as in the method of producing compound (21) from compound (26) in the aforementioned reaction scheme 3.

The thus-obtained compound (30) can be isolated and purified by a known separation and purification means, for example, concentration, concentration under reduced pressure, solvent extraction, crystallization, recrystallization, phase transfer, chromatography and the like.

In addition, compound (44) can be produced in 2 steps by using compound (42) as a starting material.

In step 1, compound (45) is produced from compound (42). The reaction is performed in the same manner as in the method of producing compound (39) from compound (36) in the aforementioned reaction scheme 6 or a method analogous thereto.

In step 2, compound (45) is reacted with compound (46) to give compound (44). The reaction is performed in the same manner as in the method of producing compound (16) from compound (13) in the aforementioned reaction scheme 2 or a method analogous thereto.

The thus-obtained compound (44) can be isolated and purified by a known separation and purification means, for example, concentration, concentration under reduced pressure, solvent extraction, crystallization, recrystallization, phase transfer, chromatography and the like.

Compound (50) can be produced by introducing a protecting group generally used as a protecting group of $W^1$ into compound (45) by a known method. The thus-obtained compound (50) can be isolated and purified by a known separation and purification means, for example, concentration, concentration under reduced pressure, solvent extraction, crystallization, recrystallization, phase transfer, chromatography and the like.

Compounds (41), (43), (46), (47), (48) and (49) to be used as starting materials in reaction scheme 7 can each be produced by a method known per se.

In the above-mentioned production method, when the starting compound or the compound of the present invention has an amino group, a carboxyl group, a hydroxy group or a carbonyl group as a substituent, a protecting group generally used in peptide chemistry and the like may be introduced into these groups. The protecting group can be removed according to a conventional method in any step in each scheme.

Examples of the amino-protecting group include a formyl group; a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, an N,N-dimethylaminomethylene group, a tri-substituted silyl group (e.g., trimethylsilyl, triethylsilyl, dimethylphenylsilyl, tert-butyldimethylsilyl, tert-butyldimethylsilyl), a $C_{2-6}$ alkenyl group (e.g., 1-allyl) and the like can be mentioned. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-10}$ aralkyl group (e.g., benzyl), a phenyl group, a trityl group, a tri-substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like can be mentioned. These groups are optionally substituted by 1 to 3 substituents selected from a halogen atom, a $C_{1-6}$ alkyl group, a $C_{1-6}$ alkoxy group or a nitro group.

Examples of the mercapto-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylamino-carbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The above-mentioned protecting groups can be removed by a method known per se, for example, the method described in Protective Groups in Organic Synthesis, John Wiley and Sons (1980), and the like. Specifically, employed is a method using acid, base, UV light, hydrazine, phenyl hydrazine, sodium N-methyldithiocarbamate, tetrabutylammonium fluoride, palladium acetate, trialkylsilyl halide (e.g., trimethylsilyl iodide, trimethylsilyl bromide and the like) and the like, reduction and the like.

Compound (I) of the present invention obtained according to the above-mentioned production method can be isolated and purified by a known means, for example, concentration, concentration under reduced pressure, solvent extraction, crystallization, recrystallization, phase transfer, chromatography and the like. In addition, each starting compound used in each of the above-mentioned production methods can be isolated and purified by a known means such as those mentioned above and the like. Alternatively, the starting compounds may be directly used in the form of a reaction mixture as starting materials of the next step without isolation.

When compound (I) contains isomers such as optical isomer, stereoisomer, positional isomer, rotamer and the like, any one of the isomers and mixtures is encompassed in compound (I). For example, when compound (I) contains an optical isomer, an optical isomer resolved from a racemate is also encompassed in compound (I). Each of these isomers can be obtained as a single product by a synthesis method, a separation method (e.g., concentration, solvent extraction, column chromatography, recrystallization etc.), an optical resolution method (e.g., fractional recrystallization, chiral column method, diastereomer method etc.) and the like known per se.

Compound (I) may be a crystal and the crystal is encompassed in compound (I), whether it is a single crystal form or a crystal mixture. Crystal can be produced by crystallization of the compound of the present invention according to a crystallization method known per se.

Compound (I) may be a pharmaceutically acceptable cocrystal or cocrystal salt. Here, the cocrystal and cocrystal salt mean crystalline substances consisting of two or more kinds of distinctive solids at room temperature, each having different physical properties (e.g., structure, melting point, melting heat, hygroscopicity, dissolution property and stability etc.). The cocrystal and cocrystal salt can be produced by a cocrystallization method known per se.

Compound (I) can also be produced by further subjecting the object compound obtained in each production method mentioned above to a substituent conversion reaction known per se.

EXAMPLES

The present invention is explained in more detail by way of the following Examples, Experimental Examples and Formulation Examples, which do not limit the present invention and may be changed without departing from the scope of the present invention.

The term "room temperature" in the following Reference Examples and Examples indicates the range of generally from about 10° C. to about 35° C. As for "%", the yield is in mol/mol %, the solvent used for chromatography is in % by volume and other "%" is in % by weight. OH proton, NH proton etc. on proton NMR spectrum that could not be confirmed due to broad peak are not included in the data.

The other symbols used herein mean the following:
s: singlet
d: doublet
t: triplet
q: quartet
m: multiplet
br: broad
brs: broad singlet
J: coupling constant
Hz: Hertz
$CDCl_3$: deuterated chloroform
DMSO-$d_6$: dimethyl sulfoxide-$d_6$
$^1$H-NMR: proton nuclear magnetic resonance
TFA: trifluoroacetic acid In the following Reference Examples and Examples, nuclear magnetic resonance spectrum (NMR) was measured under the following conditions.
NMR measurement tools: Varian Inc. Varian Gemini 200 (200 MHz), Varian Gemini 300 (300 MHz), Bruker BioSpin Corp. ADVANCE 300.

In the following Reference Examples and Examples, high performance liquid chromatography—mass spectrum (LC-MS) was measured under the following conditions.
measurement tools: Micromass Ltd., Quattro Micro and Agilent Technologies, Inc. HP1100, or Waters Corporation, MUX system (Micromass Ltd., ZQ)
Column: Shiseido Co., Ltd., Capcelpak C18 UG-120, 1.5×35 mm
solvent: SOLUTION A; 5 mM ammonium acetate/2% acetonitrile/water, SOLUTION B; 5 mM ammonium acetate/ 95% acetonitrile/water gradient cycle: 0.00 min (SOLUTION A 100%), 2.00 min (SOLUTION B 100%), 3.00 min (SOLUTION B 100%), 3.01 min (SOLUTION A 100%), 3.80 min (SOLUTION A 100%)
flow rate: 0.5 ml/min, detection: UV 220 nm
ionization method: Electron Spray Ionization: ESI
In the following Reference Examples and Examples, purification by preparative high performance liquid chromatography (HPLC) was performed under the following conditions. In the case of a compound having a basic functional group, however, when trifluoroacetic acid is used in this operation, neutralization and the like may be necessary to obtain a free compound.
tools: Gilson, Inc., high through-put purification system
Column: Shiseido Co., Ltd., Capcelpak O18 UG-120, S-5 µM, 20×50 mm
solvent: SOLUTION A; 0.1% trifluoroacetic acid-containing water, SOLUTION B; 0.1% trifluoroacetic acid-containing acetonitrile
gradient cycle: 0.00 min (SOLUTION A/SOLUTION B=95/5), 1.10 min (SOLUTION A/SOLUTION B=95/5), 5.00 min (SOLUTION A/SOLUTION B=0/100), 6.40 min (SOLUTION A/SOLUTION B=0/100), 6.50 min (SOLUTION A/SOLUTION B=95/5).
flow rate: 20 ml/min, detection: UV 220 nm
Alternatively,
tools: Waters mass preparative system (UV Purification System)
Column: Develosil ODS-UG-10
solvent: SOLUTION A; 0.1% trifluoroacetic acid-containing water, SOLUTION B; 0.1% trifluoroacetic acid-containing acetonitrile
gradient cycle: 0.00 min (SOLUTION A/SOLUTION B=95/5), 1.00 min (SOLUTION A/SOLUTION B=95/5), 2.00 min (SOLUTION A/SOLUTION B=80/20), 5.00 min (SOLUTION A/SOLUTION B=5/95), 5.10 min (SOLUTION A/SOLUTION B=0/100), 7.00 min (SOLUTION A/SOLUTION B 100/0)
flow rate: 150 ml/min, detection: UV 220 nm
In the following Reference Examples and Examples, preparative high performance liquid chromatography (HPLC) for chiral resolution was performed using K-Prep manufactured by YMC Co., Ltd. and preparative supercritical fluid chromatography (SFC) was performed using Multigram II manufactured by METTLER-TOLEDO K.K.

Reference Example 1

2-(Benzyloxy)-4-fluoro-1-nitrobenzene

To a mixture of 5-fluoro-2-nitrophenol (50.0 g), potassium carbonate (44.0 g) and N,N-dimethylformamide (150 mL) was added under ice-cooling benzyl bromide (59.9 g), and the mixture was stirred at room temperature for 15 hr. The reaction solution was concentrated under reduced pressure, water was added, and the mixture was extracted with ethyl acetate. The organic layer was washed with saturated brine, dried over magnesium sulfate, filtered and concentrated under reduced pressure. The obtained solid was washed with hexane to give the title compound (77.1 g, yield 98%) as pale-yellow crystals.
$^1$H NMR (CDCl$_3$) δ 5.23 (2H, s), 6.64-6.79 (1H, m), 6.83 (1H, dd, J=10.2, 2.5 Hz), 7.28-7.57 (5H, m), 7.97 (1H, dd, J=9.0, 6.0 Hz).

Reference Example 2

2-(Benzyloxy)-4-[4-(methylthio)phenoxy]-1-nitrobenzene

A mixture of 2-(benzyloxy)-4-fluoro-1-nitrobenzene (16.8 g), 4-methylthiophenol (10.0 g), potassium carbonate (14.1 g), and N,N-dimethylformamide (150 mL) was stirred at 80° C. for 2 hr. The reaction solution was concentrated under reduced pressure, water was added, and the mixture was extracted with ethyl acetate. The organic layer was washed successively with water and saturated brine, dried over magnesium sulfate, filtered and concentrated under reduced pressure. The obtained solid was washed with diethyl ether to give the title compound (23.2 g, yield 93%) as a pale-yellow solid. The pale-yellow solid was recrystallized from ethanol to give pale-yellow crystals.
melting point 81-82° C.

Reference Example 3

2-(Benzyloxy)-4-[4-(methylsulfonyl)phenoxy]-1-nitrobenzene 2-(Benzyloxy)-4-[4-(methylthio)phenoxy]-1-nitrobenzene (10.3 g) was dissolved in a mixed solvent of tetrahydrofuran (200 mL)-methanol (100 mL)-water (50 mL), Oxone (trade mark) (42.0 g) was added under ice-cooling, and the mixture was stirred at room temperature for 4 hr. The reaction solution was filtered to remove a white solid, and the filtrate was concentrated. Water was added to the residue, and the mixture was extracted with ethyl acetate. The organic layer was washed successively with water and saturated brine, dried over magnesium sulfate, filtered and concentrated under reduced pressure. The obtained solid was washed with a diethyl ether-hexane mixed solvent to give the title compound (11.0 g, yield 98%) as pale-yellow crystals.
melting point 142-143° C.

Reference Example 4

2-(Benzyloxy)-4-[4-(methylsulfonyl)phenoxy]aniline

A mixture of 2-(benzyloxy)-4-[4-(methylsulfonyl)phenoxy]-1-nitrobenzene (11.0 g), iron powder (7.6 g), calcium chloride (0.3 g), water (30 mL), and ethanol (120 mL) was stirred at 80° C. for 2 hr. The reaction solution was filtered through celite, and the filtrate was concentrated. Water was added to the residue, and the mixture was extracted with ethyl acetate. The organic layer was washed successively with water and saturated brine, dried over magnesium sulfate, filtered and concentrated under reduced pressure. The obtained crude product was crystallized from toluene and the obtained crystals were washed with diethyl ether to give the title compound (9.3 g, yield 92%) as pale-brown crystals.
MS 370 (MH$^+$).

Reference Example 5

Ethyl (2E)-2-({2-(benzyloxy)-4-[4-(methylsulfonyl)phenoxy]phenyl}hydrazono)propanoate 2-(Benzyloxy)-4-[4-(methylsulfonyl)phenoxy]aniline (43.8 g) was suspended in a mixed solvent of acetonitrile(50 mL)-ethanol (400 mL), and concentrated hydrochloric acid (25 mL) was added at 10° C. Moreover, ethanol (100 mL) was added. Sodium nitrite (9.8 g) dissolved in water (16 mL) was added dropwise at −5 to 0° C., and the mixture was stirred at −5° C. for 30 min. To the reaction mixture was added water (100 mL), and the mixture was added dropwise to a mixture of ethyl 2-methyl-3-oxobutanoate (18.8 mL), potassium hydroxide (85%, 23 g), water (100 mL), and ethanol (100 mL) at −13 to −11° C. over 2 hr. The reaction mixture was stirred at −11° C. for 40 min, and the precipitated orange solid was collected by filtration. The obtained solid was washed with ethanol and diethyl ether to give the title compound (52.3 g, yield 91%) as orange crystals.
$^1$H NMR (CDCl$_3$) δ 1.38 (3H, t, J=7.0 Hz), 2.06 (3H, s), 3.05 (3H, s), 4.32 (2H, q, J=6.9 Hz), 5.11 (2H, s), 6.67-6.77 (2H, m), 7.00 (2H, d, J=8.7 Hz), 7.33-7.42 (5H, m), 7.62 (1H, d, J=8.7 Hz), 7.84 (2H, d, J=8.7 Hz), 8.10 (1H,s).

Reference Example 6

Ethyl 7-(benzyloxy)-5-[4-(methylsulfonyl)phenoxy]-1H-indole-2-carboxylate p-Toluenesulfonic acid monohydrate (16.1 g) was refluxed for 1.5 hr in a toluene solvent, and water was removed by azeotropic distillation with dehydration. This solution was cooled to 80° C., ethyl [4-(methylsulfonyl)phenoxy]phenyl)hydrazono)propanoate (37.2 g) was added, and the mixture was stirred at 80° C. for 10 min. The reaction solution was washed successively with water, saturated aqueous sodium hydrogen carbonate solution and saturated brine, dried over magnesium sulfate, filtered and concentrated under reduced pressure. The obtained crude product was subjected to silica gel column chromatography (ethyl acetate:hexane=5:95 to 50:50, volume ratio), and the obtained solid was washed with diethyl ether to give the title compound (4.9 g, yield 14%) as a pale-yellow solid. The pale-yellow solid was recrystallized from ethyl acetate-hexane to give pale-yellow crystals.
melting point 148-149° C.

Reference Example 7

Ethyl 7-hydroxy-5-[4-(methylsulfonyl)phenoxy]-1H-indole-2-carboxylate

Ethyl 7-(benzyloxy)-5-[4-(methylsulfonyl)phenoxy]-1H-indole-2-carboxylate (0.40 g) was dissolved in a tetrahydrofuran (5 mL)-ethanol (5 mL) mixed solvent, 10% palladium-carbon (containing water (50%), 0.80 g) was added, and the mixture was stirred under a hydrogen atmosphere at room temperature for 4 hr. The reaction mixture was filtered, and the filtrate was concentrated under reduced pressure. The residue was crystallized from diethyl ether and the obtained solid was washed with a diethyl ether-hexane mixed solvent to give the title compound (0.31 g, yield 96%) as a pale-yellow solid. The pale-yellow solid was recrystallized from ethanol-hexane to give pale-yellow crystals.
melting point 197-198° C.

Reference Example 8

Ethyl 5-[4-(methylsulfonyl)phenoxy]-7-(tetrahydro-2H-pyran-4-yloxy)-1H-indole-2-carboxylate A mixture of ethyl 7-hydroxy-5-[4-(methylsulfonyl)phenoxy]-1H-indole-2-carboxylate (2.0 g), tetrahydro-2H-pyran-4-ol (2.02 mL), 1,1'-(azodicarbonyl)dipiperidine (5.3 g), tributylphosphine (5.3 mL), and tetrahydrofuran(60 mL) was stirred at 70° C. for 6 hr. To the reaction solution were added tetrahydro-2H-pyran-4-ol (1.02 mL), 1,1'-(azodicarbonyl)dipiperidine (2.5 g) and tributylphosphine (2.5 mL) and the mixture was stirred at 70° C. for 14 hr. The reaction solution was concentrated under reduced pressure to a half volume and the precipitated solid was filtered off. The filtrate was concentrated under reduced pressure, and the residue was subjected to silica gel column chromatography (volume ratio, ethyl acetate:hexane=5:95 to 50:50), and then basic silica gel column chromatography (volume ratio, methanol:ethyl acetate:hexane=0:2:98 to 20:80:0) to give the title compound (5.33 g) as a yellow oily crude product.
MS 460 (MH$^+$).

Reference Example 9

5-[4-(Methylsulfonyl)phenoxy]-7-(tetrahydro-2H-pyran-4-yloxy)-1H-indole-2-carboxylic acid A mixture of ethyl 5-{[5-(methylsulfonyl)pyridin-2-yl]oxy}-7-(tetrahydro-2H-pyran-4-yloxy)-1H-indole-2-carboxylate (5.33 g), 1M aqueous sodium hydroxide solution (20 mL), tetrahydrofuran (20 mL), and ethanol (20 mL) was stirred at 60° C. for 40 min. The reaction solution was concentrated under reduced pressure, and the residue was dissolved in water, and washed with ethyl acetate. To the aqueous layer was added 1M hydrochloric acid (30 mL), and the mixture was extracted with ethyl acetate. The organic layer was washed with saturated brine, dried over magnesium sulfate, filtered and concentrated under reduced pressure to give the title compound (1.95 g, yield 74%) as an orange amorphous solid.
MS 432 (MH$^+$).

Reference Example 10

5-[4-(Methylsulfonyl)phenoxy]-7-(tetrahydro-2H-pyran-4-yloxy)-1H-indole-2-carboxamide A mixture of 5-[4-(methylsulfonyl)phenoxy]-7-(tetrahydro-2H-pyran-4-yloxy)-1H-indole-2-carboxylic acid (1.95 g), 1-[3-(dimethylamino)propyl]-3-ethylcarbodiimide hydrochloride (1.73 g), 1-hydroxybenzotriazole ammonium salt (1.37 g), and N,N-dimethylformamide (50 mL) was stirred at room temperature for 12 hr. Water was added to the reaction solution, and the mixture was extracted with ethyl acetate. The organic layer was washed with saturated brine, dried over magnesium sulfate, filtered and concentrated under reduced pressure. The obtained crude product was subjected to silica gel column chromatography (methanol:ethyl acetate:hexane=0:85:15 to 10:90:0, volume ratio) to give the title compound (2.06 g, yield 100%) as a white solid.
MS 431 (MH$^+$).

Reference Example 11

2-(Methoxymethyl)-5-[4-nitro-3-(tetrahydro-2H-pyran-4-yloxy)phenoxy]pyridine

To a solution of 6-(bromomethyl)pyridin-3-yl benzenesulfonate (49.9 g) in methanol (800 mL) was added sodium methoxide (41.1 g) at 70° C., and the mixture was heated under reflux for 6 hr. The reaction mixture was cooled to room temperature, acidified with hydrogen chloride methanol solution (10%, 480 g), and the mixture was stirred at room temperature for 15 min. The reaction mixture was concentrated, toluene was added to the residue and the mixture was concentrated again. A mixture of the obtained residue, 4-(5-fluoro-2-nitrophenoxy)tetrahydro-2H-pyran (36.7 g), potassium carbonate (103.7 g) and N,N-dimethylformamide (500 mL) was stirred at 100° C. for 12 hr. The reaction mixture was concentrated, water was added to the residue, and the mixture was extracted with ethyl acetate. The organic layer was washed successively with water and saturated brine, dried over magnesium sulfate, filtered and concentrated under reduced pressure. The obtained crude product was subjected to silica gel column chromatography (hexane:ethyl acetate=2:1 to 1:4, volume ratio) to give the title compound (39.8 g, yield 73%) as a yellow oil.
MS 361 (MH$^+$).

Reference Example 12

4-{[6-(Methoxymethyl)pyridin-3-yl]oxy}-2-(tetrahydro-2H-pyran-4-yloxy)aniline

A mixture of 2-(methoxymethyl)-5-[4-nitro-3-(tetrahydro-2H-pyran-4-yloxy)phenoxy]pyridine (680 mg), iron powder (530 mg), calcium chloride (20 mg), water (3 mL), and ethanol (15 mL) was heated under reflux for 3 hr. The reaction solution was cooled to room temperature, filtered through celite, and the filtrate was concentrated. Water was added to the residue, and the mixture was extracted with ethyl acetate. The organic layer was washed with saturated brine, dried over magnesium sulfate, filtered and concentrated under reduced pressure. The obtained crude product was subjected to silica gel column chromatography (hexane:ethyl acetate=4:1 to 1:4, volume ratio) to give the title compound (480 mg, yield 76%) as a brown oil.
$^1$H NMR (CDCl$_3$) δ1.72-1.89 (2H, m), 1.94-2.13 (2H, m), 3.47 (3H, s), 3.56 (2H, ddd, J=11.74, 8.71, 3.03 Hz), 3.75 (2H, brs), 3.92-4.03 (2H, m), 4.42 (1H, tt, J=8.05, 3.88 Hz), 4.53 (2H, s), 6.47-6.54 (1H, m), 6.58 (1H, d, J=2.27 Hz), 6.71 (1H, d, J=8.33 Hz), 7.17-7.24 (1H, m), 7.29-7.34 (1H, m), 8.29 (1H, d, J=2.27 Hz).

Reference Example 13

Ethyl (2E)-2-{[4-{[6-(methoxymethyl)pyridin-3-yl]oxy}-2-(tetrahydro-2H-pyran-4-yloxy)phenyl]hydrazono}propanoate 4-{[6-(Methoxymethyl)pyridin-3-yl]oxy}-2-(tetrahydro-2H-pyran-4-yloxy)aniline (23.4 g) was dissolved in 2N hydrochloric acid (55 mL) and acetonitrile (30 mL), and aqueous solution (70 mL) of sodium nitrite (5.86 g) was added dropwise under ice-cooling. After the completion of the dropwise addition, the reaction mixture was stirred under ice-cooling for 30 min. The reaction mixture was added dropwise to a solution of ethyl 2-methylacetoacetate (10.72 g) and potassium hydroxide (11.2 g) in water (100 mL) and ethanol (100 mL) at −20° C. After stirring at −20° C. for 30 min, water was added to the reaction mixture, and the mixture was extracted with ethyl acetate. The organic layer was washed with saturated brine, dried over magnesium sulfate, filtered and concentrated under reduced pressure. The obtained crude product was subjected to silica gel column chromatography (ethyl acetate:hexane=0:100 to 100:0, volume ratio) to give the title compound (26 g, yield 83%) as a yellow oil.
MS 444 (MH$^+$).

Reference Example 14

Ethyl 5-{[6-(methoxymethyl)pyridin-3-yl]oxy}-7-(tetrahydro-2H-pyran-4-yloxy)-1H-indole-2-carboxylate p-Toluenesulfonic acid monohydrate (25.7 g) was heated under reflux in toluene (100 mL), and water was removed by azeotropic distillation with dehydration. The reaction mixture was cooled to 90° C., and a solution of ethyl (2E)-2-{[4-{[6-(methoxymethyl)pyridin-3-yl]oxy}-2-(tetrahydro-2H-pyran-4-yloxy)phenyl]hydrazono}propanoate (30 g) in toluene (50 mL) was added dropwise. The reaction mixture was stirred at 90° C. for 1 hr, and cooled to room temperature. To the reaction mixture was added saturated aqueous sodium hydrogen carbonate solution, and the mixture was extracted with ethyl acetate. The organic layer was washed with saturated brine, dried over magnesium sulfate, filtered and concentrated under reduced pressure. The obtained crude product was subjected to silica gel column chromatography (ethyl acetate:hexane=0:100 to 100:0, volume ratio), and further to basic silica gel column chromatography (ethyl acetate:hexane=0:100 to 50:50, volume ratio) to give the title compound (5.8 g, yield 20%) as a yellow amorphous solid.
MS 427 (MH$^+$).

Reference Example 15

5-{[6-(Methoxymethyl)pyridin-3-yl]oxy}-7-(tetrahydro-2H-pyran-4-yloxy)-1H-indole-2-carboxylic acid To a solution of ethyl 5-{[6-(methoxymethyl)pyridin-3-yl]oxy}-7-(tetrahydro-2H-pyran-4-yloxy)-1H-indole-2-carboxylate (5.8 g) in ethanol (100 mL) and tetrahydrofuran (100 mL) was added 1N aqueous sodium hydroxide solution (27 mL), and the mixture was stirred at room temperature for 15 hr. The reaction mixture was concentrated, 1N hydrochloric acid (27 mL) was added, and the mixture was extracted with ethyl acetate. The organic layer was washed with saturated brine, dried over magnesium sulfate, filtered and concentrated under reduced pressure. The obtained crude product was recrystallized from ethyl acetate-diethyl ether to give the title compound (3.2 g, yield 59%) as yellow crystals.
MS 399 (MH$^+$).

Reference Example 16

5-{[6-(Methoxymethyl)pyridin-3-yl]oxy}-7-(tetrahydro-2H-pyran-4-yloxy)-1H-indole-2-carboxamide To a solution of 5-{[6-(methoxymethyl)pyridin-3-yl]oxy}-7-(tetrahydro-2H-pyran-4-yloxy)-1H-indole-2-carboxylic acid (2.2 g) in N,N-dimethylformamide (20 mL) were added 1-hydroxybenzotriazole monohydrate (1.27 g), 1-ethyl-3-(3-dimethylaminopropyl)carbodiimide hydrochloride (1.6 g) and 25% aqueous ammonia (10 mL) and the mixture was stirred at room temperature for 1 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was crystallized from diethyl ether to give the title compound (2.99 g, yield 45%) as white crystals.
MS 398 (MH$^+$).

Reference Example 17

5-{[6-(Methoxymethyl)pyridin-3-yl]oxy}-7-(tetrahydro-2H-pyran-4-yloxy)-1H-indole-2-carbothioamide To a solution of 5-{[6-(methoxymethyl)pyridin-3-yl]oxy}-7-(tetrahydro-2H-pyran-4-yloxy)-1H-indole-2-carboxamide (1.45 g) in tetrahydrofuran (20 mL) was added a Lawesson's reagent (1.6 g), and the mixture was stirred with heating under reflux for 1 hr. The reaction mixture was cooled, and concentrated under reduced pressure. The obtained crude product was subjected to silica gel column chromatography (ethyl acetate:hexane=0:100 to 100:0, volume ratio) to give the title compound (1.5 g, yield 99%) as a yellow amorphous solid.

MS 414 (MH$^+$).

Reference Example 18

2-Fluoro-4-(methoxymethoxy)-1-nitrobenzene

To a solution of 3-fluoro-4-nitrophenol (120 g) in N,N-dimethylformamide (500 mL) was added sodium hydride (oily, 60%) (22 g) under ice-cooling, and the mixture was stirred for 30 min. To the reaction solution was added chloromethyl methyl ether (64 mL) and the mixture was stirred for 1 hr. Water was added to the reaction mixture, and the mixture was extracted with ethyl acetate. The organic layer was washed with saturated brine, dried over magnesium sulfate, filtered and concentrated under reduced pressure. The obtained crude product was subjected to basic column chromatography (ethyl acetate) to give the title compound (98 g, yield 64%) as a yellow oil.

$^1$H NMR (CDCl$_3$) δ3.49 (3H, s), 5.24 (2H, s), 6.91-6.95 (2H, m), 8.10 (1H, d, J=8.3 Hz).

Reference Example 19

4-Nitro-3-(tetrahydro-2H-pyran-4-yloxy)phenol

To a solution of tetrahydro-2H-pyran-4-ol (54.7 g) in N,N-dimethylformamide (500 mL) was added under ice-cooling sodium hydride (oily, 60%) (14 g), and the mixture was stirred for 30 min. To the reaction solution was added 2-fluoro-4-(methoxymethoxy)-1-nitrobenzene (98 g) and the mixture was stirred at 120° C. for 4 hr. The reaction mixture was cooled to room temperature, water was added, and the mixture was extracted with ethyl acetate. The organic layer was washed with saturated brine, dried over magnesium sulfate, filtered and concentrated under reduced pressure. The obtained crude product was dissolved in tetrahydrofuran (300 mL), 1N hydrochloric acid (500 mL) was added and the mixture was stirred at room temperature for 2 hr. Water was added to the reaction mixture, and the mixture was extracted with ethyl acetate. The organic layer was washed with saturated brine, dried over magnesium sulfate, filtered and concentrated under reduced pressure. The obtained crude product was subjected to column chromatography (ethyl acetate:hexane=0:100 to 50:50, volume ratio) to give the title compound (27 g, yield 23%) as pale-yellow crystals.

$^1$H NMR (CDCl$_3$) δ1.80-1.96 (2H, m), 1.99-2.11 (2H, m), 3.60-3.71 (2H, m), 4.01 (2H, ddd, J=11.5, 8.0, 3.5 Hz), 4.58-4.71 (1H, m), 5.97 (1H, brs.), 6.43 (1H, dd, J=9.0, 2.4 Hz), 6.51 (1H, d, J=2.3 Hz), 7.92 (1H, d, J=9.0 Hz).

Reference Example 20

5-(Methylsulfonyl)-2-[4-nitro-3-(tetrahydro-2H-pyran-4-yloxy)phenoxy]pyridine

A mixture of 4-nitro-3-(tetrahydro-2H-pyran-4-yloxy)phenol (23.0 g), 2-bromo-5-(methylsulfonyl)pyridine (22.7 g), cesium carbonate (62.6 g), and N,N-dimethylformamide (200 mL) was stirred at 100° C. for 1.5 hr. The reaction solution was concentrated under reduced pressure, water was added to the residue, and the mixture was extracted with ethyl acetate-tetrahydrofuran. The organic layer was washed with saturated brine, dried over magnesium sulfate, filtered and concentrated under reduced pressure. The obtained solid was washed with diethyl ether-hexane to give the title compound (30.0 g, yield 81%) as a brown solid.

$^1$H NMR (CDCl$_3$) δ1.82-1.97 (2H, m), 1.97-2.12 (2H, m), 3.11 (3H, s), 3.56-3.71 (2H, m), 3.99 (2H, ddd, J=11.5, 7.9 3.4 Hz), 4.59-4.72 (1H, m), 6.82 (1H, dd, J=9.0, 2.4 Hz), 6.90 (1H, d, J=2.3 Hz), 7.17 (1H, d, J=8.1 Hz), 7.98 (1H, d, J=8.9 Hz), 8.26 (1H, dd, J=8.7, 2.5 Hz), 8.71 (1H, d, J=1.9 Hz).

Reference Example 21

4-{([5-(Methylsulfonyl)pyridin-2-yl]oxy}-2-(tetrahydro-2H-pyran-4-yloxy)aniline

A mixture of 5-(methylsulfonyl)-2-[4-nitro-3-(tetrahydro-2H-pyran-4-yloxy)phenoxy]pyridine (30.0 g), iron powder (21.0 g), calcium chloride (0.8 g), water (75 mL), and ethanol (300 mL) was stirred at 80° C. for 4 hr. The reaction solution was filtered through celite, and the filtrate was concentrated. Water was added to the residue, and the mixture was extracted with ethyl acetate. The organic layer was dried over magnesium sulfate, filtered and concentrated under reduced pressure. The residue was solidified with tetrahydrofuran-diethyl ether. The obtained solid was washed with ethyl acetate-diethyl ether to give the title compound (24.9 g, yield 90%) as a brown solid.

MS 365(MH$^+$).

Reference Example 22

Ethyl (2E)-2-{[4-{[5-(methylsulfonyl)pyridin-2-yl]oxy}-2-(tetrahydro-2H-pyran-4-yloxy)phenyl]hydrazono}propanoate 4-{[5-(Methylsulfonyl)pyridin-2-yl]oxy}-2-(tetrahydro-2H-pyran-4-yloxy)aniline (25.7 g) was suspended in a mixed solvent of acetonitrile (50 mL)-ethanol (100 mL), and concentrated hydrochloric acid (21 mL) was added at 10° C. To a mixture was added dropwise sodium nitrite (5.8 g) dissolved in water (15 mL) at −5° C., and the mixture was stirred at −10° C. to −5° C. for 1 hr. The mixture was added to a mixture of ethyl 2-methyl-3-oxobutanoate (11.2 mL), potassium hydroxide (85%, 8.6 g), water (70 mL), and ethanol (100 mL) at −40 to −30° C. and the mixture was stirred at −28° C. for 30 min. To the reaction solution was added 1M hydrochloric acid (110 mL), and the mixture was extracted with ethyl acetate. The organic layer was washed with saturated brine, dried over magnesium sulfate, filtered and concentrated under reduced pressure. The obtained crude product was subjected to silica gel column chromatography (ethyl acetate:hexane=30:70 to 100:0, volume ratio) to give the title compound (25.8 g, yield 77%) as a yellow amorphous solid.

$^1$H NMR (CDCl$_3$) δ1.38 (3H, t, J=6.8 Hz), 1.74-1.92 (2H, m), 2.00-2.17 (5H, m), 3.09 (3H, s), 3.60 (2H, ddd, J=11.6, 8.4, 3.0 Hz), 3.89-4.02 (2H, m), 4.33 (2H, q, J=7.1 Hz), 4.52 (1H, tt, J=8.0, 7.8 Hz), 6.71 (1H, d, J=2.3 Hz), 6.78 (1H, dd, J=8.7, 2.3 Hz), 7.02 (1H, d, J=8.7 Hz), 7.64 (1H, d, J=8.7 Hz), 8.11 (1H, s), 8.16 (1H, dd, J=8.7, 2.7 Hz), 8.71 (1H, d, J=2.7 Hz).

Reference Example 23

Ethyl 5-{[5-(methylsulfonyl)pyridin-2-yl]oxy}-7-(tetrahydro-2H-pyran-4-yloxy)-1H-indole-2-carboxylate p-Toluenesulfonic acid monohydrate (25.7 g) was refluxed in a toluene (100 mL) solvent for 2 hr, and water was removed by azeotropic distillation with dehydration. This solution was cooled to 90° C., ethyl (2E)-2-{[4-{[5-(methylsulfonyl)pyridin-2-yl]oxy}-2-(tetrahydro-2H-pyran-4-yloxy)phenyl]hydrazono}propanoate (25.8 g) dissolved toluene (100 mL) was added, and the mixture was stirred at 90° C. for 4 hr.

The reaction solution was cooled to room temperature, an aqueous sodium hydrogen carbonate solution was added, and the mixture was extracted with ethyl acetate. The organic layer was washed with saturated brine, dried over magnesium sulfate, filtered and concentrated under reduced pressure. The obtained crude product was subjected to basic silica gel column chromatography (ethyl acetate:hexane=10:90 to 65:35, volume ratio) to give a yellow amorphous solid, which was solidified with ethyl acetate-hexane. The obtained solid was washed with hexane to give the title compound (4.1 g, yield 16%) as a pale-yellow solid.

MS 461 (MH$^+$).

Reference Example 24

5-{[5-(Methylsulfonyl)pyridin-2-yl]oxy}-7-(tetrahydro-2H-pyran-4-yloxy)-1H-indole-2-carboxylic acid A mixture of ethyl 5-{[5-(methylsulfonyl)pyridin-2-yl]oxy}-7-(tetrahydro-2H-pyran-4-yloxy)-1H-indole-2-carboxylate (4.0 g), 1M aqueous sodium hydroxide solution (13 mL), tetrahydrofuran (20 mL), and ethanol (20 mL) was stirred at 50° C. for 50 min. The reaction solution was concentrated under reduced pressure, and the residue was dissolved in water. 1M Hydrochloric acid (13.2 mL) was added and the precipitated yellow solid was collected by filtration. The obtained solid was washed with water and diethyl ether to give the title compound (4.1 g, yield 100%) as a yellow solid.

MS 433 (MH$^+$).

Reference Example 25

5-{[5-(methylsulfonyl)pyridin-2-yl]oxy}-7-(tetrahydro-2H-pyran-4-yloxy)-1H-indole-2-carboxamide A mixture of 5-{[5-(methylsulfonyl)pyridin-2-yl]oxy}-7-(tetrahydro-2H-pyran-4-yloxy)-1H-indole-2-carboxylic acid (2.5 g), 1-[3-(dimethylamino)propyl]-3-ethylcarbodiimide hydrochloride (2.2 g), 1-hydroxybenzotriazole (1.6 g), and N,N-dimethylformamide (25 mL) was stirred at 50° C. for 30 min. The reaction mixture was cooled to room temperature, 10% aqueous ammonia (4 mL) was added and the mixture was stirred at room temperature for 1.5 hr. The reaction solution was concentrated under reduced pressure, water was added to the residue, and ethyl acetate-tetrahydrofuran was added. The precipitated solid was collected by filtration to give the title compound (0.69 g) as a pale-yellow solid. The filtrate was concentrated under reduced pressure to evaporate the organic solvent. The precipitate was collected by filtration to give the title compound (0.72 g) as a pale-yellow solid (total yield 1.41 g, 64%).

MS 432 (MH$^+$).

Reference Example 26

2-[(2-Methoxyethoxy)methyl]-5-[4-nitro-3-(tetrahydro-2H-pyran-4-yloxy)phenoxy]pyridine To a solution of 6-(bromomethyl)pyridin-3-yl benzenesulfononate (2.0 g) in 2-methoxyethanol (50 mL) was added sodium hydride (60% in oil, 1.22 g) at 0° C., and the mixture was stirred at 80° C. for 15 hr, and then at room temperature for 24 hr. The reaction mixture was cooled to 0° C., 2 M hydrogen chloride ethanol solution (24.4 mL) was added, and the mixture was stirred at 0° C. for 10 min. The reaction mixture was concentrated, toluene was added to the residue and the mixture was concentrated again. A mixture of the obtained residue, 4-(5-fluoro-2-nitrophenoxy)tetrahydro-2H-pyran (1.47 g), potassium carbonate (4.21 g) and N,N-dimethylformamide (30 mL) was stirred at 90° C. for 20 hr. To the reaction mixture was added water, and the mixture was extracted with ethyl acetate. The organic layer was washed successively with water and saturated brine, dried over magnesium sulfate, filtered and concentrated under reduced pressure. The obtained crude product was subjected to silica gel column chromatography (hexane:ethyl acetate=3:2 to 1:4, volume ratio) to give the title compound (2.02 g, yield 82%) as a pale-yellow oil.

MS 405 (MH$^+$).

Reference Example 27

4-({6-[(2-Methoxyethoxy)methyl]pyridin-3-yl}oxy)-2-(tetrahydro-2H-pyran-4-yloxy)aniline To a solution of 2-[(2-methoxyethoxy)methyl]-5-[4-nitro-3-(tetrahydro-2H-pyran-4-yloxy)phenoxy]pyridine (11.5 g) in ethanol (100 mL) and water (25 mL) were added iron powder (8 g) and calcium chloride (0.3 g), and the mixture was stirred with heating under reflux for 4 hr. The reaction mixture was cooled, and insoluble material was filtered off through celite. Water was added to the filtrate, and the mixture was extracted with ethyl acetate. The organic layer was washed with saturated brine, dried over magnesium sulfate, filtered and concentrated under reduced pressure. The obtained crude product was subjected to silica gel column chromatography (ethyl acetate:hexane=0:100 to 50:50, volume ratio) to give the title compound (7.84 g, yield 74%) as an orange oil.

MS 375 (MH$^+$).

Reference Example 28

Ethyl (2E)-2-{[4-({6-[(2-methoxyethoxy)methyl]pyridin-3-yl}oxy)-2-(tetrahydro-2H-pyran-4-yloxy)phenyl]hydrazono}propanoate 4-({6-[(2-Methoxyethoxy)methyl]pyridin-3-yl}oxy)-2-(tetrahydro-2H-pyran-4-yloxy)aniline (7.84 g) was dissolved in 2N hydrochloric acid (20 mL) and acetonitrile (15 mL), and aqueous solution (20 mL) of sodium nitrite (1.73 g) was added dropwise under ice-cooling. After the completion of the dropwise addition, the reaction mixture was stirred under ice-cooling for 30 min. The reaction mixture was added dropwise to a solution of ethyl 2-methylacetoacetate (3.17 g) and potassium hydroxide (3.3 g) in water (70 mL) and ethanol (70 mL) at −20° C. After stirring at −20° C. for 30 min, water was added to the reaction mixture, and the mixture was extracted with ethyl acetate. The organic layer was washed with saturated brine, dried over magnesium sulfate, filtered and concentrated under reduced pressure. The obtained crude product was subjected to silica gel column chromatography (ethyl acetate:hexane=0:100 to 85:15, volume ratio) to give the title compound (6.0 g, yield 59%) as a yellow oil.

MS 488 (MH$^+$).

Reference Example 29

Ethyl 5-({6-[(2-methoxyethoxy)methyl]pyridin-3-yl}oxy)-7-(tetrahydro-2H-pyran-4-yloxy)-1H-indole-2-carboxylate p-Toluenesulfonic acid monohydrate (4.68 g) was heated under reflux in toluene (50 mL), and water was removed by azeotropic distillation with dehydration. The reaction mixture was cooled to 90° C., and a solution of ethyl (2E)-2-{([4-({6-[(2-methoxyethoxy)methyl]pyridin-3-yl}oxy)-2-(tetrahydro-2H-pyran-4-yloxy)phenyl]hydrazono}propanoate (6.0 g) in toluene (10 mL) was added dropwise. The reaction mixture was stirred at 90° C. for 1 hr, and cooled to room temperature. To the reaction mixture was added saturated aqueous sodium hydrogen carbonate solution, and the mixture was extracted with ethyl acetate. The organic layer was washed with saturated brine, dried over magnesium sulfate, filtered and concentrated under reduced pressure. The obtained crude product was subjected to silica gel column chromatography (ethyl acetate:hexane=0:100 to 50:50, volume ratio) to give the title compound (1.88 g, yield 32%) as a brown oil.

MS 471 (MH$^+$).

Reference Example 30

5-({6-[(2-Methoxyethoxy)methyl]pyridin-3-yl}oxy)-7-(tetrahydro-2H-pyran-4-yloxy)-1H-indole-2-carboxamide To a solution of ethyl 5-({6-[(2-methoxyethoxy)methyl]pyridin-3-yl}oxy)-7-(tetrahydro-2H-pyran-4-yloxy)-1H-indole-2-carboxylate (1.88 g) in ethanol (50 mL) and tetrahydrofuran (50 mL) was added 1N aqueous sodium hydroxide solution (5 mL), and the mixture was stirred at room temperature for 15 hr. To the reaction mixture was added 1N hydrochloric acid (5 mL) and the mixture was concentrated. To a solution of the residue in N,N-dimethylformamide (20 mL) were added 1-hydroxybenzotriazole monohydrate (1.22 g), 1-ethyl-3-(3-dimethylaminopropyl)carbodiimide hydrochloride (1.53 g), and 25% aqueous ammonia (5 mL), and the mixture was stirred at room temperature for 1 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure to give the title compound (1.1 g, yield 47%) as a yellow amorphous solid.

MS 442 (MH$^+$).

Reference Example 31

5-{[6-[(2-Methoxyethoxy)methyl]pyridin-3-yl}oxy)-7-(tetrahydro-2H-pyran-4-yloxy)-1H-indole-2-carbothioamide To a solution of 5-({6-[(2-methoxyethoxy)methyl]pyridin-3-yl}oxy)-7-(tetrahydro-2H-pyran-4-yloxy)-1H-indole-2-carboxamide (1.1 g) in tetrahydrofuran (20 mL) was added a Lawesson's reagent (1.1 g), and the mixture was stirred with heating under reflux for 1 hr. The reaction mixture was cooled, and concentrated under reduced pressure. The obtained crude product was subjected to silica gel column chromatography (ethyl acetate:hexane=0:100 to 100:0, volume ratio) to give the title compound (1.1 g, yield 96%) as a yellow amorphous solid.

MS 458 (MH$^+$).

Reference Example 32

6-[(Methylsulfonyl)methyl]pyridin-3-yl benzenesulfonate

To a solution of 6-(bromomethyl)pyridin-3-yl benzenesulfonate (30 g) in N,N-dimethylformamide (200 mL) was added sodium methylsulfinate (11.2 g), and the mixture was stirred at room temperature for 15 hr. Water was added to the reaction mixture, and the mixture was extracted with ethyl acetate. The organic layer was washed with saturated brine, dried over magnesium sulfate, filtered and concentrated under reduced pressure to give the title compound (30 g, yield 100%) as white crystals.

MS 328 (MH$^+$).

Reference Example 33

6-[(Methylsulfonyl)methyl]pyridin-3-ol

To a solution of 6-[(methylsulfonyl)methyl]pyridin-3-yl benzenesulfonate (30 g) in ethanol (200 mL) and tetrahydrofuran (200 mL) was added 1N aqueous sodium hydroxide solution (190 mL), and the mixture was stirred at 80° C. for 3 hr. The reaction mixture was concentrated, 1N hydrochloric acid (190 mL) was added, and the mixture was extracted with ethyl acetate. The organic layer was washed with saturated brine, dried over magnesium sulfate, filtered and concentrated under reduced pressure to give the title compound (13.9 g, yield 79%) as white crystals.

MS 188 (MH$^+$).

Reference Example 34

2-[(Methylsulfonyl)methyl]-5-[4-nitro-3-(tetrahydro-2H-pyran-4-yloxy)phenoxy]pyridine To a solution of 4-(5-fluoro-2-nitrophenoxy)tetrahydro-2H-pyran (13.6 g) and 6-[(methylsulfonyl)methyl]pyridin-3-ol (13.9 g) in N,N-dimethylformamide (300 mL) was added potassium carbonate (39 g), and the mixture was stirred at 110° C. for 2 hr. Water was added to the reaction solution, and the mixture was extracted with ethyl acetate. The organic layer was washed with saturated brine, dried over magnesium sulfate, filtered and concentrated under reduced pressure. The obtained crude product was subjected to silica gel column chromatography (ethyl acetate:hexane=0:100 to 50:50, volume ratio) to give the title compound (23 g, yield 95%) as a yellow solid.

MS 409 (MH$^+$).

Reference Example 35

4-({6-[(Methylsulfonyl)methyl]pyridin-3-yl}oxy)-2-(tetrahydro-2H-pyran-4-yloxy)aniline To a solution of 2-[(methylsulfonyl)methyl]-5-[4-nitro-3-(tetrahydro-2H-pyran-4-yloxy)phenoxy]pyridine (22 g) in ethanol (250 mL) was added 10% palladium carbon (2 g), and the mixture was stirred under a hydrogen atmosphere at room temperature for 15 hr. Palladium carbon was removed, and the residue was concentrated under reduced pressure to give the title compound (20 g, yield 100%) as a colorless amorphous solid.
MS 379 (MH$^+$).

Reference Example 36

Ethyl (2E)-2-{[4-({6-[(methylsulfonyl)methyl]pyridin-3-yl}oxy)-2-(tetrahydro-2H-pyran-4-yloxy)phenyl]hydrazono}propanoate 4-({6-[(Methylsulfonyl)methyl]pyridin-3-yl}oxy)-2-(tetrahydro-2H-pyran-4-yloxy)aniline (21 g) was dissolved in 2N hydrochloric acid (55 mL) and acetonitrile (20 mL), and aqueous solution (50 mL) of sodium nitrite (4.59 g) was added dropwise under ice-cooling. After the completion of the dropwise addition, the reaction mixture was stirred under ice-cooling for 30 min. The reaction mixture was added dropwise to a solution of ethyl 2-methylacetoacetate (8.4 g) and potassium hydroxide (8.8 g) in water (100 mL) and ethanol (100 mL) at −20° C. After stirring at −20° C. for 30 min, water was added to the reaction mixture, and the mixture was extracted with ethyl acetate. The organic layer was washed with saturated brine, dried over magnesium sulfate, filtered and concentrated under reduced pressure. The obtained crude product was subjected to silica gel column chromatography (ethyl acetate:hexane=0:100 to 85:15, volume ratio) to give the title compound (27 g, yield 99%) as a yellow amorphous solid.
MS 492 (MH$^+$).

Reference Example 37

Ethyl 5-({6-[(methylsulfonyl)methyl]pyridin-3-yl}oxy)-7-(tetrahydro-2H-pyran-4-yloxy)-1H-indole-2-carboxylate p-Toluenesulfonic acid monohydrate (20.9 g) was heated under reflux in toluene (100 mL), water was removed by azeotropic distillation with dehydration. The reaction mixture was cooled to 90° C., a solution of ethyl (2E)-2-{[4-({6-[(methylsulfonyl)methyl]pyridin-3-yl}oxy)-2-(tetrahydro-2H-pyran-4-yloxy)phenyl]hydrazono}propanoate (27 g) in toluene (50 mL) was added dropwise. The reaction mixture was stirred at 90° C. for 1 hr, and cooled to room temperature. To the reaction mixture was added saturated aqueous sodium hydrogen carbonate solution, and the mixture was extracted with ethyl acetate. The organic layer was washed with saturated brine, dried over magnesium sulfate, filtered and concentrated under reduced pressure. The obtained crude product was subjected to basic silica gel column chromatography (ethyl acetate:hexane=0:100 to 50:50, volume ratio), and further basic silica gel column chromatography (ethyl acetate:hexane=0:100 to 50:50, volume ratio) to give the title compound (5.2 g, yield 20%) as a brown oil.
MS 475 (MH$^+$).

Reference Example 38

5-{[6-(Methylsulfonylmethyl)pyridin-3-yl]oxy}-7-(tetrahydro-2H-pyran-4-yloxy)-1H-indole-2-carboxylic acid To a solution of ethyl 5-({6-[(methylsulfonyl)methyl]pyridin-3-yl}oxy)-7-(tetrahydro-2H-pyran-4-yloxy)-1H-indole-2-carboxylate_(5.2 g) in ethanol (100 mL) and tetrahydrofuran (100 mL) was added 1N aqueous sodium hydroxide solution (30 mL), and the mixture was stirred at room temperature for 3 hr. The reaction mixture was concentrated, 1N hydrochloric acid (30 mL) was added, and the mixture was extracted with ethyl acetate. The organic layer was washed with saturated brine, dried over magnesium sulfate, filtered and concentrated under reduced pressure to give the title compound (4.9 g, yield 100%) as a yellow oil.
MS 447 (MH$^+$).

Reference Example 39

5-({6-[(Methylsulfonyl)methyl]pyridin-3-yl}oxy)-7-(tetrahydro-2H-pyran-4-yloxy)-1H-indole-2-carboxamide To a solution of 5-{[6-(methylsulfonylmethyl)pyridin-3-yl]oxy}-7-(tetrahydro-2H-pyran-4-yloxy)-1H-indole-2-carboxylic acid (4.9 g) in N,N-dimethylformamide (20 mL) were added 1-hydroxybenzotriazole monohydrate (2.68 g), 1-ethyl-3-(3-dimethylaminopropyl)carbodiimide hydrochloride (3.3 g), and 25% aqueous ammonia (15 mL), and the mixture was stirred at room temperature for 2 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio) to give the title compound (3.0 g, yield 58%) as pale-yellow crystals.
MS 446 (MH$^+$).

Reference Example 40

5-({6-[(Methylsulfonyl)methyl]pyridin-3-yl}oxy)-7-(tetrahydro-2H-pyran-4-yloxy)-1H-indole-2-carbothioamide To a solution of 5-({6-[(methylsulfonyl)methyl]pyridin-3-yl}oxy)-7-(tetrahydro-2H-pyran-4-yloxy)-1H-indole-2-carboxamide (3.0 g) in tetrahydrofuran (20 mL) was added a Lawesson's reagent (3.0 g), and the mixture was stirred with heating under reflux for 1 hr. The reaction mixture was cooled, and concentrated under reduced pressure. The obtained crude product was subjected to silica gel column chromatography (ethyl acetate:hexane=0:100 to 100:0, volume ratio) to give the title compound (2.26 g, yield 73%) as a yellow amorphous solid.
MS 462 (MH$^+$).

Reference Example 41

4-(5-Fluoro-2-nitrophenoxy)tetrahydro-2H-pyran

A mixture of 5-fluoro-2-nitrophenol (100 g), tetrahydro-2H-pyran-4-yl methanesulfonate (172 g) and potassium carbonate (176 g) in N,N-dimethylformamide (1000 mL) was stirred at 50° C. for 3 days. Water was added to the reaction solution, and the mixture was extracted with ethyl acetate. The organic layer was washed with saturated brine, dried over magnesium sulfate, filtered and concentrated under reduced pressure. The obtained crude product was subjected to silica gel column chromatography (ethyl acetate:hexane=0:100 to 25:75, volume ratio) to give the title compound (138 g, yield 90%) as a yellow solid.
MS 242 (MH$^+$).

Reference Example 42

2-(Methylsulfonyl)-5-[4-nitro-3-(tetrahydro-2H-pyran-4-yloxy)phenoxy]pyridine

To a solution of 4-(5-fluoro-2-nitrophenoxy)tetrahydro-2H-pyran (19.5 g) and 6-(methylsulfonyl)pyridin-3-ol (14 g) in N,N-dimethylformamide (250 mL) was added potassium carbonate (22.3 g), and the mixture was stirred at 110° C. for 4 hr. 1N HCl was added to the reaction solution, and the mixture was extracted with ethyl acetate. The organic layer was washed with saturated brine, dried over magnesium sulfate, filtered and concentrated under reduced pressure. The obtained crude product was subjected to silica gel column chromatography (ethyl acetate:hexane=0:100 to 50:50, volume ratio) to give the title compound (26.4 g, yield 83%) as a yellow solid.
MS 395 (MH+).

Reference Example 43

4-{[6-(Methylsulfonyl)pyridin-3-yl]oxy}-2-(tetrahydro-2H-pyran-4-yloxy)aniline

To a solution of 2-(methylsulfonyl)-5-[4-nitro-3-(tetrahydro-2H-pyran-4-yloxy)phenoxy]pyridine (25.8 g) in ethanol (250 mL) and tetrahydrofuran (250 mL) was added 10% palladium carbon (3 g), and the mixture was stirred under hydrogen pressure of 0.5 MPa at 50° C. for 6 hr. Palladium carbon was removed, and the mixture was concentrated under reduced pressure to give the title compound (24 g, yield 100%) as a white powder.
MS 365 (MH+).

Reference Example 44

Ethyl 2-{[4-{[6-(methylsulfonyl)pyridin-3-yl]oxy}-2-(tetrahydro-2H-pyran-4-yloxy)phenyl]hydrazono}propanoate (E,Z mixture)

4-{[6-(Methylsulfonyl)pyridin-3-yl]oxy}-2-(tetrahydro-2H-pyran-4-yloxy)aniline (20 g) was dissolved in 2N hydrochloric acid (55 mL) and acetonitrile (30 mL), and aqueous solution (50 mL) of sodium nitrite (4.54 g) was added dropwise at −10° C. After the completion of the dropwise addition, the reaction mixture was stirred at −10° C. for 30 min, and the reaction solution was filtered through celite. The filtrate was added dropwise to a solution of ethyl 2-methylacetoacetate (8.31 g) and potassium hydroxide (8.7 g) in water (100 mL) and ethanol (100 mL) at −20° C. After stirring at −20° C. for 30 min, the mixture was neutralized with 6N hydrochloric acid and extracted with ethyl acetate. The organic layer was washed with saturated brine, dried over magnesium sulfate, filtered and concentrated under reduced pressure. The obtained crude product was subjected to silica gel column chromatography (ethyl acetate:hexane=0:100 to 50:50, volume ratio) to give the title compound (26 g, yield 99%) as a yellow oil.
MS 476 (M-H)−.

Reference Example 45

Ethyl 5-{[6-(methylsulfonyl)pyridin-3-yl]oxy}-7-(tetrahydro-2H-pyran-4-yloxy)-1H-indole-2-carboxylate p-Toluenesulfonic acid monohydrate (20.7 g) was heated under reflux in toluene (100 mL) for 2 hr, and water was removed by azeotropic distillation with dehydration. The reaction mixture was cooled to 90° C., and a solution of ethyl 2-{[4-[([6-(methylsulfonyl)pyridin-3-yl]oxy}-2-(tetrahydro-2H-pyran-4-yloxy)phenyl]hydrazono}propanoate (E,Z mixture) (26 g) in toluene (50 mL) was added dropwise. The reaction mixture was stirred at 90° C. for 1 hr, and cooled to room temperature. To the reaction mixture was added water, and the mixture was extracted with ethyl acetate. The organic layer was washed with saturated brine, dried over magnesium sulfate, filtered and concentrated under reduced pressure. The obtained crude product was subjected to silica gel column chromatography (ethyl acetate:hexane=50:50 to 100:0, volume ratio), and further basic silica gel column chromatography (ethyl acetate:hexane=0:100 to 50:50, volume ratio) to give the title compound (7.3 g, yield 29%) as a yellow amorphous solid.
MS 461 (MH+).

Reference Example 46

5-{[6-(Methylsulfonyl)pyridin-3-yl]oxy}-7-(tetrahydro-2H-pyran-4-yloxy)-1H-indole-2-carboxylic acid To a solution of ethyl 5-{[6-(methylsulfonyl)pyridin-3-yl]oxy}-7-(tetrahydro-2H-pyran-4-yloxy)-1H-indole-2-carboxylate (7.3 g) in ethanol (100 mL) and tetrahydrofuran (100 mL) was added 1N aqueous sodium hydroxide solution (32 mL), and the mixture was stirred at room temperature for 15 hr. To the reaction mixture, 1N hydrochloric acid (32 mL) was added, and the mixture was extracted with ethyl acetate. The organic layer was washed with saturated brine, dried over magnesium sulfate, filtered and concentrated under reduced pressure. The obtained crude product was crystallized from ethyl acetate-diethyl ether to give the title compound (5.9 g, yield 86%) as yellow powder.
MS 433 (MH+).

Reference Example 47

5-{[6-(Methylsulfonyl)pyridin-3-yl]oxy}-7-(tetrahydro-2H-pyran-4-yloxy)-1H-indole-2-carboxamide To a solution of 5-{[6-(methylsulfonyl)pyridin-3-yl]oxy}-7-(tetrahydro-2H-pyran-4-yloxy)-1H-indole-2-carboxylic acid (3 g) in N,N-dimethylformamide (20 mL) were added 1-hydroxybenzotriazole monohydrate (1.6 g), 1-ethyl-3-(3-dimethylaminopropyl)carbodiimide hydrochloride (2 g), and 10% aqueous ammonia (27 mL), and the mixture was stirred at room temperature for 1 hr. 1N HCl was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was crystallized from diethyl ether to give the title compound (1.35 g, yield 45%) as yellow powder.
MS 432 (MH+).

Reference Example 48

5-{[6-(Methylsulfonyl)pyridin-3-yl]oxy}-7-(tetrahydro-2H-pyran-4-yloxy)-1H-indole-2-carbothioamide To a solution of 5-{[6-(methylsulfonyl)pyridin-3-yl]oxy}-7-(tetrahydro-2H-pyran-4-yloxy)-1H-indole-2-carboxamide (1.35 g) in tetrahydrofuran (20 mL) was added a Lawesson's reagent (1.4 g), and the mixture was stirred with heating under reflux for 1 hr. The reaction mixture was cooled, and concentrated under reduced pressure. The obtained crude product was subjected to silica gel column chromatography (ethyl acetate:hexane=0:100 to 100:0, volume ratio) to give the title compound (1.4 g, yield 100%) as a yellow amorphous solid.
MS 448 (MH$^+$).

Reference Example 49

2-(Methylsulfonyl)-5-(4-nitrophenoxy)pyridine

To a solution of 4-fluoronitrobenzene (4.74 g) and 6-(methylsulfonyl)pyridin-3-ol (6.4 g) in N,N-dimethylformamide (50 mL) was added potassium carbonate (9.3 g), and the mixture was stirred at 100° C. for 3 hr. Water was added to the reaction solution, and the mixture was extracted with ethyl acetate. The organic layer was washed with saturated brine, dried over magnesium sulfate, filtered and concentrated under reduced pressure. The obtained crude product was crystallized from diethyl ether to give the title compound (9.88 g, yield 100%) as a yellow solid.
$^1$H NMR (DMSO-d$_6$) δ3.30 (3H, s), 7.38-7.41 (2H, m), 7.89 (1H, dd, J=8.7, 3.0 Hz), 8.13 (1H, d, J=8.7 Hz), 8.30-8.35 (2H, m), 8.72 (1H, d, J=2.7 Hz).

Reference Example 50

4-{[6-(Methylsulfonyl)pyridin-3-yl]oxy}aniline

To a solution of 2-(methylsulfonyl)-5-(4-nitrophenoxy)pyridine (9.88 g) in ethanol (150 mL) and tetrahydrofuran (150 mL) was added 10% palladium carbon (1 g), and the mixture was stirred under a hydrogen atmosphere for 15 hr. Palladium carbon was removed, and the residue was concentrated under reduced pressure to give the title compound (8.9 g, yield 100%) as a pale-yellow oil.
MS 265 (MH$^+$).

Reference Example 51

Ethyl(2E)-2-[(4-{[6-(methylsulfonyl)pyridin-3-yl]oxy}phenyl)hydrazono]propanoate 4-{[6-(Methylsulfonyl)pyridin-3-yl]oxy}aniline (8.9 g) was dissolved in 2N hydrochloric acid (35 mL) and acetonitrile (15 mL), and aqueous solution (10 mL) of sodium nitrite (2.79 g) was added dropwise under ice-cooling. After the completion of the dropwise addition, the reaction mixture was stirred under ice-cooling for 30 min, and the reaction solution was filtered through celite. The filtrate was added dropwise to a solution of ethyl 2-methylacetoacetate (5.1 g) and potassium hydroxide (5.3 g) in water (50 mL) and ethanol (100 mL) at −20° C. After stirring at −20° C. for 30 min, water was added to the reaction mixture, and the mixture was extracted with ethyl acetate. The organic layer was washed with saturated brine, dried over magnesium sulfate, filtered and concentrated under reduced pressure. The obtained crude product was subjected to basic silica gel column chromatography (ethyl acetate:hexane=0:100 to 50:50, volume ratio) to give the title compound (11.8 g, yield 93%) as a yellow amorphous solid.
MS 378 (MH$^+$).

Reference Example 52

Ethyl 5-{[6-(methylsulfonyl)pyridin-3-yl]oxy}-1H-indole-2-carboxylate p-Toluenesulfonic acid monohydrate (11.9 g) was heated under reflux in toluene (50 mL) for 2-15 hr, and water was removed by azeotropic distillation with dehydration. The reaction mixture was cooled to 90° C., a solution of ethyl (2E)-2-[(4-{[6-(methylsulfonyl)pyridin-3-yl]oxy}phenyl)hydrazono]propanoate (11.8 g) in toluene (50 mL) was added dropwise. The reaction mixture was stirred at 90° C. for 1 hr, and cooled to room temperature. To the reaction mixture was added saturated aqueous sodium hydrogen carbonate solution, and the mixture was extracted with ethyl acetate. The organic layer was washed with saturated brine, dried over magnesium sulfate, filtered and concentrated under reduced pressure. The obtained crude product was subjected to basic silica gel column chromatography (ethyl acetate:hexane=0:100 to 50:50, volume ratio) and crystallized from diethyl ether to give the title compound (5.65 g, yield 50%) as pale-yellow powder.
MS 361 (MH$^+$).

Reference Example 53

5-{[6-(Methylsulfonyl)pyridin-3-yl]oxy}-1H-indole-2-carboxylic acid

To a solution of ethyl 5-{[6-(methylsulfonyl)pyridin-3-yl]oxy}-1H-indole-2-carboxylate (5.6 g) in ethanol (100 mL) and tetrahydrofuran (100 mL) was added 1N aqueous sodium hydroxide solution (31.1 mL), and the mixture was stirred at room temperature for 15 hr. The reaction mixture was concentrated, 1N hydrochloric acid (32 mL) was added, and the precipitated crystals were filtered and concentrated under reduced pressure to give the title compound (5.2 g, yield 100%) as white crystals.
$^1$H NMR (DMSO-d$_6$) δ3.24 (3H, s), 7.05-7.18 (2H, m), 7.40-7.57 (3H, m), 7.99 (1H, d, J=8.7 Hz), 8.54 (1H, d, J=2.7 Hz), 11.95 (1H, s), 13.06 (1H, brs.).

Reference Example 54

5-{[6-(Methylsulfonyl)pyridin-3-yl]oxy}-1H-indole-2-carboxamide

A mixture of 5-{[6-(methylsulfonyl)pyridin-3-yl]oxy}-1H-indole-2-carboxylic acid (5.2 g), 1-hydroxybenzotriazole monohydrate (3.6 g) and 1-ethyl-3-(3-dimethylaminopropyl)carbodiimide hydrochloride (4.5 g) and N,N-dimethylformamide (200 mL) was stirred at 80° C. for 1 hr. The reaction mixture was cooled to room temperature and 10% aqueous ammonia (12 mL) was added, and the mixture was stirred at room temperature for 1 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was crystallized from diethyl ether to give the title compound (5.18 g, yield 100%) as pale-yellow powder.
MS 332 (MH$^+$).

Reference Example 55

5-{[6-(Methylsulfonyl)pyridin-3-yl]oxy}-1H-indole-2-carbothioamide

To a solution of 5-{[6-(methylsulfonyl)pyridin-3-yl]oxy}-1H-indole-2-carboxamide (4.5 g) in tetrahydrofuran (100 mL) was added a Lawesson's reagent (6 g), and the mixture was stirred with heating under reflux for 1 hr. The reaction mixture was cooled, and concentrated under reduced pressure. The obtained crude product was subjected to basic silica gel column chromatography (ethyl acetate:hexane=0:100 to 100:0, volume ratio) to give the title compound (3.7 g, yield 78%) as yellow powder.
MS 348 (MH$^+$).

Reference Example 56

2-Ethenyl-4-fluoro-1-nitrobenzene

Methyltriphenylphosphonium bromide (12.7 g) was dissolved in dry tetrahydrofuran (200 mL) and ice-cooled. To this solution was added dropwise 1.6M-butyllithium hexane solution (22.0 mL). After the completion of the dropwise addition, the mixture was stirred under ice-cooling for 40 min and 5-fluoro-2-nitrobenzaldehyde (5.0 g) was added to the reaction solution. This solution was warmed to room temperature, and was stirred for 3 hr. To the reaction solution was added aqueous citric acid solution, and tetrahydrofuran was evaporated under reduced pressure. The residue was extracted with ethyl acetate. The organic layer was washed with saturated brine, dried over magnesium sulfate, filtered and concentrated under reduced pressure. The obtained crude product was subjected to silica gel column chromatography (ethyl acetate:hexane=1:4, volume ratio) to give the title compound (3.7 g, yield 75%) as a brown oil.
$^1$H NMR (CDCl$_3$) δ 5.55 (1H, d, J=11.4 Hz), 5.75 (1H, d, J=16.5 Hz), 7.04-7.26 (2H,m), 7.28 (1H, dd, J=3.0, 9.6 Hz), 8.02 (1H, dd, J=5.1, 9.6 Hz).

Reference Example 57

5-(3-Ethenyl-4-nitrophenoxy)-2-(methylsulfonyl)pyridine

A mixture of 2-ethenyl-4-fluoro-1-nitrobenzene (9.6 g), 6-(methylsulfonyl)pyridin-3-ol (10.0 g), potassium carbonate (8.3 g), and N,N-dimethylformamide (90 mL) was stirred at 60° C. for 25 hr. The reaction solution was concentrated under reduced pressure, to the obtained residue was added an aqueous citric acid solution, and the mixture was extracted with ethyl acetate. The organic layer was washed with aqueous citric acid solution and saturated brine, dried over magnesium sulfate, filtered and concentrated under reduced pressure. The obtained pale-yellow oil was crystallized from ethyl acetate-hexane to give the title compound (14.5 g, yield 79%) as pale-yellow crystals.
$^1$H NMR (CDCl$_3$) δ3.26 (3H, s), 5.55 (1H, dd, J=0.9, 10.8 Hz), 5.70 (1H, dd, J=0.9, 17.4 Hz), 7.05 (1H, dd, J=3.0, 9.0 Hz), 7.18-7.28 (2H, m), 7.54 (1H, dd, J=3.0, 8.7 Hz), 8.08 (1H, d, J=9.0 Hz), 8.13 (1H, d, J=8.7 Hz), 8.52 (1H, dd, J=0.6, 3.0 Hz).

Reference Example 58

2-Ethyl-4-{[6-(methylsulfonyl)pyridin-3-yl]oxy}aniline

A mixture of 5-(3-ethenyl-4-nitrophenoxy)-2-(methylsulfonyl)pyridine (5.0 g), 10% palladium carbon (1.0 g, containing water (50%)), tetrahydrofuran (100 mL), and methanol (50 mL) was stirred under a hydrogen atmosphere (balloon pressure) at room temperature for 3 days. The catalyst was filtered off, and the obtained filtrate was concentrated under reduced pressure. The obtained crude product was subjected to silica gel column chromatography (ethyl acetate:hexane=25:75 to 60:40, volume ratio) to give the title compound (4.05 g, yield 89%) as a pale-yellow oil.
MS 293 (MH$^+$).

Reference Example 59

Ethyl(2E)-2-[(2-ethyl-4-{[6-(methylsulfonyl)pyridin-3-yl]oxy}phenyl)hydrazono]propanoate A mixture of 2-ethyl-4-{[6-(methylsulfonyl)pyridin-3-yl]oxy}aniline (11.3 g), concentrated hydrochloric acid (6.8 mL), ethanol (150 mL), and water (15 mL) was cooled to −5 to −10° C., and aqueous solution (15 mL) of sodium nitrite (3.0 g) was added dropwise. After the completion of the dropwise addition, the mixture was stirred at the same temperature for 40 min. The reaction solution was added dropwise to a solution of ethyl 2-methylacetoacetate (6.1 mL) and potassium hydroxide (8.0 g) in water (100 mL) and ethanol (60 mL) at −5 to −10° C. After stirring at −10° C. for 30 min, water was added to the reaction solution, and the mixture was extracted with ethyl acetate. The organic layer was washed with saturated brine, dried over magnesium sulfate, filtered and concentrated under reduced pressure. The obtained crude product was subjected to silica gel column chromatography (ethyl acetate:hexane=25:75 to 40:60, volume ratio) to give the title compound (10.4 g, yield 66%) as a dark-red oil.
MS 406 (MH$^+$).

Reference Example 60

Ethyl 7-ethyl-5-{[6-(methylsulfonyl)pyridin-3-yl]oxy}-1H-indole-2-carboxylate p-Toluenesulfonic acid monohydrate (14.1 g) was heated under reflux in toluene (200 mL), and water was removed by azeotropic distillation with dehydration. The reaction mixture was cooled to 50° C., and a solution of ethyl(2E)-2-[(2-ethyl-4-{[6-(methylsulfonyl)pyridin-3-yl]oxy}phenyl)hydrazono]propanoate (10.4 g) in toluene (30 mL) was added dropwise. The reaction mixture was stirred at 55° C. for 3 hr, and cooled to room temperature. To the reaction mixture was added aqueous sodium hydrogen carbonate solution, and the mixture was extracted with ethyl acetate. The organic layer was washed with water and saturated brine, dried over magnesium sulfate, filtered and concentrated under reduced pressure. The obtained crude product was subjected to silica gel column chromatography (ethyl acetate:hexane=25:75 to 50:50, volume ratio), and the obtained yellow crystals were recrystallized from ethyl acetate-hexane to give the title compound (3.65 g, yield 37%) as pale-yellow crystals.
melting point 140-141° C.
MS 389 (MH$^+$).

Reference Example 61

7-Ethyl-5-{[6-(methylsulfonyl)pyridin-3-yl]oxy}-1H-indole-2-carboxylic acid

To a solution of ethyl 7-ethyl-5-{[6-(methylsulfonyl)pyridin-3-yl]oxy}-1H-indole-2-carboxylate (3.64 g), methanol (20 mL), and tetrahydrofuran (40 mL) was added an aqueous solution (10 mL) of potassium hydroxide (1.6 g), and the mixture was stirred at room temperature for 4 hr. The reaction solution was concentrated, acidified with aqueous citric acid solution, and extracted with ethyl acetate. The organic layer was washed with saturated brine, dried over magnesium sulfate, filtered and concentrated under reduced pressure. The obtained pale-yellow crystals were washed with ethyl acetate-hexane to give the title compound (3.4 g, yield 100%) as pale-yellow crystals.

melting point 184-186° C.

MS 361 (MH$^+$).

Reference Example 62

7-Ethyl-5-{[6-(methylsulfonyl)pyridin-3-yl]oxy}-1H-indole-2-carboxamide

To a solution of 7-ethyl-5-{[6-(methylsulfonyl)pyridin-3-yl]oxy}-1H-indole-2-carboxylic acid (3.4 g) in N,N-dimethylformamide (40 mL) were added under ice-cooling 1-hydroxybenzotriazole ammonium salt (2.2 g) and 1-ethyl-3-(3-dimethylaminopropyl)carbodiimide hydrochloride (2.8 g), and the mixture was stirred from under ice-cooling to room temperature for 15 hr. The reaction solution was concentrated under reduced pressure, water was added to the obtained residue, and the mixture was extracted with ethyl acetate. The organic layer was washed with aqueous sodium hydrogen carbonate solution and saturated brine, dried over magnesium sulfate, filtered and concentrated under reduced pressure to give the title compound (3.4 g, yield 100%) as a pale-yellow amorphous solid.

MS 360(MH$^+$).

Reference Example 63

7-Ethyl-5-{[6-(methylsulfonyl)pyridin-3-yl]oxy}-1H-indole-2-carbothioamide

A mixture of 7-ethyl-5-{[6-(methylsulfonyl)pyridin-3-yl]oxy}-1H-indole-2-carboxamide (3.4 g), a Lawesson's reagent (2.3 g), and dry tetrahydrofuran (70 mL) was stirred at 55° C. for 3 hr. The reaction solution was concentrated under reduced pressure, and the obtained residue was subjected to silica gel column chromatography (ethyl acetate:hexane=25:75 to 60:40, volume ratio), and the obtained yellow crystals were washed with ethyl acetate-hexane to give the title compound (2.8 g, yield 79%) as pale-yellow crystals.

MS 376 (MH$^+$).

Reference Example 64

5-(3-Methyl-4-nitrophenoxy)-2-(methylsulfonyl)pyridine

A mixture of 4-fluoro-2-methyl-1-nitrobenzene (9.4 g), 6-(methylsulfonyl)pyridin-3-ol (10.0 g), potassium carbonate (8.8 g), and N,N-dimethylformamide (100 mL) was stirred at 60° C. for 24 hr. The reaction solution was concentrated under reduced pressure, and the obtained residue was added to a mixture of ethyl acetate-water. The precipitated solid was collected by filtration, washed with water and ethyl acetate and dried to give the title compound (8.28 g) as a pale-yellow solid. The filtrate was extracted with ethyl acetate, washed successively with aqueous citric acid solution, water and brine, dried over magnesium sulfate, filtered and concentrated under reduced pressure. The obtained solid was washed with ethyl acetate to give the title compound (4.30 g) as a pale-yellow solid.

total yield: 12.58 g (yield: 67%).

melting point 138-140° C.

Reference Example 65

2-Methyl-4-{[6-(methylsulfonyl)pyridin-3-yl]oxy}aniline

A mixture of 5-(3-methyl-4-nitrophenoxy)-2-(methylsulfonyl)pyridine (12.58 g), 10% palladium carbon (2.5 g, containing water (50%)), tetrahydrofuran (200 mL), and methanol (50 mL) was stirred under a hydrogen atmosphere (balloon pressure) at room temperature for 18 hr. The catalyst was filtered off, and the obtained filtrate was concentrated under reduced pressure to give the title compound (11.4 g, yield 100%) as a pale-yellow oil.

MS 279 (MH$^+$).

Reference Example 66

Ethyl(2E)-2-[(2-methyl-4-{[6-(methylsulfonyl)pyridin-3-yl]oxy}phenyl)hydrazono]propanoate A mixture of 2-methyl-4-{[6-(methylsulfonyl)pyridin-3-yl]oxy}aniline (11.4 g), concentrated hydrochloric acid (7.2 ethanol (100 mL), and water (10 mL) was cooled to −5° C., and aqueous solution (15 mL) of sodium nitrite (3.1 g) was added dropwise. After the completion of the dropwise addition, the mixture was stirred at the same temperature for 40 min. The reaction solution was added dropwise to a solution of ethyl 2-methylacetoacetate (6.5 mL) and potassium hydroxide (8.4 g) in water (50 mL) and ethanol (100 mL) at −5° C. After stirring at −5° C. for 30 min, water was added to the reaction solution, and the mixture was extracted with ethyl acetate. The organic layer was washed with saturated brine, dried over magnesium sulfate, filtered and concentrated under reduced pressure. The obtained crude product was subjected to silica gel column chromatography (ethyl acetate:hexane=35:65 to 60:40, volume ratio) to give the title compound (11.0 g, yield 69%) as a red oil.

MS 392 (MH$^+$).

Reference Example 67

Ethyl 7-methyl-5-{[6-(methylsulfonyl)pyridin-3-yl]oxy}-1H-indole-2-carboxylate p-Toluenesulfonic acid monohydrate (16.0 g) was heated under reflux in toluene (200 mL), and water was removed by azeotropic distillation with dehydration. The reaction mixture was cooled to 55° C., and a solution of ethyl(2E)-2-[(2-methyl-4-{[6-(methylsulfonyl)pyridin-3-yl]oxy}phenyl)hydrazono]propanoate (11.0 g) in toluene (30 mL) was added dropwise. The reaction mixture was stirred at 55° C. for 2.5 hr, and cooled to room temperature. To the reaction mixture was added aqueous sodium hydrogen carbonate solution, and the mixture was extracted with ethyl acetate. The organic layer was washed with aqueous sodium hydrogen carbonate solution and saturated brine, dried over magnesium sulfate, filtered and concentrated under reduced pressure. The obtained crude product was subjected to silica gel column chromatography (ethyl acetate:hexane=25:75 to 45:55, volume ratio), and the obtained yellow crystals were recrystallized from tetrahydrofuran-ethyl acetate-hexane to give the title compound (3.90 g, yield 37%) as pale-yellow crystals.

MS 375 (MH$^+$).

Reference Example 68

7-Methyl-5-{[6-(methylsulfonyl)pyridin-3-yl]oxy}-1H-indole-2-carboxylic acid To a solution of ethyl 7-methyl-5-{[6-(methylsulfonyl)pyridin-3-yl]oxy}-1H-indole-2-carboxylate (3.9 g), methanol (30 mL), and tetrahydrofuran (50 mL) was added aqueous solution (20 mL) of potassium hydroxide (2.0 g), and the mixture was stirred at room temperature for 15 hr. The reaction solution was concentrated, acidified with aqueous citric acid solution, and the mixture was extracted with ethyl acetate. The organic layer was washed with saturated brine, dried over magnesium sulfate, filtered and concentrated under reduced pressure. The obtained pale-yellow crystals were washed with ethyl acetate-hexane to give the title compound (3.30 g, yield 92%) as pale-yellow crystals.

MS 347 (MH$^+$).

Reference Example 69

7-Methyl-5-{[6-(methylsulfonyl)pyridin-3-yl]oxy}-1H-indole-2-carboxamide

To a solution (35 mL) of 7-methyl-5-{[6-(methylsulfonyl)pyridin-3-yl]oxy}-1H-indole-2-carboxylic acid (3.3 g) in N,N-dimethylformamide were added under ice-cooling 1-hydroxybenzotriazole ammonia salt (2.0 g) and 1-ethyl-3-(3-dimethylaminopropyl)carbodiimide hydrochloride (2.5 g), and the mixture was stirred from under ice-cooling to room temperature for 15 hr. The reaction solution was concentrated under reduced pressure, water was added to the obtained residue, and the mixture was extracted with ethyl acetate. The organic layer was washed with aqueous sodium hydrogen carbonate solution and saturated brine, dried over magnesium sulfate, filtered and concentrated under reduced pressure. The obtained pale-yellow oil was crystallized from ethyl acetate to give the title compound (2.95 g, yield 90%) as pale-yellow crystals.

MS 346(MH$^+$)

Reference Example 70

7-Methyl-5-{[6-(methylsulfonyl)pyridin-3-yl]oxy}-1H-indole-2-carbothioamide

A mixture of 7-methyl-5-{[6-(methylsulfonyl)pyridin-3-yl]oxy}-1H-indole-2-carboxamide (2.95 g), a Lawesson's reagent (2.1 g), and dry tetrahydrofuran (70 mL) was stirred at 55° C. for 2 hr. The reaction solution was concentrated under reduced pressure, and the obtained residue was subjected to silica gel column chromatography (ethyl acetate:hexane=40:60 to 55:45, volume ratio). The obtained yellow oil was crystallized from ethyl acetate-hexane to give the title compound (2.6 g, yield 84%) as pale-yellow crystals.

MS 362 (MH$^+$).

Example 1

Ethyl(2-{5-[4-(methylsulfonyl)phenoxy]-7-(tetrahydro-2H-pyran-4-yloxy)-1H-indol-2-yl}-4,5-dihydro-1,3-thiazol-5-yl)acetate

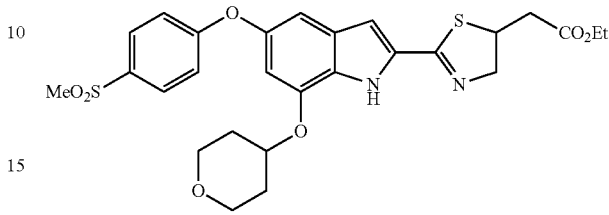

A mixture of 5-[4-(methylsulfonyl)phenoxy]-7-(tetrahydro-2H-pyran-4-yloxy)-1H-indole-2-carboxamide (1.95 g), a Lawesson's reagent (1.83 g), and tetrahydrofuran (80 mL) was stirred at 60° C. for 1 hr. The reaction solution was concentrated under reduced pressure, and the residue was subjected to silica gel column chromatography (ethyl acetate:hexane=10:90 to 100:0, volume ratio) to give thioamide derivative (1.81 g) as a yellow amorphous solid. The obtained thioamide derivative was dissolved in tetrahydrofuran (20 mL)-toluene (30 mL), tri-n-butylphosphine (1.2 mL) and ethyl 2-butynoate (1.18 mL) were added and the mixture was stirred at 60° C. for 3.5 hr. The reaction solution was concentrated under reduced pressure, and the obtained crude product was subjected to silica gel column chromatography (ethyl acetate:hexane=5:95 to 90:10, volume ratio) to give the title compound (1.17 g, yield 52%) as a pale-yellow amorphous solid.

MS 559 (MH$^+$).

Example 2

2-(2-{5-[4-(Methylsulfonyl)phenoxy]-7-(tetrahydro-2H-pyran-4-yloxy)-1H-indol-2-yl}-4,5-dihydro-1,3-thiazol-5-yl)ethanol

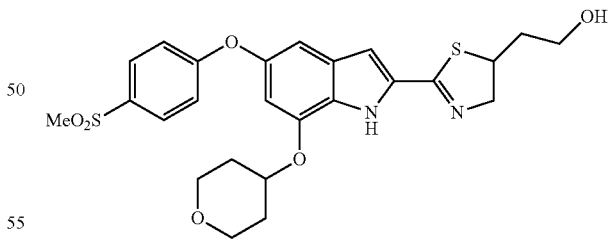

Ethyl(2-{5-[4-(methylsulfonyl)phenoxy]-7-(tetrahydro-2H-pyran-4-yloxy)-1H-indol-2-yl}-4,5-dihydro-1,3-thiazol-5-yl)acetate (300 mg) was dissolved in tetrahydrofuran (10 mL), lithium tetrahydroborate (29 mg) was added under ice-cooling, and the mixture was stirred at 50° C. for 30 min. To the reaction solution was added lithium tetrahydroborate (29 mg), and the mixture was stirred at 50° C. for 2.5 hr. Furthermore, lithium tetrahydroborate (29 mg) was added, and the mixture was stirred at 50° C. for 3 hr. Water was added to the reaction solution, and the mixture was extracted with ethyl acetate. The organic layer was washed with saturated brine, dried over magnesium sulfate, filtered and concentrated under reduced pressure. The obtained crude product was subjected to silica gel column chromatography (methanol:ethyl acetate:hexane=0:90:10 to 10:90:0, volume ratio) to give the title compound (150 mg, yield 54%) as a pale-yellow amorphous solid. The amorphous solid was crystallized from ethyl acetate-diethyl ether-hexane, and the obtained crystals were recrystallized from ethyl acetate-hexane to give the title compound as pale-yellow crystals.

melting point 116-117° C.

MS 517(MH$^+$).

Example 3

2-Methyl-1-(2-{5-[4-(methylsulfonyl)phenoxy]-7-(tetrahydro-2H-pyran-4-yloxy)-1H-indol-2-yl}-4,5-dihydro-1,3-thiazol-5-yl)propan-2-ol

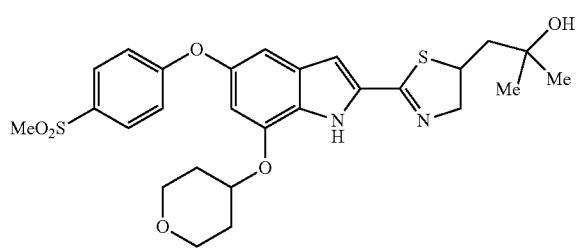

Ethyl(2-{5-[4-(methylsulfonyl)phenoxy]-7-(tetrahydro-2H-pyran-4-yloxy)-1H-indol-2-yl}-4,5-dihydro-1,3-thiazol-5-yl)acetate (400 mg) was dissolved in tetrahydrofuran (10 mL), methylmagnesium bromide (1M tetrahydrofuran solution, 3.6 mL) was added and the mixture was stirred under ice-cooling for 30 min, and then at room temperature for 1 hr. To the reaction solution was added methylmagnesium bromide (1M tetrahydrofuran solution, 1.4 mL), and the mixture was stirred at room temperature for 1 hr. Methylmagnesium bromide (1M tetrahydrofuran solution, 1.4 mL) was further added, and the mixture was stirred at room temperature for 1 hr. Methylmagnesium bromide (1M tetrahydrofuran solution, 1.4 mL) was further added, and the mixture was stirred at room temperature for 1 hr. Moreover, methylmagnesium bromide (1M tetrahydrofuran solution, 1.4 mL) was added, and the mixture was stirred at room temperature for 1 hr. To the reaction solution was added saturated aqueous ammonium chloride solution, and the mixture was extracted with ethyl acetate. The organic layer was washed with saturated brine, dried over magnesium sulfate, filtered and concentrated under reduced pressure. The obtained crude product was subjected to silica gel column chromatography (methanol:ethyl acetate:hexane=0:50:50 to 20:80:0, volume ratio), then basic silica gel column chromatography (methanol:ethyl acetate:hexane=0:50:50 to 10:90:0, volume ratio) to give the title compound as a yellow oil (81 mg, yield 21%). The obtained yellow oil was crystallized from diethyl ether-hexane and recrystallized from ethyl acetate-hexane to give pale-yellow crystals.

melting point 163-164° C.

MS 545 (MH$^+$).

Example 4

(2-{5-[4-(Methylsulfonyl)phenoxy]-7-(tetrahydro-2H-pyran-4-yloxy)-1H-indol-2-yl}-4,5-dihydro-1,3-thiazol-5-yl)acetic acid

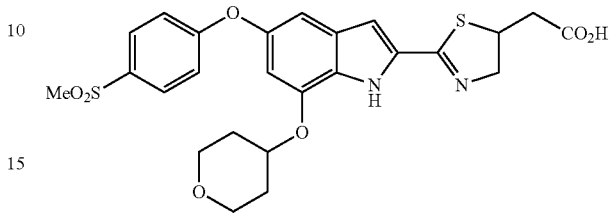

A mixture of ethyl(2-{5-[4-(methylsulfonyl)phenoxy]-7-(tetrahydro-2H-pyran-4-yloxy)-1H-indol-2-yl}-4,5-dihydro-1,3-thiazol-5-yl)acetate (424 mg), 1M aqueous sodium hydroxide solution (2 mL), tetrahydrofuran (10 mL), and ethanol (10 mL) was stirred at room temperature for 2 hr. The reaction solution was concentrated under reduced pressure, water was added, and the mixture was washed with ethyl acetate. The aqueous layer was neutralized with 1M hydrochloric acid, and the mixture was extracted with ethyl acetate. The organic layer was washed with saturated brine, dried over magnesium sulfate, filtered and concentrated under reduced pressure. The residue was solidified with diethyl ether, and the obtained solid was washed with diethyl ether-hexane to give the title compound (270 mg, yield 67%) as a yellow solid.

MS 529 (MH$^+$).

Example 5

2-(2-{5-[4-(Methylsulfonyl)phenoxy]-7-(tetrahydro-2H-pyran-4-yloxy)-1H-indol-2-yl}-4,5-dihydro-1,3-thiazol-5-yl)acetamide

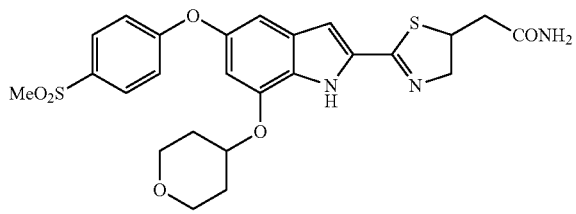 [SMILES: CS(=O)(=O)c1ccc(Oc2cc(OC3CCOCC3)c3[nH]c(C4=NCC(CC(N)=O)S4)cc3c2)cc1]

A mixture of (2-{5-[4-(methylsulfonyl)phenoxy]-7-(tetrahydro-2H-pyran-4-yloxy)-1H-indol-2-yl}-4,5-dihydro-1,3-thiazol-5-yl)acetic acid (370 mg), 1-[3-(dimethylamino)propyl]-3-ethylcarbodiimide hydrochloride (268 mg), 1-hydroxybenzotriazole (189 mg), and N,N-dimethylformamide (20 mL) was stirred at 50° C. for 30 min. The reaction solution was cooled to room temperature, 10% aqueous ammonia solution (1.0 mL) was added, and the mixture was stirred at room temperature for 1 hr. Water was added to the reaction solution, and the mixture was extracted with ethyl acetate. The organic layer was washed with saturated brine, dried over magnesium sulfate, filtered and concentrated under reduced pressure. The obtained crude product was subjected to basic silica gel column chromatography (methanol:ethyl acetate:hexane=0:50:50 to 10:90:0, volume ratio) to give the title compound (200 mg, yield 54%) as a white amorphous solid. The white amorphous solid was crystallized from diethyl ether and the obtained crystals were recrystallized from ethyl acetate-diethyl ether to give the title compound as colorless crystals.

melting point 176-177° C.

MS 530 (MH$^+$).

Example 6

Ethyl{2-[5-{[6-(methoxymethyl)pyridin-3-yl]oxy}-7-(tetrahydro-2H-pyran-4-yloxy)-1H-indol-2-yl]-4,5-dihydro-1,3-thiazol-5-yl}acetate

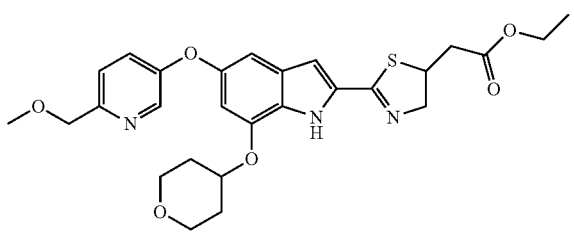 [SMILES: CCOC(=O)CC1CN=C(c2cc3cc(Oc4ccc(COC)nc4)cc(OC4CCOCC4)c3[nH]2)S1]

To a solution of 5-{[6-(methoxymethyl)pyridin-3-yl]oxy}-7-(tetrahydro-2H-pyran-4-yloxy)-1H-indole-2-carbothioamide (1.5 g) in tetrahydrofuran (10 mL) and toluene (15 mL) were added ethyl 2-butynoate (1.02 g) and tri-n-butylphosphine (0.73 g), and the mixture was stirred at 90° C. for 1 hr. The reaction mixture was cooled, and concentrated under reduced pressure. The obtained crude product was subjected to silica gel column chromatography (ethyl acetate:hexane=0:100 to 100:0, volume ratio) to give the title compound (1.25 g, yield 66%) as a yellow amorphous solid.

MS 526 (MH$^+$).

$^1$H NMR (CDCl$_3$) δ1.28 (3H, td, J=7.1, 1.1 Hz), 1.75-1.93 (2H, m), 2.09 (2H, dd, J=9.3, 4.2 Hz), 2.72 (2H, d, J=7.0 Hz), 3.48 (3H, s), 3.58 (2H, t, J=8.9 Hz), 4.00 (2H, t, J=10.5 Hz), 4.19 (2H, q, J=7.2, 1.1 Hz), 4.24-4.49 (3H, m), 4.49-4.69 (3H, m), 6.49 (1H, s), 6.81 (1H, s), 6.84 (1H, s), 7.26 (1H, d, J=1.3 Hz), 7.30-7.39 (1H, m), 8.34 (1H, d, J=2.6 Hz), 9.26 (1H, brs).

Example 7

2-{2-[5-{[6-(Methoxymethyl)pyridin-3-yl]oxy}-7-(tetrahydro-2H-pyran-4-yloxy)-1H-indol-2-yl]-4,5-dihydro-1,3-thiazol-5-yl}ethanol

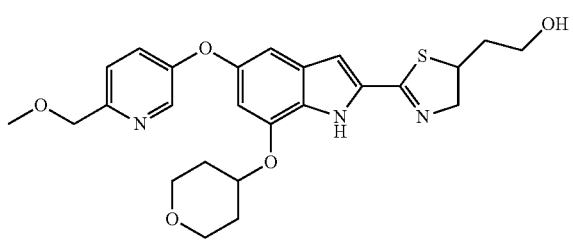 [SMILES: COCc1ccc(Oc2cc(OC3CCOCC3)c3[nH]c(C4=NCC(CCO)S4)cc3c2)cn1]

To a solution of ethyl{2-[5-{[6-(methoxymethyl)pyridin-3-yl]oxy}-7-(tetrahydro-2H-pyran-4-yloxy)-1H-indol-2-yl]-4,5-dihydro-1,3-thiazol-5-yl}acetate (500 mg) in tetrahydrofuran (10 mL) and methanol (15 mL) was added lithium tetrahydroborate (80 mg) at room temperature 3 times at 30 min intervals, and the mixture was stirred at room temperature for 1 hr. Water was added to the reaction mixture, and the mixture was extracted with ethyl acetate. The organic layer was washed with saturated brine, dried over magnesium sulfate, filtered and concentrated under reduced pressure. The obtained crude product was subjected to basic silica gel column chromatography (ethyl acetate:hexane=0:100 to 100:0, volume ratio), and further to silica gel column chromatography (methanol:ethyl acetate:hexane=0:0:100 to 10:90:0, volume ratio). The obtained crude product was purified by preparative HPLC to give the title compound (122 mg, yield 26%) as a colorless amorphous solid.

MS 484 (MH$^+$).

$^1$H NMR (CDCl$_3$) δ1.77-2.17 (6H, m), 3.48 (3H, s), 3.58 (2H, ddd, J=11.7, 8.7, 3.0 Hz), 3.79 (2H, brs.), 4.01 (2H, dd, J=6.8, 5.3 Hz), 4.09-4.32 (2H, m), 4.36-4.48 (1H, m), 4.51-4.69 (3H, m), 6.49 (1H, d, J=1.9 Hz), 6.84 (2H, dd, J=8.2, 1.8 Hz), 7.20-7.28 (1H, m), 7.31-7.38 (1H, m), 8.34 (1H, d, J=2.6 Hz), 9.32 (1H, brs).

Example 8

1-{2-[5-{[6-(Methoxymethyl)pyridin-3-yl]oxy}-7-(tetrahydro-2H-pyran-4-yloxy)-1H-indol-2-yl]-4,5-dihydro-1,3-thiazol-5-yl}-2-methylpropan-2-ol

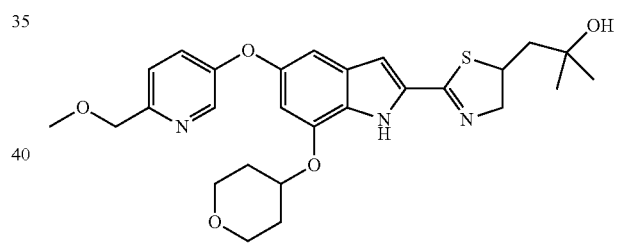

To a solution of ethyl{2-[5-{[6-(methoxymethyl)pyridin-3-yl]oxy}-7-(tetrahydro-2H-pyran-4-yloxy)-1H-indol-2-yl]-4,5-dihydro-1,3-thiazol-5-yl}acetate (500 mg) in tetrahydrofuran (10 mL) was added 1M methylmagnesium bromide tetrahydrofuran solution (5 mL) twice at 30 min intervals at room temperature, and the mixture was stirred at room temperature for 3 hr. To the reaction mixture was added saturated aqueous ammonium chloride solution, and the mixture was extracted with ethyl acetate. The organic layer was washed with saturated brine, dried over magnesium sulfate, filtered and concentrated under reduced pressure. The obtained crude product was subjected to basic silica gel column chromatography (ethyl acetate:hexane=0:100 to 100:0, volume ratio) and further to silica gel column chromatography (methanol:ethyl acetate:hexane=0:0:100 to 10:90:0, volume ratio). The obtained crude product was purified by preparative HPLC to give the title compound (75 mg, yield 15%) as white crystals.

MS 512 (MH$^+$).

melting point 108-110° C.

$^1$H NMR (CDCl$_3$) δ1.31 (6H, d, J=6.2 Hz), 1.73-1.92 (2H, m), 1.97-2.15 (4H, m), 3.48 (3H, s), 3.52-3.64 (2H, m), 3.90-4.14 (3H, m), 4.15-4.32 (1H, m), 4.47-4.70 (4H, m), 6.49 (1H, d, J=1.5 Hz), 6.83 (2H, d, J=10.5 Hz), 7.21-7.38 (2H, m), 8.35 (1H, d, J=2.8 Hz), 9.24 (1H, brs).

Example 9

{2-[5-{[6-(Methoxymethyl)pyridin-3-yl]oxy}-7-(tetrahydro-2H-pyran-4-yloxy)-1H-indol-2-yl]-4,5-dihydro-1,3-thiazol-5-yl}acetic acid

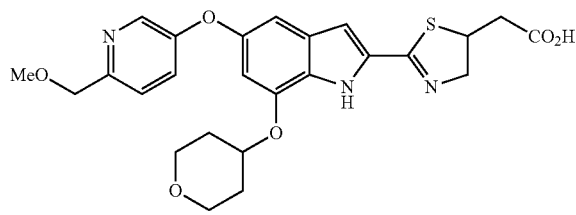 [SMILES: COCc1ccc(Oc2cc(OC3CCOCC3)c3[nH]c(C4=NCC(CC(=O)O)S4)cc3c2)cn1]

A mixture of ethyl{2-[5-{[6-(methoxymethyl)pyridin-3-yl]oxy}-7-(tetrahydro-2H-pyran-4-yloxy)-1H-indol-2-yl]-4,5-dihydro-1,3-thiazol-5-yl}acetate (1.04 g), 1M aqueous sodium hydroxide solution (6 mL), tetrahydrofuran (10 mL), and ethanol (10 mL) was stirred at room temperature for 1 hr. The reaction solution was concentrated under reduced pressure, water was added, and the mixture was washed with ethyl acetate. The aqueous layer was neutralized with 1M hydrochloric acid, and the mixture was extracted with ethyl acetate. The organic layer was washed with saturated brine, dried over magnesium sulfate, filtered and concentrated under reduced pressure to give the title compound (700 mg, yield 71%) as a white amorphous solid.

MS 498 (MH$^+$).

Example 10

2-{2-[5-{[6-(Methoxymethyl)pyridin-3-yl]oxy}-7-(tetrahydro-2H-pyran-4-yloxy)-1H-indol-2-yl]-4,5-dihydro-1,3-thiazol-5-yl}acetamide

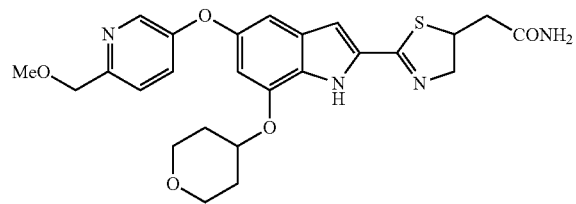 [SMILES: COCc1ccc(Oc2cc(OC3CCOCC3)c3[nH]c(C4=NCC(CC(N)=O)S4)cc3c2)cn1]

A mixture of {2-[5-{[6-(methoxymethyl)pyridin-3-yl]oxy}-7-(tetrahydro-2H-pyran-4-yloxy)-1H-indol-2-yl]-4,5-dihydro-1,3-thiazol-5-yl}acetic acid (400 mg), 1-[3-(dimethylamino)propyl]-3-ethylcarbodiimide hydrochloride (308 mg), 1-hydroxybenzotriazole (135 mg), and N,N-dimethylformamide (15 mL) was stirred at 50° C. for 30 min. The reaction solution was cooled to room temperature, 10% aqueous ammonia solution (1.5 mL) was added, and the mixture was stirred at room temperature for 2.5 hr. Water was added to the reaction solution, and the mixture was extracted with ethyl acetate. The organic layer was washed with saturated brine, dried over magnesium sulfate, filtered and concentrated under reduced pressure. The obtained crude product was subjected to basic silica gel column chromatography (methanol:ethyl acetate:hexane=0:50:50 to 15:85:0, volume ratio) to give an orange oil. The obtained orange oil was purified by preparative HPLC to give the title compound (180 mg, yield 45%) as a white amorphous solid.

MS 497 (MH$^+$).

$^1$H NMR (CDCl$_3$) δ1.74-1.93 (2H, m), 2.02-2.15 (2H, m), 2.53-2.71 (2H, m), 3.48 (3H, s), 3.58 (2H, ddd, J=11.8, 8.8 3.2 Hz), 3.94-4.07 (2H, m), 4.29-4.47 (3H, m), 4.53-4.62 (3H, m), 5.38 (1H, s), 5.42 (1H, s), 6.50 (1H, d, J=1.9 Hz), 6.83 (2H, dd, J=8.7, 1.9 Hz), 7.23-7.29 (1H, m), 7.31-7.37 (1H, m), 8.34 (1H, d, J=2.3 Hz), 9.16 (1H, s).

Example 11

2-{2-[5-{[6-(Methoxymethyl)pyridin-3-yl]oxy}-7-(tetrahydro-2H-pyran-4-yloxy)-1H-indol-2-yl]-4,5-dihydro-1,3-thiazol-5-yl}-N-methylacetamide

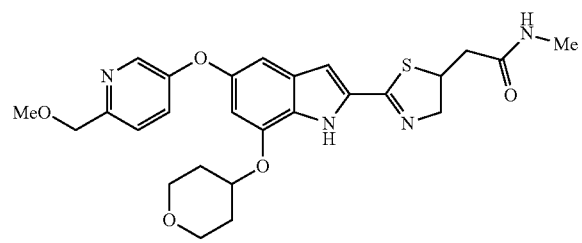 [SMILES: CNC(=O)CC1CN=C(c2cc3cc(Oc4ccc(COC)nc4)cc(OC4CCOCC4)c3[nH]2)S1]

A mixture of {2-[5-{[6-(methoxymethyl)pyridin-3-yl]oxy}-7-(tetrahydro-2H-pyran-4-yloxy)-1H-indol-2-yl]-4,5-dihydro-1,3-thiazol-5-yl}acetic acid (300 mg), 1-[3-(dimethylamino)propyl]-3-ethylcarbodiimide hydrochloride (231 mg), 1-hydroxybenzotriazole (162 mg), methylamine hydrochloride (81 mg), triethylamine (0.2 mL), and N,N-dimethylformamide (15 mL) was stirred at room temperature for 2 hr. Water was added to the reaction solution, and the mixture was extracted with ethyl acetate. The organic layer was washed with saturated brine, dried over magnesium sulfate, filtered and concentrated under reduced pressure. The obtained crude product was subjected to basic silica gel column chromatography (methanol:ethyl acetate:hexane=0:50:50 to 10:90:0, volume ratio) to give an orange oil. The obtained orange oil was purified by preparative HPLC to give the title compound (150 mg, yield 49%) as a white amorphous solid.

MS 511 (MH$^+$).

$^1$H NMR (CDCl$_3$) δ1.76-1.91 (2H, m), 2.03-2.17 (2H, m), 2.44-2.64 (2H, m), 2.84 (3H, d, J=4.9 Hz), 3.48 (3H, s), 3.58 (2H, ddd, J=11.8, 9.0, 3.0 Hz), 3.94-4.08 (2H, m), 4.27-4.48 (3H, m), 4.52-4.64 (3H, m), 5.46 (1H, d, J=4.5 Hz), 6.49 (1H, d, J=1.9 Hz), 6.83 (2H, dd, J=9.8, 1.9 Hz), 7.21-7.29 (1H, m), 7.31-7.37 (1H, m), 8.34 (1H, d, J=2.3 Hz), 9.16 (1H, s).

Example 12

Ethyl{2-[5-{[5-(methylsulfonyl)pyridin-2-yl]oxy}-7-(tetrahydro-2H-pyran-4-yloxy)-1H-indol-2-yl]-4,5-dihydro-1,3-thiazol-5-yl}acetate

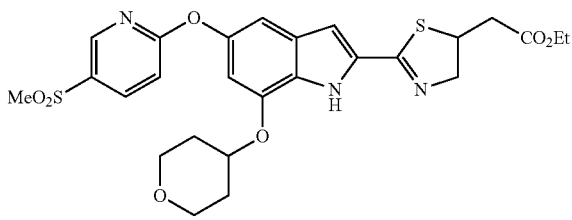 [SMILES: CCOC(=O)CC1CN=C(c2cc3cc(Oc4ccc(S(C)(=O)=O)cn4)cc(OC4CCOCC4)c3[nH]2)S1]

A mixture of 5-{[5-(methylsulfonyl)pyridin-2-yl]oxy}-7-(tetrahydro-2H-pyran-4-yloxy)-1H-indole-2-carboxamide (1.41 g), a Lawesson's reagent (1.45 g), and tetrahydrofuran (20 mL) was stirred at 70° C. for 2 hr. To the reaction solution was added a Lawesson's reagent (0.7 g), and the mixture was stirred at 70° C. for 3 hr. Furthermore, a Lawesson's reagent (0.7 g) was added, and the mixture was stirred at 50° C. for 3 days. Furthermore, a Lawesson's reagent (0.7 g) was added, and the mixture was stirred at 70° C. for 2 hr. The reaction solution was concentrated, and the residue was suspended in tetrahydrofuran (10 mL)-toluene (15 mL), tri-n-butylphosphine (1.6 mL) and ethyl 2-butynoate (1.14 mL) were added and the mixture was stirred at 70° C. for 40 min. The reaction solution was diluted with tetrahydrofuran (250 mL), tri-n-butylphosphine (1.6 mL) and ethyl 2-butynoate (1.14 mL) were added, and the mixture was stirred at 70° C. for 2.5 hr. Furthermore, tri-n-butylphosphine (0.8 mL) and ethyl 2-butynoate (1.0 mL) were added, and the mixture was stirred at 70° C. for 2 hr. The reaction solution was concentrated under reduced pressure, and the obtained crude product was subjected to basic silica gel column chromatography (ethyl acetate:hexane=10:90 to 70:30, volume ratio) to give the title compound as a brown amorphous solid (500 mg, yield 27%).
MS 558 (MH$^+$).

Example 13

2-{2-[5-{[5-(Methylsulfonyl)pyridin-2-yl]oxy}-7-(tetrahydro-2H-pyran-4-yloxy)-1H-indol-2-yl]-4,5-dihydro-1,3-thiazol-5-yl}ethanol

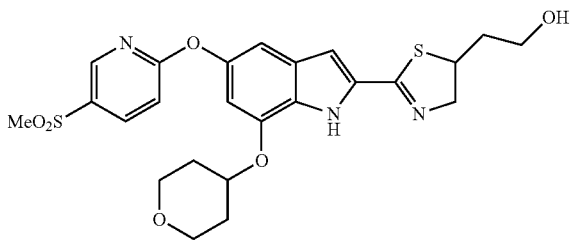 [SMILES: CS(=O)(=O)c1ccc(Oc2cc(OC3CCOCC3)c3[nH]c(C4=NCC(CCO)S4)cc3c2)nc1]

Ethyl{2-[5-{[5-(methylsulfonyl)pyridin-2-yl]oxy}-7-(tetrahydro-2H-pyran-4-yloxy)-1H-indol-2-yl]-4,5-dihydro-1,3-thiazol-5-yl}acetate (207 mg) was dissolved in tetrahydrofuran (5 mL)-methanol (2 mL), lithium tetrahydroborate (22 mg) was added under ice-cooling, and the mixture was stirred at room temperature for 50 min. To the reaction solution were added lithium tetrahydroborate (32 mg) and methanol (1 mL), and the mixture was stirred at room temperature for 1 hr. Furthermore, lithium tetrahydroborate (15 mg) was added, and the mixture was stirred at room temperature for 1 hr. Water was added to the reaction solution, and the mixture was extracted with ethyl acetate. The organic layer was washed with saturated brine, dried over magnesium sulfate, filtered and concentrated under reduced pressure. The obtained crude product was subjected to silica gel column chromatography (methanol:ethyl acetate:hexane=0:50:50 to 20:80:0, volume ratio) to give the title compound as a yellow amorphous solid (99 mg, yield 52%). The obtained amorphous solid was crystallized from diethyl ether, and the obtained crystals were recrystallized from ethyl acetate-diethyl ether to give the title compound as colorless crystals.

melting point 165-166° C.

MS 518 (MH$^+$).

Example 14

2-Methyl-1-{2-[5-{[5-(methylsulfonyl)pyridin-2-yl]oxy}-7-(tetrahydro-2H-pyran-4-yloxy)-1H-indol-2-yl]-4,5-dihydro-1,3-thiazol-5-yl}propan-2-ol

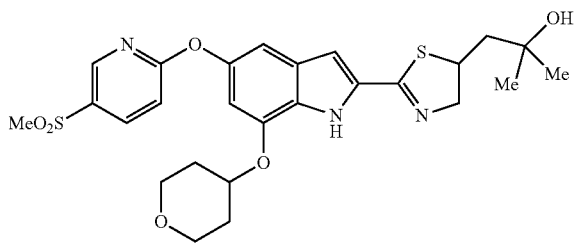 [SMILES: CC(C)(O)CC1CN=C(c2cc3cc(Oc4ccc(S(C)(=O)=O)cn4)cc(OC4CCOCC4)c3[nH]2)S1]

Ethyl{2-[5-{[5-(methylsulfonyl)pyridin-2-yl]oxy}-7-(tetrahydro-2H-pyran-4-yloxy)-1H-indol-2-yl]-4,5-dihydro-1,3-thiazol-5-yl}acetate (292 mg) was dissolved in tetrahydrofuran (15 mL), methylmagnesium bromide (1M tetrahydrofuran solution, 2.0 mL) was added and the mixture was stirred at room temperature for 30 min. To the reaction solution was further added methylmagnesium bromide (1M tetrahydrofuran solution, 3.0 mL) at room temperature and the mixture was stirred for 40 min. To the reaction solution was added saturated aqueous ammonium chloride solution, and the mixture was extracted with ethyl acetate. The organic layer was washed with saturated brine, dried over magnesium sulfate, filtered and concentrated under reduced pressure. The obtained crude product was subjected to silica gel column chromatography (methanol:ethyl acetate:hexane=0:50:50 to 10:90:0, volume ratio) to give the title compound as an orange amorphous solid (72 mg, yield 25%). The obtained amorphous solid was crystallized from diethyl ether and the obtained crystals were recrystallized from ethyl acetate-diethyl ether to give the title compound as pale-yellow crystals.

melting point 129-130° C.

MS 546 (MH$^+$).

Example 15

{2-[5-{[5-(Methylsulfonyl)pyridin-2-yl]oxy}-7-(tetrahydro-2H-pyran-4-yloxy)-1H-indol-2-yl]-4,5-dihydro-1,3-thiazol-5-yl}acetic acid

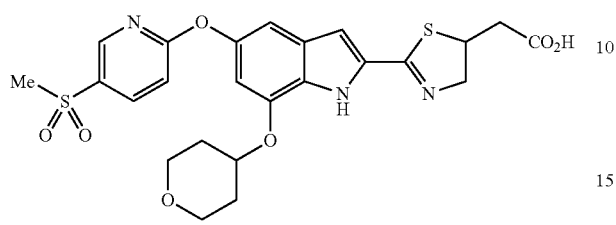

A mixture of ethyl{2-[5-{[5-(methylsulfonyl)pyridin-2-yl]oxy}-7-(tetrahydro-2H-pyran-4-yloxy)-1H-indol-2-yl]-4,5-dihydro-1,3-thiazol-5-yl}acetate (690 mg), 1M aqueous sodium hydroxide solution (5 mL), ethanol (5 mL) and tetrahydrofuran (5 mL) was stirred at room temperature for 15 hr. To the reaction solution was added 1M hydrochloric acid (5 mL) and water, and the mixture was extracted with ethyl acetate. The organic layer was washed with saturated brine, dried over magnesium sulfate, filtered and concentrated under reduced pressure. The obtained crystals were washed with hexane-ethyl acetate mixed solvent to give the title compound (610 mg, yield 95%) as brown crystals.

MS 532 (MH$^+$).

$^1$H NMR (DMSO-d$_6$) δ1.63-1.80 (2H, m), 1.87-2.03 (2H, m), 2.53-2.66 (1H, m), 2.74-2.90 (1H, m), 3.27 (3H, s), 3.41-3.53 (2H, m), 3.88-4.01 (2H, m), 4.18-4.34 (2H, m), 4.35-4.51 (1H, m), 4.71 (1H, dt, J=7.25, 3.72 Hz), 6.74 (1H, d, J=1.88 Hz), 6.84 (1H, d, J=1.88 Hz), 6.99 (1H, d, J=1.88 Hz), 7.13 (1H, d, J=8.29 Hz), 8.27 (1H, dd, J=8.67, 2.64 Hz), 8.63 (1H, d, J=2.26 Hz), 11.84 (1H, d, J=1.51 Hz), 12.48 (1H, brs).

Example 16

2-{2-[5-{[5-(Methylsulfonyl)pyridin-2-yl]oxy}-7-(tetrahydro-2H-pyran-4-yloxy)-1H-indol-2-yl]-4,5-dihydro-1,3-thiazol-5-yl}acetamide

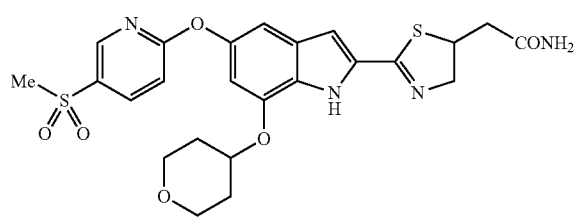 [SMILES: CS(=O)(=O)c1ccc(Oc2cc(OC3CCOCC3)c3[nH]c(C4=NCC(CC(N)=O)S4)cc3c2)nc1]

A mixture of {2-[5-{[5-(methylsulfonyl)pyridin-2-yl]oxy}-7-(tetrahydro-2H-pyran-4-yloxy)-1H-indol-2-yl]-4,5-dihydro-1,3-thiazol-5-yl}acetic acid (210 mg), 1H-1,2,3-benzotriazol-1-ol (80 mg), N-[3-(dimethylamino)propyl]-N'-ethylcarbodiimide hydrochloride (120 mg) and N,N-dimethylformamide (5 mL) was stirred at 50° C. for 30 min and cooled to 0° C. 10% Aqueous ammonia (1 mL) was added to the mixture, and the mixture was stirred at room temperature for 2.5 days. To the reaction mixture was added water and the mixture was extracted with ethyl acetate. The organic layer was washed successively with saturated aqueous sodium hydrogen carbonate and saturated brine, dried over magnesium sulfate, and subjected to silica gel short column chromatography (eluted with ethyl acetate-methanol (95/5, volume ratio)) to give pale-yellow crystals. The crystals were recrystallized from acetone-hexane to give the title compound (130 mg, yield 62%) as pale-yellow prism crystals.

melting point 188-190° C.

MS 531 (MH$^+$).

Example 17

N-Methyl-2-{2-[5-{[5-(methylsulfonyl)pyridin-2-yl]oxy}-7-(tetrahydro-2H-pyran-4-yloxy)-1H-indol-2-yl]-4,5-dihydro-1,3-thiazol-5-yl}acetamide

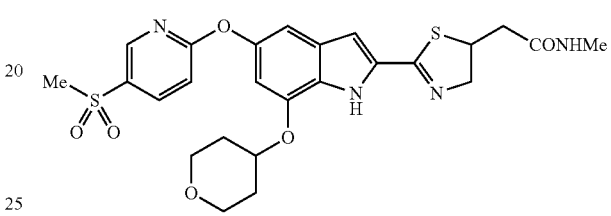

A mixture of {2-[5-{[5-(methylsulfonyl)pyridin-2-yl]oxy}-7-(tetrahydro-2H-pyran-4-yloxy)-1H-indol-2-yl]-4,5-dihydro-1,3-thiazol-5-yl}acetic acid (200 mg), 1H-1,2,3-benzotriazol-1-ol (80 mg), N-[3-(dimethylamino)propyl]-N'-ethylcarbodiimidehydrochloride (110 mg), methylamine hydrochloride (50 mg), triethylamine (85 mg) and N,N-dimethylformamide (3 mL) was stirred at room temperature for 2.5 days. To the reaction mixture was added saturated aqueous sodium hydrogen carbonate and the mixture was extracted with ethyl acetate. The organic layer was washed with saturated brine, dried over magnesium sulfate, filtered and concentrated under reduced pressure. The residue was subjected to silica gel chromatography, and eluted with ethyl acetate-methanol (100/0 to 95/5, volume ratio) to give colorless crystals. The crystals were recrystallized from acetone-hexane to give the title compound (110 mg, yield 52%) as colorless prism crystals.

melting point 170-172° C.

MS 545 (MH$^+$).

Example 18

1-({2-[5-{[5-(Methylsulfonyl)pyridin-2-yl]oxy}-7-(tetrahydro-2H-pyran-4-yloxy)-1H-indol-2-yl]-4,5-dihydro-1,3-thiazol-5-yl}acetyl)azetidin-3-ol

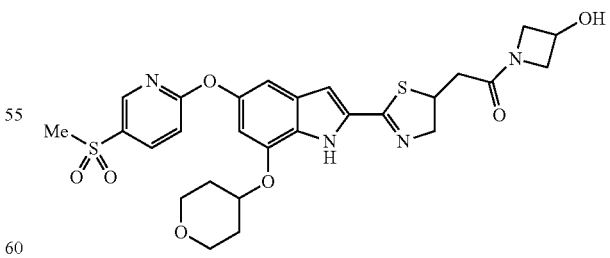

A mixture of {2-[5-{[5-(methylsulfonyl)pyridin-2-yl]oxy}-7-(tetrahydro-2H-pyran-4-yloxy)-1H-indol-2-yl]-4,5-dihydro-1,3-thiazol-5-yl}acetic acid (190 mg), 1H-1,2,3-benzotriazol-1-ol (70 mg), N-[3-(dimethylamino)propyl]-N'-ethylcarbodiimide hydrochloride (100 mg), azetidin-3-ol hydrochloride (80 mg), triethylamine (80 mg) and N,N-dimethylformamide (3 mL) was stirred at room temperature for 15 hr. To the reaction mixture was added water and the mixture was extracted with ethyl acetate. The organic layer was washed successively with saturated aqueous sodium hydrogen carbonate and saturated brine, dried over magnesium sulfate, filtered and concentrated under reduced pressure. The residue was subjected to silica gel chromatography, and eluted with ethyl acetate-methanol (100/0 to 90/10, volume ratio) to give colorless crystals. The crystals were recrystallized from acetone-hexane to give the title compound (130 mg, yield 62%) as colorless prism crystals.

melting point 180-181° C.
MS 587 (MH$^+$).

Example 19

Ethyl{2-[5-({6-[(2-methoxyethoxy)methyl]pyridin-3-yl}oxy)-7-(tetrahydro-2H-pyran-4-yloxy)-1H-indol-2-yl]-4,5-dihydro-1,3-thiazol-5-yl}acetate

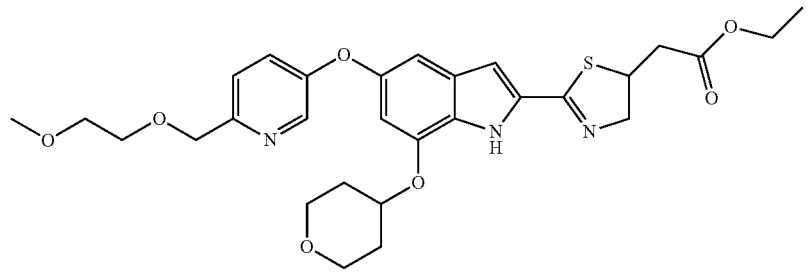 [SMILES: CCOC(=O)CC1CN=C(c2cc3cc(Oc4ccc(COCCOC)nc4)cc(OC4CCOCC4)c3[nH]2)S1]

To a solution of 5-({6-[(2-methoxyethoxy)methyl]pyridin-3-yl}oxy)-7-(tetrahydro-2H-pyran-4-yloxy)-1H-indole-2-carbothioamide (1.1 g) in tetrahydrofuran (10 mL) and toluene (15 mL) were added ethyl 2-butynoate (0.67 g) and tri-n-butylphosphine (0.49 g), and the mixture was stirred at 90° C. for 1 hr. The reaction mixture was cooled, and concentrated under reduced pressure. The obtained crude product was subjected to basic silica gel column chromatography (ethyl acetate:hexane=0:100 to 50:50, volume ratio) to give the title compound (445 mg, yield 32%) as a yellow oil.

MS 570 (MH$^+$).

$^1$H NMR (CDCl$_3$) δ 0.94 (3H, t, J=7.2 Hz), 1.73-1.91 (2H, m), 2.01-2.15 (2H, m), 2.73 (2H, d, J=6.4 Hz), 3.40 (3H, s), 3.51-3.68 (4H, m), 3.70-3.77 (2H, m), 3.94-4.07 (2H, m), 4.12 (2H, q, J=7.2 Hz), 4.24-4.48 (3H, m), 4.51-4.63 (1H, m), 4.66 (2H, s), 6.49 (1H, d, J=1.9 Hz), 6.83 (2H, dd, J=9.5, 1.9 Hz), 7.19-7.30 (1H, m), 7.40 (1H, d, J=8.3 Hz), 8.33 (1H, d, J=3.0 Hz), 9.18 (1H, brs).

Example 20

2-{2-[5-({6-[(2-Methoxyethoxy)methyl]pyridin-3-yl}oxy)-7-(tetrahydro-2H-pyran-4-yloxy)-1H-indol-2-yl]-4,5-dihydro-1,3-thiazol-5-yl}ethanol

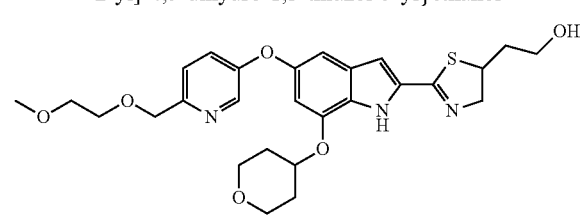

To a solution of ethyl{2-[5-({6-[(2-methoxyethoxy)methyl]pyridin-3-yl}oxy)-7-(tetrahydro-2H-pyran-4-yloxy)-1H-indol-2-yl]-4,5-dihydro-1,3-thiazol-5-yl}acetate (190 mg) in tetrahydrofuran (5 mL) and methanol (5 mL) was added at room temperature lithium tetrahydroborate (22 mg) 3 times at 30 min intervals, and the mixture was stirred at room temperature for 1 hr. Water was added to the reaction mixture, and the mixture was extracted with ethyl acetate. The organic layer was washed with saturated brine, dried over magnesium sulfate, filtered and concentrated under reduced pressure. The obtained crude product was subjected to basic silica gel column chromatography (ethyl acetate:hexane=0:100 to 100:0, volume ratio), and further to silica gel column chromatography (methanol:ethyl acetate:hexane=0:0:100 to 10:90:0, volume ratio). The obtained crude product was purified by preparative HPLC to give the title compound (52 mg, yield 30%) as a pale-yellow oil.

MS 528 (MH$^+$).

$^1$H NMR (CDCl$_3$) δ 1.73-2.15 (6H, m), 3.40 (3H, s), 3.51-3.65 (4H, m), 3.69-3.75 (2H, m), 3.79 (2H, brs), 3.95-4.07 (2H, m), 4.08-4.47 (3H, m), 4.58 (1H, m), 4.66 (2H, s), 6.48 (1H, d, J=1.9 Hz), 6.83 (2H, dd, J=7.7, 1.7 Hz), 7.23 (1H, d, J=2.6 Hz), 7.40 (1H, d, J=8.7 Hz), 8.33 (1H, d, J=2.6 Hz), 9.20 (1H, brs).

Example 21

{2-[5-({6-[(2-Methoxyethoxy)methyl]pyridin-3-yl}oxy)-7-(tetrahydro-2H-pyran-4-yloxy)-1H-indol-2-yl]-4,5-dihydro-1,3-thiazol-5-yl}acetic acid

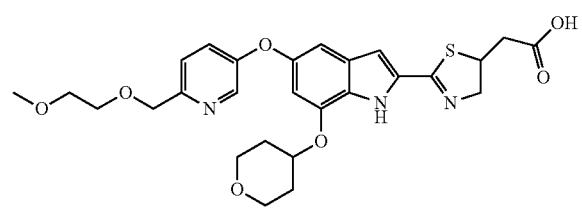 [SMILES: COCCOCc1ccc(Oc2cc(OC3CCOCC3)c3[nH]c(C4=NCC(CC(=O)O)S4)cc3c2)cn1]

To a solution of ethyl{2-[5-({6-[(2-methoxyethoxy)methyl]pyridin-3-yl}oxy)-7-(tetrahydro-2H-pyran-4-yloxy)-1H-indol-2-yl]-4,5-dihydro-1,3-thiazol-5-yl}acetate (190 mg) in ethanol (3 mL) and tetrahydrofuran (3 mL) was added 1N aqueous sodium hydroxide solution (3 mL), and the mixture was stirred at room temperature for 1 hr. The reaction mixture was concentrated, and the concentrate was washed with ethyl acetate. To the aqueous layer was added 1N hydrochloric acid (3 mL), and the mixture was extracted with ethyl acetate. The organic layer was washed with saturated brine, dried over magnesium sulfate, filtered and concentrated under reduced pressure to give the title compound (157 mg, yield 87%) as a brown oil.

MS 542 (MH$^+$).

Example 22

2-{2-[5-({6-[(2-Methoxyethoxy)methyl]pyridin-3-yl}oxy)-7-(tetrahydro-2H-pyran-4-yloxy)-1H-indol-2-yl]-4,5-dihydro-1,3-thiazol-5-yl}-N-methylacetamide

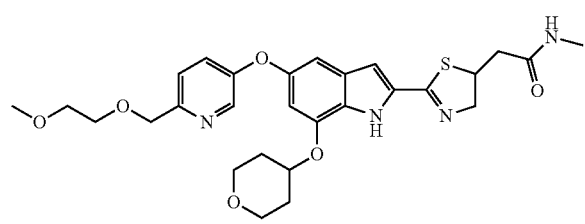

To a solution of {2-[5-({6-[(2-methoxyethoxy)methyl]pyridin-3-yl}oxy)-7-(tetrahydro-2H-pyran-4-yloxy)-1H-indol-2-yl]-4,5-dihydro-1,3-thiazol-5-yl}acetic acid (157 mg) in N,N-dimethylformamide (5 mL) were added 1-hydroxybenzotriazole monohydrate (67 mg), 1-ethyl-3-(3-dimethylaminopropyl)carbodiimide hydrochloride (83 mg), methylamine hydrochloride (30 mg), and triethylamine (0.060 mL), and the mixture was stirred at room temperature for 1 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio) to give the title compound (84 mg, yield 52%) as a yellow oil.

MS 555 (MH$^+$).

$^1$H NMR (CDCl$_3$) δ1.74-1.91 (2H, m), 1.99-2.16 (2H, m), 2.41-2.66 (2H, m), 2.84 (3H, d, J=4.5 Hz), 3.40 (3H, s), 3.50-3.64 (4H, m), 3.69-3.77 (2H, m), 3.93-4.08 (2H, m), 4.23-4.47 (3H, m), 4.51-4.62 (1H, m), 4.66 (2H, s), 5.50 (1H, brs), 6.49 (1H, d, J=1.9 Hz), 6.82 (2H, dd, J=8.7, 1.9 Hz), 7.23 (1H, d, J=2.6 Hz), 7.40 (1H, d, J=8.7 Hz), 8.32 (1H, d, J=2.6 Hz), 9.20 (1H, brs).

Example 23

Ethyl{2-[5-({6-[(methylsulfonyl)methyl]pyridin-3-yl}oxy)-7-(tetrahydro-2H-pyran-4-yloxy)-1H-indol-2-yl]-4,5-dihydro-1,3-thiazol-5-yl}acetate

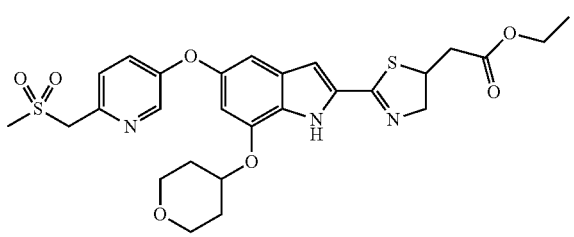 [SMILES: CCOC(=O)CC1CN=C(c2cc3cc(Oc4ccc(CS(C)(=O)=O)nc4)cc(OC4CCOCC4)c3[nH]2)S1]

To a solution of 5-({6-[(methylsulfonyl)methyl]pyridin-3-yl}oxy)-7-(tetrahydro-2H-pyran-4-yloxy)-1H-indole-2-carbothioamide (2.25 g) in tetrahydrofuran (10 mL) and toluene (15 mL) were added ethyl 2-butynoate (1.37 g) and tri-n-butylphosphine (0.99 g), and the mixture was stirred at 90° C. for 1 hr. The reaction mixture was cooled, and concentrated under reduced pressure. The obtained crude product was subjected to silica gel column chromatography (methanol:ethyl acetate:hexane=0:0:100 to 5:95:0, volume ratio) to give the title compound (1.72 g, yield 61%) as a yellow amorphous solid.

MS 574 (MH$^+$).

$^1$H NMR (CDCl$_3$) δ1.28 (3H, t, J=7.2 Hz), 1.85 (2H, qd, J=8.7, 4.3 Hz), 2.02-2.16 (2H, m), 2.61-2.77 (2H, m), 2.93 (3H, s), 3.59 (2H, ddd, J=11.9, 8.9, 3.0 Hz), 4.01 (2H, dd, J=12.1, 4.9 Hz), 4.19 (2H, q, J=6.9 Hz), 4.25-4.50 (5H, m), 4.56-4.65 (1H, m), 6.49 (1H, d, J=1.9 Hz), 6.84 (1H, d, J=2.3 Hz), 6.90 (1H, d, J=1.9 Hz), 7.24 (1H, dd, J=8.5, 2.8 Hz), 7.39 (1H, d, J=8.7 Hz), 8.35 (1H, d, J=2.3 Hz), 9.26 (1H, s).

Example 24

2-{2-[5-({6-[(Methylsulfonyl)methyl]pyridin-3-yl}oxy)-7-(tetrahydro-2H-pyran-4-yloxy)-1H-indol-2-yl]-4,5-dihydro-1,3-thiazol-5-yl}ethanol

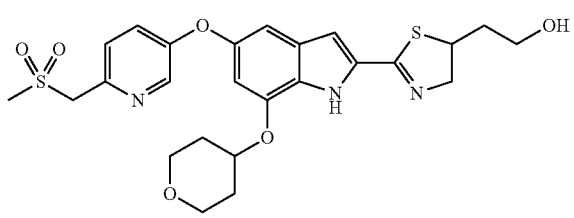 [SMILES: CS(=O)(=O)Cc1ccc(Oc2cc(OC3CCOCC3)c3[nH]c(C4=NCC(CCO)S4)cc3c2)cn1]

To a solution of ethyl{2-[5-({6-[(methylsulfonyl)methyl]pyridin-3-yl}oxy)-7-(tetrahydro-2H-pyran-4-yloxy)-1H-indol-2-yl]-4,5-dihydro-1,3-thiazol-5-yl}acetate (290 mg) in tetrahydrofuran (10 mL) and methanol (15 mL) was added lithium tetrahydroborate (132 mg) at room temperature, and the mixture was stirred at room temperature for 1 hr. Water was added to the reaction mixture, and the mixture was extracted with ethyl acetate. The organic layer was washed with saturated brine, dried over magnesium sulfate, filtered and concentrated under reduced pressure. The obtained crude product was subjected to basic silica gel column chromatography (ethyl acetate:hexane=0:100 to 100:0, volume ratio), and recrystallized from ethyl acetate to give the title compound (142 mg, yield 53%) as white crystals.

MS 532 (MH$^+$).

$^1$H NMR (DMSO-d$_6$) δ1.59-1.78 (3H, m), 1.80-2.02 (3H, m), 2.99 (3H, s), 3.39-3.57 (4H, m), 3.88-4.02 (2H, m), 4.06-4.29 (2H, m), 4.34-4.48 (1H, m), 4.59 (2H, s), 4.70-4.76 (1H, m), 6.73 (1H, d, J=1.9 Hz), 6.82 (1H, d, J=1.9 Hz), 6.90 (1H, d, J=1.9 Hz), 7.28-7.42 (1H, m), 7.42-7.50 (1H, m), 8.32 (1H, d, J=3.0 Hz), 11.82 (1H, s).

Example 25

{2-[5-({6-[(Methylsulfonyl)methyl]pyridin-3-yl}oxy)-7-(tetrahydro-2H-pyran-4-yloxy)-1H-indol-2-yl]-4,5-dihydro-1,3-thiazol-5-yl}acetic acid

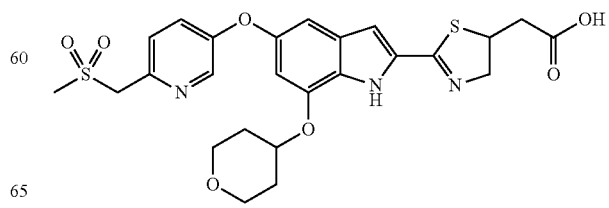

To a solution of ethyl{2-[5-({6-[(methylsulfonyl)methyl]pyridin-3-yl}oxy)-7-(tetrahydro-2H-pyran-4-yloxy)-1H-indol-2-yl]-4,5-dihydro-1,3-thiazol-5-yl}acetate (1.0 g) in ethanol (10 mL) and tetrahydrofuran (10 mL) was added 1N aqueous sodium hydroxide solution (5 mL), and the mixture was stirred at room temperature for 15 hr. To the reaction mixture was added 1N hydrochloric acid (5 mL), and the mixture was extracted with ethyl acetate. The organic layer was washed with saturated brine, dried over magnesium sulfate, filtered and concentrated under reduced pressure to give the title compound (0.95 g, yield 100%) as a yellow amorphous solid.

MS 546 (MH+).

$^1$H NMR (CDCl$_3$) δ1.79-1.96 (2H, m), 2.01-2.16 (2H, m), 2.79 (2H, d, J=7.2 Hz), 2.92 (3H, s), 3.60 (2H, ddd, J=11.6, 8.4, 3.0 Hz), 3.99-4.09 (2H, m), 4.25-4.50 (5H, m), 4.59-4.64 (1H, m), 6.50 (1H, d, J=1.9 Hz), 6.84-6.92 (2H, m), 7.21-7.30 (1H, m), 7.40 (1H, d, J=8.3 Hz), 8.34 (1H, d, J=2.7 Hz), 9.92 (1H, brs).

Example 26

2-{2-[5-({6-[(Methylsulfonyl)methyl]pyridin-3-yl}oxy)-7-(tetrahydro-2H-pyran-4-yloxy)-1H-indol-2-yl]-4,5-dihydro-1,3-thiazol-5-yl}acetamide

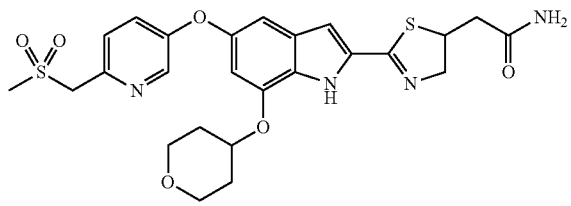 [SMILES: CS(=O)(=O)Cc1ccc(Oc2cc(OC3CCOCC3)c3[nH]c(C4=NCC(CC(N)=O)S4)cc3c2)cn1]

To a solution of {2-[5-({6-[(methylsulfonyl)methyl]pyridin-3-yl}oxy)-7-(tetrahydro-2H-pyran-4-yloxy)-1H-indol-2-yl]-4,5-dihydro-1,3-thiazol-5-yl}acetic acid (200 mg) in N,N-dimethylformamide (5 mL) were added 1-hydroxybenzotriazole monohydrate (84 mg), 1-ethyl-3-(3-dimethylaminopropyl)carbodiimide hydrochloride (105 mg), and 25% aqueous ammonia (2 mL), and the mixture was stirred at room temperature for 1 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio) and crystallized from acetonitrile. The obtained crystals were recrystallized from ethyl acetate and diethyl ether to give the title compound (136 mg, yield 68%) as white crystals.

MS 545 (MH+).

melting point 164-167° C.

$^1$H NMR (DMSO-d$_6$) δ1.63-1.78 (2H, m), 1.95 (2H, td, J=6.5, 3.2 Hz), 2.36-2.64 (2H, m), 2.99 (3H, s), 3.47 (2H, ddd, J=11.4, 8.0, 3.4 Hz), 3.96 (2H, ddd, J=11.1, 6.5, 4.0 Hz), 4.14-4.45 (3H, m), 4.59 (2H, s), 4.70-4.75 (1H, m), 6.73 (1H, d, J=1.9 Hz), 6.82 (1H, d, J=1.9 Hz), 6.89 (1H, d, J=1.9 Hz), 6.95 (1H, brs), 7.31-7.38 (1H, m), 7.41 (1H, brs), 7.43-7.48 (1H, m), 8.32 (1H, d, J=3.0 Hz), 11.83 (1H, s).

Example 27

N-Methyl-2-{2-[5-({6-[(methylsulfonyl)methyl]pyridin-3-yl}oxy)-7-(tetrahydro-2H-pyran-4-yloxy)-1H-indol-2-yl]-4,5-dihydro-1,3-thiazol-5-yl}acetamide

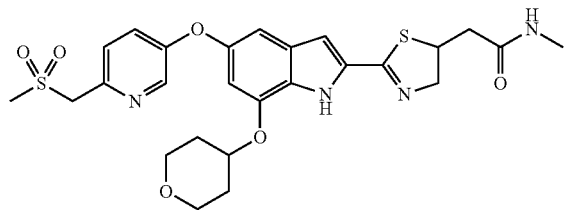

To a solution of {2-[5-({6-[(methylsulfonyl)methyl]pyridin-3-yl}oxy)-7-(tetrahydro-2H-pyran-4-yloxy)-1H-indol-2-yl]-4,5-dihydro-1,3-thiazol-5-yl}acetic acid (200 mg) in N,N-dimethylformamide (5 mL) were added 1-hydroxybenzotriazole monohydrate (84 mg), 1-ethyl-3-(3-dimethylaminopropyl)carbodiimide hydrochloride (105 mg), methylamine hydrochloride (37 mg), and triethylamine (0.080 mL), and the mixture was stirred at room temperature for 1 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio) and crystallized from acetonitrile. The obtained crystals were recrystallized from ethyl acetate and diethyl ether to give the title compound (148 mg, yield 72%) as white crystals.

MS 559 (MH+).

melting point 157-158° C.

$^1$H NMR (DMSO-d$_6$) δ1.60-1.79 (2H, m), 1.86-2.01 (2H, m), 2.33-2.56 (2H, m), 2.59 (3H, d, J=4.5 Hz), 2.99 (3H, s), 3.47 (2H, ddd, J=11.3, 8.0, 3.0 Hz), 3.96 (2H, ddd, J=11.1, 6.7, 3.8 Hz), 4.16-4.44 (3H, m), 4.59 (2H, s), 4.71-4.76 (1H, m), 6.73 (1H, d, J=1.9 Hz), 6.82 (1H, d, J=1.5 Hz), 6.89 (1H, d, J=1.9 Hz), 7.28-7.39 (1H, m), 7.42-7.49 (1H, m), 7.89 (1H, q, J=4.3 Hz), 8.32 (1H, d, J=2.7 Hz), 11.83 (1H, s).

Example 28

Ethyl{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetate

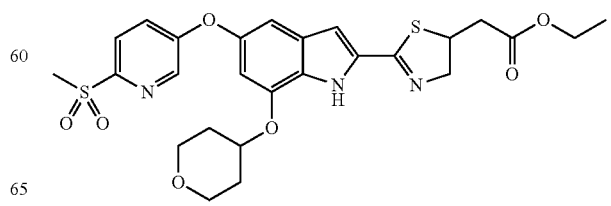

To a solution of 5-{[6-(methylsulfonyl)pyridin-3-yl]oxy}-7-(tetrahydro-2H-pyran-4-yloxy)-1H-indole-2-carbothioamide (1.4 g) in tetrahydrofuran (10 mL) and toluene (15 mL) were added ethyl 2-butynoate (0.88 g) and tri-n-butylphosphine (0.63 g), and the mixture was stirred at 90° C. for 1 hr. The reaction mixture was cooled, and concentrated under reduced pressure. The obtained crude product was subjected to silica gel column chromatography (ethyl acetate:hexane=0:100 to 100:0, volume ratio) to give the title compound (1.05 g, yield 60%) as a yellow amorphous solid.

MS 560 (MH$^+$).

$^1$H NMR (CDCl$_3$) δ1.29 (3H, t, J=7.2 Hz), 1.77-1.97 (2H, m), 2.01-2.16 (2H, m), 2.74 (2H, d, J=6.0 Hz), 3.21 (3H, s), 3.51-3.71 (2H, m), 3.95-4.08 (2H, m), 4.12-4.50 (5H, m), 4.52-4.69 (1H, m), 6.46 (1H, d, J=1.9 Hz), 6.86 (1H, d, J=2.1 Hz), 6.95 (1H, d, J=1.7 Hz), 7.33 (1H, dd, J=8.7, 2.6 Hz), 8.00 (1H, d, J=8.7 Hz), 8.44 (1H, d, J=2.6 Hz), 9.31 (1H, brs).

Example 29

2-{2-[5-{[6-(Methylsulfonyl)pyridin-3-yl]oxy}-7-(tetrahydro-2H-pyran-4-yloxy)-1H-indol-2-yl]-4,5-dihydro-1,3-thiazol-5-yl}ethanol

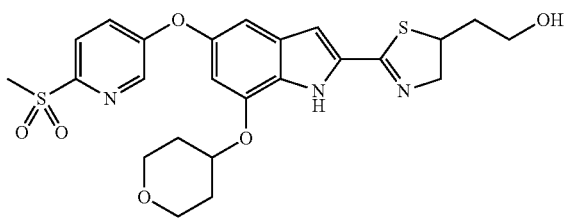 [SMILES: CS(=O)(=O)c1ccc(Oc2cc(OC3CCOCC3)c3[nH]c(C4=NCC(CCO)S4)cc3c2)cn1]

To a solution of ethyl{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetate (500 mg) in tetrahydrofuran (10 mL) and methanol (15 mL) was added at room temperature lithium tetrahydroborate (80 mg) 3 times at 30 min intervals, and the mixture was stirred at room temperature for 3 hr. Water was added to the reaction mixture, and the mixture was extracted with ethyl acetate. The organic layer was washed with saturated brine, dried over magnesium sulfate, filtered and concentrated under reduced pressure. The obtained crude product was subjected to basic silica gel column chromatography (ethyl acetate:hexane=0:100 to 100:0, volume ratio) and further to silica gel column chromatography (methanol:ethyl acetate:hexane=0:0:100 to 10:90:0, volume ratio). The obtained crude product was purified by preparative HPLC to give the title compound (112 mg, yield 24%) as a colorless amorphous solid.

MS 518 (MH$^+$).

$^1$H NMR (CDCl$_3$) δ1.76-2.16 (5H, m), 3.21 (3H, s), 3.48 (1H, qd, J=7.0, 2.0 Hz), 3.59 (2H, t, J=10.0 Hz), 3.79 (2H, brs), 4.02 (2H, t, J=9.9 Hz), 4.13-4.35 (2H, m), 4.37-4.50 (1H, m), 4.51-4.66 (1H, m), 6.42-6.49 (1H, m), 6.87 (1H, s), 6.95 (1H, t, J=1.8 Hz), 7.33 (1H, dt, J=8.7, 2.4 Hz), 7.99 (1H, dd, J=8.7, 1.5 Hz), 8.44 (1H, t, J=2.1 Hz), 9.36 (1H, brs).

Example 30

{2-[5-{[6-(Methylsulfonyl)pyridin-3-yl]oxy}-7-(tetrahydro-2H-pyran-4-yloxy)-1H-indol-2-yl]-4,5-dihydro-1,3-thiazol-5-yl}acetic acid

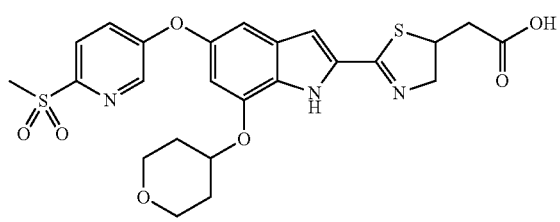 [SMILES: CS(=O)(=O)c1ccc(Oc2cc(OC3CCOCC3)c3[nH]c(C4=NCC(CC(=O)O)S4)cc3c2)cn1]

To a solution of ethyl {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetate (16.1 g) in ethanol (100 mL) and tetrahydrofuran (100 mL) was added 1N aqueous sodium hydroxide solution (58 mL), and the mixture was stirred at room temperature for 3 hr. The reaction mixture was concentrated, water was added to the residue, and the mixture was washed with ethyl acetate. To the aqueous layer was added 1N hydrochloric acid (58 mL), and the mixture was extracted with ethyl acetate. The organic layer was washed with saturated brine, dried over magnesium sulfate, filtered and concentrated under reduced pressure to give the title compound (15 g, yield 98%) as a brown amorphous solid.

MS 532 (MH$^+$).

From the obtained title compound, 200 mg was purified by preparative HPLC to give the title compound (96 mg) as a yellow powder.

MS 532 (MH$^+$).

$^1$H NMR (DMSO-d$_6$) δ1.72 (2H, dd, J=16.7, 4.2 Hz), 1.87-1.99 (2H, m), 2.58 (1H, dd, J=16.8, 8.9 Hz), 2.80 (1H, dd, J=17.0, 5.3 Hz), 3.24 (3H, s), 3.47 (2H, ddd, J=11.5, 8.0, 3.2 Hz), 3.96 (2H, dd, J=14.8, 3.4 Hz), 4.17-4.33 (2H, m), 4.35-4.50 (1H, m), 4.65-4.84 (1H, m), 6.79 (1H, d, J=1.9 Hz), 6.85 (1H, d, J=1.9 Hz), 7.01 (1H, d, J=1.5 Hz), 7.46 (1H, dd, J=8.7, 3.0 Hz), 7.99 (1H, d, J=8.7 Hz), 8.52 (1H, d, J=2.7 Hz), 11.92 (1H, s), 12.47 (1H, brs).

Example 31

2-{2-[5-{[6-(Methylsulfonyl)pyridin-3-yl]oxy}-7-(tetrahydro-2H-pyran-4-yloxy)-1H-indol-2-yl]-4,5-dihydro-1,3-thiazol-5-yl}acetamide

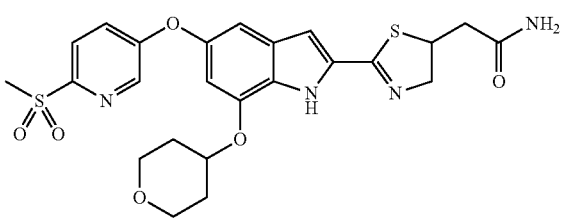 [SMILES: CS(=O)(=O)c1ccc(Oc2cc(OC3CCOCC3)c3[nH]c(C4=NCC(CC(N)=O)S4)cc3c2)cn1]

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (365 mg) in N,N-dimethylformamide (5 mL) were added 1-hydroxybenzotriazole monohydrate (158 mg), 1-ethyl-3-(3-dimethylaminopropyl)

carbodiimide hydrochloride (198 mg), and 25% aqueous ammonia (2.7 mL), and the mixture was stirred at room temperature for 1 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio), and crystallized from acetonitrile. The obtained crystals were recrystallized from ethyl acetate and diethyl ether to give the title compound (127 mg, yield 35%) as white crystals.

MS 531 (MH+).

melting point 136-138° C.

$^1$H NMR (DMSO-$d_6$) δ1.60-1.81 (2H, m), 1.95 (2H, ddd, J=9.7, 6.2, 3.0 Hz), 2.37-2.50 (1H, m), 2.53-2.62 (1H, m), 3.24 (3H, s), 3.47 (2H, ddd, J=11.4, 8.0, 3.4 Hz), 3.97 (2H, ddd, J=11.2, 6.6, 3.8 Hz), 4.16-4.48 (3H, m), 4.74 (1H, m), 6.79 (1H, d, J=1.9 Hz), 6.85 (1H, d, J=1.9 Hz), 6.96 (1H, brs), 7.01 (1H, d, J=1.9 Hz), 7.41 (1H, brs), 7.46 (1H, dd, J=8.7, 2.7 Hz), 7.99 (1H, d, J=8.7 Hz), 8.52 (1H, d, J=2.7 Hz), 11.92 (1H, s).

Example 32

2-{2-[5-{[6-(Methylsulfonyl)pyridin-3-yl]oxy}-7-(tetrahydro-2H-pyran-4-yloxy)-1H-indol-2-yl]-4,5-dihydro-1,3-thiazol-5-yl}acetamide

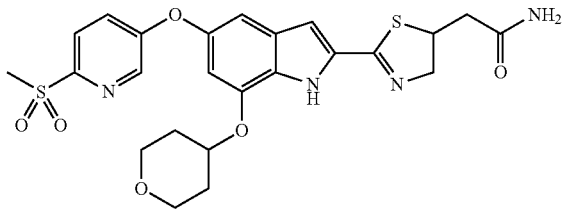 [SMILES: CS(=O)(=O)c1ccc(Oc2cc(OC3CCOCC3)c3[nH]c(C4=NCC(CC(N)=O)S4)cc3c2)cn1]

2-{2-[5-{[6-(Methylsulfonyl)pyridin-3-yl]oxy}-7-(tetrahydro-2H-pyran-4-yloxy)-1H-indol-2-yl]-4,5-dihydro-1,3-thiazol-5-yl}acetamide (12.0 mg) was dissolved in 2-propanol (12.0 mL), and the solution was subjected to supercritical fluid chromatography using CHIRALPAK AD-H (manufactured by DAICEL CHEMICAL INDUSTRIES, LTD.) and eluted with mobile phase: carbon dioxide-2-propanol (700:300, volume ratio) at 100 bar, 35° C., flow rate 50 mL/min. The peak at retention time 8.86 min was separated, concentrated and freeze-dried to give the title compound (5.7 mg) as a white solid.

MS 531 (MH+).

Example 33

2-{2-[5-{[6-(Methylsulfonyl)pyridin-3-yl]oxy}-7-(tetrahydro-2H-pyran-4-yloxy)-1H-indol-2-yl]-4,5-dihydro-1,3-thiazol-5-yl}acetamide

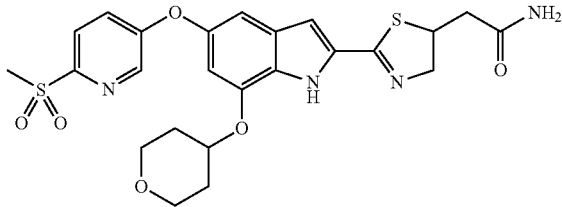 [SMILES: CS(=O)(=O)c1ccc(Oc2cc(OC3CCOCC3)c3[nH]c(C4=NCC(CC(N)=O)S4)cc3c2)cn1]

2-{2-[5-{[6-(Methylsulfonyl)pyridin-3-yl]oxy}-7-(tetrahydro-2H-pyran-4-yloxy)-1H-indol-2-yl]-4,5-dihydro-1,3-thiazol-5-yl}acetamide (12.0 mg) was dissolved in 2-propanol (12.0 mL), and the solution was subjected to supercritical fluid chromatography using CHIRALPAK AD-H (manufactured by DAICEL CHEMICAL INDUSTRIES, LTD.) and eluted with mobile phase: carbon dioxide-2-propanol (700:300, volume ratio) at 100 bar, 35° C., flow rate 50 mL/min. The peak at retention time 11.45 min was separated, concentrated and freeze-dried to give the title compound (6.1 mg) as a white solid.

MS 531 (MH+).

Example 34

N-methyl-2-{2-[5-{[6-(Methylsulfonyl)pyridin-3-yl]oxy}-7-(tetrahydro-2H-pyran-4-yloxy)-1H-indol-2-yl]-4,5-dihydro-1,3-thiazol-5-yl}acetamide

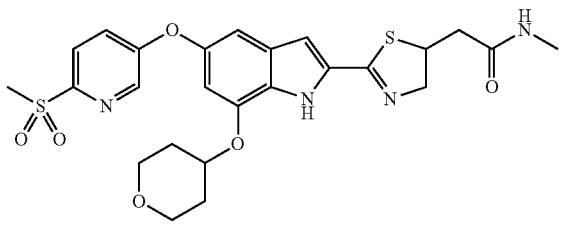

To a solution of (2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl]acetic acid (365 mg) in N,N-dimethylformamide (5 mL) were added 1-hydroxybenzotriazole monohydrate (158 mg), 1-ethyl-3-(3-dimethylaminopropyl)carbodiimide hydrochloride (198 mg), methylamine hydrochloride (70 mg), and triethylamine (0.144 mL), and the mixture was stirred at room temperature for 1 hr. 1N HCl was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio), and crystallized from acetonitrile. The obtained crystals were recrystallized from ethyl acetate and diethyl ether to give the title compound (115 mg, yield 31%) as white powder.

MS 545 (MH+).

melting point 143-144° C.

$^1$H NMR (DMSO-$d_6$) δ1.60-1.80 (2H, m), 1.88-2.00 (2H, m), 2.36-2.47 (1H, m), 2.53-2.62 (1H, m), 2.59 (3H, d, J=4.5 Hz), 3.24 (3H, s), 3.41-3.54 (2H, m), 3.97 (2H, ddd, J=11.0, 6.4, 3.8 Hz), 4.14-4.47 (3H, m), 4.72-4.74 (1H, m), 6.79 (1H, d, J=1.5 Hz), 6.85 (1H, d, J=1.5 Hz), 7.01 (1H, d, J=1.5 Hz), 7.45 (1H, dd, J=8.7, 2.7 Hz), 7.89 (1H, d, J=4.5 Hz), 7.99 (1H, d, J=9.1 Hz), 8.52 (1H, d, J=2.7 Hz), 11.91 (1H, s).

Example 35

N-Methyl-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide

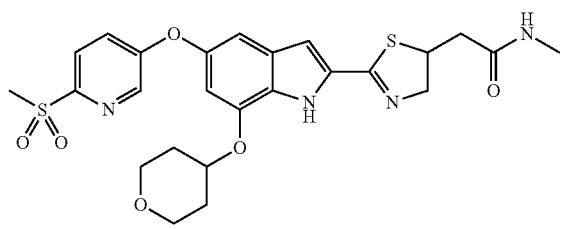

N-Methyl-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide (12.8 mg) was dissolved in ethanol (2.4 mL), and the solution was subjected to supercritical fluid chromatography using CHIRALPAK AD-H (manufactured by DAICEL CHEMICAL INDUSTRIES, LTD.) and eluted with mobile phase: carbon dioxide-ethanol (600:400, volume ratio) at 100 bar, 35° C., flow rate 60 mL/min. The peak at retention time 6.64 min was separated, concentrated and freeze-dried to give the title compound (6.2 mg) as a white solid.

MS 545 (MH$^+$).

Example 36

N-Methyl-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide

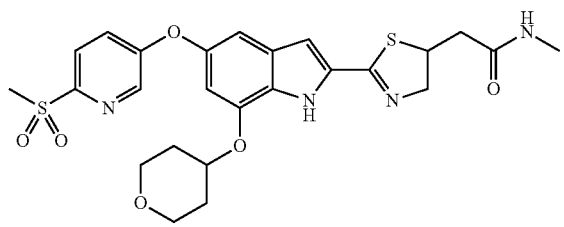

N-methyl-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide (12.8 mg) was dissolved in ethanol (2.4 mL), and the solution was subjected to supercritical fluid chromatography using CHIRALPAK AD-H (manufactured by DAICEL CHEMICAL INDUSTRIES, LTD.) and eluted with mobile phase: carbon dioxide-ethanol (600:400, volume ratio) at 100 bar, 35° C., flow rate 60 mL/min. The peak at retention time 10.55 min was separated, concentrated and freeze-dried to give the title compound (6.5 mg) as a white solid.

MS 545 (MH$^+$).

Example 37

N-Cyclopropyl-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide

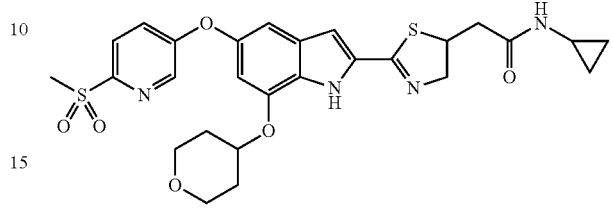

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (150 mg) in N,N-dimethylformamide (5 mL) were added 1-hydroxybenzotriazole monohydrate (65 mg), 1-ethyl-3-(3-dimethylaminopropyl)carbodiimide hydrochloride (81 mg), and cyclopropylamine (32 mg), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio), and crystallized from acetonitrile. The obtained crystals were recrystallized from ethyl acetate and diethyl ether to give the title compound (67 mg, yield 42%) as white crystals.

MS 571 (MH$^+$).

melting point 175-176° C.

$^1$H NMR (DMSO-d$_6$) δ0.32-0.42 (2H, m), 0.55-0.65 (2H, m), 1.63-1.79 (2H, m), 1.86-2.03 (2H, m), 2.34-2.46 (1H, m), 2.53-2.74 (2H, m), 3.24 (3H, s), 3.47 (2H, ddd, J=11.4, 8.0, 3.2 Hz), 3.90-4.02 (2H, m), 4.16-4.47 (3H, m), 4.68-4.80 (1H, m), 6.79 (1H, d, J=1.9 Hz), 6.85 (1H, d, J=1.9 Hz), 7.01 (1H, d, J=1.9 Hz), 7.45 (1H, dd, J=8.7, 2.6 Hz), 7.99 (1H, d, J=8.7 Hz), 8.02 (1H, d, J=4.5 Hz), 8.52 (1H, d, J=2.6 Hz), 11.91 (1H, s).

Example 38

5-{[6-(Methylsulfonyl)pyridin-3-yl]oxy}-2-[5-(2-morpholin-4-yl-2-oxoethyl)-4,5-dihydro-1,3-thiazol-2-yl]-7-(tetrahydro-2H-pyran-4-yloxy)-1H-indole

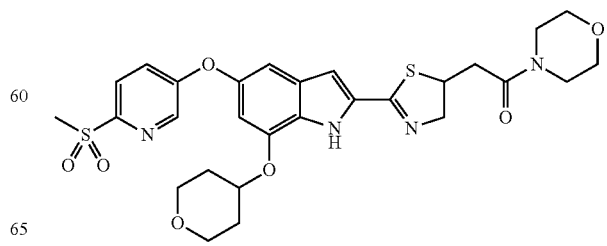

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (150 mg) in N,N-dimethylformamide (5 mL) were added 1-hydroxybenzotriazole monohydrate (65 mg), 1-ethyl-3-(3-dimethylaminopropyl) carbodiimide hydrochloride (81 mg), and morpholine (49 mg), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio) to give the title compound (102 mg, yield 60%) as a pale-yellow amorphous solid.

MS 601 (MH$^+$).

$^1$H NMR (DMSO-d$_6$) δ1.59-1.82 (2H, m), 1.87-1.99 (2H, m), 2.65-2.95 (2H, m), 3.24 (3H, s), 3.36-3.63 (10H, m), 3.88-4.02 (2H, m), 4.17-4.56 (3H, m), 4.64-4.82 (1H, m), 6.78 (1H, d, J=1.9 Hz), 6.84 (1H, d, J=1.9 Hz), 7.01 (1H, d, J=1.9 Hz), 7.45 (1H, dd, J=8.9, 2.8 Hz), 7.99 (1H, d, J=8.7 Hz), 8.52 (1H, d, J=2.6 Hz), 11.89 (1H, s).

Example 39

N-(2-Hydroxy-2-methylpropyl)-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide

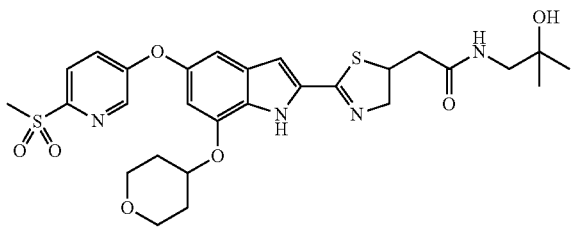 [SMILES: CC(C)(O)CNC(=O)CC1CN=C(c2cc3cc(Oc4ccc(S(C)(=O)=O)nc4)cc(OC4CCOCC4)c3[nH]2)S1]

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (150 mg) in N,N-dimethylformamide (5 mL) were added 1-hydroxybenzotriazole monohydrate (65 mg), 1-ethyl-3-(3-dimethylaminopropyl) carbodiimide hydrochloride (81 mg), and 1-amino-2-methylpropan-2-ol (50 mg), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio), and crystallized from acetonitrile. The obtained crystals were recrystallized from ethyl acetate and diethyl ether to give the title compound (97 mg, yield 57%) as white crystals.

MS 603 (MH$^+$).

melting point 195-196° C.

$^1$H NMR (DMSO-d$_6$) δ1.06 (6H, s), 1.60-1.80 (2H, m), 1.88-2.01 (2H, m), 2.52-2.73 (2H, m), 3.04 (2H, d, J=6.0 Hz), 3.24 (3H, s), 3.47 (2H, ddd, J=11.3, 7.9, 3.4 Hz), 3.87-4.04 (2H, m), 4.14-4.44 (4H, m), 4.66-4.82 (1H, m), 6.79 (1H, d, J=2.3 Hz), 6.84 (1H, d, J=2.3 Hz), 7.01 (1H, d, J=1.9 Hz), 7.45 (1H, dd, J=8.7, 3.0 Hz), 7.86 (1H, t, J=6.0 Hz), 7.99 (1H, d, J=8.7 Hz), 8.52 (1H, d, J=2.3 Hz), 11.92 (1H, s).

Example 40

N-[(3-Methyloxetan-3-yl)methyl]-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide

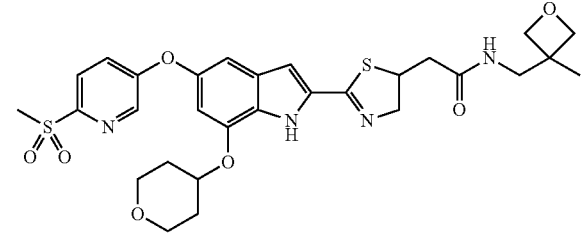

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (150 mg) in N,N-dimethylformamide (5 mL) were added 1-hydroxybenzotriazole monohydrate (65 mg), 1-ethyl-3-(3-dimethylaminopropyl) carbodiimide hydrochloride (81 mg), and 1-(3-methyloxetan-3-yl)methanamine (57 mg), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio), and crystallized from acetonitrile. The obtained crystals were recrystallized from ethyl acetate and diethyl ether to give the title compound (106 mg, yield 61%) as white crystals.

MS 615 (MH$^+$).

melting point 189-190° C.

$^1$H NMR (DMSO-d$_6$) δ1.21 (3H, s), 1.59-1.80 (2H, m), 1.85-2.03 (2H, m), 2.51-2.79 (2H, m), 3.24 (3H, s), 3.28 (2H, d, J=6.0 Hz), 3.47 (2H, ddd, J=11.3, 7.9, 3.4 Hz), 3.89-4.03 (2H, m), 4.17 (2H, d, J=5.7 Hz), 4.21-4.47 (5H, m), 4.64-4.84 (1H, m), 6.79 (1H, d, J=1.9 Hz), 6.84 (1H, d, J=1.9 Hz), 7.01 (1H, d, J=1.9 Hz), 7.45 (1H, dd, J=8.9, 2.8 Hz), 7.99 (1H, d, J=9.0 Hz), 8.14 (1H, t, J=6.2 Hz), 8.52 (1H, d, J=2.6 Hz), 11.93 (1H, s).

Example 41

N,N-Dimethyl-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide

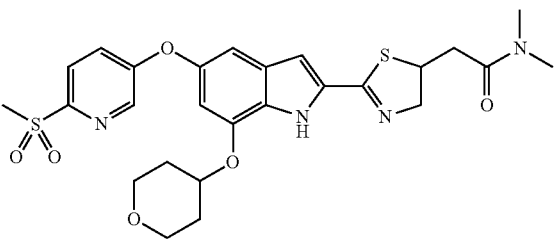

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (150 mg) in N,N-dimethylformamide (5 mL) were added 1-hydroxybenzotriazole monohydrate (65 mg), 1-ethyl-3-(3-dimethylaminopropyl) carbodiimide hydrochloride (81 mg), and 2M dimethylamine tetrahydrofuran solution (0.29 mL), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio) to give the title compound (102 mg, yield 60%) as a pale-yellow amorphous solid.

MS 559(MH$^+$).

$^1$H NMR (DMSO-d$_6$) δ1.60-1.80 (2H, m), 1.87-2.01 (2H, m), 2.63-2.79 (1H, m), 2.84 (3H, s), 2.85-2.92 (1H, m), 2.93 (3H, s), 3.24 (3H, s), 3.47 (2H, ddd, J=11.3, 7.9, 3.4 Hz), 3.97 (2H, ddd, J=10.9, 6.4, 3.8 Hz), 4.15-4.32 (2H, m), 4.35-4.52 (1H, m), 4.72-4.74 (1H, m), 6.78 (1H, d, J=1.9 Hz), 6.83 (1H, d, J=1.9 Hz), 7.00 (1H, d, J=1.9 Hz), 7.45 (1H, dd, J=8.9, 2.8 Hz), 7.99 (1H, d, J=9.0 Hz), 8.52 (1H, d, J=2.6 Hz), 11.89 (1H, s).

Example 42

N-Ethyl-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide

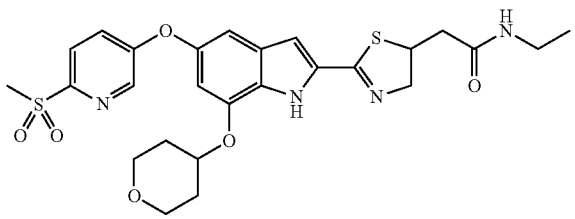

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (150 mg) in N,N-dimethylformamide (5 mL) were added 1-hydroxybenzotriazole monohydrate (65 mg), 1-ethyl-3-(3-dimethylaminopropyl) carbodiimide hydrochloride (81 mg), and 2M ethylamine tetrahydrofuran solution (0.29 mL), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio), and crystallized from acetonitrile. The obtained crystals were recrystallized from ethyl acetate and diethyl ether to give the title compound (80 mg, yield 51%) as white crystals.

MS 559 (MH$^+$).

melting point 197-198° C.

$^1$H NMR (DMSO-d$_6$) δ1.02 (3H, t, J=7.3 Hz), 1.60-1.79 (2H, m), 1.88-2.01 (2H, m), 2.38-2.48 (1H, m), 2.52-2.62 (1H, m), 2.99-3.16 (2H, m), 3.24 (3H, s), 3.47 (2H, ddd, J=11.2, 7.8, 3.2 Hz), 3.91-4.02 (2H, m), 4.17-4.48 (3H, m), 4.65-4.82 (1H, m), 6.79 (1H, d, J=1.9 Hz), 6.85 (1H, d, J=1.1 Hz), 7.01 (1H, d, J=1.9 Hz), 7.45 (1H, dd, J=8.9, 2.8 Hz), 7.95 (1H, t, J=5.5 Hz), 7.99 (1H, d, J=9.0 Hz), 8.52 (1H, d, J=2.6 Hz), 11.92 (1H, s).

Example 43

2-{2-[5-{[6-(Methylsulfonyl)pyridin-3-yl]oxy}-7-(tetrahydro-2H-pyran-4-yloxy)-1H-indol-2-yl]-4,5-dihydro-1,3-thiazol-5-yl}-N-(2,2,2-trifluoroethyl)acetamide

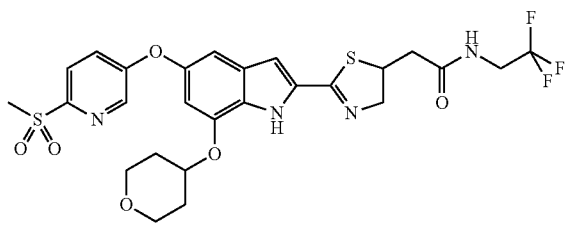 [SMILES: CS(=O)(=O)c1ccc(Oc2cc(OC3CCOCC3)c3[nH]c(C4=NCC(CC(=O)NCC(F)(F)F)S4)cc3c2)cn1]

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (150 mg) in N,N-dimethylformamide (5 mL) were added 1-hydroxybenzotriazole monohydrate (65 mg), 1-ethyl-3-(3-dimethylaminopropyl) carbodiimide hydrochloride (81 mg), and 2,2,2-trifluoroethylamine (56 mg), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio) to give the title compound (102 mg, yield 60%) as a pale-yellow amorphous solid.

MS 613(MH$^+$).

$^1$H NMR (DMSO-d$_6$) δ1.60-1.82 (2H, m), 1.87-2.01 (2H, m), 2.51-2.62 (1H, m), 2.65-2.77 (1H, m), 3.24 (3H, s), 3.47 (2H, ddd, J=11.2, 8.0, 3.0 Hz), 3.77-4.07 (4H, m), 4.17-4.47 (3H, m), 4.68-4.83 (1H, m), 6.79 (1H, d, J=1.9 Hz), 6.85 (1H, d, J=1.9 Hz), 7.01 (1H, d, J=1.9 Hz), 7.45 (1H, dd, J=8.7, 2.6 Hz), 7.99 (1H, d, J=8.7 Hz), 8.52 (1H, d, J=2.6 Hz), 8.66 (1H, t, J=6.2 Hz), 11.94 (1H, s).

Example 44

N-(2-Hydroxyethyl)-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide

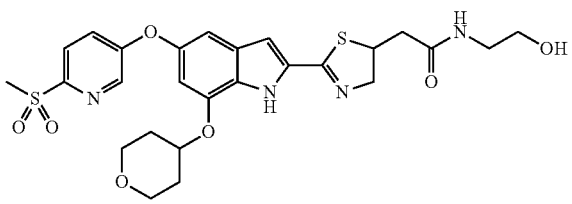 [SMILES: CS(=O)(=O)c1ccc(Oc2cc(OC3CCOCC3)c3[nH]c(C4=NCC(CC(=O)NCCO)S4)cc3c2)cn1]

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (150 mg) in N,N-dimethylformamide (5 mL) were added 1-hydroxybenzotriazole monohydrate (65 mg), 1-ethyl-3-(3-dimethylaminopropyl)carbodiimide hydrochloride (81 mg), and 2-aminoethanol (35 mg), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio), and crystallized from acetonitrile. The obtained crystals were recrystallized from ethyl acetate and diethyl ether to give the title compound (86 mg, yield 53%) as white crystals.

MS 575 (MH$^+$).

melting point 157-158° C.

$^1$H NMR (DMSO-d$_6$) δ1.58-1.79 (2H, m), 1.87-2.02 (2H, m), 2.40-2.55 (1H, m), 2.55-2.67 (1H, m), 3.13 (2H, ddd, J=11.6, 6.2, 5.9 Hz), 3.24 (3H, s), 3.34-3.54 (4H, m), 3.88-4.02 (2H, m), 4.15-4.48 (3H, m), 4.66 (1H, t, J=5.3 Hz), 4.74 (1H, brs), 6.79 (1H, s), 6.85 (1H, s), 7.01 (1H, s), 7.45 (1H, dd, J=8.7, 2.6 Hz), 7.99 (1H, d, J=8.3 Hz), 7.96 (1H, brs), 8.52 (1H, d, J=2.3 Hz), 11.92 (1H, brs.).

Example 45

N-(2-Hydroxyethyl)-N-methyl-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide

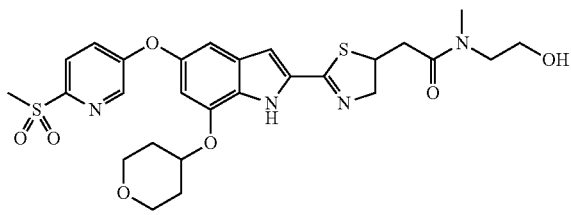 [SMILES: CN(CCO)C(=O)CC1CN=C(c2cc3cc(Oc4ccc(S(C)(=O)=O)nc4)cc(OC4CCOCC4)c3[nH]2)S1]

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (150 mg) in N,N-dimethylformamide (5 mL) were added 1-hydroxybenzotriazole monohydrate (65 mg), 1-ethyl-3-(3-dimethylaminopropyl)carbodiimide hydrochloride (81 mg), and 2-(methylamino)ethanol (42 mg), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio) to give the title compound (102 mg, yield 60%) as a pale-yellow amorphous solid.

MS 589(MH$^+$).

Anal. Calcd for C$_{27}$H$_{32}$N$_4$O$_7$S$_2$: C,55.09;H,5.48; N,9.52. Found: C,54.76;H,5.58; N,9.79.

Example 46

N-(2-Methoxyethyl)-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide

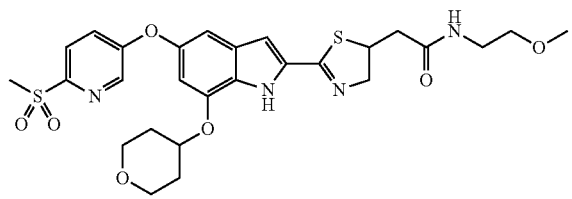

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (150 mg) in N,N-dimethylformamide (5 mL) were added 1-hydroxybenzotriazole monohydrate (65 mg), 1-ethyl-3-(3-dimethylaminopropyl)carbodiimide hydrochloride (81 mg), and 2-methoxyethylamine (42 mg), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio), and crystallized from hexane to give the title compound (102 mg, yield 60%) as a pale-yellow amorphous solid.

MS 589(MH$^+$).

$^1$H NMR (DMSO-d$_6$) δ1.61-1.82 (2H, m), 1.86-2.02 (2H, m), 2.42-2.49 (1H, m), 2.53-2.66 (1H, m), 3.15-3.27 (2H, m), 3.24 (3H, s), 3.25 (3H, s), 3.29-3.38 (2H, m), 3.47 (2H, ddd, J=11.3, 7.9, 3.4 Hz), 3.89-4.03 (2H, m), 4.12-4.48 (3H, m), 4.65-4.83 (1H, m), 6.79 (1H, d, J=1.9 Hz), 6.85 (1H, d, J=2.3 Hz), 7.01 (1H, d, J=1.9 Hz), 7.45 (1H, dd, J=8.7, 3.0 Hz), 7.99 (1H, d, J=9.0 Hz), 8.06 (1H, t, J=5.5 Hz), 8.52 (1H, d, J=2.6 Hz), 11.92 (1H, s).

Example 47

2-{5-[2-(1,1-Dioxidothiomorpholin-4-yl)-2-oxoethyl]-4,5-dihydro-1,3-thiazol-2-yl}-5-{[6-(methylsulfonyl)pyridin-3-yl]oxy}-7-(tetrahydro-2H-pyran-4-yloxy)-1H-indole

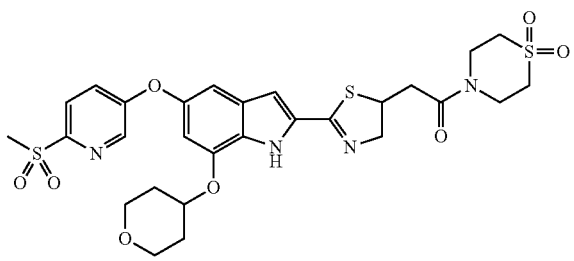 [SMILES: CS(=O)(=O)c1ccc(Oc2cc(OC3CCOCC3)c3[nH]c(C4=NCC(CC(=O)N5CCS(=O)(=O)CC5)S4)cc3c2)cn1]

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (150 mg) in N,N-dimethylformamide (5 mL) were added 1-hydroxybenzotriazole monohydrate (65 mg), 1-ethyl-3-(3-dimethylaminopropyl) carbodiimide hydrochloride (81 mg), and thiomorpholine-1,1-dioxide (76 mg), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio) and crystallized from acetonitrile to give the title compound (136 mg, yield 74%) as white crystals.

MS 649 (MH$^+$).

$^1$H NMR (DMSO-d$_6$) δ1.62-1.80 (2H, m), 1.87-2.02 (2H, m), 2.83-3.04 (2H, m), 3.10 (2H, t, J=5.3 Hz), 3.24 (5H, s), 3.47 (2H, ddd, J=11.3, 7.9, 3.0 Hz), 3.67-4.07 (6H, m), 4.19-4.35 (2H, m), 4.38-4.53 (1H, m), 4.64-4.81 (1H, m), 6.79 (1H, d, J=1.9 Hz), 6.83 (1H, d, J=1.5 Hz), 7.01 (1H, d, J=1.9 Hz), 7.45 (1H, dd, J=8.7, 3.0 Hz), 7.99 (1H, d, J=8.7 Hz), 8.52 (1H, d, J=2.6 Hz), 11.90 (1H, s).

Example 48

N-[2-(Methylsulfonyl)ethyl]-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide

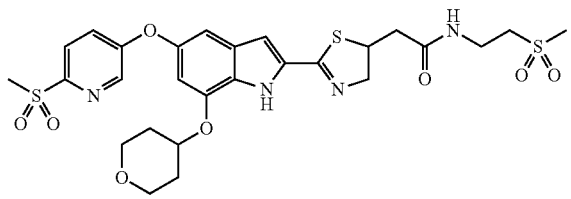

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (150 mg) in N,N-dimethylformamide (5 mL) were added 1-hydroxybenzotriazole monohydrate (65 mg), 1-ethyl-3-(3-dimethylaminopropyl) carbodiimide hydrochloride (81 mg), 2-(methylsulfonyl)ethaneamine hydrochloride (90 mg), and triethylamine (120 μL), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (methanol:ethyl acetate:hexane=0:0:100 to 10:90:0, volume ratio) to give the title compound (111 mg, yield 62%) as a pale-yellow amorphous solid.

MS 637(MH$^+$).

$^1$H NMR (DMSO-d$_6$) δ1.61-1.80 (2H, m), 1.86-2.02 (2H, m), 2.41-2.49 (1H, m), 2.56-2.66 (1H, m), 3.01 (3H, s), 3.24 (3H, s), 3.24-3.29 (2H, m), 3.37-3.57 (4H, m), 3.97 (2H, ddd, J=11.0, 6.7, 3.8 Hz), 4.14-4.44 (3H, m), 4.64-4.81 (1H, m), 6.79 (1H, d, J=1.9 Hz), 6.85 (1H, d, J=1.9 Hz), 7.01 (1H, d, J=1.9 Hz), 7.45 (1H, dd, J=8.7, 2.6 Hz), 7.99 (1H, d, J=8.7 Hz), 8.27 (1H, t), 8.52 (1H, d, J=2.6 Hz), 11.93 (1H, s).

Example 49

N-(Cyanomethyl)-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide

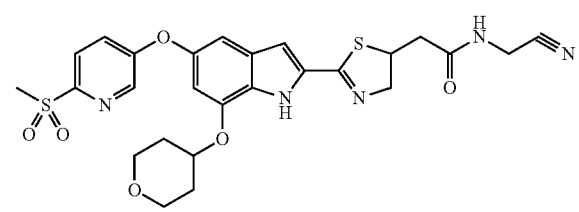 [SMILES: CS(=O)(=O)c1ccc(Oc2cc(OC3CCOCC3)c3[nH]c(C4=NCC(CC(=O)NCC#N)S4)cc3c2)cn1]

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (150 mg) in N,N-dimethylformamide (5 mL) were added 1-hydroxybenzotriazole monohydrate (65 mg), 1-ethyl-3-(3-dimethylaminopropyl) carbodiimide hydrochloride (81 mg), aminoacetonitrile hydrochloride (52 mg), and triethylamine (120 μL), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (methanol:ethyl acetate:hexane=0:0:100 to 10:90:0, volume ratio), and crystallized from acetonitrile to give the title compound (103 mg, yield 64%) as white crystals.

MS 570 (MH$^+$).

$^1$H NMR (DMSO-d$_6$) δ1.60-1.80 (2H, m), 1.87-2.03 (2H, m), 2.52-2.75 (2H, m), 3.24 (3H, s), 3.38-3.60 (2H, m), 3.87-4.04 (2H, m), 4.17 (2H, d, J=5.7 Hz), 4.20-4.47 (3H, m), 4.63-4.84 (1H, m), 6.79 (1H, d, J=1.9 Hz), 6.86 (1H, d, J=1.9 Hz), 7.01 (1H, d, J=1.9 Hz), 7.45 (1H, dd, J=8.7, 2.6 Hz), 7.99 (1H, d, J=8.7 Hz), 8.52 (1H, d, J=2.6 Hz), 8.72 (1H, t, J=5.7 Hz), 11.94 (1H, s).

Example 50

N-(1-Methylethyl)-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide

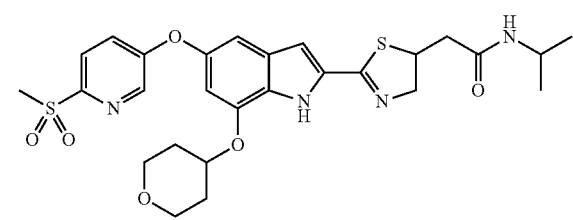 [SMILES: CC(C)NC(=O)CC1CN=C(c2cc3cc(Oc4ccc(S(C)(=O)=O)nc4)cc(OC4CCOCC4)c3[nH]2)S1]

To a solution of {2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetic acid (150 mg) in N,N-dimethylformamide (5 mL) were added 1-hydroxybenzotriazole monohydrate (65 mg), 1-ethyl-3-(3-dimethylaminopropyl)carbodiimide hydrochloride (81 mg), and isopropylamine (34 mg), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate:hexane=0:100 to 100:0, volume ratio) and crystallized from acetonitrile to give the title compound (128 mg, yield 79%) as white crystals.

MS 573(MH$^+$).

$^1$H NMR (DMSO-d$_6$) δ1.05 (6H, dd, J=6.4, 1.5 Hz), 1.60-1.81 (2H, m), 1.86-2.01 (2H, m), 2.35-2.58 (2H, m), 3.24 (3H, s), 3.47 (2H, ddd, J=11.3, 7.9, 3.0 Hz), 3.76-3.91 (1H, m), 3.91-4.09 (2H, m), 4.16-4.47 (3H, m), 4.66-4.82 (1H, m), 6.79 (1H, d, J=1.9 Hz), 6.85 (1H, d, J=1.9 Hz), 7.01 (1H, d, J=1.9 Hz), 7.45 (1H, dd, J=8.7, 3.0 Hz), 7.83 (1H, d, J=7.5 Hz), 7.99 (1H, d, J=8.7 Hz), 8.52 (1H, d, J=2.3 Hz), 11.92 (1H, s).

Example 51

Ethyl[2-(5-{[6-(methylsulfonyl)pyridin-3-yl]oxy}-1H-indol-2-yl)-4,5-dihydro-1,3-thiazol-5-yl]acetate

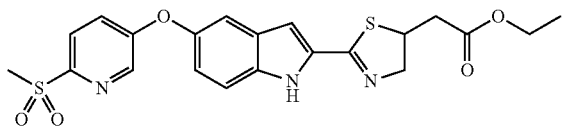 [SMILES: CCOC(=O)CC1CN=C(c2cc3cc(Oc4ccc(S(C)(=O)=O)nc4)ccc3[nH]2)S1]

To a solution of 5-{([6-(methylsulfonyl)pyridin-3-yl]oxy}-1H-indole-2-carbothioamide (3.7 g) in tetrahydrofuran (50 mL) and toluene (75 mL) were added ethyl 2-butynoate (3 g) and tri-n-butylphosphine (2.16 g); and the mixture was stirred at 90° C. under argon atmosphere for 15 min. The reaction mixture was cooled, and concentrated under reduced pressure. The obtained crude product was subjected to basic silica gel column chromatography (ethyl acetate:hexane=0:100 to 70:30, volume ratio) to give the title compound (4.0 g, yield 82%) as a brown amorphous solid.

MS 460 (MH$^+$).

$^1$H NMR (CDCl$_3$) δ1.28 (3H, t, J=7.5 Hz), 2.74 (2H, d, J=6.0 Hz), 3.21 (3H, s), 4.14-4.49 (5H, m), 6.90 (1H, d, J=1.5 Hz), 7.02 (1H, dd, J=8.7, 2.3 Hz), 7.31 (1H, dd, J=8.7, 2.6 Hz), 7.36 (1H, d, J=2.3 Hz), 7.43 (1H, d, J=9.0 Hz), 7.99 (1H, d, J=8.7 Hz), 8.45 (1H, d, J=2.3 Hz), 9.44 (1H, brs).

Example 52

[2-(5-{[6-(Methylsulfonyl)pyridin-3-yl]oxy}-1H-indol-2-yl)-4,5-dihydro-1,3-thiazol-5-yl]acetic acid

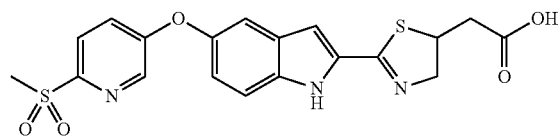 [SMILES: CS(=O)(=O)c1ccc(Oc2ccc3[nH]c(C4=NCC(CC(=O)O)S4)cc3c2)cn1]

To a solution of ethyl [2-(5-{[6-(methylsulfonyl)pyridin-3-yl]oxy}-1H-indol-2-yl)-4,5-dihydro-1,3-thiazol-5-yl]acetate (4 g) in ethanol (50 mL) and tetrahydrofuran (50 mL) was added 1N aqueous sodium hydroxide solution (17.4 mL), and the mixture was stirred at room temperature for 15 hr. The reaction mixture was concentrated, and water was added to the residue, and the mixture was washed with ethyl acetate. To the aqueous layer was added 1N hydrochloric acid for neutralization, and the mixture was extracted with ethyl acetate. The organic layer was washed with saturated brine, dried over magnesium sulfate, filtered and concentrated under reduced pressure, and crystallized from ethyl acetate and diethyl ether to give the title compound (2.2 g, yield 59%) as yellow powder.

MS 432 (MH$^+$).

melting point 205-208° C.

$^1$H NMR (DMSO-d$_6$) δ2.59 (1H, dd, J=17.0, 9.1 Hz), 2.72-2.88 (1H, m), 3.24 (3H, s), 4.13-4.51 (3H, m), 6.87 (1H, d, J=1.9 Hz), 7.08 (1H, dd, J=8.9, 2.5 Hz), 7.38-7.56 (3H, m), 8.00 (1H, d, J=8.7 Hz), 8.53 (1H, d, J=3.0 Hz), 11.95 (1H, d, J=1.5 Hz), 12.50 (1H, brs).

Example 53

N-Methyl-2-[2-(5-{[6-(methylsulfonyl)pyridin-3-yl]oxy}-1H-indol-2-yl)-4,5-dihydro-1,3-thiazol-5-yl]acetamide

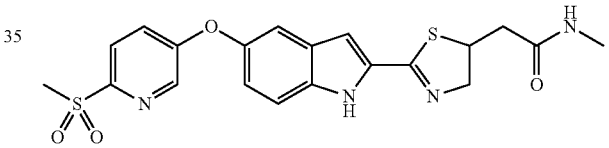

To a solution of [2-(5-{[6-(methylsulfonyl)pyridin-3-yl]oxy}-1H-indol-2-yl)-4,5-dihydro-1,3-thiazol-5-yl]acetic acid (150 mg) in N,N-dimethylformamide (5 mL) were added 1-hydroxybenzotriazole monohydrate (80 mg), 1-ethyl-3-(3-dimethylaminopropyl)carbodiimide hydrochloride (100 mg), methylamine hydrochloride (47 mg), and triethylamine (100 μL), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (methanol:ethyl acetate:hexane=0:0:100 to 10:90:0, volume ratio) and crystallized from acetonitrile to give the title compound (64 mg, yield 41%) as white crystals.

MS 445 (MH$^+$).

melting point 150-152° C.

$^1$H NMR (DMSO-d$_6$) δ2.36-2.48 (1H, m), 2.52-2.63 (4H, m), 3.24 (3H, s), 4.10-4.48 (3H, m), 6.87 (1H, d, J=1.5 Hz), 7.08 (1H, dd, J=8.7, 2.3 Hz), 7.38-7.55 (3H, m), 7.89 (1H, q, J=8.7 Hz), 8.53 (1H, d, J=2.6 Hz), 11.95 (1H, s).

Example 54

N-Ethyl-2-[2-(5-{[6-(methylsulfonyl)pyridin-3-yl]oxy}-1H-indol-2-yl)-4,5-dihydro-1,3-thiazol-5-yl]acetamide

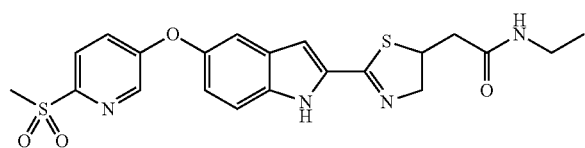 [SMILES: CCNC(=O)CC1CN=C(c2cc3cc(Oc4ccc(S(C)(=O)=O)nc4)ccc3[nH]2)S1]

To a solution of [2-(5-{[6-(methylsulfonyl)pyridin-3-yl]oxy}-1H-indol-2-yl)-4,5-dihydro-1,3-thiazol-5-yl]acetic acid (150 mg) in N,N-dimethylformamide (5 mL) were added 1-hydroxybenzotriazole monohydrate (80 mg), 1-ethyl-3-(3-dimethylaminopropyl)carbodiimide hydrochloride (100 mg), and 2M ethylamine tetrahydrofuran solution (0.35 mL), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (methanol:ethyl acetate:hexane=0:0:100 to 10:90:0, volume ratio) and crystallized from acetonitrile to give the title compound (89 mg, yield 56%) as white crystals.

MS 459 (MH$^+$).

melting point 216-217° C.

$^1$H NMR (DMSO-d$_6$) δ1.02 (3H, t, J=7.2 Hz), 2.38-2.48 (1H, m), 2.53-2.62 (1H, m), 2.94-3.16 (2H, m), 3.24 (3H, s), 4.11-4.47 (3H, m), 6.87 (1H, s), 7.08 (1H, dd, J=8.9, 2.4 Hz), 7.36-7.54 (3H, m), 7.89-8.03 (2H, m), 8.53 (1H, d, J=2.6 Hz), 11.95 (1H, s).

Example 55

N,N-Dimethyl-2-[2-(5-{[6-(methylsulfonyl)pyridin-3-yl]oxy}-1H-indol-2-yl)-4,5-dihydro-1,3-thiazol-5-yl]acetamide

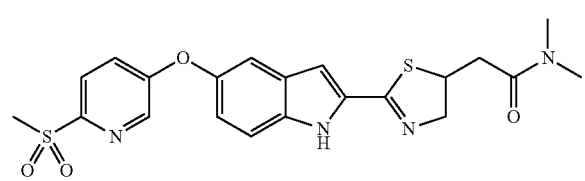

To a solution of [2-(5-{[6-(methylsulfonyl)pyridin-3-yl]oxy}-1H-indol-2-yl)-4,5-dihydro-1,3-thiazol-5-yl]acetic acid (150 mg) in N,N-dimethylformamide (5 mL) were added 1-hydroxybenzotriazole monohydrate (80 mg), 1-ethyl-3-(3-dimethylaminopropyl)carbodiimide hydrochloride (100 mg), and 2M dimethylamine tetrahydrofuran solution (0.35 mL), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (methanol:ethyl acetate:hexane=0:0:100 to 10:90:0, volume ratio) and crystallized from acetonitrile to give the title compound (112 mg, yield 70%) as white crystals.

MS 459 (MH$^+$).

melting point 162-164° C.

$^1$H NMR (DMSO-d$_6$) δ2.67-2.80 (1H, m), 2.84 (3H, s), 2.86-2.91 (1H, m), 2.93 (3H, s), 3.24 (3H, s), 4.06-4.49 (3H, m), 6.85 (1H, d, J=1.5 Hz), 7.07 (1H, dd, J=8.9, 2.4 Hz), 7.34-7.58 (3H, m), 7.99 (1H, d, J=8.7 Hz), 8.53 (1H, d, J=2.6 Hz), 11.93 (1H, s).

Example 56

2-[2-(5-{[6-(Methylsulfonyl)pyridin-3-yl]oxy}-1H-indol-2-yl)-4,5-dihydro-1,3-thiazol-5-yl]-N-(2,2,2-trifluoroethyl)acetamide

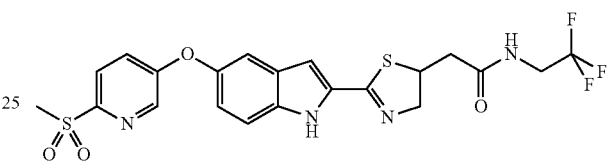

To a solution of [2-(5-{[6-(methylsulfonyl)pyridin-3-yl]oxy}-1H-indol-2-yl)-4,5-dihydro-1,3-thiazol-5-yl]acetic acid (150 mg) in N,N-dimethylformamide (5 mL) were added 1-hydroxybenzotriazole monohydrate (80 mg), 1-ethyl-3-(3-dimethylaminopropyl)carbodiimide hydrochloride (100 mg), and 2,2,2-trifluoroethylamine (69 mg), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (methanol:ethyl acetate:hexane=0:0:100 to 10:90:0, volume ratio) and crystallized from acetonitrile to give the title compound (115 mg, yield 65%) as white crystals.

MS 513 (MH$^+$).

melting point 234-235° C.

$^1$H NMR (DMSO-d$_6$) δ2.52-2.63 (1H, m), 2.65-2.78 (1H, m), 3.24 (3H, s), 3.74-4.09 (2H, m), 4.15-4.49 (3H, m), 6.87 (1H, d, J=1.5 Hz), 7.08 (1H, dd, J=8.9, 2.4 Hz), 7.40-7.55 (3H, m), 8.00 (1H, d, J=8.7 Hz), 8.53 (1H, d, J=2.6 Hz), 8.66 (1H, t, J=6.4 Hz), 11.97 (1H, s).

Example 57

N-(2-Methoxyethyl)-2-[2-(5-{[6-(methylsulfonyl)pyridin-3-yl]oxy}-1H-indol-2-yl)-4,5-dihydro-1,3-thiazol-5-yl]acetamide

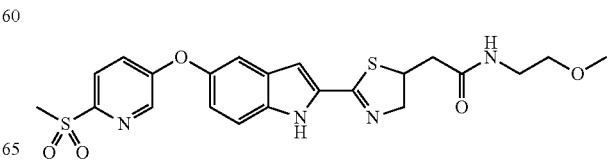

To a solution of [2-(5-{[6-(methylsulfonyl)pyridin-3-yl]oxy}-1H-indol-2-yl)-4,5-dihydro-1,3-thiazol-5-yl]acetic acid (150 mg) in N,N-dimethylformamide (5 mL) were added 1-hydroxybenzotriazole monohydrate (80 mg), 1-ethyl-3-(3-dimethylaminopropyl)carbodiimide hydrochloride (100 mg), and 2-methoxyethylamine (52 mg), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (methanol:ethyl acetate:hexane=0:0:100 to 10:90:0, volume ratio), and crystallized from acetonitrile to give the title compound (101 mg, yield 60%) as white crystals.

MS 489 (MH$^+$).

melting point 155-156° C.

$^1$H NMR (DMSO-d$_6$) δ2.41-2.50 (1H, m), 2.54-2.65 (1H, m), 3.08-3.28 (8H, m), 3.32-3.37 (2H, m), 3.95-4.49 (3H, m), 6.87 (1H, s), 7.08 (1H, dd, J=9.0, 2.3 Hz), 7.37-7.48 (2H, m), 7.51 (1H, d, J=8.7 Hz), 8.00 (1H, d, J=8.7 Hz), 8.06 (1H, t, J=5.3 Hz), 8.53 (1H, d, J=2.6 Hz), 11.96 (1H, s).

Example 58

5-{[6-(Methylsulfonyl)pyridin-3-yl]oxy}-2-[5-(2-morpholin-4-yl-2-oxoethyl)-4,5-dihydro-1,3-thiazol-2-yl]-1H-indole

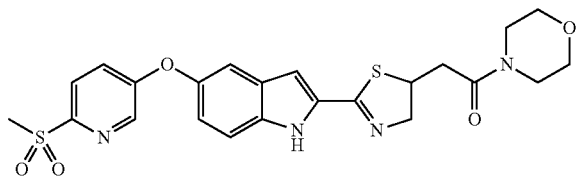 [SMILES: CS(=O)(=O)c1ccc(Oc2ccc3[nH]c(C4=NCC(CC(=O)N5CCOCC5)S4)cc3c2)cn1]

To a solution of [2-(5-{[6-(methylsulfonyl)pyridin-3-yl]oxy}-1H-indol-2-yl)-4,5-dihydro-1,3-thiazol-5-yl]acetic acid (150 mg) in N,N-dimethylformamide (5 mL) were added 1-hydroxybenzotriazole monohydrate (80 mg), 1-ethyl-3-(3-dimethylaminopropyl)carbodiimide hydrochloride (100 mg), and morpholine (61 mg), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (methanol:ethyl acetate:hexane=0:0:100 to 10:90:0, volume ratio) and crystallized from acetonitrile to give the title compound (106 mg, yield 61%) as white crystals.

MS 501 (MH$^+$).

melting point 190-191° C.

$^1$H NMR (DMSO-d$_6$) δ2.66-2.96 (2H, m), 3.24 (3H, s), 3.36-3.49 (4H, m), 3.50-3.59 (4H, m), 4.04-4.55 (3H, m), 6.85 (1H, d, J=1.5 Hz), 7.08 (1H, dd, J=8.9, 2.4 Hz), 7.27-7.60 (3H, m), 8.00 (1H, d, J=8.7 Hz), 8.53 (1H, d, J=3.0 Hz), 11.94 (1H, s).

Example 59

Ethyl[2-(7-ethyl-5-{[6-(methylsulfonyl)pyridin-3-yl]oxy}-1H-indol-2-yl)-4,5-dihydro-1,3-thiazol-5-yl]acetate

To a mixed solution of 7-ethyl-5-{[6-(methylsulfonyl)pyridin-3-yl]oxy}-1H-indole-2-carbothioamide (2.8 g), ethyl 2-butynoate (1.8 mL), tetrahydrofuran (40 mL), and toluene (60 mL), tri-n-butylphosphine (2.2 mL) was added under an argon atmosphere at room temperature, and the mixture was stirred at 40° C. for 3 hr. The reaction solution was concentrated under reduced pressure, and the obtained residue was subjected to silica gel column chromatography (ethyl acetate:hexane=25:75 to 60:40, volume ratio) to give the title compound (3.05 g, yield 84%) as a pale-yellow amorphous solid.

MS 488 (MH$^+$).

$^1$H NMR (CDCl$_3$) δ1.29 (3H, t, J=7.2 Hz), 1.35 (3H, t, J=7.2 Hz), 2.72-2.77 (2H, m), 2.87 (2H, q, J=7.2 Hz), 3.20 (3H, s), 4.19 (2H, q, J=7.2 Hz), 4.26-4.48 (3H, m), 6.86 (1H, d, J=2.1 Hz), 6.89 (1H, d, J=2.1 Hz), 7.20 (1H, d, J=2.1 Hz), 7.30 (1H, dd, J=2.7, 8.7 Hz), 7.98 (1H, d, J=8.7 Hz), 8.43 (1H, d, J=2.7 Hz), 9.11 (1H, brs).

Example 60

[2-(7-Ethyl-5-{[6-(methylsulfonyl)pyridin-3-yl]oxy}-1H-indol-2-yl)-4,5-dihydro-1,3-thiazol-5-yl]acetic acid

To a solution of ethyl[2-(7-ethyl-5-{[6-(methylsulfonyl)pyridin-3-yl]oxy}-1H-indol-2-yl)-4,5-dihydro-1,3-thiazol-5-yl]acetate (3.0 g), methanol (15 mL), and tetrahydrofuran (30 mL) was added an aqueous solution (10 mL) of potassium hydroxide (1.1 g), and the mixture was stirred at room temperature for 15 hr. The reaction solution was concentrated, acidified with aqueous citric acid solution, and the mixture was extracted with ethyl acetate. The organic layer was washed with saturated brine, dried over magnesium sulfate, filtered and concentrated under reduced pressure. The obtained pale-yellow crystals were washed with ethyl acetate-hexane to give the title compound (2.5 g, yield 88%) as pale-yellow crystals.

melting point 230-232° C.

MS 460 (MH$^+$).

Example 61

2-[2-(7-Ethyl-5-{[6-(methylsulfonyl)pyridin-3-yl]oxy}-1H-indol-2-yl)-4,5-dihydro-1,3-thiazol-5-yl]acetamide

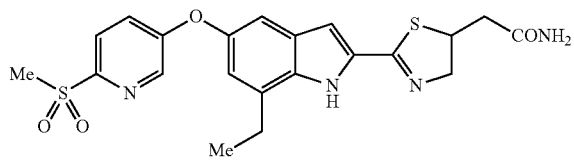 [SMILES: CCc1cc(Oc2ccc(S(C)(=O)=O)nc2)cc2cc(C3=NCC(CC(N)=O)S3)[nH]c12]

To a solution (10 mL) of [2-(7-ethyl-5-{[6-(methylsulfonyl)pyridin-3-yl]oxy}-1H-indol-2-yl)-4,5-dihydro-1,3-thiazol-5-yl]acetic acid (200 mg) in N,N-dimethylformamide were added under ice-cooling 1-hydroxybenzotriazole ammonium salt (100 mg) and 1-ethyl-3-(3-dimethylaminopropyl)carbodiimide hydrochloride (125 mg), and the mixture was stirred from under ice-cooling to room temperature for 20 hr. Water was added to the reaction solution, and the mixture was extracted with ethyl acetate. The organic layer was washed with aqueous sodium hydrogen carbonate solution and saturated brine, dried over magnesium sulfate, filtered and concentrated under reduced pressure. The obtained pale-yellow amorphous solid was crystallized from ethyl acetate-hexane to give pale-yellow crystals (188 mg). The crystals were recrystallized from tetrahydrofuran-ethyl acetate to give the title compound (163 mg, yield 82%) as pale-yellow crystals.

melting point 190-191° C.
MS 459 (MH$^+$).

Example 62

2-[2-(7-Ethyl-5-{[6-(methylsulfonyl)pyridin-3-yl]oxy}-1H-indol-2-yl)-4,5-dihydro-1,3-thiazol-5-yl]-N-methylacetamide

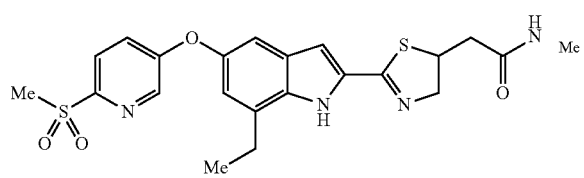

To a mixed solution of methylamine hydrochloride (147 mg), triethylamine (0.31 mL), and N,N-dimethylformamide (25 mL) were added [2-(7-ethyl-5-{[6-(methylsulfonyl)pyridin-3-yl]oxy}-1H-indol-2-yl)-4,5-dihydro-1,3-thiazol-5-yl]acetic acid (500 mg), 1-hydroxybenzotriazole (300 mg), and 1-ethyl-3-(3-dimethylaminopropyl)carbodiimide hydrochloride (420 mg) under ice-cooling, and the mixture was stirred under ice-cooling and then at room temperature for 2 days. Water was added to the reaction solution, and the mixture was extracted with ethyl acetate. The organic layer was washed with aqueous sodium hydrogen carbonate solution and saturated brine, dried over magnesium sulfate, filtered and concentrated under reduced pressure. The obtained residue was subjected to silica gel column chromatography (ethyl acetate:methanol=100:0 to 90:10, volume ratio), and the obtained colorless oil was crystallized from ethyl acetate-hexane to give the title compound (490 mg, yield 95%) as colorless crystals.

melting point 189-190° C.
MS 473 (MH$^+$).

Example 63

N-Ethyl-2-[2-(7-ethyl-5-{[6-(methylsulfonyl)pyridin-3-yl]oxy}-1H-indol-2-yl)-4,5-dihydro-1,3-thiazol-5-yl]acetamide

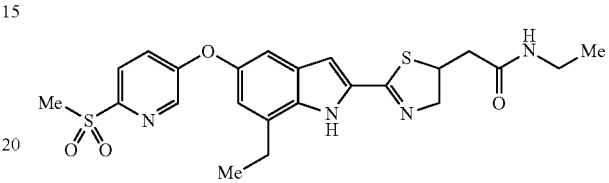

To a mixed solution of 2.0M-ethylamine tetrahydrofuran solution (0.33 mL), [2-(7-ethyl-5-{[6-(methylsulfonyl)pyridin-3-yl]oxy}-1H-indol-2-yl)-4,5-dihydro-1,3-thiazol-5-yl]acetic acid (200 mg), and N,N-dimethylformamide (10 mL) were added 1-hydroxybenzotriazole (89 mg), and 1-ethyl-3-(3-dimethylaminopropyl)carbodiimide hydrochloride (125 mg) under ice-cooling, and the mixture was stirred under ice-cooling and then at room temperature for 15 hr. Water was added to the reaction solution, and the mixture was extracted with ethyl acetate. The organic layer was washed with aqueous sodium hydrogen carbonate solution and saturated brine, dried over magnesium sulfate, filtered and concentrated under reduced pressure. The obtained residue was subjected to silica gel column chromatography (ethyl acetate:methanol=100:0 to 90:10, volume ratio), and the obtained pale-yellow oil was recrystallized from ethyl acetate-hexane to give the title compound (92 mg, yield 44%) as colorless crystals.

melting point 227-229° C.
MS 487 (MH$^+$).

Example 64

N,N-Dimethyl-2-[2-(5-{[6-(methylsulfonyl)pyridin-3-yl]oxy}-1H-indol-2-yl)-4,5-dihydro-1,3-thiazol-5-yl]acetamide

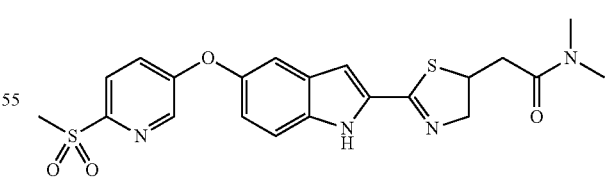

N,N-Dimethyl-2-[2-(5-{[6-(methylsulfonyl)pyridin-3-yl]oxy}-1H-indol-2-yl)-4,5-dihydro-1,3-thiazol-5-yl]acetamide (205 mg) was dissolved in methanol (70 mL), and the solution was subjected to supercritical fluid chromatography using CHIRALPAK AS-H (manufactured by DAICEL CHEMICAL INDUSTRIES, LTD.) and eluted with mobile phase: carbon dioxide-methanol-acetonitrile (600:200:200, volume ratio) at 100 bar, 35° C., flow rate 60 mL/min. The peak at retention time 4.0 min was separated, and concentrated to give white crystals (101 mg). The white crystals were recrystallized from ethyl acetate/hexane to give the title compound (91 mg, yield 44%) as white crystals.

MS 459 (MH+).

melting point 190-191° C.

$^1$H NMR (DMSO-d$_6$) δ2.68-2.79 (1H, m), 2.84 (3H, s), 2.89 (1H, d, J=4.9 Hz), 2.93 (3H, s), 3.24 (3H, s), 4.13-4.53 (3H, m), 6.85 (1H, s), 7.07 (1H, dd, J=8.7, 2.3 Hz), 7.37-7.47 (2H, m), 7.50 (1H, d, J=9.1 Hz), 7.99 (1H, d, J=8.7 Hz), 8.53 (1H, d, J=2.7 Hz), 11.93 (1H, s).

Example 65

N,N-Dimethyl-2-[2-(5-{[6-(methylsulfonyl)pyridin-3-yl]oxy}-1H-indol-2-yl)-4,5-dihydro-1,3-thiazol-5-yl]acetamide

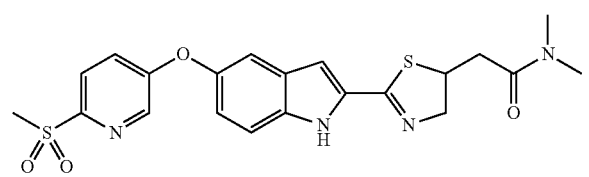

N,N-Dimethyl-2-[2-(5-{[6-(methylsulfonyl)pyridin-3-yl]oxy}-1H-indol-2-yl)-4,5-dihydro-1,3-thiazol-5-yl]acetamide (205 mg) was dissolved in methanol (70 mL), and the solution was subjected to supercritical fluid chromatography using CHIRALPAK AS-H (manufactured by DAICEL CHEMICAL INDUSTRIES, LTD.) and eluted with mobile phase: carbon dioxide-methanol-acetonitrile (600:200:200, volume ratio) at 100 bar, 35° C., flow rate 60 mL/min. The peak at retention time 6.0 min was separated, and concentrated to give white crystals (90 mg). The white crystals were recrystallized from ethyl acetate/hexane to give the title compound (81 mg, yield 39%) as white crystals.

MS 459 (MH+).

melting point 190-191° C.

$^1$H NMR (DMSO-d$_6$) δ2.68-2.79 (1H, m), 2.84 (3H, s), 2.89 (1H, d, J=4.9 Hz), 2.93 (3H, s), 3.24 (3H, s), 4.13-4.53 (3H, m), 6.85 (1H, s), 7.07 (1H, dd, J=8.7, 2.3 Hz), 7.37-7.47 (2H, m), 7.50 (1H, d, J=9.1 Hz), 7.99 (1H, d, J=8.7 Hz), 8.53 (1H, d, J=2.7 Hz), 11.93 (1H, s).

Example 66

N-(2-Methoxyethyl)-2-[2-(5-{[6-(methylsulfonyl)pyridin-3-yl]oxy}-1H-indol-2-yl)-4,5-dihydro-1,3-thiazol-5-yl]acetamide

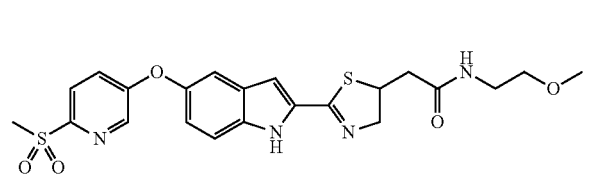

N-(2-Methoxyethyl)-2-[2-(5-{[6-(methylsulfonyl)pyridin-3-yl]oxy}-1H-indol-2-yl)-4,5-dihydro-1,3-thiazol-5-yl]acetamide (300 mg) was dissolved in methanol-acetonitrile (500:500, 70 mL), and the solution was subjected to supercritical fluid chromatography using CHIRALCEL OD-H (manufactured by DAICEL CHEMICAL INDUSTRIES, LTD.) and eluted with mobile phase: carbon dioxide-methanol-acetonitrile (600:200:200, volume ratio) at 100 bar, 30° C., flow rate 50 mL/min. The peak at retention time 5.2 min was separated, and concentrated to give the title compound (143 mg) as crystals. The obtained crystals were washed with diethyl ether-hexane and recrystallized from acetone-hexane to give the title compound (126 mg) as colorless prism crystals.

MS 489 (MH+).

melting point 174-175° C.

Example 67

N-(2-Methoxyethyl)-2-[2-(5-{[6-(methylsulfonyl)pyridin-3-yl]oxy}-1H-indol-2-yl)-4,5-dihydro-1,3-thiazol-5-yl]acetamide

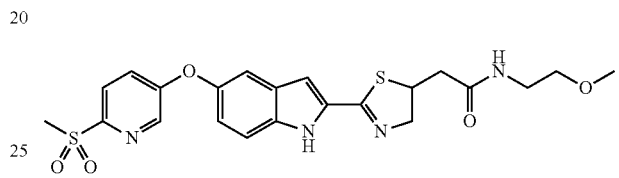

N-(2-Methoxyethyl)-2-[2-(5-{[6-(methylsulfonyl)pyridin-3-yl]oxy}-1H-indol-2-yl)-4,5-dihydro-1,3-thiazol-5-yl]acetamide (300 mg) was dissolved in methanol-acetonitrile (500:500, 70 mL), and the solution was subjected to supercritical fluid chromatography using CHIRALCEL OD-H (manufactured by DAICEL CHEMICAL INDUSTRIES, LTD.) and eluted with mobile phase: carbon dioxide-methanol-acetonitrile (600:200:200, volume ratio) at 100 bar, 30° C., flow rate 50 mL/min. The peak at retention time 6.4 min was separated, and concentrated to give the title compound (143 mg) as crystals. The obtained crystals were washed with diethyl ether-hexane and recrystallized from acetone-hexane to give the title compound (118 mg) as colorless prism crystals.

MS 489 (MH+).

melting point 174-175° C.

Example 68

5-{[6-(Methylsulfonyl)pyridin-3-yl]oxy}-2-[5-(2-morpholin-4-yl-2-oxoethyl)-4,5-dihydro-1,3-thiazol-2-yl]-1H-indole

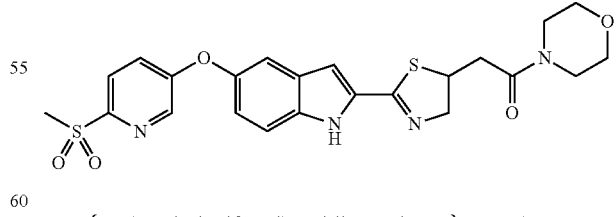

5-{[6-(Methylsulfonyl)pyridin-3-yl]oxy}-2-[5-(2-morpholin-4-yl-2-oxoethyl)-4,5-dihydro-1,3-thiazol-2-yl]-1H-indole (310 mg) was dissolved in methanol-acetonitrile (500:500, 100 mL), and the solution was subjected to supercritical fluid chromatography using CHIRALPAK AS-H (manufactured by DAICEL CHEMICAL INDUSTRIES, LTD.) and eluted with mobile phase: carbon dioxide-methanol-acetonitrile (600:200:200, volume ratio) at 100 bar, 30° C., flow rate 50 mL/mina The peak at retention time 5.0 min was separated, and concentrated to give white crystals (145 mg). The white crystals were recrystallized from acetone/hexane to give the title compound (130 mg, yield 42%) as white crystals.

MS 501 (MH+).

melting point 168-169° C.

$^1$H NMR (DMSO-d$_6$) δ2.68-2.79 (1H, m), 2.84 (3H, s), 2.89 (1H, d, J=4.9 Hz), 2.93 (3H, s), 3.24 (3H, s), 4.13-4.53 (3H, m), 6.85 (1H, s), 7.07 (1H, dd, J=8.7, 2.3 Hz), 7.37-7.47 (2H, m), 7.50 (1H, d, J=9.1 Hz), 7.99 (1H, d, J=8.7 Hz), 8.53 (1H, d, J=2.7 Hz), 11.93 (1H, s).

Example 69

5-{[6-(Methylsulfonyl)pyridin-3-yl]oxy}-2-[5-(2-morpholin-4-yl-2-oxoethyl)-4,5-dihydro-1,3-thiazol-2-yl]-1H-indole

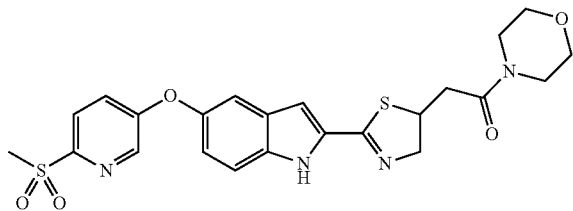 [SMILES: CS(=O)(=O)c1ccc(Oc2ccc3[nH]c(C4=NCC(CC(=O)N5CCOCC5)S4)cc3c2)cn1]

5-{[6-(Methylsulfonyl)pyridin-3-yl]oxy}-2-[5-(2-morpholin-4-yl-2-oxoethyl)-4,5-dihydro-1,3-thiazol-2-yl]-1H-indole (310 mg) was dissolved in methanol-acetonitrile (500: 500, 100 mL), and the solution was subjected to supercritical fluid chromatography using CHIRALPAK AS-H (manufactured by DAICEL CHEMICAL INDUSTRIES, LTD.) and eluted with mobile phase: carbon dioxide-methanol-acetonitrile (600:200:200, volume ratio) at 100 bar, 30° C., flow rate 50 mL/min. The peak at retention time 6.2 min was separated, and concentrated to give white crystals (150 mg). The white crystals were recrystallized from acetone/hexane to give the title compound (107 mg, yield 34%) as white crystals.

MS 501 (MH+).

melting point 167-168° C.

$^1$H NMR (DMSO-d$_6$) δ2.68-2.79 (1H, m), 2.84 (3H, s), 2.89 (1H, d, J=4.9 Hz), 2.93 (3H, s), 3.24 (3H, s), 4.13-4.53 (3H, m), 6.85 (1H, s), 7.07 (1H, dd, J=8.7, 2.3 Hz), 7.37-7.47 (2H, m), 7.50 (1H, d, J=9.1 Hz), 7.99 (1H, d, J=8.7 Hz), 8.53 (1H, d, J=2.7 Hz), 11.93 (1H, s).

Example 70

Ethyl[2-(7-methyl-5-{[6-(methylsulfonyl)pyridin-3-yl]oxy}-1H-indol-2-yl)-4,5-dihydro-1,3-thiazol-5-yl]acetate

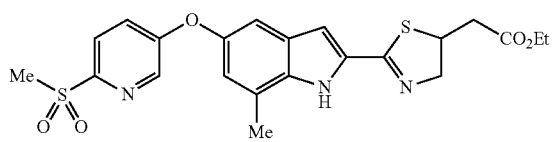 [SMILES: CCOC(=O)CC1CN=C(c2cc3cc(Oc4ccc(S(C)(=O)=O)nc4)cc(C)c3[nH]2)S1]

To a mixed solution of 7-methyl-5-{[6-(methylsulfonyl)pyridin-3-yl]oxy}-1H-indole-2-carbothioamide (2.6 g), ethyl 2-butynoate (1.7 mL), tetrahydrofuran (40 mL), and toluene (60 mL) was added tri-n-butylphosphine (2.2 mL) under an argon atmosphere at room temperature, and the mixture was stirred at 40° C. for 2.5 hr. The reaction solution was concentrated under reduced pressure, and the obtained residue was subjected to silica gel column chromatography (ethyl acetate:hexane=40:60 to 65:35, volume ratio) to give the title compound (2.59 g, yield 76%) as a pale-yellow amorphous solid.

MS 474 (MH+).

$^1$H NMR (CDCl$_3$) δ1.29 (3H, t, J=7.2 Hz), 2.51 (3H, s), 2.72-2.76 (2H, m), 3.20 (3H, s), 4.29 (2H, q, J=7.2 Hz), 4.25-4.48 (3H, m), 6.83 (1H, d, J=2.1 Hz), 6.89 (1H, d, J=2.1 Hz), 7.20 (1H, d, J=2.1 Hz), 7.30 (1H, dd, J=2.7, 8.7 Hz), 7.98 (1H, d, J=8.7 Hz), 8.43 (1H, d, J=2.7 Hz), 9.09 (1H, brs).

Example 71

[2-(7-Methyl-5-{[6-(methylsulfonyl)pyridin-3-yl]oxy}-1H-indol-2-yl)-4,5-dihydro-1,3-thiazol-5-yl]acetic acid

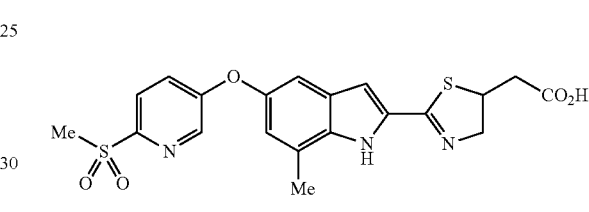

To a solution of ethyl[2-(7-methyl-5-{[6-(methylsulfonyl)pyridin-3-yl]oxy}-1H-indol-2-yl)-4,5-dihydro-1,3-thiazol-5-yl]acetate (2.59 g), methanol (25 mL), and tetrahydrofuran (25 mL) was added an aqueous solution (15 mL) of potassium hydroxide (1.0 g), and the mixture was stirred at room temperature for 6 hr. The reaction solution was concentrated, acidified with aqueous citric acid solution, and the mixture was extracted with ethyl acetate. The organic layer was washed with water, dried over magnesium sulfate, filtered and concentrated under reduced pressure. The obtained pale-yellow crystals were washed with ethyl acetate-hexane to give the title compound (2.33 g, yield 96%) as pale-yellow crystals.

melting point 248-249° C.

MS 446 (MH+).

Example 72

2-[2-(7-Methyl-5-{[6-(methylsulfonyl)pyridin-3-yl]oxy}-1H-indol-2-yl)-4,5-dihydro-1,3-thiazol-5-yl]acetamide

To a solution of [2-(7-methyl-5-{[6-(methylsulfonyl)pyridin-3-yl]oxy}-1H-indol-2-yl)-4,5-dihydro-1,3-thiazol-5-yl]acetic acid (300 mg) in N,N-dimethylformamide (12 mL) were added 1-hydroxybenzotriazole ammonium salt (154 mg) and 1-ethyl-3-(3-dimethylaminopropyl)carbodiimide hydrochloride (194 mg) under ice-cooling, and the mixture was stirred from under ice-cooling to room temperature for 2 days. Water was added to the reaction solution, and the mixture was extracted with ethyl acetate. The organic layer was washed with aqueous sodium hydrogen carbonate solution and saturated brine, dried over magnesium sulfate, filtered and concentrated under reduced pressure. The obtained residue was subjected to silica gel column chromatography (ethyl acetate:methanol=100:0 to 90:10, volume ratio) to give pale-yellow crystals. The obtained crystals were recrystallized from methanol-ethyl acetate to give the title compound (224 mg, yield 75%) as colorless crystals.
melting point 202-203° C.
MS 444 (MH$^+$).

Example 73

2-[2-(7-Methyl-5-{[6-(methylsulfonyl)pyridin-3-yl]oxy}-1H-indol-2-yl)-4,5-dihydro-1,3-thiazol-5-yl]-N-methylacetamide

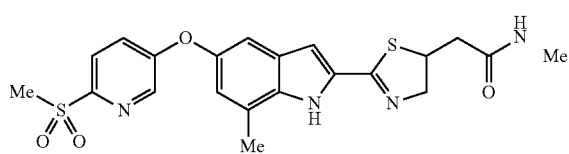

To a mixed solution of methylamine hydrochloride (120 mg), triethylamine (0.24 mL) and N,N-dimethylformamide (20 mL) were added [2-(7-methyl-5-{[6-(methylsulfonyl)pyridin-3-yl]oxy}-1H-indol-2-yl)-4,5-dihydro-1,3-thiazol-5-yl]acetic acid (500 mg), 1-hydroxybenzotriazole (230 mg), and 1-ethyl-3-(3-dimethylaminopropyl)carbodiimide hydrochloride (330 mg) under ice-cooling, and the mixture was stirred from under ice-cooling to room temperature for 2 days. Water was added to the reaction solution, and the mixture was extracted with ethyl acetate. The organic layer was washed with aqueous sodium hydrogen carbonate solution and saturated brine, dried over magnesium sulfate, filtered and concentrated under reduced pressure. The obtained residue was subjected to silica gel column chromatography (ethyl acetate:methanol=100:0 to 85:15, volume ratio), and the obtained colorless oil was crystallized from ethyl acetate-hexane to give the title compound (436 mg, yield 85%) as colorless crystals.
melting point 183-184° C.
MS 458 (MH$^+$).

Example 74

N-(2-Hydroxy-2-methylpropyl)-2-[2-(5-{[6-(methylsulfonyl)pyridin-3-yl]oxy}-1H-indol-2-yl)-4,5-dihydro-1,3-thiazol-5-yl]acetamide

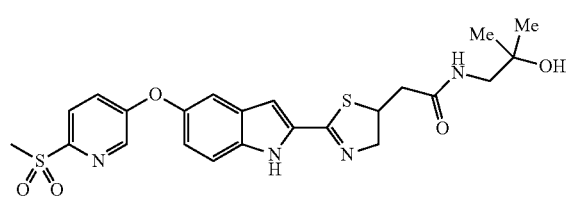 [SMILES: CC(C)(O)CNC(=O)CC1CN=C(c2cc3cc(Oc4ccc(S(C)(=O)=O)nc4)ccc3[nH]2)S1]

To a solution of [2-(5-{[6-(methylsulfonyl)pyridin-3-yl]oxy}-1H-indol-2-yl)-4,5-dihydro-1,3-thiazol-5-yl]acetic acid (600 mg) in N,N-dimethylformamide (10 mL) were added 1-hydroxybenzotriazole monohydrate (319 mg), 1-ethyl-3-(3-dimethylaminopropyl)carbodiimide hydrochloride (400 mg), and 1-amino-2-methyl-2-propanol (242 mg), and the mixture was stirred at room temperature for 15 hr. Water was added to the reaction mixture, and the mixture was extracted with ethyl acetate. The organic layer was washed with saturated aqueous sodium hydrogen carbonate solution and saturated brine, dried over magnesium sulfate, filtered and concentrated under reduced pressure. The obtained crude product was subjected to basic silica gel column chromatography (ethyl acetate) and crystallized from acetonitrile to give the title compound (601 mg, yield 86%) as white crystals.
MS 459 (MH$^+$).
melting point 178-179° C.
$^1$H NMR (DMSO-d$_6$) δ1.06 (6H, s), 2.53-2.77 (2H, m), 3.04 (2H, d, J=6.0 Hz), 3.24 (3H, s), 4.17-4.46 (4H, m), 6.86 (1H, s), 7.08 (1H, dd, J=9.0, 2.3 Hz), 7.37-7.54 (3H, m), 7.87 (1H, t, J=5.8 Hz), 8.00 (1H, d, J=8.7 Hz), 8.53 (1H, d, J=2.6 Hz), 11.98 (1H, s).

Example 75

N-(2-Hydroxy-2-methylpropyl)-2-[2-(7-methyl-5-{[6-(methylsulfonyl)pyridin-3-yl]oxy}-1H-indol-2-yl)-4,5-dihydro-1,3-thiazol-5-yl]acetamide

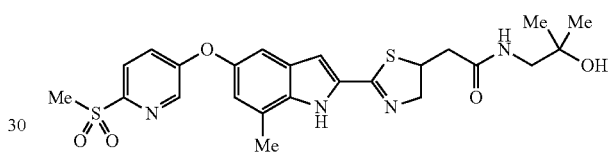

To a solution of [2-(7-methyl-5-{[6-(methylsulfonyl)pyridin-3-yl]oxy}-1H-indol-2-yl)-4,5-dihydro-1,3-thiazol-5-yl]acetic acid (300 mg) and 2-amino-2-methyl-2-propanol (90 mg) in N,N-dimethylformamide (20 mL) were added 1-hydroxybenzotriazole (137 mg) and 1-ethyl-3-(3-dimethylaminopropyl)carbodiimide hydrochloride (194 mg) under ice-cooling, and the mixture was stirred under ice-cooling and then at room temperature for 15 hr. Water was added to the reaction solution, and the mixture was extracted with ethyl acetate. The organic layer was washed with aqueous sodium hydrogen carbonate solution and saturated brine, dried over magnesium sulfate, filtered and concentrated under reduced pressure. The obtained residue was subjected to silica gel column chromatography (ethyl acetate:methanol=100:0 to 90:10, volume ratio) to give colorless crystals. The obtained crystals were recrystallized from tetrahydrofuran-ethyl acetate to give the title compound (280 mg, yield 81%) as colorless crystals.
melting point 184-186° C.
MS 517 (MH$^+$).

Example 76

N-[(2S)-2-Hydroxypropyl]-2-[2-(7-methyl-5-{[6-(methylsulfonyl)pyridin-3-yl]oxy}-1H-indol-2-yl)-4,5-dihydro-1,3-thiazol-5-yl]acetamide

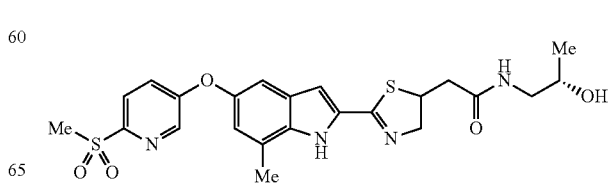

To a solution of [2-(7-methyl-5-{[6-(methylsulfonyl)pyridin-3-yl]oxy}-1H-indol-2-yl)-4,5-dihydro-1,3-thiazol-5-yl]acetic acid (300 mg) and (S)-(+)-1-amino-2-propanol (78 mg) in N,N-dimethylformamide (20 mL) were added 1-hydroxybenzotriazole (137 mg) and 1-ethyl-3-(3-dimethylaminopropyl)carbodiimide hydrochloride (194 mg) under ice-cooling, and the mixture was stirred under ice-cooling and then at room temperature for 15 hr. Water was added to the reaction solution, and the mixture was extracted with ethyl acetate. The organic layer was washed with aqueous sodium hydrogen carbonate solution and saturated brine, dried over magnesium sulfate, filtered and concentrated under reduced pressure. The obtained pale-yellow crystals were recrystallized from tetrahydrofuran-ethyl acetate to give the title compound (230 mg, yield 68%) as colorless crystals.

melting point 170-171° C.
MS 503 (MH$^+$).

Example 77

N-[(2R)-2-Hydroxypropyl]-2-[2-(7-methyl-5-{[6-(methylsulfonyl)pyridin-3-yl]oxy}-1H-indol-2-yl)-4,5-dihydro-1,3-thiazol-5-yl]acetamide

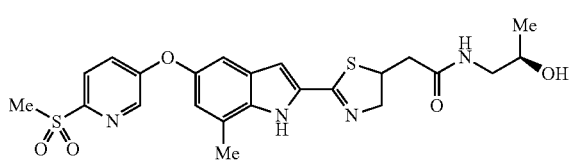 [SMILES: Cc1cc(Oc2ccc(S(C)(=O)=O)nc2)cc2cc(C3=NCC(CC(=O)NC[C@@H](C)O)S3)[nH]c12]

To a solution of [2-(7-methyl-5-{[6-(methylsulfonyl)pyridin-3-yl]oxy}-1H-indol-2-yl)-4,5-dihydro-1,3-thiazol-5-yl]acetic acid (300 mg) and (R)-(-)-1-amino-2-propanol (78 mg) in N,N-dimethylformamide (20 mL) were added 1-hydroxybenzotriazole (137 mg) and 1-ethyl-3-(3-dimethylaminopropyl)carbodiimide hydrochloride (194 mg) under ice-cooling, and the mixture was stirred under ice-cooling and then at room temperature for 15 hr. Water was added to the reaction solution, and the mixture was extracted with ethyl acetate. The organic layer was washed with aqueous sodium hydrogen carbonate solution and saturated brine, dried over magnesium sulfate, filtered and concentrated under reduced pressure. The obtained pale-yellow crystals were washed with ethyl acetate-hexane and recrystallized from tetrahydrofuran-ethyl acetate to give the title compound (264 mg, yield 78%) as colorless crystals.

melting point 168-169° C.
MS 503 (MH$^+$).

Example 78

N-Methyl-2-[2-(5-{[6-(methylsulfonyl)pyridin-3-yl]oxy}-1H-indol-2-yl)-4,5-dihydro-1,3-thiazol-5-yl]acetamide

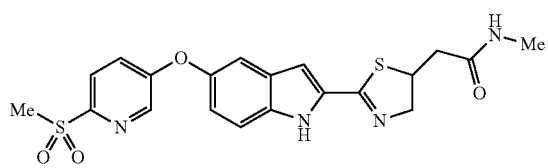 [SMILES: CNC(=O)CC1CN=C(c2cc3cc(Oc4ccc(S(C)(=O)=O)nc4)ccc3[nH]2)S1]

N-Methyl-2-[2-(5-{[6-(methylsulfonyl)pyridin-3-yl]oxy}-1H-indol-2-yl)-4,5-dihydro-1,3-thiazol-5-yl]acetamide (260 mg) was dissolved in methanol-acetonitrile (500:500, 100 mL), and the solution was subjected to supercritical fluid chromatography using CHIRALCELL OJ-H (manufactured by DAICEL CHEMICAL INDUSTRIES, LTD.) and eluted with mobile phase: carbon dioxide-methanol-acetonitrile (600:200:200, volume ratio) at 100 bar, 30° C., flow rate 50 mL/min. The peak at retention time 5.6 min was separated, and concentrated to give crystals (131 mg). The crystals were recrystallized from ethyl acetate/hexane to give the title compound (104 mg, yield 40%) as colorless crystals.

MS 445 (MH$^+$).
melting point 178-180° C.

Example 79

N-Methyl-2-[2-(5-{[6-(methylsulfonyl)pyridin-3-yl]oxy}-1H-indol-2-yl)-4,5-dihydro-1,3-thiazol-5-yl]acetamide

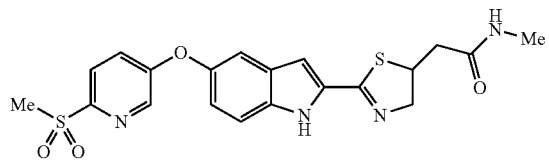 [SMILES: CNC(=O)CC1CN=C(c2cc3cc(Oc4ccc(S(C)(=O)=O)nc4)ccc3[nH]2)S1]

N-Methyl-2-[2-(5-{[6-(methylsulfonyl)pyridin-3-yl]oxy}-1H-indol-2-yl)-4,5-dihydro-1,3-thiazol-5-yl]acetamide (260 mg) was dissolved in methanol-acetonitrile (500:500, 100 mL), and the solution was subjected to supercritical fluid chromatography using CHIRALCELL OJ-H (manufactured by DAICEL CHEMICAL INDUSTRIES, LTD.) and eluted with mobile phase: carbon dioxide-methanol-acetonitrile (600:200:200, volume ratio) at 100 bar, 30° C., flow rate 50 mL/min. The peak at retention time 7.8 min was separated, and concentrated to give crystals (125 mg). The crystals were recrystallized from ethyl acetate/hexane to give the title compound (104 mg, yield 40%) as colorless crystals.

MS 445 (MH$^+$).
melting point 172-173° C.

Example 80

7-Methyl-5-{[6-(methylsulfonyl)pyridin-3-yl]oxy}-2-[5-(2-morpholin-4-yl-2-oxoethyl)-4,5-dihydro-1,3-thiazol-2-yl]-1H-indole

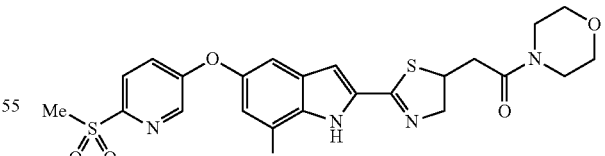

To a solution of [2-(7-methyl-5-{[6-(methylsulfonyl)pyridin-3-yl]oxy}-1H-indol-2-yl)-4,5-dihydro-1,3-thiazol-5-yl]acetic acid (300 mg) and morpholine (0.088 mL) in N,N-dimethylformamide (20 mL) were added 1-hydroxybenzotriazole (137 mg) and 1-ethyl-3-(3-dimethylaminopropyl)carbodiimide hydrochloride (194 mg) under ice-cooling, and the mixture was stirred under ice-cooling and then at room temperature for 15 hr. Water was added to the reaction solution, and the mixture was extracted with ethyl acetate. The organic layer was washed with aqueous sodium hydrogen carbonate solution and saturated brine, dried over magnesium sulfate, filtered and concentrated under reduced pressure. The obtained residue was subjected to silica gel column chromatography (ethyl acetate:methanol=100:0 to 90:10, volume ratio), and the obtained pale-yellow oil was crystallized from ethyl acetate-diethyl ether to give the title compound (286 mg, yield 83%) as colorless crystals.

melting point 152-154° C.
MS 515 (MH$^+$).

Example 81

7-Methyl-5-{[6-(methylsulfonyl)pyridin-3-yl]oxy}-2-{5-[2-(1-oxidothiomorpholin-4-yl)-2-oxoethyl]-4,5-dihydro-1,3-thiazol-2-yl}-1H-indole

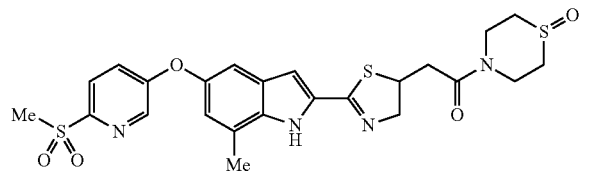 [SMILES: Cc1cc(Oc2ccc(S(C)(=O)=O)nc2)cc2cc(C3=NCC(CC(=O)N4CCS(=O)CC4)S3)[nH]c12]

To a solution of thiomorpholine 1-oxide hydrochloride (140 mg) and triethylamine (0.125 mL) in N,N-dimethylformamide (15 mL) were added [2-(7-methyl-5-{[6-(methylsulfonyl)pyridin-3-yl]oxy}-1H-indol-2-yl)-4,5-dihydro-1,3-thiazol-5-yl]acetic acid (200 mg), 1-hydroxybenzotriazole (121 mg) and 1-ethyl-3-(3-dimethylaminopropyl)carbodiimide hydrochloride (172 mg) under ice-cooling, and the mixture was stirred under ice-cooling and then at room temperature for 15 hr. Water was added to the reaction solution, and the mixture was extracted with ethyl acetate. The organic layer was washed with aqueous sodium hydrogen carbonate solution and saturated brine, dried over magnesium sulfate, filtered and concentrated under reduced pressure. The obtained residue was subjected to silica gel column chromatography (ethyl acetate:methanol=100:0 to 75:25, volume ratio), and the obtained pale-yellow crystals were recrystallized from ethyl acetate-hexane to give the title compound (104 mg, yield 42%) as colorless crystals.

melting point 157-160° C.
MS 547 (MH$^+$).

Example 82

7-Ethyl-5-{[6-(methylsulfonyl)pyridin-3-yl]oxy}-2-{5-[2-(1-oxidothiomorpholin-4-yl)-2-oxoethyl]-4,5-dihydro-1,3-thiazol-2-yl}-1H-indole

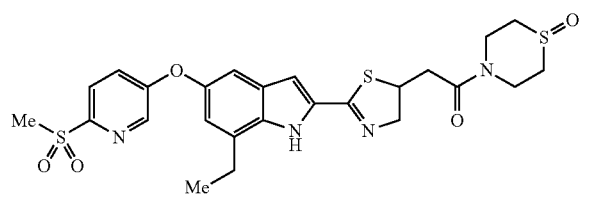 [SMILES: CCc1cc(Oc2ccc(S(C)(=O)=O)nc2)cc2cc(C3=NCC(CC(=O)N4CCS(=O)CC4)S3)[nH]c12]

To a solution of thiomorpholine 1-oxide hydrochloride (340 mg) and triethylamine (0.31 mL) in N,N-dimethylformamide (25 mL) were added [2-(7-ethyl-5-{[6-(methylsulfonyl)pyridin-3-yl]oxy}-1H-indol-2-yl)-4,5-dihydro-1,3-thiazol-5-yl]acetic acid (500 mg), 1-hydroxybenzotriazole (300 mg) and 1-ethyl-3-(3-dimethylaminopropyl)carbodiimide hydrochloride (420 mg) under ice-cooling, and the mixture was stirred under ice-cooling and then at room temperature for 15 hr. Water was added to the reaction solution, and the mixture was extracted with ethyl acetate. The organic layer was washed with aqueous sodium hydrogen carbonate solution and saturated brine, dried over magnesium sulfate, filtered and concentrated under reduced pressure. The obtained residue was subjected to silica gel column chromatography (ethyl acetate:methanol=100:0 to 80:20, volume ratio), and the obtained pale-yellow crystals were recrystallized from tetrahydrofuran-ethyl acetate to give the title compound (354 mg, yield 58%) as colorless crystals. melting point 194-196° C.

MS 561 (MH$^+$).

Experimental Example 1

(1) Construction of Glucokinase (GK) Expression Vector

Plasmid DNA to be used for the expression of a protein (GST-hLGK1) containing GST (Glutathione S-transferase) added to the amino terminal of human liver GK in *Escherichia coli* was prepared as follows.

First, PCR was performed using human liver cDNA (Marathon Ready cDNA, Clontech Laboratories, Inc.) as a template and two kinds of synthetic DNAs (5'-CAGCTCTCCATCCAAGCAGCCGTTGCT-3' (SEQ ID NO: 1) and 5'-GGCG-GCCTGGGTCCTGACAAG-3' (SEQ ID NO: 2)), and the obtained DNA fragment was closed using a TOPO TA Cloning Kit (Invitrogen Corporation). PCR was performed using the obtained plasmid DNA as a template and a synthetic DNA (5'-GGATCCATGCCCAGACCAAGATC-CCAACTCCCACAACCCAACTCCCAGGTA-GAGCAGATCCTGG CAGAG-3' (SEQ ID NO: 3)) with a BamHI site added to immediately before the initiation codon, and a synthetic DNA (5'-GAATTCCTGGCCCAGCATA-CAGGC-3' (SEQ ID NO: 4)) with an EcoRI site added to immediately after the stop codon. The obtained DNA fragment was subcloned to pGEX6P-2 (Amersham Biosciences K.K.) cleaved with BamHI and EcoRI to give a plasmid (pGEX6P-2/hLGK1) for expression of human liver GK.

(2) Expression and Purification of GST-hLGK1

BL21 strain (Stratagene) transformed with pGEX6P-2/hLGK1 obtained in (1) was cultured with shaking at 37° C. for 14 hr in a 200 ml Erlenmeyer flask containing 50 ml of 100 μg/ml ampicillin-containing LB medium. The culture medium (25 ml) was diluted with 225 ml of 100 μg/ml ampicillin-containing LB medium, and further cultured with shaking at 37° C. for 1 hr in a 1 L Erlenmeyer flask. After culture, the Erlenmeyer flask was cooled on ice, 125 μL of 100 mM isopropyl-thio-β-D-galactopyranoside (IPTG) was added (final concentration 50 μM), and cultured at 17° C. for 20 hr. The culture medium was centrifuged, and the obtained fungus was disrupted by ultrasonication. The object protein (GST-hLGK1) was purified from the supernatant using Glutathione Sepharose 4B (Amersham Biosciences K.K.).

(3) Determination of GK Activity Value

A solution (5 μL) of test compound in 50% dimethyl sulfoxide was added to each well of 384 well black plate (Nalge Nunc International K.K.). Then, a solution (35 μL) obtained by diluting GST-hLGK1 obtained in (2) with measurement buffer (containing 50 mM HEPES (pH 7.4), 200 mM KCl, 5 mM MgCl$_2$, 2.5 mM DTT and 50 μM 2'-(or-3')-O—(N-methylanthraniloyl)adenosine 5'-triphosphate (Mant-ATP) (Jena Bioscience GmbH)) to 6 μg/mL was added to each well.

Each well was stood at 37° C. for 10 min, and 25 mM D-glucose solution (10 μL) was added to start the reaction.

Each well after the reaction was stood at 37° C. for 60 min, and the reaction was quenched by adding 25 μL of a quenching solution (containing 200 mM HEPES (pH 7.4), 20 mM $MgCl_2$, 200 mM EDTA, 0.03% Triton-X 100, 0.3% Coating 3 reagent (Caliper Life Sciences, Inc.)).

2'-(or -3')-O—(N-methylanthraniloyl)adenosine 5'-triphosphate (Mant-ATP, substrate) and Mant-ADP (reaction resultant product) were separated from each well after the reaction by a microchip type capillary electrophoresis apparatus 250 HTS (Caliper Life Sciences, Inc.). The reaction rate [(reaction resultant product peak height)/(reaction resultant product peak height+substrate peak height)×100(%)] was calculated from the ratio of the substrate peak height and reaction resultant product peak height obtained by fluorescence detection (excitation wavelength 355 nm, measurement wavelength 460 nm) and used as the index of GK activity.

3.5 As a control group, the reaction rate was calculated in the same manner as above except that "solution in 50% dimethyl sulfoxide (without test compound)" was used instead of "solution of test compound in 50% dimethyl sulfoxide".

A concentration dependency curve of the test compound was drawn with the percentage obtained by dividing the reaction rate of the well added with the test compound (test compound addition group) by the reaction rate of the control group was taken as the GK activity value of the test compound, and the concentration of the test compound at the midpoint between the maximum activity value of the test compound addition group and the control group activity value is shown as $EC_{50}$ value. The results are shown in Table 1.

TABLE 1

| test compound (Example No.) | $EC_{50}$ value (μM) |
|---|---|
| 2 | 0.018 |
| 3 | 0.015 |
| 7 | 0.014 |
| 8 | 0.018 |
| 14 | 0.061 |
| 17 | 0.09 |
| 20 | 0.027 |
| 24 | 0.019 |
| 32 | 0.016 |
| 33 | 0.026 |
| 35 | 0.031 |
| 36 | 0.016 |
| 37 | 0.016 |
| 42 | 0.021 |
| 53 | 0.13 |
| 54 | 0.12 |
| 55 | 0.18 |
| 56 | 0.073 |
| 57 | 0.16 |
| 58 | 0.12 |
| 61 | 0.016 |
| 65 | 0.066 |
| 67 | 0.089 |
| 69 | 0.028 |
| 72 | 0.029 |
| 73 | 0.033 |
| 78 | 0.08 |
| 80 | 0.054 |
| 81 | 0.048 |
| 82 | 0.018 |

As is clear from Table 1, the compound of the present invention has a superior glucokinase activation action.

Formulation Example 1

Production of Capsule

| | |
|---|---|
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2

Production of Tablet

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3), and 30 g of 4) are kneaded with water, vacuum dried and sized. The sieved powder is mixed with 14 g of 4) and 1 g of 5), and the mixture is punched by a tableting machine. In this way, 1000 tablets containing 30 mg of the compound of Example 1 per tablet are obtained.

INDUSTRIAL APPLICABILITY

The compound of the present invention has a superior glucokinase activating action, and is useful as a medicament such as an agent for the prophylaxis or treatment of diabetes, obesity and the like, and the like.

This application is based on a provisional application No. 61/193,826 filed in US, the contents of which are incorporated in full herein.

Although the present invention have been presented or described by referring to preferred embodiments of this invention, it will, however, be understood by those of ordinary skill in the art that various modifications may be made to the forms and details without departing from the scope of the invention as set forth in the appended claims. All patents, patent publications and other publications indicated or cited in the Specification are hereby incorporated in their entireties by reference.

The invention claimed is:

1. A compound represented by the formula (I):

wherein ring A is a 6-membered ring which is optionally further substituted;
ring B is an optionally substituted 5- to 7-membered non-aromatic nitrogen-containing heterocycle;
$W^1$ is O, S, SO, $SO_2$, an optionally substituted $C_{1-6}$ alkylene group or $NR^4$ wherein $R^4$ is a hydrogen atom or a $C_{1-6}$ alkyl group;
$R^1$ is an optionally substituted $C_{6-14}$ aryl group or an optionally substituted heterocyclic group;
$R^3$ is a hydrogen atom or a halogen atom;
(1) when $W^2$ is O, S, SO or $SO_2$, $R^2$ is an optionally substituted heterocyclic group; and
(2) when $W^2$ is a bond, $R^2$ is a hydrogen atom, a halogen atom, an optionally substituted $C_{1-6}$ alkyl group, an optionally substituted $C_{3-10}$ cycloalkyl group or an optionally substituted heterocyclic group,
or a salt thereof.

2. The compound or salt according to claim 1, wherein $W^2$ is O, S, SO or $SO_2$.

3. The compound or salt according to claim 1, wherein ring A is a benzene ring.

4. The compound or salt according to claim 1, wherein $R^3$ is a hydrogen atom.

5. The compound or salt according to claim 1, wherein ring B is a thiazoline ring optionally substituted by a $C_{1-6}$ alkyl group optionally substituted by 1 to 3 substituents selected from the group consisting of:
- (1) a hydroxy group,
- (2) a carbamoyl group optionally mono- or di-substituted by $C_{1-6}$ alkyl group(s) optionally substituted by 1 to 3 substituents selected from the group consisting of:
  - (i) a hydroxy group,
  - (ii) a halogen atom,
  - (iii) a $C_{1-6}$ alkoxy group,
  - (iv) a $C_{1-6}$ alkylsulfonyl group, and
  - (v) a cyano group,
- (3) a carboxy group, and
- (4) a $C_{1-6}$ alkoxy-carbonyl group.

6. The compound or salt according to claim 1, wherein $W^1$ is O.

7. The compound or salt according to claim 1, wherein $R^1$ is a phenyl group or a pyridyl group each optionally substituted by 1 to 3 substituents selected from the group consisting of:
- (1) a $C_{1-6}$ alkyl group optionally substituted by 1 to 3 substituents selected from the group consisting of:
  - (i) a $C_{1-6}$ alkoxy group optionally substituted by a $C_{1-6}$ alkoxy group, and
  - (ii) a $C_{1-6}$ alkylsulfonyl group, and
- (2) a $C_{1-6}$ alkylsulfonyl group.

8. The compound or salt according to claim 1, wherein $W^2$ is O, and $R^2$ is a tetrahydropyranyl group.

9. The compound or salt according to claim 1, wherein $W^2$ is a bond, and $R^2$ is a hydrogen atom or a $C_{1-6}$ alkyl group.

10. The compound or salt according to claim 1, wherein
ring A is a benzene ring;
ring B is a thiazoline ring optionally substituted by a $C_{1-6}$ alkyl group optionally substituted by 1 to 3 substituents selected from the group consisting of:
- (1) a hydroxy group,
- (2) a carbamoyl group optionally mono- or di-substituted by $C_{1-6}$ alkyl group(s) optionally substituted by 1 to 3 substituents selected from the group consisting of:
  - (i) a hydroxy group,
  - (ii) a halogen atom,
  - (iii) a $C_{1-6}$ alkoxy group,
  - (iv) a $C_{1-6}$ alkylsulfonyl group, and
  - (v) a cyano group,
- (3) a carboxy group, and
- (4) a $C_{1-6}$ alkoxy-carbonyl group;

$W^1$ is O;
$R^1$ is a phenyl group or a pyridyl group each optionally substituted by 1 to 3 substituents selected from the group consisting of:
- (1) a $C_{1-6}$ alkyl group optionally substituted by 1 to 3 substituents selected from the group consisting of:
  - (i) a $C_{1-6}$ alkoxy group optionally substituted by a $C_{1-6}$ alkoxy group, and
  - (ii) a $C_{1-6}$ alkylsulfonyl group, and
- (2) a $C_{1-6}$ alkylsulfonyl group;

$R^3$ is a hydrogen atom;
$W^2$ is O; and
$R^2$ is a tetrahydropyranyl group.

11. The compound or salt according to claim 1, wherein
ring A is a benzene ring;
ring B is a thiazoline ring optionally substituted by a $C_{1-6}$ alkyl group optionally substituted by 1 to 3 substituents selected from the group consisting of:
- (1) a hydroxy group,
- (2) a carbamoyl group optionally mono- or di-substituted by $C_{1-6}$ alkyl group(s) optionally substituted by 1 to 3 substituents selected from the group consisting of:
  - (i) a hydroxy group,
  - (ii) a halogen atom,
  - (iii) a $C_{1-6}$ alkoxy group,
  - (iv) a $C_{1-6}$ alkylsulfonyl group, and
  - (v) a cyano group,
- (3) a carboxy group, and
- (4) a $C_{1-6}$ alkoxy-carbonyl group;

$W^1$ is O;
$R^1$ is a phenyl group or a pyridyl group each optionally substituted by 1 to 3 substituents selected from the group consisting of:
- (1) a $C_{1-6}$ alkyl group optionally substituted by 1 to 3 substituents selected from the group consisting of:
  - (i) a $C_{1-6}$ alkoxy group optionally substituted by a $C_{1-6}$ alkoxy group, and
  - (ii) a $C_{1-6}$ alkylsulfonyl group, and
- (2) a $C_{1-6}$ alkylsulfonyl group;

$R^3$ is a hydrogen atom;
$W^2$ is a bond; and
$R^2$ is a hydrogen atom or a $C_{1-6}$ alkyl group.

12. N-M ethyl-2-{2-[5-{[6-(methylsulfonyl)pyridin-3-yl]oxy}-7-(tetrahydro-2H-pyran-4-yloxy)-1H-indol-2-yl]-4,5-dihydro-1,3-thiazol-5-yl}acetamide or a salt thereof.

13. N-Methyl-2-[2-(5-{[6-(methylsulfonyl)pyridin-3-yl]oxy}-1H-indol-2-yl)-4,5-dihydro-1,3-thiazol-5-yl]acetamide or a salt thereof.

14. N,N-Dimethyl-2-[2-(5-{[6-(methylsulfonyl)pyridin-3-yl]oxy}-1H-indol-2-yl)-4,5-dihydro-1,3-thiazol-5-yl]acetamide or a salt thereof.

15. N-(2-Methoxyethyl)-2-[2-(5-{[6-(methylsulfonyl)pyridin-3-yl]oxy}-1H-indol-2-yl)-4,5-dihydro-1,3-thiazol-5-yl]acetamide or a salt thereof.

16. 2-[2-(7-Ethyl-5-{[6-(methylsulfonyl)pyridin-3-yl]oxy}-1H-indol-2-yl)-4,5-dihydro-1,3-thiazol-5-yl]-N-methylacetamide or a salt thereof.

17. A prodrug of the compound or salt according to claim 1.

18. A pharmaceutical composition comprising the compound or salt according to claim 1 or a prodrug thereof and a pharmaceutically acceptable carrier.

19. The pharmaceutical composition according to claim 18, which is a glucokinase activator.

20. The pharmaceutical composition according to claim 18, which is an agent for the treatment of diabetes or obesity.

21. A method for the treatment of diabetes or obesity in a mammal, comprising administering an effective amount of the compound or salt according to claim 1 or a prodrug thereof to the mammal.

* * * * *